US011492630B2

(12) United States Patent
Harling et al.

(10) Patent No.: US 11,492,630 B2
(45) Date of Patent: Nov. 8, 2022

(54) METHODS AND HYBRIDS FOR TARGETED NUCLEIC ACID EDITING IN PLANTS USING CRISPR/CAS SYSTEMS

(71) Applicant: KWS SAAT SE & CO. KGAA, Einbeck (DE)

(72) Inventors: Hinrich Harling, Bovenden (DE); Susana Martin-Ortigosa, Einbeck (DE); Markus Niessen, Hannover (DE); Corinna Streitner, Melle (DE); Nadine Schumann, Einbeck (DE); Erik Jongedijk, Lokeren (BE)

(73) Assignee: KWS SAAT SE & CO. KGAA, Einbeck (DE)

( * ) Notice: Subject to any disclaimer, the term of this patent is extended or adjusted under 35 U.S.C. 154(b) by 453 days.

(21) Appl. No.: 15/575,167

(22) PCT Filed: May 19, 2016

(86) PCT No.: PCT/EP2016/061237
§ 371 (c)(1),
(2) Date: Apr. 16, 2018

(87) PCT Pub. No.: WO2016/184955
PCT Pub. Date: Nov. 24, 2016

(65) Prior Publication Data

US 2018/0223295 A1 Aug. 9, 2018

(30) Foreign Application Priority Data

May 19, 2015 (DE) ......................... 102015006335.9
Nov. 5, 2015 (DE) ......................... 102015014252.6

(51) Int. Cl.
*C12N 15/82* (2006.01)
*C12N 15/113* (2010.01)
*A01H 5/04* (2018.01)
*A01H 5/12* (2018.01)

(52) U.S. Cl.
CPC ........... *C12N 15/8213* (2013.01); *A01H 5/04* (2013.01); *A01H 5/12* (2013.01); *C12N 15/113* (2013.01); *C12N 15/8201* (2013.01); *C12N 15/8203* (2013.01); *C12N 15/8205* (2013.01); *C12N 15/8207* (2013.01); *C12N 2310/20* (2017.05)

(58) Field of Classification Search
None
See application file for complete search history.

(56) References Cited

U.S. PATENT DOCUMENTS 5,500,360 A * 3/1996 Ahlquist et al. ....... C12N 15/85 435/468
5,736,369 A * 4/1998 Bowen et al. ..... C12N 15/8207 800/293
5,910,631 A 6/1999 Topfer et al.
6,187,994 B1 2/2001 Baszczynski et al.
6,410,329 B1 6/2002 Hansen et al.
6,583,335 B1 6/2003 Peffley et al.
6,603,061 B1 8/2003 Armstrong et al.
6,846,970 B1 1/2005 Christou et al.
8,399,218 B2 3/2013 Gupta et al.
8,697,359 B1 4/2014 Zhang
2003/0135891 A1 7/2003 Gould et al.
2005/0039228 A1 * 2/2005 Ding ..................... C12N 15/86 800/278
2011/0189775 A1 8/2011 Ainley et al.
2013/0145488 A1 6/2013 Wang et al.
2013/0263324 A1 10/2013 Lassner et al.
2014/0068797 A1 3/2014 Doudna et al.
2014/0096284 A1 4/2014 Martin-Ortigosa et al.
2014/0170753 A1 6/2014 Zhang
2014/0242702 A1 * 8/2014 Chen ................. A61K 31/5377 435/462
2015/0059010 A1 2/2015 Cigan et al.
2015/0067922 A1 3/2015 Yang
2016/0145631 A1 5/2016 Voytas et al.
2017/0260536 A1 9/2017 Vainstein et al.

FOREIGN PATENT DOCUMENTS

CN 1541270 A 10/2004
CN 102558309 A 7/2012
CN 102812034 A 12/2012
CN 103343120 A 10/2013
(Continued)

OTHER PUBLICATIONS

Ma et al., KR029113 (2015).*
Springer et al. (1979) Protoplasma 101:269-81.*
Al-Abed et al. (2006) Planta 223:1355-60.*
Ušák, D, "Regeneration and transformation of mature embryos of B73 maize line," (2020) B.A. Thesis, Palachy Univ. Olomouc.*
Elhiti & Stasolla (2011) "The use of zygotic embryos as explants for in vitro propagation: an overview," in: Plant Embryo Culture, Thorpe, T.A. & Yeung, E.C., eds. Meth Mol Biol, Humana Press (Totowa, NJ) 229-55.*
Maruyama et al. (2015) Nat Biotech 33:538-42.*
Ma et al., Plant multiplex genome editing vector pYLCRISPR/Cas9P35s-B; GenBank: KR029113.1 (2015).*
(Continued)

*Primary Examiner* — Russell T Boggs
(74) *Attorney, Agent, or Firm* — Troutman Pepper Hamilton Sanders LLP

(57) ABSTRACT

The present invention relates to methods and hybrids for the targeted modification of a nucleic acid-target region in a plant target structure using CRISPR/Cas systems. The invention specifically relates to methods and hybrids for directly obtaining a plant or plant material which comprises an editing of a nucleic acid introduced in a targeted manner into a meristematic cell. The hybrids can be introduced in a transient and/or stable manner. The invention also relates to novel plant-optimized introduction strategies. The invention further relates to a method for carrying out an in vitro screening assay in order to first check the suitable gRNA candidates in vitro with respect to their efficiency.

13 Claims, 27 Drawing Sheets

Specification includes a Sequence Listing.

(56) References Cited

FOREIGN PATENT DOCUMENTS

| | | | |
|---|---|---|---|
| CN | 103382468 | A | 11/2013 |
| CN | 103555711 | A | 2/2014 |
| CN | 103667338 | A | 3/2014 |
| CN | 103898099 | A | 7/2014 |
| CN | 103952405 | A | 7/2014 |
| CN | 104212778 | A | 12/2014 |
| CN | 104293828 | A | 1/2015 |
| DE | 10 2015 004 187 | A1 | 10/2016 |
| EP | 2 274 973 | A1 | 1/2011 |
| JP | 2010-539930 | A | 12/2010 |
| KR | 1020150006469 | | 1/2015 |
| WO | 00/66746 | A1 | 11/2000 |
| WO | 2004/009761 | A2 | 1/2004 |
| WO | 2009/042164 | A1 | 4/2009 |
| WO | 2011/072246 | | 6/2011 |
| WO | 2013/096567 | | 6/2013 |
| WO | 2013/1452578 | A1 | 9/2013 |
| WO | 2013/166315 | A1 | 11/2013 |
| WO | 2013/169802 | A1 | 11/2013 |
| WO | 2013/176772 | A1 | 11/2013 |
| WO | 2014/018423 | | 1/2014 |
| WO | 2014/039872 | A1 | 3/2014 |
| WO | 2014/065596 | A1 | 5/2014 |
| WO | 2014/104878 | A1 | 7/2014 |
| WO | 2014/144155 | | 9/2014 |
| WO | 2014/161821 | A1 | 10/2014 |
| WO | 2014/194190 | | 12/2014 |
| WO | 2014/199358 | A1 | 12/2014 |
| WO | 2015/026886 | A1 | 2/2015 |
| WO | WO2015/026885 | A1 * | 2/2015 |
| WO | 2015/066637 | A1 | 5/2015 |
| WO | 2015/077290 | A2 | 5/2015 |
| WO | 2016/021973 | A1 | 12/2016 |
| WO | 2017/092201 | A1 | 6/2017 |

OTHER PUBLICATIONS

International Search Report and Written Opinion issued by the International Searching Authority in International Application No. PCT/EP2016/061237, dated Feb. 20, 2017.

Baltes, N.J. et al., "DNA Replicons for Plant Genome Engineering," The Plant Cell, 2014, vol. 26, No. 1, pp. 151-163.

Quinn, T.P. et al., "A Streamlined Method for the Production, Screening, and Application of sgRNAs for CRISPR/Cas Gene Editing," (available at http://info.clontech.com/rs/clontech/images/633702_Guide_It_PS-0514_web.pdf).

Maruyama, T. et al., "Increasing the Efficiency of Precise Genome Editing with CRISPR-Cas9 by Inhibition of Nonhomologous End Joining," Nature Biotechnology, 2015, vol. 33, No. 5, pp. 538-542.

Zahir, A. et al., "Efficient Virus-Mediated Genome Editing in Plants Using the CRISPR/Cas9 System," Molecular Plant, 2015, vol. 8, No. 8, pp. 1288-1291.

Xing, H.-L., et al., "A CRISPR/Cas9 Toolkit for Multiplex Genome Editing in Plants," BMC Plant Biology, 2014, vol. 14, No. 1, pp. 327, 12 pages total.

Hyun Y. et al., "Site-Directed Mutagenesis in *Arabidopsis thaliana* Using Dividing Tissue-Targeted RGEN of the CRISPR/Cas System to Generate Heritable Null Alleles," Planta, 2015, vol. 241, No. 1, pp. 271-284.

Jacobs, T.B. et al., "Targeted Genome Modifications in Soybean with CRISPR/Cas9," BMC Biotechnology, 2015, vol. 15, No. 1, pp. 10 pages total.

Jiang, W. et al., "Demonstration of CRISPR/Cas9/sgRNA-Mediated Targeted Gene Modification in *Arabidopsis*, Tobacco, Sorghum and Rice," Nucleic Acids Research, 2013, vol. 41, No. 20, p. e188, 12 pages total.

Zhang, H. et al., "The CRISPR/Cas9 System Produces Specific and Homozygous Targeted Gene Editing in Rice in One Generation," Plant Biotechnology Journal, 2014, vol. 12, No. 6, pp. 797-807.

Bortesi, L. et al., "The CRISPR/Cas9 System for Plant Genome Editing and Beyond," Biotechnology Advances, 2014, vol. 33, No. 1, pp. 41-52.

Biotechniques, "A Streamlined Method for the Production, Screening, and Application of sgRNAs for CRISPR/Cas9 Gene Editing," 2014, vol. 57, No. 3, p. 157.

Zetsche, B. et al., "Cpfl is a Single RNA-Guided Endonuclease of a Class 2 CRISPR-Cas System," Cell, 2015, vol. 163, No. 3, pp. 759-771, 14 pages total.

Barrangou et al., "CRISPR provides acquired resistance against viruses in prokaryotes", Science, 2007, vol. 315, 1709-1712.

Clough et al., "Floral Dip: a simplified method for Agrobacterium-mediated transformation of *Arabidopsis thaliana*", The Plant Journal, vol. 16, No. 6, 1998, pp. 735-743.

Gelvin, "Viral-mediated plant transformation gets a boost", Nature Biotechnology, vol. 23, No. 6, 2005, pp. 684-685.

Guilinger et al., "Fusion of catalytically inactive Cas9 to Fokl nuclease improves the specificity of genome modification", Nat Biotechnol., 2014, vol. 32, No. 6, pp. 577-582.

Helenius et al., "Gene delivery into intact plants using the Helios Gene Gun", Plant Molecular Biology Reporter, 2000, vol. 18, No. 3, pp. 287a-287l.

Deltcheva et al., "CRISPR RNA maturation by trans-encoded small RNA and host factor RNase III", Nature, 2011, vol. 471, No. 7340, pp. 602-607.

Jansen et al., "Identification of genes that are associated with DNA repeats in pokaryotes", Molecular Microbiology, 2002, vol. 43, No. 6, pp. 1565-1575.

Jinek et al. "A programmable dual-RNA-guided DNA Endonuclease in Adaptive Bacterial Immunity", Science, 2012, vol. 337, pp. 816-821.

Kim et al., "Highly efficient RNA-guided genome editing in human cells via delivery of purified Cas9 ribonucleoproteins", Genome Research, 2014, vol. 24, No. 6, pp. 1012-1019.

Krens et al., "Transformation and regeneration in sugar beet (*Beta vulgaris* L.) induced by 'shooter' mutants of Agrobacterium tumefaciens", Euphytica, 1988, vol. 39, No. 3, pp. 185-194.

Leduc et al., "Gene transfer to inflorescence and flower meristems using ballistic micro-targeting", Sexual Plant Reproduction, 1994, vol. 7, No. 2, pp. 135-143.

Mahn et al., "Transient gene expression in shoot apical meristems of sugarbeet seedlings after particle bombardment", Journal of Experimental Botany, 1995, vol. 46, No. 291, pp. 1625-1628.

Makarova et al., "An updated evolutionary classification of CRISPR-Cas systems", Nature Rev. Microbial., 2015, vol. 13, No. 11, pp. 722-736.

Makraova et al., "Annotation and Classification of CRISPR-Cas Systems", Methods Mol. Biol., 2015, vol. 1311, pp. 47-75.

Makraova et al., "Unification of Cas protein families and a simple scenario for the origin and evolution of CRISPR-Cas systems", Biology Direct, vol. 6, No. 38, 2011, 27 pages.

Mali et al., "CAS9 transcriptional activators for target specificity screening and paired nickases for cooperative genome engineering", Nat Biotechnol., 2013, vol. 31, No. 9, pp. 833-838.

Martin-Ortigosa et al., "Proteolistics: a biolistic method for Intracellular delivery of proteins", Transgenic Research, 2014, vol. 23, pp. 743-756.

Ramakrishna et al., "Gene disruption by cell-penetrating peptide-mediated delivery of Cas9 protein and guide RNA", Genome Research, 2014, vol. 24, No. 6, pp. 1020-1027.

Sapranaukas et al., "The *Streptococcus thermophilus* CRISPR/Cas system provides immunity in *Escherichia coli*", Nucleic Acids Research, 2011, vol. 39, No. 21, pp. 9275-9282.

Van der Oost et al., "Unravelling the structural of mechanistic basis of CRISPR-Cas systems", Nat Rev Microbiol., 2014, vol. 12, No. 7, pp. 479-492.

Wiedenheft et al., "Structures of the RNA-guided surveillance complex from a bacterial immune system", Nature, 2011, vol. 477, No. (7365), pp. 486-489.

International Search Report and Written Opinion issued by the International Searching Authority in International Application No. PCT/EP2016/061338, dated Aug. 5, 2016.

(56) References Cited

OTHER PUBLICATIONS

Abhishek et al., "Tissue Culture Independent Agrobacterium tumefaciens Mediated In Planta Transformation Method for Tropical Maize (*Zea mays.* L)", Proceedings of the National Academy of Sciences, India, Section B, Biological Sciences, 2016, vol. 86, No. 2, pp. 375-384.
Bent et al., "*Arabidopsis* in Planta Transformation. Uses, mechanisms, and Prospects for Transformation of Other Species", Plant Physiology, 2000, vol. 124, No. 4, p. 1540-1547.
Chowrira et al., "Transgenic Grain Legumes Obtained by In Planta Electroporation-Mediated Gene Transfer", Molecular Biotechnology, vol. 5, No. 2, 1996, pp. 85-96.
Razzaq et al., "Development of in planta transformation protocol for wheat", African Journal of Biotechnology, vol. 10. No. 5, 2011, pp. 740-750.
Collins et al., "The Effect of Cotyledon Excision on Reproductive Development in Pea (*Pisum sativum* L.)", Annals of Botany, vol. 38, No. 1, 1974, pp. 181-188.
European Search Report issued in EP 15202060 dated Aug. 5, 2016.
Hu et al., "Agrobacterium-mediated vacuum infiltration and floral dip transformation of rapid-cycling *Brassica rapa*", BMC Plant Biology, 2019, vol. 19, 9 pages.
Ghedira et al., "The Efficiency of *Arabidopsis thaliana* Floral Dip Transformation is Determined Not Only by the Agrobacterium Strain Used but Also by the Physiology and the Ecotype of the Dipped Plant", MPMI, vol. 26, No. 7, 2013, pp. 823-832.
Takacs et al., "Ontogeny of the Maize Shoot Apical Meristem", The Plant Cell, vol. 24, Aug. 2012, pp. 3219-3234.
Yoo et al., "*Arabidopsis mesophyll* protoplasts: a versatile cell system for transient gene expression analysis", Nature Protocols, 2007, vol. 2, No. 7, pp. 1565-1572.
Liang et al., "Efficient DNA-free genome editing of bread wheat using CRISPR/Cas9 ribonucieoprotein complexes", Nature Communications, 2017, vol. 8, Article 14261, 15 pages.
Svitashev et al., "Genome editing in maize directed by CRISPR-Cas9 ribonucieoprotein complexes", Nature Communications, 2016, vol. 7, Article 13274, 7 pages.
Zhang et al., "Efficient and transgene-free genome editing in wheat through transient expression CRISPR/Cas9 DNA or RNA", Nature Communications, 2016, vol. 7, Article 12617, 8 pages.
Nathalia Maira Cabral de Medeiros et al., "Recent Advances in Plant DNA Repair", Intech, 2015, pp. 3-42 (available at http://dx.doi.org/10.5772/59998).
Yoshiyama, "SOG1: a master regulator of the DNA damage response in plants", Genes & Genetic Systems, 2015, vol. 90, pp. 209-216.
Feng et al., "Efficient genome editing in plants using a CRISPR/Cas System", Cell Research, 2013, vol. 23, No. 10, pp. 1229-1232.
Woo et al., "DNA-free genome editing in plants with preassembled CRISPR-Cas9 ribonucleoproteins," Nature Biotechnology, vol. 33, No. 11, 2015, pp. 1162-1165.
Curtin et al., "Targeted Mutagenesis of Duplicated Genes in Soybean with Zinc-Finger Nucleases", Plant Physiology, 2011, vol. 156, No. 2, pp. 466-473.
Fang et al., "New Method of Genome Editing Derived from CRISPR/Cas9", Progress in Biochemistry and Biophysics, 2013, vol. 40, No. 8, pp. 691-702 and English Abstract Thereof.
International Search Report and Written Opinion issued in PCT/CN2016/076244, dated Jun. 15, 2016 and English Translation thereof, 22 pages.
Liang et al., "Targeted Mutagenesis in *Zea mays* Using TALENs and the CRISPR/Cas System", Journal of Genetics and Genomics, 2013, vol. 41, No. 2, pp. 63-68.
Xiao et al., "Progress in Zinc Finger Nuclease Engineering for Targeted Genome Modification", Hereditas, 2011, vol. 33, No. 7, pp. 665-683 and English Abstract Thereof.
Zhang et al., "TALENs: A New Genome Site-Specific Modification Technology", Chinese Bulletin of Life Sciences, 2013, vol. 25, No. 12, pp. 126-132 and English Abstract Thereof.
Armstrong et al., "Development and availability of germplasm with high Type II culture formation response", https://mnl.maizegdb.org/mn1/65/146armstrong.html. 3 pages.

Wang, et al., "Simultaneous editing of three homoeoalleles in hexaploid bread wheat confers heritable resistance to powdery mildew", Nature Biotechnology, 2014, vol. 32, No. 9, pp. 947-952.
Weeks et al., "Rapid production of multiple independent lines offertile transgenic wheat (*Triticum aestivum*)", Plant Physiol., 1993, vol. 102, pp. 1077-1084.
Chang et al., "Genome editing with RNA-guided Cas9 nuclease in Zebrafish embryos", Cell Research, 2013, vol. 23, No. 4, pp. 465-472.
Shan et al., "Rapid and Efficient Gene Modification in Rice and Brachypodium Using TALENs", Molecular Plant, 2013, vol. 6, No. 4, pp. 1365-1368.
Song et al., "Application of a transformation method via the pollen-tube pathway in agriculture molecular breeeding", Life Science Journal, 2007, vol. 4, No. 1, pp. 77-79.
Gasiunas et al., "Cas9-crRNA ribonucleoprotein complex mediates specific DNA cleavage for adaptive immunity in bacteria", Proc. Natl Acad Sci USA, 2012, vol. 109, No. 39, pp. E2579-E2586.
Wang et al., "One-step generation of mice carrying mutations in multiple genes by CRISPR/Cas-mediated genome engineering", Cell, 2013, vol. 153, No. 4, pp. 910-918.
Klein et al.,"Transformation of microbes, plants and animals by particle bombardment", Biotechnology, 1992, vol. 10, No. 3, pp. 286-291.
Barcelo et al., "Transgenic cereal (tritodeum) plants obtained at high efficiency by microprojectile bombardment of inflorescence tissue", The Plant Journal, 1994, vol. 5, No. 4, pp. 583-592.
Wang et al., "Cotton transformation via pollen tube pathway", Methods in Molecular Biology, 2013, vol. 958, pp. 71-77.
Dudas et al., "DNA double-strand break repair by homologous recombination", Mutation Research, 2004, vol. 566, No. 2, pp. 131-167.
Kim et al., "A guide to genome engineering with programmable nucleases", Nt. Rev. Genet, 2014, vol. 15, No. 5, pp. 321-334.
Vainstein et al., "Permanent genome modifications in plant cells by transient viral vectors", Trends in Biotechnology, 2011, vol. 29, No. 8, pp. 363-369.
Martin-Ortigosa et al., "Mesoporous silica nanoparticle-mediated intracellular cre protein delivery for maize genome editing via loxP site excision", Plant Physiology, 2014, vol. 164, No. 2, pp. 537-547.
Lee et al., "RNA-guided genome editing in *Drosophila* with the purified Cas9 protein", G3, 2014, vol. 4, No. 7, pp. 1291-1295.
Bassett et al., "Highly efficient targeted mutagenesis of *Drosophila* with the CRISPR/Cas9 system", Cell Reports, 2013, vol. 4, No. 1, pp. 220-228.
Fernando et al., "Transient gene expression in pine pollen tubes following particle bombardment", Plant Cell Reports, 2000, vol. 19, pp. 224-228.
Jiang et al., "Efficient CRISPR/Cas9-mediated gene editing in *Arabidopsis thaliana* and inheritance of modified genes in the T2 and T3 generations", PloS one, 2014, vol. 9, Issue 6, pp. 1-10.
Shan et al., "Targeted genome modification of crop plants using a CRISPR-Cas System", Nature Biotechnology, vol. 31, No. 8, Aug. 1, 2013, pp. 686-688.
Shan et al., "Supplementary Material for Targeted genome modification of crop plants using a CRISPR-Cas system", Nature Biotechnology, vol. 31, No. 8, Aug. 1, 2013, 22 pages.
Zhang et al., "Transcription Activator-Like Effector Nucleases Enable Efficient Plant Genome Engineering", Plant Physiology, 2013, vol. 161, No. 1, pp. 20-27.
Kumar et al., "The CRISPR-Cas system for plant genome editing: advances and opportunities", Journal of Experimental Botany, 2015, vol. 66, No. 1, pp. 47-57.
Voytas et al., "Precision Genome Engineering and Agriculture: Opportunites and Regulatory Challenges", PLOS Biology, Jun. 2014, vol. 12, No. 6, e1001877, pp. 1-6.
Puchta et al., "Synthetic nucleases for genome engineering in plants prospects for a bright future", The Plant Journal, vol. 78, No. 5, 2014, pp. 727-741.
Marton et al., "Nontransgenic Genome Modification in Plant Cells", Plant Physiology, 2010, vol. 154, No. 3, pp. 1079-1087.
International Search Report and Written Opinion issued PCT/CN2016/071352, dated Apr. 25, 2016, 9 pages.

(56) References Cited

OTHER PUBLICATIONS

Ling et al., "Draft genome of the wheat A-genome progenitor Triticum urartu", Nature, 2013, vol. 496, pp. 87-90.
Shan et al., "Genome editing in rice and wheat using the CRISPR/Cas system", Nature Protocols, 2014, vol. 9, No. 10, pp. 2395-2410.
Mao et al., "Overexpression of a NAC-domain protein promotes shoot branching in rice", New Phytologist, 2007, vol. 176, pp. 288-298.
Xu et al., "A PIN1 Family Gene, OsPIN1, involved in Auxin-dependent Adventitious Root Emergence and Tillering in Rice", Plant Cell Physiol., 2005, vol. 46, No. 10, pp. 1674-1681.
Feng et al., "Molecular analysis of lipoxygenase (LOX) genes in common wheat and phylogenetic investigation of LOX proteins from model and crop plants", Journal of Cereal Science, 2010, vol. 52, pp. 387-394.
Lawrenson et al., "Induction of targeted, heritable mutations in barley and *Brassica oleracea* using RNA-guided Cas9 nuclease", Genome Biology, 2015, vol. 16, 258, 13 pages.
Zhang et al., "Biolistic Genetic Transformation of a Wide Range of Chinese Elite Wheat (*Triticum aestivum* L.) Varieties", Journal of Genetics and Genomics, 2015, vol. 42, pp. 39-42.
Larsen et al., "ALS3 encodes a phloem-localized ABC transporter-like protein that is required for aluminum tolerance in *Arabidopsis*", The Plant Journal, 2005, vol. 41, No. 3, pp. 353-363.
Laursen et al., "Production of fertile transgenic maize by electroporation of suspension culture cells", Plant Molecular Biology, 1994, vol. 24, No. 1, pp. 51-61.
Aragao et al., "Particle bombardment-mediated transient expression of a Brazil nut methionine-rich albumin in bean (*Phaseolus vulgaris* L.)", Plant Molecular Biology, 1992, vol. 20, No. 2, pp. 357-359.
Brooks et al., "Efficient Gene Editing in Tomato in the First Generation Using the Clustered Regularly Interspaced Short Palindromic Repeats/CRISPR-Associated9 System", Plant Physiology, 2014, vol. 166, pp. 1292-1297.
International Search Report Issued in PCT/CN2016/072352 dated Apr. 27, 2016 and English Translation thereof 10 pages.
Russell, "Registration of B70 and B73 parental lines of maize", Crop Sci., 1972, vol. 12, p. 721.
Koornneef at al., "Linkage map of *Arabidopsis thaliana*", The Journal of Heredity, 1983, vol. 74, pp. 265-272.
Li et al., "Multiplex and homologous recombination-mediated plant genome editing via guide RNA/Cas9", Nature Biotechnology, 2013, vol. 31, No. 8, pp. 688-691.
Written Opinion issued in PCT/CN2016/072352 dated Apr. 27, 2016 and English Translation thereof.
Luo et al., "A Simple Method for the Transformation of Rice Via the Pollen-Tube Pathway", Plant Molecular Biology Reporter, 1988, vol. 6, No. 3, pp. 165-174.
Yang et al., "Transgenic soybean with low phytate content constructed by Agrobacterium transformation and pollen-tube pathway", Euphytica, 2011, vol. 177, pp. 375-382.
Naito et al., "CRISPRdirect: software for designing CRISPR/Cas guide RNA with reduced off-target sites", Bioinfomatics, 2015, vol. 31, No. 7, pp. 1120-1123.
Basic knowledge of the database DIAM biotechnology, (a) Bioindustry Association, "Select temperature," URL:<http://togodb.biosciencedbc.jp/togodb/show/diam_bioterm_list/96>.
Ishida et al., "Agrobacterium-mediated transformation of maize", Nature Protocols, 2007, vol. 2, No. 7, pp. 1614-1621.
International Search Report and Written Opinion by the International Searching Authority in International Application No. PCT/CN2016/095307 dated Nov. 23, 2016.
Weinthal et al., "Nonhomologous End Joining-Mediated Gene Replacement in Plant Cells", Plant Physiology, 2013, vol. 162, pp. 390-400.
Chen et al., "TALENs: Customizable Molecular DNA Scissors for Genome Engineering of Plants", Journal of Genetics and Genomics, 2013, vol. 40, No. 6, pp. 271-279.
Gilles et al., "Efficient CRISPR-mediated gene targeting and transgene replacement in the beetle *Tribolium castaneum*", Development, vol. 142, No. 16, 2015, pp. 2832-2839.
Li et al., "Gene replacements and insertions in rice by intron targeting using CRISPR-Cas9", Nature Plants, vol. 2, No. 10, 2016, Article No. 16139, 6 pages.
Zu et al., "TALEN-mediated precise genome modification by homologous recombination in zebrafish", Nature Methods, 2013, vol. 10, No. 4, pp. 329-331.
Kanchiswamy et al., "Non-GMO genetically edited crop plants", Trends in Biotechnology, 2015, vol. 33, No. 9, pp. 489-491.
Xu et al., "Cloning of genomic DAN of rice 5-enolpyruvlshikimate 3-phsphate synthase gene and chromosomal localization of the gene", Science in China, 2002, vol. 45, No. 3, pp. 251-259.
Vasil et al., "Transformation of wheat via particle bombardment", Methods in Molecular Biology, 2006, vol. 318, pp. 273-283.
Doshi et al., "Anthocyanin expression in marker free transgenic wheat and triticale embryos", In Vitro Cell Dev. Biol.—Plant, 2007, vol. 43, pp. 429-435.
De Vetten et al., "A transformation method for obtaining marker-free plants of a cross-pollinating and vegetatively propagated crop", Nature Biotechnology, 2003, vol. 21, No. 4, pp. 439-442.
Pastori et al., "Age-dependent transformation frequency in elite wheat varieties", Journal of Experimental Botany, 2001, vol. 52, No. 357, pp. 857-863.
Carroll, "Genome Engineering with Targetable Nucleases", Annu. Rev. Biochem., 2014, vol. 83, pp. 409-439.
Hamada et al., "Biolistic-delivery-bsed transient CRISPR/Cas9 expression enables in planta genome editing in wheat", Scientific Reports, 2018, vol. 8, Article 14422, 7 pages.

* cited by examiner (A) (B)

(A) (B)

Column:

(B)

(A)

(B)

(A)

(A) (B)

(A) (B)

(A)

(B)

dpi: days after infiltration (E)

(F)

(G)

(H)

(A) (B)

SEQUENCE LISTING

```
<160> NUMBER OF SEQ ID NOS: 61

<210> SEQ ID NO 1
<211> LENGTH: 259
<212> TYPE: DNA
<213> ORGANISM: Artificial sequence
<220> FEATURE:
<223> OTHER INFORMATION: VP16 activator comprising sequence

<400> SEQUENCE: 1

ctaagctttc gacggccccc ccgaccgacg tcagcctggg ggacgagctc cacttagacg      60

gcgaggacgt ggcgatggcg catgccgacg cgctagacga tttcgatctg gacatgttgg     120

gggacgggga ttccccgggg ccgggattta ccccccacga ctccgccccc tacggcgctc     180

tggatacggc cgacttcgag tttgagcaga tgtttaccga tgcccttgga attgacgagt     240

acggtgggta gagatcttc                                                  259


<210> SEQ ID NO 2
<211> LENGTH: 11
<212> TYPE: PRT
<213> ORGANISM: Artificial sequence
<220> FEATURE:
<223> OTHER INFORMATION: VP16 activator

<400> SEQUENCE: 2

Asp Ala Leu Asp Asp Phe Asp Leu Asp Met Leu
1               5                   10


<210> SEQ ID NO 3
<211> LENGTH: 50
<212> TYPE: PRT
<213> ORGANISM: Artificial sequence
<220> FEATURE:
<223> OTHER INFORMATION: VP64 activator with glycine serine spacers

<400> SEQUENCE: 3

Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45
```

Met Leu
50

<210> SEQ ID NO 4
<211> LENGTH: 615
<212> TYPE: DNA
<213> ORGANISM: Arabidopsis thaliana
<220> FEATURE:
<221> NAME/KEY: misc_feature
<222> LOCATION: (1)..(615)
<223> OTHER INFORMATION: EAR 1 repressor

<400> SEQUENCE: 4
atggagagat caaacagcat agagttgagg aacagcttct atggccgtgc aagaacttca 60
ccatggagct atggagatta tgataattgc caacaggatc atgattatct tctagggttt 120
tcatggccac caagatccta cacttgcagc ttctgcaaaa gggaattcag atcggctcaa 180
gcacttggtg gccacatgaa tgttcacaga agagacagag caagactcag attacaacag 240
tctccatcat catcttcaac accttctcct ccttacccta accctaatta ctcttactca 300
accatggcaa actctcctcc tcctcatcat tctcctctaa ccctatttcc aaccctttct 360
cctccatcct caccaagata tagggcaggt ttgatccgtt ccttgagccc caagtcaaaa 420
catacaccag aaaacgcttg taagactaag aaatcatctc ttttagtgga ggctggagag 480
gctacaaggt tcaccagtaa agatgcttgc aagatcctga ggaatgatga aatcatcagc 540
ttggagcttg agattggttt gattaacgaa tcagagcaag atctggatct agaactccgt 600
ttgggtttcg cttaa 615

<210> SEQ ID NO 5
<211> LENGTH: 972
<212> TYPE: DNA
<213> ORGANISM: Petroselinum crispum
<220> FEATURE:
<221> NAME/KEY: misc_feature
<222> LOCATION: (1)..(972)
<223> OTHER INFORMATION: Parsley_Ubi4

<400> SEQUENCE: 5
aaaaattacg gatatgaata taggcatatc cgtatccgaa ttatccgttt gacagctagc 60
aacgattgta caattgcttc tttaaaaaag gaagaaagaa agaaagaaaa gaatcaacat 120
cagcgttaac aaacggcccc gttacggccc aaacggtcat atagagtaac ggcgttaagc 180
gttgaaagac tcctatcgaa atacgtaacc gcaaacgtgt catagtcaga tcccctcttc 240
cttcaccgcc tcaaacacaa aaataatctt ctacagccta tatatacaac cccccttct 300 atctctcctt tctcacaatt catcatcttt ctttctctac ccccaatttt aagaaatcct 360
ctcttctcct cttcatttc aaggtaaatc tctctctctc tctctctctc tgttattcct 420
tgttttaatt aggtatgtat tattgctagt ttgttaatct gcttatctta tgtatgcctt 480
atgtgaatat ctttatcttg ttcatctcat ccgtttagaa gctataaatt tgttgatttg 540
actgtgtatc tacacgtggt tatgtttata tctaatcaga tatgaatttc ttcatattgt 600
tgcgtttgtg tgtaccaatc cgaaatcgtt gatttttttc atttaatcgt gtagctaatt 660
gtacgtatac atatggatct acgtatcaat tgttcatctg tttgtgtttg tatgtataca 720
gatctgaaaa catcacttct ctcatctgat tgtgttgtta catacataga tatagatctg 780
ttatatcatt ttttttatta attgtgtata tatatatgtg catagatctg gattacatga 840
ttgtgattat ttacatgatt ttgttattta cgtatgtata tatgtagatc tggacttttt 900
ggagttgttg acttgattgt atttgtgtgt gtatatgtgt gttctgatct tgatatgtta 960
tgtatgtgca gc 972

<210> SEQ ID NO 6
<211> LENGTH: 384
<212> TYPE: DNA
<213> ORGANISM: Arabidopsis thaliana
<220> FEATURE:
<221> NAME/KEY: misc_feature
<222> LOCATION: (1)..(384)
<223> OTHER INFORMATION: Arabidopsis_U6

<400> SEQUENCE: 6 cttttttttct tcttcttcgt tcatacagtt tttttttgtt tatcagctta cattttcttg 60
aaccgtagct ttcgtttttct tctttttaac tttccattcg gagtttttgt atcttgtttc 120
atagtttgtc ccaggattag aatgattagg catcgaacct tcaagaattt gattgaataa 180
aacatcttca ttcttaagat atgaagataa tcttcaaaag gcccctggga atctgaaaga 240
agagaagcag gcccatttat atgggaaaga acaatagtat ttcttatata ggcccattta 300
agttgaaaac aatcttcaaa agtcccacat cgcttagata agaaaacgaa gctgagttta 360
tatacagcta gagtcgaagt agtg 384

<210> SEQ ID NO 7
<211> LENGTH: 1502
<212> TYPE: DNA
<213> ORGANISM: Zea spp.
<220> FEATURE:
<221> NAME/KEY: misc_feature
<222> LOCATION: (1)..(1502)
<223> OTHER INFORMATION: Maize_Ubi_Intron

<400> SEQUENCE: 7
tgcagcgtga cccggtcgtg cccctctcta gagataatga gcattgcatg tctaagttat 60
aaaaaattac cacatatttt ttttgtcaca cttgtttgaa gtgcagttta tctatcttta 120
tacatatatt taaactttac tctacgaata atataatcta tagtactaca ataatatcag 180
tgttttagag aatcatataa atgaacagtt agacatggtc taaaggacaa ttgagtattt 240
tgacaacagg actctacagt tttatctttt tagtgtgcat gtgttctcct ttttttttgc 300
aaatagcttc acctatataa tacttcatcc attttattag tacatccatt tagggtttag 360
ggttaatggt ttttatagac taattttttt agtacatcta ttttattcta ttttagcctc 420
taaattaaga aaactaaaac tctattttag tttttttatt taataattta gatataaaat 480
agaataaaat aaagtgacta aaaattaaac aaataccctt taagaaatta aaaaaactaa 540
ggaaacattt ttcttgtttc gagtagataa tgccagcctg ttaaacgccg tcgatcgacg 600
agtctaacgg acaccaacca gcgaaccagc agcgtcgcgt cgggccaagc gaagcagacg 660
gcacggcatc tctgtcgctg cctctggacc cctctcgaga gttccgctcc accgttggac 720
ttgctccgct gtcggcatcc agaaattgcg tggcggagcg gcagacgtga gccggcacgg 780
caggcggcct cctcctcctc tcacggcacc ggcagctacg gggggattcct ttcccaccgc 840 tccttcgctt tcccttcctc gcccgccgta ataaatagac accccctcca caccctcttt 900
ccccaacctc gtgttgttcg gagcgcacac acacacaacc agatctcccc caaatccacc 960
cgtcggcacc tccgcttcaa ggtacgccgc tcgtcctccc cccccccccc tctctacctt 1020
ctctagatcg gcgttccggt ccatggttag ggcccggtag ttctacttct gttcatgttt 1080
gtgttagatc cgtgtttgtg ttagatccgt gctgctagcg ttcgtacacg gatgcgacct 1140
gtacgtcaga cacgttctga ttgctaactt gccagtgttt ctctttgggg aatcctggga 1200
tggctctagc cgttccgcag acgggatcga tctaggatag gtatacatgt tgatgtgggt 1260
tttactgatg catatacatg atggcatatg cagcatctat tcatatgctc taaccttgag 1320
tacctatcta ttataataaa caagtatgtt ttataattat tttgatcttg atatacttgg 1380
atgatggcat atgcagcagc tatatgtgga tttttttagc cctgccttca tacgctattt 1440
atttgcttgg tactgtttct tttgtcgatg ctcaccctgt tgtttggtgt tacttctgca 1500
gg 1502

<210> SEQ ID NO 8
<211> LENGTH: 360
<212> TYPE: DNA
<213> ORGANISM: Triticum spp.
<220> FEATURE:
<221> NAME/KEY: misc_feature
<222> LOCATION: (1)..(360)
<223> OTHER INFORMATION: U6

<400> SEQUENCE: 8
gaccaagccc gttattctga cagttctggt gctcaacaca tttatattta tcaaggagca 60
cattgttact cactgctagg agggaatcga actaggaata ttgatcagag gaactacgag 120
agagctgaag ataactgccc tctagctctc actgatctgg gcgcatagtg agatgcagcc 180
cacgtgagtt cagcaacggt ctagcgctgg gcttttaggc ccgcatgatc gggctttgtc 240
gggtggtcga cgtgttcacg attggggaga gcaacgcagc agttcctctt agtttagtcc 300
cacctcgcct gtccagcaga gttctgaccg gtttataaac tcgcttgctg catcagactt 360

<210> SEQ ID NO 9
<211> LENGTH: 377
<212> TYPE: DNA
<213> ORGANISM: Oryza spp.
<220> FEATURE:
<221> NAME/KEY: misc_feature
<222> LOCATION: (1)..(377)
<223> OTHER INFORMATION: U3

<400> SEQUENCE: 9
aaggaatctt taaacatacg aacagatcac ttaaagttct tctgaagcaa cttaaagtta 60
tcaggcatgc atggatcttg gaggaatcag atgtgcagtc agggaccata gcacaagaca 120
ggcgtcttct actggtgcta ccagcaaatg ctggaagccg ggaacactgg gtacgttgga 180
aaccacgtga tgtggagtaa gataaactgt aggagaaaag catttcgtag tgggccatga 240
agcctttcag gacatgtatt gcagtatggg ccggcccatt acgcaattgg acgacaacaa 300
agactagtat tagtaccacc tcggctatcc acatagatca aagctggttt aaaagagttg 360
tgcagatgat ccgtggc 377

<210> SEQ ID NO 10
<211> LENGTH: 763
<212> TYPE: DNA
<213> ORGANISM: Zea spp.
<220> FEATURE:
<221> NAME/KEY: misc_feature
<222> LOCATION: (1)..(763)
<223> OTHER INFORMATION: U3

<400> SEQUENCE: 10
gaattccatc taagtatctt ggtaaagcat ggattaattt ggatgcccac ttcaggtcta 60

```
tgcagctccg gtgccttgtg attgtgagtt gtgaccgatg ctcatgctat tctgcatttc    120

tgcgatgtat gtagctagta gatcttcaaa actaacaccg catgccatca tcatccactg    180

cttgatttta gtctcaccgc tggccaaaaa tgtgatgatg ccagaaacct caactacctt    240

gaatcaacac gggcccaaca gtgtgatgac gacagaaaca aaaaaaaatg agccaatagt    300

tcagaaggag gcactatgca gaaactacat ttctgaaggt gactaaaagg tgagcgtaga    360

gtgtaattac tagtagttta gccaccatta cccaaatgct ttcgagcttg tattaagatt    420

tcctaagctg agcatcatca ctgatctgca ggccaccctc gcttcgctgc caagatcaac    480

agcaaccatg tggcggcaac atccagcatt gcacatgggc taaagattga gctttgtgcc    540

tcgtctaggg atcagctgag gttatcagtc tttccttttt ttcatccagg tgaggcatca    600

agctactact gcctcgattg gctggacccg aagcccacat gtaggatacc agaatgggcc    660

gacccaggac gcagtatgtt ggccagtccc accggttagt gccatctcgg ttgctcacat    720

gcgtagaagc cagcttaaaa atttagcttt ggtgactcac agc                      763
```

```
<210> SEQ ID NO 11
<211> LENGTH: 1880
<212> TYPE: DNA
<213> ORGANISM: Brachypodium spp.
<220> FEATURE:
<221> NAME/KEY: misc_feature
<222> LOCATION: (1)..(1880)
<223> OTHER INFORMATION: EF1

<400> SEQUENCE: 11

cttcaccgcc attgcaaaaa ttgtcaataa atatttagag tgggtggcat cagaaaaaca     60

tctctagtgg actctcttcc tatcatagct actcgggctg tagatagaac gagggcacaa    120

gagttgggtg gcgtaggttt actcgtgacc tcaactcttt tggctgtgtc ttacgtctaa    180

gatgggtttg gcatgtgaga aacataggtc taagcaattc atgttagggc tgttgcattg    240

ttgttgcatc aaccaaatgt ccagatagca gttcatgcta catctagttg aaaaccctca    300

tcattaggcg gaacatgtgt tcttttttag catagtcaaa gtcagattgc ggcactcgct    360

catccacgga aagaatttc cctgtgcagg catctcgatc aaaagacgca aattaatttt     420

tgaatagcga tataacaata tctaattaac gtttcttgtt ttctgcgaaa tgtctttcat    480

cataaaatga gtcatctcga tgagcccaag tgacatagcc caacacccca ccccaccaat    540

aaaagtgaag aaaacatgtt gggaaaacta taccaagtaa aatacgagtt gttctaaaga    600

aaaagtaaag tacgagttag atcgcaccct gtcctggagt gtggcttgat gatccaactc    660

ctagcattgt atccctgttt ttggatgatg taactattat ttacaatgaa taaagaggtg    720

ttttactagt aaaaaaatct tgaggggagg agaaaataat ggaggtcttt tttcaaaccg    780

atggactatt atttttagtg aaagagaata atattattgg aaaaattatt ctatccactt    840

attttatatt ggcagaatac aaagaatggt ggggtccacg cggaacttgc ggcccccgaa    900

acctatcgag ggcgcggtac ccaagcaagg aacggaggaa acttgcgggg cccgaaacct    960

agtgataaaa ggcatatcat ccacacgatg aagatctgac ggaccatatc tcccaccacg   1020

gaaagccatc agacgaggat cagacggcca ggaaggaacc ctagcgcccg ccggtgccaa   1080

tataaagcgc cactctctct cgtcttaagc cccagcctct ccattcccct ctccctctcg   1140

ccgccgccgt ctccttctcc tactcccttc gaggtgtgtt gttcatccgt cccgaatcca   1200

tccatcccct cttcagatgt gttgttcatg gctctaatag ctctagatct gcttgtttgt   1260
```

```
gttgtttagc tctagatcta ctcgcgcgcg cttctctctc gatctcctgt agaacaattt   1320

tggttggttt tttgtgcata tccatggtaa ttttgtctgc aatatggagg aggctttcta   1380

agctcctacg tagcatcgat ctttagaatt ccctcggttt ctgtttattt cttcgcgagg   1440

gctctctgtt atctgtagga gtagctgtaa gcgcggttcg ttacggatta atcgtcatgc   1500

ttagttgaac ctatcggtcg aaggatttgt gtgggttgtc gtgtagaatt gacaccatct   1560

acttactgta ctgatatgcc gatctgtagg atactcttca ttacttttgt ttactgctag   1620

ttgtggtgta gatttagcat tctcaaaccc atgctgtagc gtttctaata ttgttacata   1680

gatctaccgg tgcctgttaa ttgtattcga tcgggcgttt ctacatctgt ccgcccacct   1740

agttttatat gtggtaatca aaattgcgtt gacttcgtga tgctgtctgt gtactgtttt   1800

taatcgctct tacttagatg atcaacatgg tgatggttac gatttactgt tttctaatcc   1860

ctgttacttc gatgctgcag                                               1880
```

<210> SEQ ID NO 12
<211> LENGTH: 2690
<212> TYPE: DNA
<213> ORGANISM: Maize Streak Virus (MSV) South African Strain

<400> SEQUENCE: 12

```
atggatccac agaacgccct gtattatcag ccgcgggtac ccactgcagc tccgacatcc     60

ggaggagtgc cgtggagtcg cgtaggcgag gtagctattt tgagctttgt tgcattgatt    120

tgcttttacc tgctttacct ttgggtgctg agagacctta tcttagttct gaaggctcga    180

caaggcagat ccacggagga gctgatattt ggtggacaag ctgtggatag gagcaaccct    240

atccctaatc taccagcacc accaagtcag ggcaatcccg ggccatttgt tccaggcacg    300

ggataagcaa tcagccatgt ccacgtccaa gaggaagcgg ggagatgatg cgaattggag    360

taagcgggtg cctaagaaga agccttcttc agctgggctg aagagggctg gaagcaaggc    420

cgataggcca tccctccaaa tccagacact ccagcatgct gggaccacca tgataactgt    480

cccatccgga ggagtatgtg acctcatcaa cacctatgcc cgaggatctg acgagggcaa    540

ccgccacacc agcgagactc tgacgtacaa gatcgccgtc gactaccact tcgttgccga    600

cgcggctgcc tgccgctact ccaacaccgg aaccggtgta atgtggctgg tgtatgacac    660

cactcccggc ggacaagctc cgaccccgca aactatattt gcctaccctg acacgctaaa    720

agcgtggccg gccacatgga aagtgagccg ggagctgtgt catcgcttcg tggtgaaacg    780

gcgatggttg ttcaacatgg agaccgacgg tcggattggt tcggatatcc ctccctcgaa    840

tacaagttgg aagccttgca agcgcaacat ctacttccac aagttcacga gtgggttggg    900

agtgagaacg cagtggaaga atgtaacgga cggaggagtt ggtgccatcc agagaggagc    960

tttgtacatg gtcattgccc ccggcaatgg ccttacattt actgcccatg ggcagacccg   1020

cctgtacttt aagagtgttg gcaaccagta atgaataaaa acgcccgttt tattatatct   1080

gatgaatgct gaaagcttac attaatatgt cgtgcgatgg cacgaaaaaa cacacgcaat   1140

caatacaggg gggtagtcgg cgggcggcta agggtggtgc tcggcgggca aaacatcgaa   1200

aaatcaagat ctatatgaat tacacttcct ccgtaggagg aagcacaggg ggagaatacc   1260

acttctcccc cggcgacata atgtaaatga tgcagtttgc ctcgaaatac tccagctgcc   1320

ctggagtcat ttccttcatc caatcttcat ccgagttggc gaggattatt gtaggcttag   1380

acttcttctg cacctttttc ttcttaccat acttggggtt tacaatgaaa tccctctgac   1440

agccaactaa ctgtttccaa caaggacaga atttaaacgg aatatcatct acgatgttgt   1500
```

```
agattgcgtc ttcgttgtat gaagaccaat caacattatt ttgccagtaa ttatgaaccc   1560

ctaggcttct ggcccaagta gattttccgg ttcttgttgg gccgacgatg tagaggctct   1620

gctttcttga tctttcatct gatgactgga tacagaatcc atccattgga ggtcagagat   1680

tgcatcctcg agggtataac aggtaggttg aaggagcatg taagcttcgg gactaacctg   1740

gaagatgtta ggctggagcc aatcattgat tgactcatta caaagtaaat caggtgagga   1800

gggtggatga ggattggtga actcttcctg aatctcagga aaaagcttat ttgcagagta   1860

ttcaaaatac tgcaattttg tggaccaatc aaagggaagc tctttctgga tcatggagag   1920

gtactctgct ttggaagtag cgtgtgaaat aatgtctcgc attatttcat ctttagaagg   1980

ctttttttcc tttacctctg aatcagattt tcctaggaag gggacttcc taggaatgaa   2040

agtacctctc tcaaacacag ccagaggttc cttgagaatg taatccctca ctctgttaac   2100

tgacttggca ctctgaatat ttgggtgaaa cccatttata tcaaagaacc ttgagtcaga   2160

tatccttacc ggcttctctg tctgaagcaa tgcatgtaaa tgcaaacttc catctttatg   2220

tgcctctcgg gcacatagaa tatacttggg aatccaacga acgacgagct cccagatcat   2280

ctgacaggcg atttcaggat tttctggaca ctttggatag gttaggaacg tgttagcgtt   2340

cctgtgtgag aactgacggt tggatgagga ggaggccata gcagacgacg gaggctgagg   2400

ctgagggatg gcagactggg agctccaaac tctatagtat acccgtgcgc cttcgaaatc   2460

cgccgctccc ttgtcttata gtggttgtaa atgggccgga ccggtccggc ccagcaggaa   2520

aagaaggcgc gcactaatat taccgcgcct tcttttcctg cgagggcccg gtagggaccg   2580

agcgctttga tttaaagcct ggttctgctt tgtatgattt atctaaagca gcccaatcta   2640

aagaaaccgg tcccgggcac tataaattgc ctaacaagtg cgattcattc              2690
```

<210> SEQ ID NO 13
<211> LENGTH: 6337
<212> TYPE: DNA
<213> ORGANISM: Maize rayado fino virus (MYDV)

<400> SEQUENCE: 13

```
gtcctctgcc cccttcttgc gcccgatcgc cgcaagtcgc attctgcacc agctctcgct     60

cgtccagaaa cagatcaatc tttcggcctc ttttcttgca ctcttcttcg ttgcacctct    120

ctagatgtct agtttcctgc gtggtggcca tctcctcagc ggagtcgagt ccctcacacc    180

aaccactcac cgcgacacca tcactgcacc catcgttgag tcccttgcca ccccccttcg    240

ccgatccctc gaacgctacc cttggtccat cccaaaggag ttccattcgt tcctccatac    300

ctgtggcgtc gacatctccg gcttcggcca tgccgctcat ccccaccctg tccacaagac    360

catcgagacc cacctccttc tcgatgtctg gcccaattac gcccggggct tgtctgatgt    420

catgttcatc aagcccgaga agttcgccaa gctccagtcc cgacagccca atttcgccca    480

cctcatcaac taccggctcg tgcctaaaga caccacccgg taccccttcca cttccacgaa    540

tctcccggac tgcgagaccg tcttcatgca tgatgcgctc atgtactaca ccccagggca    600

gatcgctgac ctcttcttcc tttgccccca gctccagaag atctacgcct cgctggtcgt    660

ccctgcagag tcgagtttca cgcatctctc gctccatccg gaactttacc gcttccgttt    720

ccagggttct gaccttgtct acgagccgga gggcaaccct gccgccaact acacgcagcc    780

gcgttcggcc ctcgactggc tccagaccac cggcttcacc gtcggtcacg aattcttctc    840

cgtcacactt ctcgactctt tcggcccggt ccattccctc ctcatccagc gtggccgccc    900
```

-continued

```
ccctgtcttt caggccgaag acgtcgcttc cttccgcgtc ccggacgccg tcgccctccc    960
tgctcctgcc tccctccacc aggacctgcg tcaccgactg gtcccccgca aggtgtacga   1020
cgcactcttc aactacgtcc gagccgtccg cacccttcgg gtcacagacc ccgctggttt   1080
cgtccggacc caggtcggta agcctgagta cagttgggtc acctcttccg cctgggacaa   1140
tctccagcac ttcgcgctcc agactgccgc cgttcgtccc aacacctcgc atcccctctt   1200
tcagtcgccc ttcgcccgtt tgtcccattg gctccgcacc cacacttggg cgctctggtg   1260
catggcttcc ccctcggcct ctgtctccgc ttgggccgct gccagcgctc ttggccggct   1320
cctcccgctt cacaccgacc gtctcaggtt gttcggcttc gacatcgttg ggcggagatt   1380
ctggcctcgt ctcccattcc atggccccga gccaaggttc ctttgggaga cccatccagc   1440
ctgccgcccg ccagtgctct tcgccgactc ggcctttgag tgccaaatcc ttgctggttt   1500
ggcaaaccgg tgttctccct ccccttctg gtcgcgcttg ttccccacgg cctctccgcc    1560
gcactgggtc gcctattcag ccttggccct agctgcagtg ccacttgctg cgttagcgtt   1620
gcgctggttt tacggcccgg attctcccca ggctcttcat gatcagtacc acgccacctt   1680
ccatcccgac ccgtggactc ttgacctccc ccgccggctt cgccgcttcg agcgcgagcc   1740
cttcatgcgg acgggttccg caccttcgcc tcagtcgctc cctccttctg gaggctctct   1800
tcttcctgtc gagcctcctc ttgcttcgag cgagcccgag cctgcccttg agccgccatc   1860
ccccgcggcc ccggtcccga ctccttctcc agctccagtt ccagagcctc ctccttctcc   1920
cgagtcagtc gcccctccag tcgccgtcgc ctcgcccgcc gtgcaacctg ttcgggctcc   1980
gtccccctct ccagcgcttt tgggcgccga gcttcgtttc ggggatcttc ctcctgtctc   2040
tgcttgggac agtgaccccg agatttcgaa gcttggtgag tccacccaag gcaccgtttt   2100
tgctgtcacc cccggccctc gcgctcctga gccagacact gcccgcttag acgctgatcc   2160
ttcggctagc ggccccgtta tggagttccg cgagcttcag aagggcgctt acatcgagcc   2220
gactggcgct ttcctcaccc gggctcgcaa ctcggtgtcc tccagcatcc cttatcctgc   2280
gagggcggct tgtcttctcg tggccgtcag tcaagcaaca gggctcccca cccgcactct   2340
ctgggctgcc ctctgtgcta atcttccgga ttccgttctt gacgacggct cgctcgccac   2400
cttgggcctc accaccgacc acttcgccgt cctcgcccgc atcttctcct tgaggtgccg   2460
cttcgtgagt gagcatggcg atgttgagct cgggctccac gacgccacct ctcgctttac   2520
gatccgccac acccccggcc acttcgagct cgtggccgac aacttctccc ttcccgctct   2580
cgtcggcgcc tcttctgttc caggctccga cctagccgaa gcgtgcaagc gtttcgtggc   2640
tccggaccgc accgttcttc cattccggga cgtccacatc catcgcaccg acgtccgccg   2700
tgccaaaaac ctcatttcca acatgaagaa cggcttcgac ggtgtcatgg cgcaggccaa   2760
tcctctggat ccgaagagtg cccgagagcg gttcctcatg ctcgactcct gcctcgacat   2820
tgccgcgcct cgccgggtcc gtcttatcca catagcgggc ttcgctggtt gcgggaaatc   2880
ctggccgatc tcccatctgc tccgtacccc cgccttccgt gttttcaagc tcgccgttcc   2940
aaccaccgag cttcgcgacg agtggaaggc cctcatggat cctcgcgacc aggacaagtg   3000
gcgcttcggc acctgggagt cctctctcct caagactgcc cgcgtccttg tcattgatga   3060
ggtgtacaag atgcctcgcg ggtaccttga tctggccatc catgcggacg ccgccattca   3120
gttcgtgatt ttgctcggcg atccaattca aggcgagtac cattccacac atcccagctc   3180
ctccaatgcc cgcctttctc ccgagcatcg gtatctccgc ccgtatgtgg acttctactg   3240
cttctggagt cgtcgcatcc ctcggaacgt ggcccgcgcc ctcgatgtgc ccacgacctc   3300
```

```
gaccgagatg ggttttgctc gctactcgca gcagttccca ttctccggga agatcctcat   3360
ctcggcgcgc gactccgcca agagcttggc tgactgtggt tatcatgctg tcaccatagc   3420
tagcagccaa gggtccacta ttgccggccc agcttatgtc cacctcgaca atcattcgag   3480
gcgcctctca catcaacatt cgcttgtcgc catcactcga tccaagtccg gcatagtatt   3540
cactggcgac aaggctgcag cggatggcac ctcctctgct aatctccttt tctccgctgt   3600
gctcctcgac cgacgcctct cggtgcgctc tctcttcagc gcgctcctgc cttgctgtcc   3660
gtttgtcacg gagcctccaa cgtctcgagc cgttctcctt cgcggagccg gctacggcgt   3720
cgctcggccc cttcgcgctc gtgacgcccc tcctctcggc cccgatttcg tcggagatgt   3780
tattctggac tcctccgccc cgattcttgg cgacggatcg gccaacgctc cccaggtcag   3840
cactcacttt cttccagaga cgcgtcggcc tttgcacttc gacatccctt ccgcccgcca   3900
tcaagtggcc gatcatcctc tcgcgcccga tcactccgcc tgcgctatcg agcccgtgta   3960
ccctggcgag agcttcgaat ctctggcctc tcttttcctc cccccctacgg atgccgagag   4020
caaggagact tacttccgag gggagatgtc gaatcaattc cctcatctcg acaagccgtt   4080
cgagttaggt gcgcagacgt cgagcctcct cgcgccactc cacaactcca aacatgatcc   4140
cacgcttctc ccggcttcca tcggtaagag actgcgcttc cgtcactcag aggctcccta   4200
cgtcatcgct cctcgcgacg agatcttggg gtcactcctc tatgaggcct ggtgtcgagc   4260
ctatcgccgt tctcctcggg acgtcgagcc gttcgaccca gacctctacg ctgagtgcat   4320
taacctcaac gagttcgcgc agctctcctc caagacccag gcgactatca tggccaacgc   4380
caaccgcagc gacccagact ggcgctggtc cgccgttcgc attttcgcca agacgcagca   4440
taaggtcaac gagggctcgc ttttcggctc ctggaaagct tgccagaccc tcgcgcttat   4500
gcacgacgcc gtcgttttgc tccttggccc cgtcaagaag tatcaacgct tcttcgacca   4560
gcgcgatcgg ccttccactc tttacgtcca tgcgggccac acccccttcg agatggctga   4620
ctggtgccgc gcccatttga cccccgcggt caagctggcc aatgactaca ccgcctttga   4680
ccagtcacag cacggcgagg ctgttgtctt cgagcgctac aagatgaatc gtctctcaat   4740
tcctgccgag ctcgtggact tgcacgtcta tctgaagacc aatgtctcca cccagtttgg   4800
cccgttgacg tgcatgcgcc tcactggtga gcccggcacc tacgacgaca acaccgacta   4860
caacatcgcc gtgctccatc tcgagtacgc tgtcggctct actccgctca tggtctctgg   4920
tgatgactcg ctgctcgact ccgagcctcc tgtccgtgac cagtggtccg ccatcgctcc   4980
catgctcgct ctcaccttca agaaggagcg cggccgttat gccactttt gcggctatta   5040
cgtcggcttc accggcgcgg tccgatcgcc tccggccctt tttgcgaagc ttatgattgc   5100
ggttgacgac ggatccatct ccgacaagct catcgcctat ctcacggagt tcaccgttgg   5160
tcattcttcc ggcgatgctt tctggaccat cctcccagtc gaagctgttc cttaccagag   5220
cgcctgcttt gacttcttct gccgtcgagc tccggcgcaa gccaaagtga tgttgcggct   5280
tggcgaggcc ccagagtctc ttctttccct ggcgttcgag ggtctgaagt gggcttccca   5340
ctcggtgtac gcccttatga attccagtca ccgacgccag ttgcttcata gctcccgccg   5400
ccctcgctct ctccccgagg accccgaagt gtcgcagctt cagggtgaat tgcttcatca   5460
gttccaatcg cttcacctcc cgcttcgtgg tggcctcatg ccaaatccgc tcgctgcgcc   5520
cttcaggctc cttcagcaaa gcagctccct tggtcccact tacgcagtcg cccccatcgc   5580
tcgcgctccc caggtccctc tgccctctat ggccgacaat gccacccaag tcgggcctgt   5640
```

tcctcctcgc gacgaccgcg ttgatcgcca gcctcctctt cctgatcctc ctcgtgtgct 5700
cgagacgacc ccgtcgcact tcctcgacct ccctttccaa tggaaggtca cggacttcac 5760
aggatacgcc gcctaccacg gaaccgacga cctgtccgcc tccgcggtac tgaccacgct 5820
ctgtgctccg taccgccacg ccgagctcct ctatgtcgag atctccgtcg ctccgtgtcc 5880
cccgtcgttc tccaagccca tcatgttcac cgtcgtctgg acaccggcca ccctgtcccc 5940
cgctgacggc aaggagaccg actactacgg gggccgtcag atcactgtgg gcgggcctgt 6000
cctgttgtcc agcaccaccg ccgtacccgc agacctggcc cgcatgaacc ccttcatcaa 6060
gtccagcgtc tcctacaatg acacgccccg ctggaccatg tctgtccccc ccgtcaccgg 6120
tggggacacc aagatcccgc tcgccactgc cttcgttcgc gggatcgtcc gcgtgtcagc 6180
cccctctggg actgccaccc cctctgcctg atccatcaag gcagcaataa tgcgagaagg 6240
aaaactcgcc cagccttgag ctggtaagct gttaaacctc cgcccatcca tgtttgcaaa 6300
atctaaggta gcaggtcggc cataagacct gtgggcc 6337

<210> SEQ ID NO 14
<211> LENGTH: 5612
<212> TYPE: DNA
<213> ORGANISM: Maize yellow dwarf virus (MYDV)

<400> SEQUENCE: 14
acaaaagggt tctagaggga ccctttatag cactcttctt tcaccagaag tttcatgcgc 60
tgtgagattc actttgacgg gacactcacg tttgctgaaa tcccccgtga tctcacaatc 120
cgccttttag agtttcaaac agctctaaga accatcgctt gttgtgttct caaccaacga 180
tacgatgctg aaactctggt gcgctctgct tttactattc tgcctctcat gctccgtgaa 240
ctcccattca cttgggagtt ccctagtgcg gtacacgccg cctttgcgaa gcatgcgtta 300
cgtaccgccg gcagaatacc tcctcccatg gaactcatct tccatggtga cacgccaaaa 360
cacatgtata gagatttcct ataccgcgtt gtcacgagag atattgcagc tagcctacag 420
agatctcacg agaatttcat ctgtggctat aaacgcttcc aactccggct ggaaagtgtt 480
tgcagaagag ttgagctcct tggtgacaca tttgcaccaa aacatatcga ggagctttca 540
tggtcttcgc ggactcgcgg tggacggggt gcaggcgctc gcaggaggct tcctgctcgc 600
tgtaatctac acctggagct acttgatatc gctgctcttt tgggttgtta caaccctggt 660
atgcagatat acgttccaga tgtcatcgat cgcctgtctc tacgtctgta caatgctctt 720
ggtccggctg gcttcaaaga tttttggagg gtggccggtt atgatcatct cgctgattgg 780
gactctgaca tcgaagctct ttcgggctct gtcattcaaa aagagctcaa tctcctttga 840
gatccctacc ccagggtaca agacagtaga gatacctcag aaaccaccca aagattgcgt 900
cttgctggtt caacacaacg acgctctcaa ttcccctgga ggatacgcat catgtgttcg 960
actcctcaac ggaagcaatg ctttgctcac tgcaaaacat gtttccaccc aggaaggtga 1020
tttgctcatc gcttcatcca gaactggaaa caggatcaag ttgtcattgt tcaacacaat 1080
cctaaccaca aagaattccg acgtgggtct ttatcaagga cctccaggtt gggaatcaat 1140
tcttggatgt aaagctgcag acatcgtacc agtggatggg ctctcatgtt gtgaggcctc 1200
catttatagg catgatggca actggatgcg ttccaacgca tccttggtcg gaacagaagg 1260
cacttttgtc tctgttttga gcaacaccat tgagggtttt agtggaactc cctattttaa 1320
cggaaaatcc attttgggag ttcatgtggg aggcaatgaa accagaacta acaatctgat 1380
ggcccccata cccagcatcc caggcctaac aaaacacaaa tatgtgtttg aatcgccaca 1440

```
actcagaggc cgcctgttta cagacgagga agttgagaaa ctcgaattcg agattgatga   1500
agctttccag aaagctcata atctcataca tttcaaatct aaaacaggaa gaaactgggc   1560
tgatgatgag gatgacatcc actttgaagc tccaaagttt cagggaaacg acgcacgcgg   1620
tcccgtccgc gaaaacaaaa cggtctctcc cacccctaca cactcgcccg tcgttacttc   1680
aggcaacgac actctcaaca aggtggtgga agcgttggtc tcgaagatcg acgtctcagt   1740
aatcgagcgg atggttgttc aaaagatctc ggaatcagct ttgaaacgcc caacgaacaa   1800
caatcggaaa cacaggcgaa agcccaaaac ttctcagcct actttgcctc cctctacaga   1860
tgggaggtac gtggcgcccg ctcgcagatc cccggcttcg aagcctgcgg atccctcccc   1920
aaatactact tcacaaaaca aaaagaagaa tcagagtggg ggaggttact tgcagaggga   1980
aacccggcgc tggcaagtaa agtcagcggc ttcgggtggc cccaattcgg acccgaggcc   2040
gaattgaaga gcctgcgcct tcaggcgcag agatggctct cacgcgcgga gtttgctaaa   2100
atcccgtcat ctgaggacag ggagcgcgtg atccggaaga ctgtggaggc atacaaaact   2160
tgccaaactc aatgccccaa gacttctcaa agcaacctgc ttgtgtggga agactttctc   2220
gaagatttca aacaagcagt gttctccctc gagcccgatg ccggtgttgg tgttcctttc   2280
gtgggatacg accggcgtac gcaccgtgga tggatcgaag atccaacact tctgccagtt   2340
cttgcccgca tgaccttcga ccgattacat aagatgtcga cggttaagtt tgagcaactt   2400
acagcagaac aattggtgca acagggcttg tgtgacccga tcagactatt tgtcaagggg   2460
gaacctcaca agcagtcaaa gctcgatgaa ggccgctacc gcctcattat gagtgtttcg   2520
ttgctggatc aactggtagc ccgggttctg tttcaaaatc agaacaagag ggaaattgca   2580
ctatggcgag ccataccctc aaaacccggt tttgggttgt ctacagacgc ccaatcgcga   2640
gaatttgtgc agaatctcgc gaaacagtgt ggggtcaaca cgactgaact tttggcaaat   2700
tggccaacct acactgttcc gactgactgc tctggtttcg actggagtgt tgcggattgg   2760
atgctccagg atgatatgga ggtccgcaac cgactcactc gcaacaacac agatctcacc   2820
aagcgcttgc gcgcttgctg gttgaaatgt atatccaatt ctgtgttgtg cttgagtgat   2880
ggcactctgc tagcccagcg catagcggga atccagaaat ctggttctta caacaccagt   2940
tcgagtaact ctcgaatccg agtgatggcc gcatatcatt gcggtgctac ctgggcgatg   3000
gctatgggtg atgatgcact cgagtcagtc gacacgaacc tagacgtgta taaaacacta   3060
ggattcaaag tcgaggtctc caaacaactg gagttttgtt ctcatatctt cgagaaggaa   3120
gaccttgctc gcccggttaa ccaaaacaag atgatctaca aactcttaca tggttacaac   3180
ccggcgaacg gctcttcgga ggtgatacag cgttatcttg acgcatgtat gagcgtactc   3240
aacgagttgc gccacgaccc cgaaaccgtt gagcttctgt accagtggct ggtcgctcca   3300
gtccagaaac aaaaagttta aaacagaagc tctcaagtca gccaggcaaa ttcgagttgc   3360
aagcactgga tgacctagtc tcgatacata aaccaccacg gattacaagt tcttagccgg   3420
gatcactctc ggcctttgca tcacattccc atttataatc cttggtgtgt acaaagtcta   3480
ccgtacggtc tccaacgata caagcaaact cgctaatgaa tttgggaggc cgtagaaatg   3540
gacgacgtgg aacacggtta cgcagacgcg tacgcattgc tcgcaccacc caaccaatgg   3600
ttgtggtcgc gcaaacccag cgtagacgcc gcatccgaag acgaggacga ccaagtggag   3660
acacttcagg aggacctcga gggcgaggag gctcgcggga gactttcgta ttttcgaagg   3720
attctatcgc gggcagtgcc tccggaaagc tcaccttcgg ggcgtctctt tctgagtgcg   3780
```

-continued

```
cagcattctc tggtggaatt ctcaaggcct accatgagta taagatcaca aaagtcatac   3840

tggagttcat ctccgaggcc ccttacaccg cagccggttc catcgcttat gagcttgatc   3900

cccacaacaa gctcagcacc ctcgcatcaa caatcaacaa attctcgatc gtcaagggtg   3960

gcaagcgtgc ctatacgtcc aaacaaatcg gaggtggagt atggcgagat tcgtccgaag   4020

accaatttgc aatactctac aagggcagtg gaaactcctc agttgccggc tcgttccgca   4080

tcacgatgga ggttcatacc caaaatccga aataggtaga cggagcttcc cctgcaccag   4140

acccaacacc gacaccaacc cccactccaa cacctactcc aactccaacg cccactcctg   4200

tgactcagga agccttctac ggctattctg gtgtcccaga atgtaagatc cagtccagaa   4260

agaactcgga attcatcgat atctattcgt tgaatttcgt taaattgttc tactggagag   4320

atgaggcgtg gagctcggag accctttcgg cgggatacat acaaaatgat tcgctccgcg   4380

caacccccta ccttttggtt ccgaccaaga agggaaaata ctctgtttat atagagtgtg   4440

agggttttca agcggttaaa gctaagggtg gtaacaacga cggcaagatg agtggttttg   4500

tcacgtatga taaagatcaa agcggttggc aagtgtactc atgggctggt tgctctctct   4560

cgcagatcaa agttaaagac actggtgtcg tggctcatcc cgacatgaag gtgaatggtt   4620

gctctttcac caaaggccaa cttattgaga gagattttat ttgttcgttc catctcgaag   4680

ctacggaaga tggatattgg gctttgcaag cccccccagt agagaagtct gatgaccaca   4740

attttattgt gtcatacggt tcttacaccg aaaagattct tgaatggggt tcagtatcca   4800

tatcaataga tgagataaat cgaacagaag ctcgcaagat tccgaaaagg gataaggatc   4860

tatcacaaag tggacgtttg gccgacatga ccaacgtccc cacagtgggg gtggttgtag   4920

cagcgaccac gaaaccggac ctgccggtag aacagccaaa ccagttggct gtggtggagc   4980

aacccactga agagcaacaa aagaaaaggg cgactatcga ccaatggctc gatgccgttg   5040

aagctcttgc tcccccagaa cctgaagggt tggtgacaca ggtgagacta ccaacagcag   5100

ctgaacgagg tttgacctcg caaaagctac ctttgcacca acgtggaacc ttcaaagacc   5160

tcgccaaccg agacgctgat acatacagtg tcgcatctcg tggattgact gggggcttga   5220

gaggaactcc cgcaacacct caggttgaaa cgattgagga gaaccccgtc caagtggacg   5280

atgattccaa atctctcgtt tcaagctcgt caaggcttac aggcggtctt cgtcttagaa   5340

cttcatatcg catgaccact caagaggcca agcaatatga tgagatcaga cgaagctttg   5400

gtaaagcacg cgcaaaagcc tattatgacg atttgtgtaa ggcgaactgg tattagccca   5460

cacaccctgg tcagggtcac agaccactcg ccggagtata aacgagatag gatggcaacc   5520

tagccactcc ccttcctccc gatgggaaat agggtgagtt ccaagcccaa ggaatgagat   5580

ttcagtgcaa tttttccact gaaatctatg gt                                5612
```

<210> SEQ ID NO 15
<211> LENGTH: 9515
<212> TYPE: DNA
<213> ORGANISM: Maize dwarf mosaic virus (MDMV)

<400> SEQUENCE: 15

```
aaaaacaaca agactcaaca caacacaacc aaacacgacc aaacacaacc aaattacacg     60

ttattggagc acattcagtt tgcaggcaac ggttcgtttg caaggtgcat cgaaaagcct    120

ctctgaacac acgatcgcaa tggcaggaac ttggacccac gttactcaca agtggcagcc    180

aaaccttgac aaccctcgtg acgtcaggag aatcatggag ctgttcgctg caaagggcca    240

ggtctatgac gagaagcgag ctctggagca caacagtaaa ttacttcgta gagctcaggt    300
```

-continued

```
ggtggatgtc gaaccaatga tcacggttca accaaagaag tgtgcacaga tatggaaaga    360
ggtggtggat cataatccaa cacaccattt cgtgtacgca cgtttctctg aggttaagaa    420
gcaacagcct accaaaccag ttgcaacctc agttaataaa ctagtgagaa agactctaga    480
aatacgagag aattttccag tgaatgttga gtttattgga aagaaacgca agaacactac    540
gagagtctca ctgaggaaag tttttaacaa aactttctta cactgtggca cgcgacatga    600
gaacaaccaa ttcaagcgag ttgacacaaa catcactcga gattggattc cagtgctatc    660
aagcgtagca aaatgttatg cgacactgtc gtctaacatg atgcacaaca tacacaaagg    720
gcacagtggt ctaacgttca ttcaaaatgg tgaacttttc atagtccgag gaagacttag    780
aggtgaacta tgcaatagct tggactgtac aaaggaagtt caggagatag aacactacgc    840
agacccacag gcagctgatt tttggaaggg atacactaat gcatatgttg agaatagaaa    900
tatttcaacg acgcatacag agcatacgcc tacaatgaac ttagaaaagt gtggcaagcg    960
tatggcgtta ttggaagttc ttttccattc aacgttcaaa atcacatgca agcattgtaa   1020
cactgatgat cttgaattat cagatgatga attcggagaa aaactttaca agaacattca   1080
gcgcatcgaa gagcaacaga gtgaatatct agccgaggac caaaaactca aacgggtgtt   1140
atcattcatc aaggctagat gcacaccaaa gtttgatcac ttacctatga attggcaagt   1200
cgcagacatc attggacatt attcagataa tcaagcaaaa caaattttag atgtcaatga   1260
agcactgatt aaagtgaaca cactcacacc ttcagatgca ttaaaggcaa gtgcagctct   1320
tctcgagtta tcgagatggt ataagaatag gaaagaatca acaaaagagg acaacttatc   1380
cactttccgc aataagatat ctccaaagag cacgattaac ttagcattaa tgtgcgacaa   1440
tcaactcgat tcaaatggta actttgtttg ggaaagaggg gaatatcatg caaaaagatt   1500
cttctcaaac tactttgaag ctgtggatcc agctgattca tatgaaaaac acgtaacacg   1560
ctttaatcca aacggacaaa gaaaattatc tatcggaaaa ttggttattc ctttggactt   1620
ccaacgtatc cgtgattcat ttgctggcat acctgtaaca aaacaaccgc tttcaaatgc   1680
ttgtctgagc agaatagaca aaacctacgt ctacccttgt tgctgtgtaa ctacagagtt   1740
tggacaacct gcatactcag aaataatacc tccgacaaag gggcatttaa ccattggtaa   1800
ttctgtggat ccgaagattg tcgatctgcc aaacacagac cctccaacga tgtatatttc   1860
gaaggacgga tattgctata taaacatttt cttggcagcc atgataaatg ttaatgagga   1920
ttcagctaag gattacacaa aattcatcag agatgaactc atagagagac ttggtaaatg   1980
gcccaaactt aaaaatgtag ctactgcatg ttatgcactt tctgtaatgt tcccagagat   2040
caagaacgct gagttacctc aaatcttggt tgatcatgaa aataagacaa tgcacgttgt   2100
ggattcatat ggatcactaa gcgttggcta tcacatcttg aaagcgaata ccgtgggaca   2160
actcatcaaa atgcagtacg agtcgatgga aagcgagatg agagaatatg cagttggtgg   2220
tacaataaca cacaaatcat tttccacctt aattagccat ctaatcaaga atatgtttaa   2280
gccacgtgaa atgcggaaaa taattgaaga agaacctttc ttaattatgc tatctgttgt   2340
atctcctact gttcttatat ctctatataa taattgtcac attgagaatg caatggcgta   2400
ttggataacg aagaatcaag gagtagcagc aatgttcgca caattggaag cccttgcaaa   2460
agaaacatca aaggcagagc ttttaatcca gcagatgaca atattagaga aagcttctaa   2520
tcagctaaaa ttggccgtga tgggtctaaa tcatgttgac ccagctaagc gattgctttg   2580
gtcacattta gaagtcatgt cgtcgagggc agccacaaat aaagatcttc tagaccaagg   2640
```

-continued

```
ctacgctcta tatagcgata ggttgtatgc catcatcgaa aaaacctatg tagatcagtt   2700
gaatcaagcg tggacagaat tatcattgtt tggaaaattc tccgaaacat ggcgtgtgta   2760
caaggacaag aaatactaca agccatcttt aatcctgcaa agaagcgtag atttaggcgc   2820
tgtctacaat atatcagtta cgcatcaaat atcaagttta gtgcagaaaa gtcgcagtcg   2880
agtcagctct actttaacca aactccacca aggttcatgt gataaactat atagtttgcg   2940
tactaaagct ataaatacaa tttattggtt tgttcctgat attttccgac ttattcacat   3000
tttcatagta ctaagtttat tatcaacagt agctaatact attatagtaa caatgcaaga   3060
ttacaagaaa ttacaaaaac aagttcgtga ggaagaatat gaaaaggaaa taagcgaagt   3120
acgcgctata cacgcgaagt tgcttaaaat acatgataac gaactcactt gcgaacagtt   3180
cctgcagtac attaacgaaa atcatccaag attaattgaa gcagctgttg aactatcagg   3240
agtgggtgtg atacatgagg gcaagtccaa ccttgaaatc aatctagagc aagcgatggc   3300
tattggaaca ctaatcacaa tgatatttga ccctacaaag agcgatgctg tatacaaagt   3360
attaaacaaa atgagaacaa ttttgagtac agttgaacaa gatgcacctt tcccacgcat   3420
tgatttcacg aatatctttc ggtcgcaggt aacccaccaa agtttagatt tggacgaccc   3480
tctcactatc aatactgata agaagcttac ggtggatttc gacacaaccc aagatcttcc   3540
agcagatact tttagtaatg atgtgacatt tgatcaatgg tggtcgaatc aactcgaaaa   3600
caatagaact gttccgcact acagacttgg tggtgagttc attgaattca cacgagaaaa   3660
agcagcatct gttagcatca gtatagcaca ttcgcaaatt gagaaagaat atttactcgg   3720
aggagcagtc ggttcgggaa aatcaacagg tttaccatac catttgagcc agcgaggaaa   3780
agttctttta ttagagccga cacgaccact cgcagaaaac gtctgtagac aactacaagg   3840
ggcaccgttc aatgtaagtc ctacgctaca gatgagaggt ttgagctcct ttggatcaac   3900
gcccattaca ataatgacat caggctttgc acttcatatg tacgcaaaca atccagacaa   3960
attgtcaaat tatgactttg tcattttcga tgaatgtcat attatggaag ccccagcaat   4020
ggccttttac tgtttgctaa aggagtacgc atttgatggg aaaataatta aggtctcagc   4080
cacaccacca ggaagggaat gtgaattctc tacgcaacac ccagtcgata ttcacgtttg   4140
cgagaattta actcaaaacc aattcgtgct tgaacttggg actggatcaa aagctgatgc   4200
cactaaatac ggtaacaaca ttctggttta cgtggctagc tacaacgatg ttgattcatt   4260
ggcaagagca ttaattgagc gacattattc agtgatcaaa gttgatggca gaacgatgaa   4320
gcagaacaca agtggaatcc atccaaacgg acatgatgga aagaaatgtt tcatagttgc   4380
caccaatatt atcgaaaacg gagtaacatt ggacgtcgac gtcgttgttg actttggcct   4440
taaggttacg gctgaattgg acgttgataa tagagcagta atgtatcgta aagtgagcat   4500
atcttatggt gagagaatcc aacgacttgg aagagttgga agaacaaaac cagggactgt   4560
cattagaatt ggaacaacca tgaagggact tcaagagata ccagctatga tagcaactga   4620
agcagctttc ctttgtttcg catatggcct caaggttata acacataacg tttcaactac   4680
acacctatcg aaatgcacgg ttaagcaagc gagaactatg atgccatttg agctttcacc   4740
attcattatg tctgaattag tcaaatttga tggctcaatg catcctcaaa tacatgagat   4800
tctcaagaaa tacaagctta gagaatccgt gatcatgttg cgaccaaatg caattcctca   4860
tacaaatgtt cacaactggt taacagttaa agactacaac aaaattggct gtgatcttga   4920
gctagacgat tatgtaaagg ttccatactt cataagaggc attcctgaga aagtgtattc   4980
agatatctat aagattgtac tcgaatatgg ttcgaccagt tgttatggaa gactatcaag   5040
```

tgcatgtgca ggaaaagtag cttacacatt acgcacggac ccctttgctt taccacgaac 5100
aatcgctatt gtgaatcagc tcatagctga ggaacacgca aaacgtgatc attataactc 5160
aatcacatca aacccatcat cttcacatgc tttttccctt acaggaattt gcaatatgtt 5220
agcctcaagg tacatgaagg accattcaag ggaaaacatt gagaaattga cacgtgttaa 5280
agaccaattg attgagttta gggggactgg aggtgagttc aaaaatccag aagatttgct 5340
tgaatttggt gggctagtta cagtcattca ccaaggctta gattccaccg cccggggtct 5400
acagctcaaa ggaaggtgga acggagactt gattcagcgc gatttgatga tatcagctgg 5460
cgttttcaca ggcggtctac tgatgctttg gttcctcttc cggaaatggt catcaacaga 5520
tgtcaaacat gaagctaaga caaaacgcag caggcaaaaa ctcaaattta ggcaagcgcg 5580
cgacagcaaa tatgcttatg acgttactgg atctaaggat gcaattgaag aaaattttgg 5640
atcagcttat gttaagaaag ataagaaaaa gggaacaaaa gttggattgg gagttaagca 5700
acataagttc tacatgctgt ataattttga tccacaagat tacaatctaa ttcgatttgt 5760
ggacccactt acaggtgcaa ctcttgatga gcaaattcac gcagatatca atatggtacg 5820
agaacatttc acagcaattc gagaagctgc cataaataat gaccaacttg agtatcaaca 5880
catttattca aatccaggaa ttaaagcata ttttatacga aatggatctc aaaatgctct 5940
caaagtcgac atgactccac acgaaccact aagggttgtt actggtaaca atatagcggg 6000
attccctgaa tacgaaggca cgctacgaca aaccggaaga gcacaagtga taccttcaga 6060
acaagtacca gcaccaaacg aggtggaagt ggagcacgaa gcaaaatcta tgttaacggg 6120
attggtggat tacacaccta tagctaatca gattggcata attgaaaatc attcagatga 6180
tgttaggctt tgcatgtatg ctataggata tggatcatac ttaatcactc ctgcacacct 6240
cttcaaagca agcaatggag agttaacatt tcgatcttcg cgaggggttt acaagatgag 6300
aaactcagtg gaagtaaagc tacaccacgt aaaggggcgc gatttggtta taattcaact 6360
ccccaaagat tttcctccat tcccacagaa actcaagttt caagcaccta atcgcgaaaa 6420
caaagtgtgc ttggttggcg tcaatttcca gcagaatcat tcttcatgtg tagtttctga 6480
gagtagcact attgcgccaa aaggaaataa tacattttgg agtcattgga tctcaacaac 6540
aggtggccaa tgtggtttac cattagttga tatgaaaacc agaagcatag ttggggtaca 6600
tagccttgca tccgtaaatg cgaacgtaaa tttcttcgta gcaatgccgg aagacttcaa 6660
cacatacctt agtgaacttg tctcgaagaa tgaatgggaa aaaggatggc aatataatcc 6720
aaatttaata tcctggagtg gactaaatct cgtatcctct gcacctaaag gcgcttttaa 6780
aacagcaaaa cttgttgagg atttatcatt tgatgttaca gaacaaggga tccaacatga 6840
aacatggcta acgaagcaca tacagcaaaa tttgcaagtt gtagccaaat gtcctggaca 6900
attggttaca aaacatgttg ttaaaggtcc gtgcccgcac tttgcactat acttatccac 6960
gcacgaggaa gctgagaagt tctttagacc gcttatgggc aaatatgata agagtagact 7020
caataaagca gctttcgtta aagatcttac aaaatatgca aaaccaactt atattggcga 7080
agtaaacact gcactatttg aaagagctgt tgagcatgtc atacaactcc tacgcaatgt 7140
tgggattcca acatgtgagt acatcacaga tgaagatgaa attttcaaat ctttaaacat 7200
gaatgctgcg gttggagcat tatacacagg aaagaagaga gaatattttt ctgaatacac 7260
acaagaggat agagcagaga taataaagca atcgtgcgaa agagtttacg aaggcaagct 7320
tggaatttgg aatgggtctc tcaaggctga aataagacct atagagaaaa cggaagcaaa 7380

-continued

```
taagacaagg acattcacag ccgcaccatt ggaaacattg ctagcgggta aggtgtgtgt   7440

cgatgatttc aataatcaat tttatgcaca ccacttaaat ggaccgtgga cagttggaat   7500

aactaaattc tacggtggtt ggaatagatt acttgagaag ctaccagatg gctggatcta   7560

ctgtgatgca gatggttcgc aactcgacag ttcgctcact ccttatctga taaatgcagt   7620

gctcaacatt cgattacaat ttatggagcc gtggaacatt ggtgaacaaa tgcttaaaaa   7680

tttatacacg gaaattgttt ttacaccaat tgcaacacct gatgggtcag tcatcaaaaa   7740

gtttaaaggc aacaatagtg gacagccatc aacagttgtt ggcaacacac taatggtgat   7800

catagccttt aactatacgt tgttatcgtg tggagttgac ttggagaagg ctgatgatgt   7860

gtgtcgaatg tatgcgaatg gagacgattt attacttgca gtgaacccaa cacatgttga   7920

cattctaaac gaatttggaa aacacttcgc agcgttaggg ttaaatttcg attttgaatc   7980

acgaacgaga gataaatcag aactttggtt catgtcaacg cgaggtatca agtacgaaga   8040

aatgtatatc ccaaaattgg aaaaagaacg aattgtagct attcttgaat gggatcgatc   8100

attaatccct caataccgtc ttgaagctgt ctgtgcagca atggttgagg catggggata   8160

taaagatttg ctccatgaga tacgtaagtt ctatgcgtgg ctgctcgaaa tgcaaccttt   8220

tgctaactta gcaaaggaag gctcagcacc gtacatagcc gagacagccc tgagaaactt   8280

gtatactggt gctaaggttt cagaagatga attgaatgtc tatgcacgac aattcttcga   8340

tgatctttca gattatttgg ccgatgaagt tatagatgtc aaacatcaag ctggtgagaa   8400

tgtcgatgct gggcagaaga ctgaagcaca gaaggaagca gagaggaagg cagctgaaga   8460

gaataaagca aaggaagctg aggctaaaca aaaggaaacc aaggagaaaa cgactgagaa   8520

agctggtgat ggcgagtcca cgggaaaaga caaagacgtg gacgccggaa cttcaggctc   8580

agtatcggta cctaagctaa aagctatgtc caaaaagatg cgtttgccac aagcgaaggg   8640

aaagaatatt ctccatcttg acttcctatt gaaatacaag ccacaacaac aagacttatc   8700

gaacacccga gcaaccaggg ctgaattcga tagatggtat gaagcagtgc agaaagaata   8760

cgaacttgat gatacacaaa tgacggttgt catgagtgga ttaatggttt ggtgcattga   8820

gaatggttgc tcaccaaaca tcaatggagt ctggacaatg atggatggag acgaacagag   8880

aacatttcct ttaaaacagg ttattggaaa tgcatctcca actttcagac aaattatgca   8940

tcattttagt gatgcagctg aagcatacat tgagtataga aattcaacag aaagatatat   9000

ggcgagatat ggacttcagc gaaacttaac cgactttagc cttgcacgct atgcatttga   9060

tttttacgag atatcatctc gaactccagc acgtgcaaag gaagcccaca tgcagatgaa   9120

ggccgcagca gtccgtggtt caaacacacg gatgtttggt cttgatggga atgtcggaga   9180

aacccaagaa aatacagaac gccacacagc tggcgacgtt agtcgcaaca tccactccct   9240

tttgggagtt cagcaggggc attgatacgg ggttcaactt ttacgcagta atttagtaat   9300

atataagtaa gctattgtgg tgaggttgta cctcgttagt tttatatata tattatgcta   9360

cgtacctact atgtctgcaa gtgagtgagg ttgcacctcg acacttatag tgggcactat   9420

tactagcttc gaatcacgag acggacggtc cattgagtgg ttctaccacg aggatgcagc   9480

gagtttcgtg gtgagagaca aaaaaaaaaa aaaaa                              9515
```

<210> SEQ ID NO 16
<211> LENGTH: 3249
<212> TYPE: DNA
<213> ORGANISM: Neisseria meningitidis
<220> FEATURE:
<221> NAME/KEY: gene
<222> LOCATION: (1)..(3249)
<223> OTHER INFORMATION: NmCas9

<400> SEQUENCE: 16
atggctgcct tcaaacctaa ttcaatcaac tacatcctcg gcctcgatat cggcatcgca 60
tccgtcggct gggcgatggt agaaattgac gaagaagaaa accccatccg cctgattgat 120
ttgggcgtgc gcgtatttga gcgtgccgaa gtaccgaaaa caggcgactc ccttgccatg 180
gcaaggcgtt tggcgcgcag tgttcgccgc ctgacccgcc gtcgcgccca ccgcctgctt 240
cggacccgcc gcctattgaa acgcgaaggc gtattacaag ccgccaattt tgacgaaaac 300
ggcttgatta aatccttacc gaatacacca tggcaacttc gcgcagccgc attagaccgc 360
aaactgacgc ctttagagtg gtcggcagtc ttgttgcatt taatcaaaca tcgcggctat 420
ttatcgcaac ggaaaaacga gggcgaaact gccgataagg agcttggcgc tttgcttaaa 480
ggcgtagccg gcaatgccca tgccttacag acaggcgatt tccgcacacc ggccgaattg 540
gctttaaata aatttgagaa agaaagcggc catatccgca atcagcgcag cgattattcg 600
catacgttca gccgcaaaga tttacaggcg gagctgattt tgctgtttga aaaacaaaaa 660
gaatttggca atccgcatgt ttcaggcggc cttaaagaag gtattgaaac cctactgatg 720
acgcaacgcc ctgccctgtc cggcgatgcc gttcaaaaaa tgttggggca ttgcaccttc 780
gaaccggcag agccgaaagc cgctaaaaac acctacacag ccgaacgttt catctggctg 840
accaagctga acaacctgcg tattttagag caaggcagcg agcggccatt gaccgatacc 900
gaacgcgcca cgcttatgga cgagccatac agaaaatcca aactgactta cgcacaagcc 960
cgtaagctgc tgggtttaga agataccgcc tttttcaaag gcttgcgcta tggtaaagac 1020
aatgccgaag cctcaacatt gatggaaatg aaggcctacc atgccatcag ccgtgcactg 1080
gaaaaagaag gattgaaaga caaaaaatcc ccattaaacc tttctcccga attacaagac 1140
gaaatcggca cggcattctc cctgttcaaa accgatgaag acattacagg ccgtctgaaa 1200
gaccgtatac agcccgaaat cttagaagcg ctgttgaaac acatcagctt cgataagttc 1260
gtccaaattt ccttgaaagc attgcgccga attgtgcctc taatggaaca aggcaaacgt 1320
tacgatgaag cctgcgccga aatctacgga gaccattacg gcaagaagaa tacggaagaa 1380
aagatttatc tgccgccgat tcccgccgac gaaatccgca accccgtcgt cttgcgcgcc 1440
ttatctcaag cacgtaaggt cattaacggc gtggtacgcc gttacggctc cccagctcgt 1500
atccatattg aaactgcaag ggaagtaggt aaatcgttta aagaccgcaa agaaattgag 1560
aaacgccaag aagaaaaccg caaagaccgg gaaaaagccg ccgccaaatt ccgagagtat 1620
ttccccaatt ttgtcggaga acccaaatcc aaagatattc tgaaactgcg cctgtacgag 1680
caacaacacg gcaaatgcct gtattcgggc aaagaaatca acttaggccg tctgaacgaa 1740
aaaggctatg tcgaaatcga ccatgccctg ccgttctcgc gcacatggga cgacagtttc 1800
aacaataaag tactggtatt gggcagcgaa aaccaaaaca aaggcaatca aacccccttac 1860 gaatacttca acggcaaaga caacagccgc gaatggcagg aatttaaagc gcgtgtcgaa 1920
accagccgtt tcccgcgcag taaaaaacaa cggattctgc tgcaaaaatt cgatgaagac 1980
ggctttaaag aacgcaatct gaacgacacg cgctacgtca accgtttcct gtgtcaattt 2040
gttgccgacc gtatgcggct gacaggtaaa ggcaagaaac gtgtctttgc atccaacgga 2100
caaattacca atctgttgcg cggcttttgg ggattgcgca aagtgcgtgc ggaaaacgac 2160
cgccatcacg ccttggacgc cgtcgtcgtt gcctgctcga ccgttgccat gcagcagaaa 2220

-continued

```
attacccgtt ttgtacgcta taaagagatg aacgcgtttg acggtaaaac catagacaaa   2280
gaaacaggag aagtgctgca tcaaaaaaca cacttcccac aaccttggga atttttcgca   2340
caagaagtca tgattcgcgt cttcggcaaa ccggacggca aacccgaatt cgaagaagcc   2400
gataccctag aaaaactgcg cacgttgctt gccgaaaaat tatcatctcg ccccgaagcc   2460
gtacacgaat acgttacgcc actgtttgtt tcacgcgcgc ccaatcggaa gatgagcggg   2520
caagggcata tggagaccgt caaatccgcc aaacgactgg acgaaggcgt cagcgtgttg   2580
cgcgtaccgc tgacacagtt aaaactgaaa gacttggaaa aaatggtcaa tcgggagcgc   2640
gaacctaagc tatacgaagc actgaaagca cggctggaag cacataaaga cgatcctgcc   2700
aaagcctttg ccgagccgtt ttacaaatac gataaagcag gcaaccgcac ccaacaggta   2760
aaagccgtac gcgtagagca agtacagaaa accggcgtat gggtgcgcaa ccataacggt   2820
attgccgaca acgcaaccat ggtgcgcgta gatgtgtttg agaaaggcga caagtattat   2880
ctggtaccga tttacagttg gcaggtagcg aaagggattt tgccggatag ggctgttgta   2940
caaggaaaag atgaagaaga ttggcaactt attgatgata gtttcaactt taaattctca   3000
ttacacccta atgatttagt cgaggttata acaaaaaaag ctagaatgtt tggttacttt   3060
gccagctgcc atcgaggcac aggtaatatc aatatacgca ttcatgatct tgatcataaa   3120
attggcaaaa atggaatact ggaaggtatc ggcgtcaaaa ccgccctttc attccaaaaa   3180
taccaaattg acgaactggg caaagaaatc agaccatgcc gtctgaaaaa acgcccgcct   3240
gtccgttaa                                                           3249
```

```
<210> SEQ ID NO 17
<211> LENGTH: 3114
<212> TYPE: DNA
<213> ORGANISM: Parvibaculum lavamentivorans

<400> SEQUENCE: 17
```

```
atggagagga ttttcggctt tgacatcggc acaacaagta tcggattcag cgtgattgat     60
tacagtagca cccagtccgc aggcaacatc cagaggctgg gcgtgcgcat tttccctgag    120
gcaagggacc cagatgggac ccccctgaac cagcagcgga gacagaaacg catgatgagg    180
cgccagctgc gacggagaag gattcgccga aaggcactga atgagacact gcacgaagcc    240
ggctttctgc cagcttacgg gtctgcagat tggcccgtgg tcatggccga cgagccttat    300
gaactgcgga gaaggggact ggaggaaggc ctgagtgctt acgagttcgg acgggcaatc    360
tatcatctgg cccagcaccg gcattttaaa ggcagagaac tggaggaatc cgatacaccc    420
gaccctgatg tggacgatga gaaggaagcc gctaacgaga gagcagccac tctgaaggcc    480
ctgaaaaatg aacagaccac actgggagca tggctggccc gccgaccccc ttctgaccgc    540
aagcgaggaa tccacgccca taggaacgtg gtcgctgagg agttcgagcg cctgtgggaa    600
gtgcagtcca agtttcaccc cgctctgaaa tctgaggaaa tgcgggcaag aatcagtgat    660
acaattttcg cccagaggcc tgtgttttgg cgcaagaaca ctctgggaga gtgcagattc    720
atgcctggcg aaccactgtg tcccaagggg tcctggctgt ctcagcagcg gagaatgctg    780
gagaaactga acaatctggc tatcgcaggc gggaatgcta ggccactgga tgcagaggaa    840
cgcgacgcca ttctgagtaa gctgcagcag caggccagca tgtcctggcc aggcgtgcgg    900
tcagctctga aggcactgta caaacagaga ggcgagcccg gggctgaaaa gagcctgaaa    960
ttcaacctgg agctgggagg cgaatccaag ctgctgggaa atgccctgga ggctaaactg   1020
gcagatatgt ttggccctga ctggccagct caccccgaa agcaggagat ccggcacgca    1080
```

-continued

```
gtgcatgaac ggctgtgggc tgcagattac ggcgagacac ccgacaagaa aagagtcatc   1140
attctgtccg agaaggatcg aaaagctcat cgggaagccg ctgcaaactc tttcgtggca   1200
gactttggaa ttactggcga gcaggcagct cagctgcagg ccctgaagct gccaaccggc   1260
tgggaacctt atagcatccc agcactgaac ctgttcctgg ccgagctgga aaagggggag   1320
aggtttggag ccctggtgaa tggacctgat tgggaaggct ggaggcgcac aaacttcccc   1380
caccgcaatc agcctactgg ggagatcctg gacaagctgc caagtcccgc ctcaaaagag   1440
gaaagggaac gcattagcca gctgcgcaac ccaaccgtgg tccgaacaca gaatgagctg   1500
agaaaggtgg tcaacaatct gatcgggctg tatggaaaac ccgatcgaat ccggattgaa   1560
gtgggccggg acgtcgggaa gtccaaaaga gaaagggagg aaatccagtc tggcattcga   1620
cggaacgaga agcagagaaa gaaagccact gaagatctga tcaaaaacgg aattgctaat   1680
cctagccggg acgatgtgga gaagtggatc ctgtggaaag agggccagga aagatgccca   1740
tacaccggcg accagattgg cttcaatgcc ctgtttagag aaggcagata tgaggtggaa   1800
cacatctggc ctcgctctcg aagttttgat aacagcccaa ggaataagac actgtgtcgc   1860
aaagacgtga acatcgagaa gggaaatagg atgcctttcg aggcatttgg ccatgacgaa   1920
gatcggtgga gcgccatcca gattagactg cagggcatgg tgtcagccaa agggggaact   1980
gggatgagcc ccggaaaggt caaacgcttc ctggctaaga ccatgcctga ggattttgca   2040
gcccggcagc tgaacgacac aagatacgct gcaaagcaga tcctggccca gctgaaaagg   2100
ctgtggccag acatgggacc tgaggctcca gtgaaggtcg aagcagtgac tggacaggtc   2160
accgcccagc tgcgcaaact gtggactctg aacaatattc tggctgacga tggggagaaa   2220
accagagcag atcacaggca ccatgccatc gacgctctga cagtggcctg cactcatcct   2280
ggaatgacca acaagctgag caggtattgg cagctgcgcg acgatccacg agcagagaag   2340
ccagctctga ctccaccctg ggataccatc cgcgccgacg ctgagaaagc cgtgtctgaa   2400
attgtggtca gtcaccgggt gagaaagaaa gtcagcggcc cactgcataa ggagactacc   2460
tacggcgata cagggactga cattaagacc aaatccggca catatagaca gttcgtgacc   2520
aggaagaaaa tcgagtcact gagcaagggg gagctggatg aaattcgcga cccccgaatc   2580
aaagaaattg tggcagctca cgtcgcagga cgaggaggcg accccaagaa ggccttccct   2640
ccatacccct gtgtgtctcc cggaggccct gagatccgga aggtcagact gaccagtaaa   2700
cagcagctga acctgatggc ccagacaggg aatggatacg ctgacctggg ctccaaccac   2760
catatcgcaa tctaccggct gcccgatggg aaggccgact tcgagattgt gtcactgttt   2820
gatgctagca gaaggctggc acagagaaat ccaatcgtgc agaggacacg agcagacgga   2880
gccagcttcg tcatgtccct ggcagccgga gaggccatca tgattcccga aggctcaaag   2940
aaagggatct ggattgtgca gggagtctgg gcaagcggac aggtggtcct ggagagggac   3000
accgatgctg accactctac aactacccgc cctatgccaa accccatcct gaaggacgat   3060
gccaagaaag tgagtatcga tcctattggc cgagtccggc catcaaatga ctaa          3114
```

<210> SEQ ID NO 18
<211> LENGTH: 3255
<212> TYPE: DNA
<213> ORGANISM: Corynebacterium diphtheriae

<400> SEQUENCE: 18

```
atgaagtacc atgtcggaat cgatgtcgga accttttctg tggggctggc tgctattgaa     60
```

-continued

```
gtggatgacg ctggaatgcc tattaagacc ctgagtctgg tgtcacacat tcatgactca    120
ggactggatc ctgacgagat caagagcgct gtgaccaggc tggcaagctc cggaatcgcc    180
cggagaacaa ggcgcctgta ccgacggaag agaaggcgcc tgcagcagct ggataagttc    240
atccagaggc agggctggcc agtgatcgag ctggaagatt acagcgaccc cctgtatcct    300
tggaaggtgc gcgccgaact ggccgcttct tatattgctg acgagaagga acggggggag    360
aaactgagtg tggctctgag acacatcgca aggcatcgcg gatggaggaa cccttacgcc    420
aaggtgtcta gtctgtatct gccagatggc ccctcagacg ccttcaaggc tattagggag    480
gaaatcaaac gcgctagcgg ccagcctgtg ccagagactg caaccgtcgg gcagatggtg    540
accctgtgcg aactgggcac actgaagctg cgaggagagg gaggagtgct gagtgcacgg    600
ctgcagcagt cagattacgc ccgcgagatc caggaaattt gtcgaatgca ggagatcggc    660
caggaactgt atcgcaagat cattgacgtg gtgttcgcag ccgagtcccc aaagggctct    720
gcctcaagcc gggtggggaa agatcctctg cagccaggaa agaacagagc actgaaagcc    780
agcgacgctt ttcagcgata ccggattgct gcactgatcg gcaatctgag agtcagggtg    840
gatggggaga agaggattct gagcgtggag gagaagaacc tggtgttcga ccacctggtg    900
aatctgactc caaagaaaga gcccgaatgg gtgaccatcg ccgaaattct gggcatcgat    960
cgcgggcagc tgatcggaac agctactatg accgacgatg gagagcgagc aggagcccga   1020
cccccctacac acgatactaa cagaagtatt gtgaacagcc ggatcgcacc actggtcgac   1080
tggtggaaaa cagctagcgc actggagcag cacgccatgg tgaaggcact gtccaacgcc   1140
gaagtcgacg attttgattc tcccgaggga gcaaaagtgc aggcattctt tgccgatctg   1200
gacgatgacg tccacgccaa gctggacagc ctgcatctgc ctgtgggacg agcagcttac   1260
tccgaggaca ctctggtcag actgacccga cggatgctga gtgatggggt ggacctgtat   1320
accgcccggc tgcaggagtt cggaattgaa cctagctgga ccccacccac accaagaatc   1380
ggagagcctg tcggcaatcc agccgtcgac cgggtgctga aacagtgag cagatggctg   1440
gaatccgcaa caaagacttg gggcgcccca gagagggtca tcattgagca cgtgcgcgaa   1500
ggcttcgtca ctgagaaacg cgctcgagaa atggatgggg acatgagaag gcgcgcagcc   1560
cggaacgcca agctgtttca ggagatgcag gaaaagctga atgtgcaggg caaacccagt   1620
cgagccgatc tgtggagata ccagtcagtg cagagacaga actgccagtg tgcctattgc   1680
gggtccccaa ttaccttttc taatagtgaa atggaccaca tcgtgcccag agcagggcag   1740
ggatccacca acacaaggga gaatctggtc gccgtgtgcc atcgctgtaa ccagtctaag   1800
ggcaatacac ccttcgctat ttgggcaaaa aacacttcta tcgaaggggt cagtgtgaag   1860
gaggccgtgg aacggaccag acattgggtc actgataccg gcatgagaag cactgacttc   1920
aagaagttca ccaaggctgt ggtcgagcgg tttcagagag caacaatgga tgaggaaatc   1980
gacgccagaa gcatggaatc cgtcgcctgg atggctaatg agctgaggag ccgcgtggct   2040
cagcacttcg catcccatgg aaccacagtc agggtgtacc gaggcagcct gacagcagag   2100
gctcgacggg catctgggat cagtggaaag ctgaaattct ttgatggcgt ggggaagtcc   2160
aggctggata gaaggcacca tgctattgac gctgcagtga tcgcattcac ctctgactat   2220
gtggccgaaa cactggctgt ccgctcaaac ctgaaacaga gccaggccca ccgacaggag   2280
gctcctcagt ggagagagtt caccggcaag gatgcagagc atcgagcagc ttggagagtg   2340
tggtgccaga agatggaaaa actgagcgcc ctgctgaccg aggacctgcg agatgaccgg   2400
gtggtcgtga tgtctaacgt gcgactgcgg ctgggaaatg gcagtgccca caaggaaacc   2460
```

attggcaaac tgtcaaaggt gaaactgtcc tctcagctgt cagtcagcga tatcgacaaa 2520
gcaagttcag aggccctgtg gtgtgctctg accagagagc ccggattcga tcctaaggaa 2580
ggcctgcccg ctaaccctga gagacacatc agggtgaatg ggacacatgt ctacgccggg 2640
gacaatattg gactgtttcc agtgtcagca ggaagcatcg cactgagggg aggatacgca 2700
gagctgggca gctccttcca ccatgctcgc gtgtataaaa ttacttccgg caagaaaccc 2760
gcatttgcca tgctgagggt gtacaccatc gatctgctgc cttatcgcaa ccaggacctg 2820
tttagcgtgg aactgaagcc acagacaatg tccatgaggc aggctgagaa gaaactgcgc 2880
gacgctctgg caactgggaa tgcagaatat ctgggatggc tggtcgtgga tgacgagctg 2940
gtcgtggata catctaagat tgccactgac caggtcaaag cagtggaggc cgaactgggg 3000
actatccgcc gatggcgggt ggatggattc ttttccccct ctaaactgag actgaggcct 3060
ctgcagatgt ccaaggaggg gatcaagaaa gagtccgctc ccgaactgtc taaaatcatt 3120
gacagaccag gatggctgcc cgccgtgaac aagctgttct ctgatggaaa tgtcaccgtc 3180
gtgcggagag actctctggg acgcgtgcga ctggagagta cagcccacct gcctgtcact 3240
tggaaggtgc agtaa 3255

<210> SEQ ID NO 19
<211> LENGTH: 3393
<212> TYPE: DNA
<213> ORGANISM: Streptococcus pasteurianus

<400> SEQUENCE: 19
atgactaacg gcaagattct ggggctggac attggcatcg caagcgtggg ggtggggatt 60
attgaggcaa aaactggaaa ggtggtgcat gccaattccc ggctgttctc tgccgctaac 120
gctgagaaca atgcagaacg gagagggttt aggggatcta ggcgcctgaa tcgacggaag 180
aaacaccgcg tgaagcgagt ccgggatctg ttcgagaaat acggaatcgt caccgacttt 240
cgcaacctga atctgaaccc ttatgagctg cgagtgaagg gcctgaccga acagctgaaa 300
aacgaggaac tgttcgcagc cctgagaaca atctctaaga gaagggggat tagttacctg 360
gacgatgccg aggacgatag taccggatca acagactatg ctaagagcat cgatgagaat 420
cgccgactgc tgaaaaacaa gacaccaggc cagattcagc tggagaggct ggaaaagtac 480
ggccagctgc gcgggaattt caccgtctat gacgagaacg gggaagccca tcgcctgatc 540
aatgtgttta gtacatcaga ttacgagaaa gaagcacgga agatcctgga gacacaggcc 600
gactacaaca agaaaatcac agctgagttc attgacgatt atgtggaaat cctgacccag 660
aaacgaaagt actatcacgg ccccgggaac gaaaagagcc ggactgacta cggacggttc 720
cggaccgatg ggaccacact ggagaatatt ttcggaatcc tgattggcaa gtgcaacttt 780
taccctgatg aatatcgagc aagcaaggcc agctacaccg cacaggagta taatttcctg 840
aacgacctga acaatctgaa ggtgagcacc gaaacaggga agctgtcaac agagcagaaa 900
gaaagcctgg tggagtttgc caagaatact gctaccctgg gacccgctaa actgctgaag 960
gagatcgcaa aaattctgga ctgtaaggtg gatgagatca aaggatacag agaggacgat 1020
aaaggcaagc cagatctgca taccttcgag ccctatagga aactgaagtt taatctggaa 1080
agcatcaaca ttgacgatct gtcccgcgaa gtgatcgaca agctggctga tattctgact 1140
ctgaacaccg agagagaagg aatcgaggac gcaattaaga ggaatctgcc aaaccagttc 1200
acagaggaac agatcagcga gatcatcaag gtgcggaaga gccagtccac tgctttcaat 1260

```
aagggctggc actcttttag tgcaaaactg atgaacgagc tgatccccga actgtacgcc   1320
acctccgacg agcagatgac aattctgact cggctggaaa aattcaaggt caataagaaa   1380
agctccaaaa acacaaagac tatcgacgag aaggaagtca ctgatgagat ctacaatcct   1440
gtggtcgcca agagcgtgag acagaccatc aaaatcatta acgctgcagt caagaaatat   1500
ggcgacttcg ataagatcgt gattgaaatg ccacgggata aaaatgctga cgatgagaag   1560
aagttcatcg acaagagaaa taaggagaac aagaaggaaa aggacgatgc cctgaaaagg   1620
gccgcttacc tgtataattc tagtgacaag ctgcccgatg aggtgttcca cggcaacaag   1680
cagctggaaa ccaaaatccg actgtggtat cagcaggggg agcggtgcct gtatagtgga   1740
aagcccatct caattcagga gctggtgcat aactctaaca atttcgaaat cgatcacatt   1800
ctgcctctgt cactgagctt tgacgatagt ctggccaata aggtgctggt ctacgcttgg   1860
acaaaccagg agaaaggcca gaaaacccct tatcaggtca tcgactccat ggatgcagcc   1920
tggtctttca gggagatgaa ggactacgtg ctgaaacaga agggactggg caagaaaaag   1980
cgcgactatc tgctgactac cgagaacatc gataagattg aagtgaagaa gaagttcatc   2040
gagaggaatc tggtggatac tcgctacgca tctcgagtgg tcctgaactc tctgcagagt   2100
gccctgagag agctggggaa agacactaag gtgtctgtgg tcaggggaca gttcaccagt   2160
cagctgcgga gaaaatggaa gatcgataag agccgcgaga cataccacca tcacgcagtg   2220
gacgccctga tcattgctgc atcaagccag ctgaaactgt gggagaagca ggacaatccc   2280
atgtttgtgg attatggcaa gaaccaggtg gtcgacaaac agactgggga gatcctgtcc   2340
gtgtctgacg atgagtacaa ggaactggtg ttccagcccc cttatcaggg ctttgtgaat   2400
accatctcct ctaaagggtt cgaggacgaa attctgttta gctaccaggt ggattccaaa   2460
tataaccgga aggtcagtga cgcaaccatc tactcaacaa gaaaagccaa gattggcaag   2520
gataagaaag aggaaaccta cgtgctggga aaaatcaagg acatctactc ccagaatggc   2580
ttcgatacct tcatcaagaa gtacaacaaa gataagactc agttcctgat gtatcagaag   2640
gactctctga catgggagaa cgtgatcgaa gtcattctga gggactaccc aacaactaag   2700
aaaagcgagg acggcaaaaa tgatgtgaag tgcaacccct ttgaggaata caggcgcgag   2760
aatgggctga tctgtaagta ttccaagaaa gggaaaggaa ctcccatcaa gagcctgaag   2820
tactatgaca agaaactggg gaactgcatc gatattaccc cagaggaatc acgcaataag   2880
gtcatcctgc agagcattaa cccttggcga gccgacgtgt acttcaatcc agagacactg   2940
aagtacgaac tgatgggcct gaaatattca gatctgagct ttgaaaaggg cactgggaac   3000
taccatatca gccaggagaa atatgacgct atcaaagaga aggaaggaat tggcaagaaa   3060
tccgagttca agtttacact gtaccgcaac gacctgatcc tgatcaagga tatcgccagt   3120
ggcgagcagg aaatctacag attcctgtca agaactatgc ccaatgtgaa ccactacgtc   3180
gagctgaagc cttacgacaa ggaaaagttc gataacgtgc aggagctggt cgaagcactg   3240
ggagaggcag ataaagtggg acgatgtatc aaaggactga ataagccaaa catcagcatc   3300
tacaaggtga gaaccgacgt cctgggaaac aaatatttcg tgaagaaaaa gggcgacaaa   3360
cccaagctgg attttaagaa caacaagaag taa                                3393
```

<210> SEQ ID NO 20
<211> LENGTH: 3249
<212> TYPE: DNA
<213> ORGANISM: Neisseria cinerea

<400> SEQUENCE: 20

-continued

```
atggctgcct tcaaacctaa tcctatgaac tacatcctgg gcctggacat tggaatcgct     60
tctgtcgggt gggctatcgt ggaaatcgac gaggaagaga accctatcag actgattgat    120
ctgggagtca gagtgtttga aagggcagag gtgccaaaga ccggcgactc cctggccgct    180
gcacggagac tggctcggtc tgtcaggcgc ctgacacgac ggagagcaca caggctgctg    240
cgagctaggc gcctgctgaa gagagagggc gtgctgcagg ccgctgactt cgatgaaaac    300
ggcctgatca agagcctgcc caatactcct tggcagctga gagcagccgc tctggacagg    360
aagctgaccc cactggagtg gtctgccgtg ctgctgcacc tgatcaagca tcgcggctac    420
ctgagtcagc gaaaaaatga aggggagaca gcagataagg agctgggagc actgctgaaa    480
ggagtggccg acaacactca tgctctgcag accggcgatt ttaggacacc cgctgagctg    540
gcactgaata agttcgaaaa agagagtgga cacattcgaa accagcgggg cgactattca    600
cataccttca accgcaagga tctgcaggcc gagctgaatc tgctgtttga aaagcagaaa    660
gagttcggga atccccacgt gtccgacggg ctgaaagaag gaatcgagac actgctgatg    720
actcagaggc ctgcactgtc tggcgatgcc gtgcagaaga tgctggggca ttgcaccttt    780
gaaccaacag agcccaaggc agccaaaaac acctacacag ccgagaggtt cgtgtggctg    840
acaaagctga acaatctgcg catcctggaa cagggcagtg agcggcccct gactgacacc    900
gaaagagcca cactgatgga tgagccttac aggaagtcta aactgactta tgcccaggct    960
cgcaagctgc tggacctgga cgatactgcc ttctttaagg gcctgaggta cgggaaagat   1020
aatgcagaag ccagcaccct gatggagatg aaggcctatc acgctatctc ccgcgccctg   1080
gaaaaagagg gcctgaagga caagaaatct cccctgaacc tgagtcctga actgcaggat   1140
gagattggga ccgcttttag cctgttcaag actgacgagg atatcaccgg acgcctgaaa   1200
gaccgagtgc agcccgaaat tctggaggca ctgctgaagc acatcagttt tgataaattc   1260
gtgcagattt cactgaaggc cctgcgacgg atcgtccctc tgatggagca gggcaatcgg   1320
tacgacgagg cctgcaccga gatctacgga gatcattatg gcaagaaaaa cacagaagag   1380
aaaatctatc tgccccctat tcctgccgac gagatccgga atccagtggt cctgagagct   1440
ctgtcacagg caagaaaagt gatcaacgga gtggtcagaa ggtacggcag ccctgctagg   1500
atccacattg aaaccgcacg cgaagtggga aagtccttta aagaccgcaa ggaaatcgag   1560
aagcgacagg aagagaatag aaaagatagg gaaaagtctg ctgcaaaatt cagggagtac   1620
tttccaaact tcgtgggcga acccaagagt aaagacatcc tgaagctgcg cctgtacgag   1680
cagcagcacg ggaagtgtct gtatagcgga aaagaaatta acctgggccg gctgaatgaa   1740
aagggctatg tggagatcga tcatgcactg cccttttcca gaacatggga cgattctttc   1800
aacaataagg tcctggctct ggggagcgag aaccagaaca agggaaatca gactccttac   1860
gaatatttca acgggaagga caatagccga gaatggcagg agtttaaagc ccgcgtggag   1920
acaagccggt tcccacgaag caagaaacag cggattctgc tgcagaagtt tgacgaagat   1980
ggattcaaag agagaaacct gaatgacacc cggtacatca acagatttct gtgccagttc   2040
gtggctgatc acatgctgct gaccggaaag ggcaaacgcc gagtctttgc aagcaacggc   2100
cagatcacaa atctgctgag gggcttctgg gggctgcgga aggtgagagc cgagaatgac   2160
cgccaccatg cactggatgc cgtggtcgtg gcttgttcca ctattgcaat gcagcagaag   2220
atcaccaggt ttgtgcgcta taaagagatg aacgccttcg acggaaagac aattgataaa   2280
gaaactggcg aggtgctgca ccagaaggca cattttcctc agccatggga gttcttcgcc   2340
```

-continued

```
caggaagtga tgatccgggt ctttgggaag cctgacggaa aaccagagtt cgaagaggcc   2400

gataccccag aaaagctgcg gacactgctg gctgaaaaac tgagctccag acccgaggca   2460

gtgcacaagt acgtcacccc cctgttcatt agcagggccc ctaatcgcaa aatgtccggg   2520

cagggacata tggagactgt gaaatcagct aagcggctgg acgaaggcat cagcgtgctg   2580

agagtcccac tgacccagct gaagctgaaa gatctggaga agatggtgaa ccgggaaaga   2640

gagcccaagc tgtatgaagc tctgaaagca agactggagg cccacaagga cgatccagct   2700

aaagcatttg ccgagccctt ctacaaatat gacaaggccg gcaatcggac acagcaggtg   2760

aaggctgtca gagtggagca ggtccagaaa actggggtct gggtgcacaa ccataatgga   2820

attgccgaca acgctacaat cgtccgggtg gatgtgttcg agaaaggcgg gaagtactat   2880

ctggtgccta tctactcctg gcaggtcgcc aagggaatcc tgccagatag agctgtcgtg   2940

cagggcaaag acgaagagga ttggactgtg atggacgatt ctttcgagtt taagttcgtc   3000

ctgtacgcaa acgacctgat caagctgaca gccaagaaaa atgaatttct ggggtatttc   3060

gtgtcactga acagggcaac tggagccatc gatattcgca cacatgacac tgatagcacc   3120

aagggaaaaa acggcatctt tcagtctgtg ggcgtcaaga ccgccctgag tttccagaaa   3180

tatcagattg acgaactggg gaaggagatc cgaccctgtc ggctgaagaa acgaccaccc   3240

gtgcggtaa                                                           3249
```

<210> SEQ ID NO 21
<211> LENGTH: 3294
<212> TYPE: DNA
<213> ORGANISM: Staphylococcus aureus

<400> SEQUENCE: 21

```
aagcggaact acatcctggg cctggacatc ggcatcacca gcgtgggcta cggcatcatc     60

gactacgaga cacgggacgt gatcgatgcc ggcgtgcggc tgttcaaaga ggccaacgtg    120

gaaaacaacg agggcaggcg gagcaagaga ggcgccagaa ggctgaagcg gcggaggcgg    180

catagaatcc agagagtgaa gaagctgctg ttcgactaca acctgctgac cgaccacagc    240

gagctgagcg gcatcaaccc ctacgaggcc agagtgaagg gcctgagcca gaagctgagc    300

gaggaagagt tctctgccgc cctgctgcac ctggccaaga gaagaggcgt gcacaacgtg    360

aacgaggtgg aagaggacac cggcaacgag ctgtccacca aagagcagat cagccggaac    420

agcaaggccc tggaagagaa atacgtggcc gaactgcagc tggaacggct gaagaaagac    480

ggcgaagtgc ggggcagcat caacagattc aagaccagcg actacgtgaa agaagccaaa    540

cagctgctga aggtgcagaa ggcctaccac cagctggacc agagcttcat cgacacctac    600

atcgacctgc tggaaacccg gcggacctac tatgagggac ctggcgaggg cagcccctte    660

ggctggaagg acatcaaaga atggtacgag atgctgatgg gccactgcac ctacttcccc    720

gaggaactgc ggagcgtgaa gtacgcctac aacgccgacc tgtacaacgc cctgaacgac    780

ctgaacaatc tcgtgatcac cagggacgag aacgagaagc tggaatatta cgagaagttc    840

cagatcatcg agaacgtgtt caagcagaag aagaagccca ccctgaagca gatcgccaaa    900

gaaatcctcg tgaacgaaga ggatattaag ggctacagag tgaccagcac cggcaagccc    960

gagttcacca acctgaaggt gtaccacgac atcaaggaca ttaccgcccg gaaagagatt   1020

attgagaacg ccgagctgct ggatcagatt gccaagatcc tgaccatcta ccagagcagc   1080

gaggacatcc aggaagaact gaccaatctg aactccgagc tgacccagga agagatcgag   1140

cagatctcta atctgaaggg ctataccggc acccacaacc tgagcctgaa ggccatcaac   1200
```

```
ctgatcctgg acgagctgtg gcacaccaac gacaaccaga tcgctatctt caaccggctg   1260
aagctggtgc ccaagaaggt ggacctgtcc cagcagaaag agatccccac caccctggtg   1320
gacgacttca tcctgagccc cgtcgtgaag agaagcttca tccagagcat caaagtgatc   1380
aacgccatca tcaagaagta cggcctgccc aacgacatca ttatcgagct ggcccgcgag   1440
aagaactcca aggacgccca gaaaatgatc aacgagatgc agaagcggaa ccggcagacc   1500
aacgagcgga tcgaggaaat catccggacc accggcaaag agaacgccaa gtacctgatc   1560
gagaagatca agctgcacga catgcaggaa ggcaagtgcc tgtacagcct ggaagccatc   1620
cctctggaag atctgctgaa caacccccttc aactatgagg tggaccacat catccccaga   1680
agcgtgtcct tcgacaacag cttcaacaac aaggtgctcg tgaagcagga agaaaacagc   1740
aagaagggca accggacccc attccagtac ctgagcagca gcgacagcaa gatcagctac   1800
gaaaccttca agaagcacat cctgaatctg gccaagggca agggcagaat cagcaagacc   1860
aagaaagagt atctgctgga agaacgggac atcaacaggt tctccgtgca gaaagacttc   1920
atcaaccgga acctggtgga taccagatac gccaccagag gcctgatgaa cctgctgcgg   1980
agctacttca gagtgaacaa cctggacgtg aaagtgaagt ccatcaatgg cggcttcacc   2040
agctttctgc ggcggaagtg gaagtttaag aaagagcgga acaaggggta caagcaccac   2100
gccgaggacg ccctgatcat tgccaacgcc gatttcatct tcaaagagtg gaagaaactg   2160
gacaaggcca aaaaagtgat ggaaaaccag atgttcgagg aaaagcaggc cgagagcatg   2220
cccgagatcg aaaccgagca ggagtacaaa gagatcttca tcaccccccca ccagatcaag   2280
cacattaagg acttcaagga ctacaagtac agccaccggg tggacaagaa gcctaataga   2340
gagctgatta acgacaccct gtactccacc cggaaggacg acaagggcaa caccctgatc   2400
gtgaacaatc tgaacggcct gtacgacaag gacaatgaca agctgaaaaa gctgatcaac   2460
aagagccccg aaaagctgct gatgtaccac cacgaccccc agacctacca gaaactgaag   2520
ctgattatgg aacagtacgg cgacgagaag aatcccctgt acaagtacta cgaggaaacc   2580
gggaactacc tgaccaagta ctccaaaaag gacaacggcc ccgtgatcaa gaagattaag   2640
tattacggca acaaactgaa cgcccatctg gacatcaccg acgactaccc caacagcaga   2700
aacaaggtcg tgaagctgtc cctgaagccc tacagattcg acgtgtacct ggacaatggc   2760
gtgtacaagt tcgtgaccgt gaagaatctg gatgtgatca aaaaagaaaa ctactacgaa   2820
gtgaatagca agtgctatga ggaagctaag aagctgaaga agatcagcaa ccaggccgag   2880
tttatcgcct ccttctacaa caacgatctg atcaagatca acggcgagct gtatagagtg   2940
atcggcgtga acaacgacct gctgaaccgg atcgaagtga acatgatcga catcacctac   3000
cgcgagtacc tggaaaacat gaacgacaag aggcccccca ggatcattaa gacaatcgcc   3060
tccaagaccc agagcattaa gaagtacagc acagacattc tgggcaacct gtatgaagtg   3120
aaatctaaga agcaccctca gatcatcaaa aagggcaaaa ggccggcggc cacgaaaaag   3180
gccggccagg caaaaaagaa aaagggatcc tacccatacg atgttccaga ttacgcttac   3240
ccatacgatg ttccagatta cgcttaccca tacgatgttc cagattacgc ttaa         3294
```

<210> SEQ ID NO 22
<211> LENGTH: 3012
<212> TYPE: DNA
<213> ORGANISM: Campylobacter lari

<400> SEQUENCE: 22

```
atgaggattc tggggtttga cattggcatt aacagcatcg ggtgggcttt tgtggagaac     60
gacgaactga aggactgcgg agtgcggatc ttcacaaagg ccgagaaccc aaaaaataag    120
gaaagcctgg cactgccccg gagaaatgca cgcagctcca ggcgccgact gaaacggaga    180
aaggcccggc tgatcgctat taagagaatc ctggccaaag agctgaagct gaactacaag    240
gactatgtcg cagctgatgg agagctgcca aaggcctacg aaggatccct ggcatctgtg    300
tacgagctgc ggtataaggc cctgacacag aacctggaaa ctaaagatct ggccagagtg    360
atcctgcaca ttgctaagca tagggggtac atgaacaaga acgagaagaa atcaaacgac    420
gctaagaaag gaaagatcct gagcgctctg aaaaacaatg cactgaagct ggagaactac    480
cagagcgtgg gcgaatactt ctacaaggag ttctttcaga aatacaagaa aaacacaaag    540
aacttcatca agatccgcaa cactaaggat aattacaaca attgcgtgct gtctagtgac    600
ctggaaaaag agctgaagct gatcctggaa aaacagaagg agttcggcta caactactct    660
gaagatttca tcaacgagat tctgaaggtc gccttctttc agcggcccct gaaggacttc    720
agtcacctgg tgggggcctg cactttcttt gaggaagaga aaagggcctg taagaacagc    780
tactctgcct gggagtttgt ggctctgacc aagatcatta acgagatcaa gagcctggag    840
aagatcagcg gcgaaattgt gccaacccag acaatcaacg aggtcctgaa tctgatcctg    900
gacaaggggt ctatcaccta caagaaattc agaagttgta tcaatctgca tgagagtatc    960
agcttcaaga gcctgaagta tgataaagaa aacgccgaga atgctaaact gatcgacttc   1020
cgcaagctgg tggagtttaa gaaagccctg ggagtccaca gcctgtcccg gcaggaactg   1080
gatcagatct ccactcatat caccctgatt aaggacaacg tgaagctgaa aaccgtcctg   1140
gagaaataca acctgagtaa tgaacagatc aacaatctgc tggaaattga gttcaacgat   1200
tatatcaacc tgagcttcaa ggccctggga atgattctgc cactgatgcg cgagggcaaa   1260
cgatacgacg aggcctgcga gatcgccaat ctgaaaccta agaccgtgga cgagaagaaa   1320
gatttcctgc cagcattttg tgattccatt ttcgcccacg agctgtctaa ccccgtggtc   1380
aatagggcta tcagcgaata ccgcaaggtg ctgaacgcac tgctgaagaa atatggaaag   1440
gtccacaaaa ttcatctgga gctggctcgc gacgtgggcc tgtccaagaa agcacgagag   1500
aagatcgaaa aagagcagaa ggaaaaccag gccgtgaatg catgggccct gaaggaatgc   1560
gagaatattg gcctgaaggc cagcgcaaag aacatcctga aactgaagct gtggaaagaa   1620
cagaaggaga tctgtatcta ctccggaaat aagatctcta ttgagcacct gaaagatgaa   1680
aaggccctgg aggtggacca tatctacccc tattctagga gtttcgacga ttcttttatc   1740
aacaaagtgc tggtgttcac caaggaaaat caggagaaac tgaacaagac acctttcgag   1800
gcctttggca agaatattga aaaatggagc aagatccaga ccctggctca gaacctgcca   1860
tacaagaaaa agaataagat tctggacgag aacttcaaag ataagcagca ggaggacttt   1920
atctctcgaa atctgaacga cacccggtat atcgctacac tgattgcaaa atacacaaag   1980
gagtatctga acttcctgct gctgagcgaa aatgagaacg ccaatctgaa gagtggcgaa   2040
aaagggtcaa agatccacgt gcagactatt agcgggatgc tgacctccgt cctgaggcac   2100
acatgggggt ttgacaaaaa ggatcgcaac aatcatctgc accatgcact ggatgccatc   2160
attgtggcct acagtacaaa ttcaatcatt aaggctttca gcgatttccg gaaaaaccag   2220
gagctgctga aggccagatt ctacgctaaa gaactgactt ccgataacta taaacatcag   2280
gtcaagttct ttgagccttt caagagtttt agagaaaaaa tcctgtcaaa gatcgacgag   2340
attttcgtgt ccaaaccacc tcgaaagcga gctaggcgcg cactgcacaa ggataccttt   2400
```

```
cattctgaga acaagatcat tgacaagtgc agctacaact ccaaggaagg cctgcagatt   2460

gccctgagct gtggaagagt gaggaaaatc ggcactaagt atgtcgagaa tgataccatc   2520

gtgagggtcg acattttcaa aaagcagaac aagttttacg ctatcccaat ctacgcaatg   2580

gattttgccc tggggatcct gcccaataag atcgtgatta ctggaaaaga taagaacaat   2640

aaccccaaac agtggcagac cattgacgaa tcatacgagt tctgctttag cctgtataag   2700

aatgacctga tcctgctgca gaaaaagaac atgcaggaac ctgagttcgc ctactataac   2760

gatttttcaa tcagcacatc aagcatttgt gtggagaaac acgacaacaa gttcgaaaat   2820

ctgactagca accagaagct gctgttttcc aatgcaaaag agggctctgt gaaggtcgaa   2880

agtctgggga tccagaacct gaaagtgttc gagaagtaca tcattacccc cctgggagat   2940

aaaattaagg ctgactttca gcctcgagaa aacatcagcc tgaaaaccag taaaaagtat   3000

ggcctgaggt aa                                                        3012
```

```
<210> SEQ ID NO 23
<211> LENGTH: 16386
<212> TYPE: DNA
<213> ORGANISM: Artificial Sequence
<220> FEATURE:
<223> OTHER INFORMATION: Vektor1_TaU6
<220> FEATURE:
<221> NAME/KEY: misc_feature
<222> LOCATION: (16239)..(16258)
<223> OTHER INFORMATION: n is a, c, g, or t

<400> SEQUENCE: 23

ttgtacaaag tggttcgata attccgatcc agcctaggcc cgggcctgag gacgcgcctt     60

actagtggat cccttcaccg ccattgcaaa aattgtcaat aaatatttag agtgggtggc    120

atcagaaaaa catctctagt ggactctctt cctatcatag ctactcgggc tgtagataga    180

acgagggcac aagagttggg tggcgtaggt ttactcgtga cctcaactct tttggctgtg    240

tcttacgtct aagatgggtt tggcatgtga gaaacatagg tctaagcaat tcatgttagg    300

gctgttgcat tgttgttgca tcaaccaaat gtccagatag cagttcatgc tacatctagt    360

tgaaaaccct catcattagg cggaacatgt gttctttttt agcatagtca aagtcagatt    420

gcggcactcg ctcatccacg gaaagaattt tccctgtgca ggcatctcga tcaaaagacg    480

caaattaatt tttgaatagc gatataacaa tatctaatta acgtttcttg ttttctgcga    540

aatgtctttc atcataaaat gagtcatctc gatgagccca agtgacatag cccaacaccc    600

caccccacca ataaaagtga agaaaacatg ttgggaaaac tataccaagt aaaatacgag    660

ttgttctaaa gaaaaagtaa agtacgagtt agatcgcacc ctgtcctgga gtgtggcttg    720

atgatccaac tcctagcatt gtatccctgt ttttggatga tgtaactatt atttacaatg    780

aataaagagg tgttttacta gtaaaaaaat cttgagggga ggagaaaata atggaggtct    840

tttttcaaac cgatggacta ttatttttag tgaaagagaa taatattatt ggaaaaatta    900

ttctatccac ttattttata ttggcagaat acaaagaatg gtggggtcca cgcggaactt    960

gcggcccccg aaacctatcg agggcgcggt acccaagcaa ggaacggagg aaacttgcgg   1020

ggcccgaaac ctagtgataa aaggcatatc atccacacga tgaagatctg acggaccata   1080

tctcccacca cggaaagcca tcagacgagg atcagacggc caggaaggaa ccctagcgcc   1140

cgccggtgcc aatataaagc gccactctct ctcgtcttaa gccccagcct ctccattccc   1200

ctctccctct cgattacgag gtgtgttgtt catccgtccc gaatccatcc atcccctctt   1260
```

-continued

```
cagatgtgtt gttcatggct ctaatagctc tagatctgct tgtttgtgtt gtttagctct   1320
agatctactc gcgcgcgctt ctctctcgat ctcctgtaga acaattttgg ttggtttttt   1380
gtgcatatcc atggtaattt tgtctgcaat atggaggagg ctttctaagc tcctacgtag   1440
catcgatctt tagaattccc tcggtttctg tttatttctt cgcgagggct ctctgttatc   1500
tgtaggagta gctgtaagcg cggttcgtta cggattaatc gtcatgctta gttgaaccta   1560
tcggtcgaag gatttgtgtg ggttgtcgtg tagaattgac accatctact tactgtactg   1620
atatgccgat ctgtaggata ctcttcatta cttttgttta ctgctagttg tggtgtagat   1680
ttagcattct caaacccatg ctgtagcgtt tctaatattg ttacatagat ctaccggtgc   1740
ctgttaattg tattcgatcg ggcgtttcta catctgtccg cccacctagt tttatatgtg   1800
gtaatcaaaa ttgcgttgac ttcgtgatgc tgtctgtgta ctgtttttaa tcgctcttac   1860
ttagatgatc aacatggtga tggttacgat ttactgtttt ctaatccctg ttacttcgat   1920
gctgcagttt gattgatggg cccagaacga cgcccggccg acatccgccg tgccaccgag   1980
gcggacatgc cggcggtctg caccatcgtc aaccactaca tcgagacaag cacggtcaac   2040
ttccgtaccg agccgcagga accgcaggag tggacggacg acctcgtccg tctgcgggag   2100
cgctatccct ggctcgtcgc cgaggtggac ggcgaggtcg ccggcatcgc ctacgcgggc   2160
ccctggaagg cacgcaacgc ctacgactgg acggccgagt cgaccgtgta cgtctccccc   2220
cgccaccagc ggacgggact gggctccacg ctctacaccc acctgctgaa gtccctggag   2280
gcacagggct tcaagagcgt ggtcgctgtc atcgggctgc ccaacgaccc gagcgtgcgc   2340
atgcacgagg cgctcggata tgccccccgc ggcatgctgc gggcggccgg cttcaagcac   2400
gggaactggc atgacgtggg tttctggcag ctggacttca gcctgccggt accgccccgt   2460
ccggtcctgc ccgtcaccga gatctgaatg ccgaatttcc ccgatcgttc aaacatttgg   2520
caataaagtt tcttaagatt gaatcctgtt gccggtcttg cgatgattat catataattt   2580
ctgttgaatt acgttaagca tgtaataatt aacatgtaat gcatgacgtt atttatgaga   2640
tgggttttta tgattagagt cccgcaatta tacatttaat acgcgataga aaacaaaata   2700
tagcgcgcaa actaggataa attatcgcgc gcggtgtcat ctatgttact agatcgctcg   2760
aagatccccc gggctgcagg aattcaagct tggcactggc cgtcgtttta caacgtcgtg   2820
actgggaaaa ccctggcgtt acccaactta atcgccttgc agcacatccc cctttcgcca   2880
gctggcgtaa tagcgaagag gcccgcaccg atcgcccttc ccaacagttg cgcagcctga   2940
atggcgaatg agcttgagct tggatcagat tgtcgtttcc cgccttcagt ttaaactatc   3000
agtgtttgac aggatatatt ggcgggtaaa cctaagagaa aagagcgttt attagaataa   3060
cggatattta aaagggcgtg aaaaggttta tccgttcgtc catttgtatg tgcatgccaa   3120
ccacagggtt cccctcggga tcaaagtact ttgatccaac ccctccgctg ctatagtgca   3180
gtcggcttct gacgttcagt gcagccgtct tctgaaaacg acatgtcgca caagtcctaa   3240
gttacgcgac aggctgccgc cctgcccttt tcctggcgtt ttcttgtcgc gtgttttagt   3300
cgcataaagt agaatacttg cgactagaac cggagacatt acgccatgaa caagagcgcc   3360
gccgctggcc tgctgggcta tgcccgcgtc agcaccgacg accaggactt gaccaaccaa   3420
cgggccgaac tgcacgcggc cggctgcacc aagctgtttt ccgagaagat caccggcacc   3480
aggcgcgacc gcccggagct ggccaggatg cttgaccacc tacgccctgg cgacgttgtg   3540
acagtgacca ggctagaccg cctggcccgc agcacccgcg acctactgga cattgccgag   3600
cgcatccagg aggccggcgc gggcctgcgt agcctggcag agccgtgggc cgacaccacc   3660
```

```
acgccggccg gccgcatggt gttgaccgtg ttcgccggca ttgccgagtt cgagcgttcc   3720
ctaatcatcg accgcacccg gagcgggcgc gaggccgcca aggcccgagg cgtgaagttt   3780
ggcccccgcc ctaccctcac cccggcacag atcgcgcacg cccgcgagct gatcgaccag   3840
gaaggccgca ccgtgaaaga ggcggctgca ctgcttggcg tgcatcgctc gaccctgtac   3900
cgcgcacttg agcgcagcga ggaagtgacg cccaccgagg ccaggcggcg cggtgccttc   3960
cgtgaggacg cattgaccga ggccgacgcc ctggcggccg ccgagaatga acgccaagag   4020
gaacaagcat gaaaccgcac caggacggcc aggacgaacc gtttttcatt accgaagaga   4080
tcgaggcgga gatgatcgcg gccgggtacg tgttcgagcc gcccgcgcac gtctcaaccg   4140
tgcggctgca tgaaatcctg gccggtttgt ctgatgccaa gctggcggcc tggccggcca   4200
gcttggccgc tgaagaaacc gagcgccgcc gtctaaaaag gtgatgtgta tttgagtaaa   4260
acagcttgcg tcatgcggtc gctgcgtata tgatgcgatg agtaaataaa caaatacgca   4320
aggggaacgc atgaaggtta tcgctgtact taaccagaaa ggcgggtcag gcaagacgac   4380
catcgcaacc catctagccc gcgccctgca actcgccggg gccgatgttc tgttagtcga   4440
ttccgatccc cagggcagtg cccgcgattg ggcggccgtg cgggaagatc aaccgctaac   4500
cgttgtcggc atcgaccgcc cgacgattga ccgcgacgtg aaggccatcg gccggcgcga   4560
cttcgtagtg atcgacggag cgccccaggc ggcggacttg gctgtgtccg cgatcaaggc   4620
agccgacttc gtgctgattc cggtgcagcc aagcccttac gacatatggg ccaccgccga   4680
cctggtggag ctggttaagc agcgcattga ggtcacggat ggaaggctac aagcggcctt   4740
tgtcgtgtcg cgggcgatca aaggcacgcg catcggcggt gaggttgccg aggcgctggc   4800
cgggtacgag ctgcccattc ttgagtcccg tatcacgcag cgcgtgagct acccaggcac   4860
tgccgccgcc ggcacaaccg ttcttgaatc agaacccgag ggcgacgctg cccgcgaggt   4920
ccaggcgctg gccgctgaaa ttaaatcaaa actcatttga gttaatgagg taaagagaaa   4980
atgagcaaaa gcacaaacac gctaagtgcc ggccgtccga gcgcacgcag cagcaaggct   5040
gcaacgttgg ccagcctggc agacacgcca gccatgaagc gggtcaactt tcagttgccg   5100
gcggaggatc acaccaagct gaagatgtac gcggtacgcc aaggcaagac cattaccgag   5160
ctgctatctg aatacatcgc gcagctacca gagtaaatga gcaaatgaat aaatgagtag   5220
atgaatttta gcggctaaag gaggcggcat ggaaaatcaa gaacaaccag gcaccgacgc   5280
cgtggaatgc cccatgtgtg gaggaacggg cggttggcca ggcgtaagcg gctgggttgt   5340
ctgccggccc tgcaatggca ctggaacccc caagcccgag gaatcggcgt gacggtcgca   5400
aaccatccgg cccggtacaa atcggcgcgg cgctgggtga tgacctggtg gagaagttga   5460
aggccgcgca ggccgcccag cggcaacgca tcgaggcaga agcacgcccc ggtgaatcgt   5520
ggcaagcggc cgctgatcga atccgcaaag aatcccggca accgccggca gccggtgcgc   5580
cgtcgattag gaagccgccc aagggcgacg agcaaccaga tttttcgtt ccgatgctct    5640
atgacgtggg cacccgcgat agtcgcagca tcatggacgt ggccgttttc cgtctgtcga   5700
agcgtgaccg acgagctggc gaggtgatcc gctacgagct tccagacggg cacgtagagg   5760
tttccgcagg gccggccggc atggccagtg tgtgggatta cgacctggta ctgatggcgg   5820
tttcccatct aaccgaatcc atgaaccgat accgggaagg gaagggagac aagcccggcc   5880
gcgtgttccg tccacacgtt gcggacgtac tcaagttctg ccggcgagcc gatggcggaa   5940
agcagaaaga cgacctggta gaaacctgca ttcggttaaa caccacgcac gttgccatgc   6000
```

agcgtacgaa gaaggccaag aacggccgcc tggtgacggt atccgagggt gaagccttga 6060
ttagccgcta caagatcgta aagagcgaaa ccgggcggcc ggagtacatc gagatcgagc 6120
tagctgattg gatgtaccgc gagatcacag aaggcaagaa cccggacgtg ctgacggttc 6180
accccgatta ctttttgatc gatcccggca tcggccgttt tctctaccgc ctggcacgcc 6240
gcgccgcagg caaggcagaa gccagatggt tgttcaagac gatctacgaa cgcagtggca 6300
gcgccggaga gttcaagaag ttctgtttca ccgtgcgcaa gctgatcggg tcaaatgacc 6360
tgccggagta cgatttgaag gaggaggcgg ggcaggctgg cccgatccta gtcatgcgct 6420
accgcaacct gatcgagggc gaagcatccg ccggttccta atgtacggag cagatgctag 6480
ggcaaattgc cctagcaggg gaaaaaggtc gaaaaggtct ctttcctgtg gatagcacgt 6540
acattgggaa cccaaagccg tacattggga accggaaccc gtacattggg aacccaaagc 6600
cgtacattgg gaaccggtca cacatgtaag tgactgatat aaaagagaaa aaaggcgatt 6660
tttccgccta aaactcttta aaacttatta aaactcttaa aacccgcctg gcctgtgcat 6720
aactgtctgg ccagcgcaca gccgaagagc tgcaaaaagc gcctaccctt cggtcgctgc 6780
gctccctacg ccccgccgct tcgcgtcggc ctatcgcggc cgctggccgc tcaaaaatgg 6840
ctggcctacg gccaggcaat ctaccagggc gcggacaagc cgcgccgtcg ccactcgacc 6900
gccggcgccc acatcaaggc accctgcctc gcgcgtttcg gtgatgacgg tgaaaacctc 6960
tgacacatgc agctcccgga gacggtcaca gcttgtctgt aagcggatgc cgggagcaga 7020
caagcccgtc agggcgcgtc agcgggtgtt ggcgggtgtc ggggcgcagc catgacccag 7080
tcacgtagcg atagcggagt gtatactggc ttaactatgc ggcatcagag cagattgtac 7140
tgagagtgca ccatatgcgg tgtgaaatac cgcacagatg cgtaaggaga aaataccgca 7200
tcaggcgctc ttccgcttcc tcgctcactg actcgctgcg ctcggtcgtt cggctgcggc 7260
gagcggtatc agctcactca aaggcggtaa tacggttatc cacagaatca ggggataacg 7320
caggaaagaa catgtgagca aaaggccagc aaaaggccag gaaccgtaaa aaggccgcgt 7380
tgctggcgtt tttccatagg ctccgccccc ctgacgagca tcacaaaaat cgacgctcaa 7440
gtcagaggtg gcgaaacccg acaggactat aaagatacca ggcgtttccc cctggaagct 7500
ccctcgtgcg ctctcctgtt ccgaccctgc cgcttaccgg atacctgtcc gcctttctcc 7560
cttcgggaag cgtggcgctt tctcatagct cacgctgtag gtatctcagt tcggtgtagg 7620
tcgttcgctc caagctgggc tgtgtgcacg aaccccccgt tcagcccgac cgctgcgcct 7680
tatccggtaa ctatcgtctt gagtccaacc cggtaagaca cgacttatcg ccactggcag 7740
cagccactgg taacaggatt agcagagcga ggtatgtagg cggtgctaca gagttcttga 7800
agtggtggcc taactacggc tacactagaa ggacagtatt tggtatctgc gctctgctga 7860
agccagttac cttcggaaaa agagttggta gctcttgatc cggcaaacaa accaccgctg 7920
gtagcggtgg tttttttgtt tgcaagcagc agattacgcg cagaaaaaaa ggatctcaag 7980
aagatccttt gatcttttct acggggtctg acgctcagtg gaacgaaaac tcacgttaag 8040
ggattttggt catgcatgat atatctccca atttgtgtag ggcttattat gcacgcttaa 8100
aaataataaa agcagacttg acctgatagt ttggctgtga gcaattatgt gcttagtgca 8160
tctaatcgct tgagttaacg ccggcgaagc ggcgtcggct tgaacgaatt tctagctaga 8220
cattatttgc cgactacctt ggtgatctcg cctttcacgt agtggacaaa ttcttccaac 8280
tgatctgcgc gcgaggccaa gcgatcttct tcttgtccaa gataagcctg tctagcttca 8340
agtatgacgg gctgatactg ggccggcagg cgctccattg cccagtcggc agcgacatcc 8400

```
ttcggcgcga ttttgccggt tactgcgctg taccaaatgc gggacaacgt aagcactaca   8460
tttcgctcat cgccagccca gtcgggcggc gagttccata gcgttaaggt ttcatttagc   8520
gcctcaaata gatcctgttc aggaaccgga tcaaagagtt cctccgccgc tggacctacc   8580
aaggcaacgc tatgttctct tgcttttgtc agcaagatag ccagatcaat gtcgatcgtg   8640
gctggctcga agatacctgc aagaatgtca ttgcgctgcc attctccaaa ttgcagttcg   8700
cgcttagctg gataacgcca cggaatgatg tcgtcgtgca caacaatggt gacttctaca   8760
gcgcggagaa tctcgctctc tccaggggaa gccgaagttt ccaaaaggtc gttgatcaaa   8820
gctcgccgcg ttgtttcatc aagccttacg gtcaccgtaa ccagcaaatc aatatcactg   8880
tgtggcttca ggccgccatc cactgcggag ccgtacaaat gtacggccag caacgtcggt   8940
tcgagatggc gctcgatgac gccaactacc tctgatagtt gagtcgatac ttcggcgatc   9000
accgcttccc ccatgatgtt taactttgtt ttagggcgac tgccctgctg cgtaacatcg   9060
ttgctgctcc ataacatcaa acatcgaccc acggcgtaac gcgcttgctg cttggatgcc   9120
cgaggcatag actgtacccc aaaaaaacat gtcataacaa gaagccatga aaaccgccac   9180
tgcgccgtta ccaccgctgc gttcggtcaa ggttctggac cagttgcgtg acggcagtta   9240
cgctacttgc attacagctt acgaaccgaa cgaggcttat gtccactggg ttcgtgcccg   9300
aattgatcac aggcagcaac gctctgtcat cgttacaatc aacatgctac cctccgcgag   9360
atcatccgtg tttcaaaccc ggcagcttag ttgccgttct tccgaatagc atcggtaaca   9420
tgagcaaagt ctgccgcctt acaacggctc tcccgctgac gccgtcccgg actgatgggc   9480
tgcctgtatc gagtggtgat tttgtgccga gctgccggtc ggggagctgt tggctggctg   9540
gtggcaggat atattgtggt gtaaacaaat tgacgcttag acaacttaat aacacattgc   9600
ggacgttttt aatgtactga attaacgccg aattgctcta gccaatacgc aaaccgcctc   9660
tccccgcgcg ttggccgatt cattaattgc agcgtgaccc ggtcgtgccc ctctctagag   9720
ataatgagca ttgcatgtct aagttataaa aaattaccac atattttttt tgtcacactt   9780
gtttgaagtg cagtttatct atctttatac atatatttaa actttactct acgaataata   9840
taatctatag tactacaata atatcagtgt tttagagaat catataaatg aacagttaga   9900
catggtctaa aggacaattg agtattttga caacaggact ctacagtttt atctttttag   9960
tgtgcatgtg ttctcctttt tttttgcaaa tagcttcacc tatataatac ttcatccatt  10020
ttattagtac atccatttag ggtttagggt taatggtttt tatagactaa tttttttagt  10080
acatctattt tattctattt tagcctctaa attaagaaaa ctaaaactct attttagttt  10140
ttttatttaa taatttagat ataaaataga ataaaataaa gtgactaaaa attaaacaaa  10200
taccctttaa gaaattaaaa aaactaagga aacatttttc ttgtttcgag tagataatgc  10260
cagcctgtta aacgccgtcg atcgacgagt ctaacggaca ccaaccagcg aaccagcagc  10320
gtcgcgtcgg gccaagcgaa gcagacggca cggcatctct gtcgctgcct ctggacccct  10380
ctcgagagtt ccgctccacc gttggacttg ctccgctgtc ggcatccaga aattgcgtgg  10440
cggagcggca gacgtgagcc ggcacggcag gcggcctcct cctcctctca cggcaccggc  10500
agctacgggg gattcctttc ccaccgctcc ttcgctttcc cttcctcgcc cgccgtaata  10560
aatagacacc ccctccacac cctctttccc caacctcgtg ttgttcggag cgcacacaca  10620
cacaaccaga tctcccccaa atccacccgt cggcacctcc gcttcaaggt acgccgctcg  10680
tcctcccccc ccccccctct ctaccttctc tagatcggcg ttccggtcca tggttagggc  10740
```

-continued

```
ccggtagttc tacttctgtt catgtttgtg ttagatccgt gtttgtgtta gatccgtgct  10800
gctagcgttc gtacacggat gcgacctgta cgtcagacac gttctgattg ctaacttgcc  10860
agtgtttctc tttggggaat cctgggatgg ctctagccgt tccgcagacg ggatcgatct  10920
aggataggta tacatgttga tgtgggtttt actgatgcat atacatgatg gcatatgcag  10980
catctattca tatgctctaa ccttgagtac ctatctatta taataaacaa gtatgtttta  11040
taattatttt gatcttgata tacttggatg atggcatatg cagcagctat atgtggattt  11100
ttttagccct gccttcatac gctatttatt tgcttggtac tgtttctttt gtcgatgctc  11160
accctgttgt ttggtgttac ttctgcaggg gtaccgccat ggataagaag tactctatcg  11220
gactcgatat cggaactaac tctgtgggat gggctgtgat caccgatgag tacaaggtgc  11280
catctaagaa gttcaaggtt ctcggaaaca ccgataggca ctctatcaag aaaaacctta  11340
tcggtgctct cctcttcgat tctggtgaaa ctgctgaggc taccagactc aagagaaccg  11400
ctagaagaag gtacaccaga agaaagaaca ggatctgcta cctccaagag atcttctcta  11460
acgagatggc taaagtggat gattcattct tccacaggct cgaagagtca ttcctcgtgg  11520
aagaagataa gaagcacgag aggcacccta tcttcggaaa catcgttgat gaggtggcat  11580
accacgagaa gtaccctact atctaccacc tcagaaagaa gctcgttgat tctactgata  11640
aggctgatct caggctcatc tacctcgctc tcgctcacat gatcaagttc agaggacact  11700
tcctcatcga gggtgatctc aaccctgata actctgatgt ggataagttg ttcatccagc  11760
tcgtgcagac ctacaaccag cttttcgaag agaaccctat caacgcttca ggtgtggatg  11820
ctaaggctat cctctctgct aggctctcta agtcaagaag gcttgagaac ctcattgctc  11880
agctccctgg tgagaagaag aacggacttt tcggaaactt gatcgctctc tctctcggac  11940
tcacccctaa cttcaagtct aacttcgatc tcgctgagga tgcaaagctc cagctctcaa  12000
aggataccta cgatgatgat ctcgataacc tcctcgctca gatcggagat cagtacgctg  12060
atttgttcct cgctgctaag aacctctctg atgctatcct cctcagtgat atcctcagag  12120
tgaacaccga gatcaccaag gctccactct cagcttctat gatcaagaga tacgatgagc  12180
accaccagga tctcacactt ctcaaggctc ttgttagaca gcagctccca gagaagtaca  12240
aagagatttt cttcgatcag tctaagaacg gatacgctgg ttacatcgat ggtggtgcat  12300
ctcaagaaga gttctacaag ttcatcaagc ctatcctcga gaagatggat ggaaccgagg  12360
aactcctcgt gaagctcaat agagaggatc ttctcagaaa gcagaggacc ttcgataacg  12420
gatctatccc tcatcagatc cacctcggag agttgcacgc tatccttaga aggcaagagg  12480
atttctaccc attcctcaag gataacaggg aaaagattga gaagattctc accttcagaa  12540
tcccttacta cgtgggacct ctcgctagag gaaactcaag attcgcttgg atgaccagaa  12600
agtctgagga aaccatcacc ccttggaact tcgaagaggt ggtggataag ggtgctagtg  12660
ctcagtcttt catcgagagg atgaccaact tcgataagaa ccttccaaac gagaaggtgc  12720
tccctaagca ctctttgctc tacgagtact tcaccgtgta caacgagttg accaaggtta  12780
agtacgtgac cgagggaatg aggaagcctg ctttttttgtc aggtgagcaa aagaaggcta  12840
tcgttgatct cttgttcaag accaacagaa aggtgaccgt gaagcagctc aaagaggatt  12900
acttcaagaa aatcgagtgc ttcgattcag ttgagatttc tggtgttgag gataggttca  12960
acgcatctct cggaacctac cacgatctcc tcaagatcat taaggataag gatttcttgg  13020
ataacgagga aaacgaggat atcttggagg atatcgttct taccctcacc ctctttgaag  13080
atagagagat gattgaagaa aggctcaaga cctacgctca tctcttcgat gataaggtga  13140
```

tgaagcagtt gaagagaaga agatacactg gttggggaag gctctcaaga aagctcatta 13200
acggaatcag ggataagcag tctggaaaga caatccttga tttcctcaag tctgatggat 13260
tcgctaacag aaacttcatg cagctcatcc acgatgattc tctcaccttt aaagaggata 13320
tccagaaggc tcaggtttca ggacagggtg atagtctcca tgagcatatc gctaacctcg 13380
ctggatctcc tgcaatcaag aagggaatcc tccagactgt gaaggttgtg gatgagttgg 13440
tgaaggtgat gggaaggcat aagcctgaga acatcgtgat cgaaatggct agagagaacc 13500
agaccactca gaagggacag aagaactcta gggaaaggat gaagaggatc gaggaaggta 13560
tcaaagagct tggatctcag atcctcaaag agcaccctgt tgagaacact cagctccaga 13620
atgagaagct ctacctctac tacctccaga acggaaggga tatgtatgtg gatcaagagt 13680
tggatatcaa caggctctct gattacgatg ttgatcatat cgtgccacag tcattcttga 13740
aggatgattc tatcgataac aaggtgctca ccaggtctga taagaacagg ggtaagagtg 13800
ataacgtgcc aagtgaagag gttgtgaaga aaatgaagaa ctattggagg cagctcctca 13860
acgctaagct catcactcag agaaagttcg ataacttgac taaggctgag aggggaggac 13920
tctctgaatt ggataaggca ggattcatca agaggcagct tgtggaaacc aggcagatca 13980
ctaagcacgt tgcacagatc ctcgattcta ggatgaacac caagtacgat gagaacgata 14040
agttgatcag ggaagtgaag gttatcaccc tcaagtcaaa gctcgtgtct gatttcagaa 14100
aggatttcca attctacaag gtgagggaaa tcaacaacta ccaccacgct cacgatgctt 14160
accttaacgc tgttgttgga accgctctca tcaagaagta tcctaagctc gagtcagagt 14220
tcgtgtacgg tgattacaag gtgtacgatg tgaggaagat gatcgctaag tctgagcaag 14280
agatcggaaa ggctaccgct aagtatttct tctactctaa catcatgaat ttcttcaaga 14340
ccgagattac cctcgctaac ggtgagatca gaaagaggcc actcatcgag acaaacggtg 14400
aaacaggtga gatcgtgtgg gataagggaa gggatttcgc taccgttaga aaggtgctct 14460
ctatgccaca ggtgaacatc gttaagaaaa ccgaggtgca gaccggtgga ttctctaaag 14520
agtctatcct ccctaagagg aactctgata agctcattgc taggaagaag gattgggacc 14580
ctaagaaata cggtggtttc gattctccta ccgtggctta ctctgttctc gttgtggcta 14640
aggttgagaa gggaaagagt aagaagctca agtctgttaa ggaacttctc ggaatcacta 14700
tcatggaaag gtcatctttc gagaagaacc caatcgattt cctcgaggct aagggataca 14760
aagaggttaa gaaggatctc atcatcaagc tcccaaagta ctcactcttc gaactcgaga 14820
acggtagaaa gaggatgctc gcttctgctg gtgagcttca aaagggaaac gagcttgctc 14880
tcccatctaa gtacgttaac tttctttacc tcgcttctca ctacgagaag ttgaagggat 14940
ctccagaaga taacgagcag aagcaacttt tcgttgagca gcacaagcac tacttggatg 15000
agatcatcga gcagatctct gagttctcta aaagggtgat cctcgctgat gcaaacctcg 15060
ataaggtgtt gtctgcttac aacaagcaca gagataagcc tatcagggaa caggcagaga 15120
acatcatcca tctcttcacc cttaccaacc tcggtgctcc tgctgctttc aagtacttcg 15180
atacaaccat cgataggaag agatacacct ctaccaaaga agtgctcgat gctaccctca 15240
tccatcagtc tatcactgga ctctacgaga ctaggatcga tctctcacag ctcggtggtg 15300
attcaagggc tgatcctaag aagaagagga aggtttgagg cgcgccgagc tccaggcctc 15360
ccagctttcg tccgtatcat cggtttcgac aacgttcgtc aagttcaatg catcagtttc 15420
attgcccaca caccagaatc ctactaagtt tgagtattat ggcattggaa aagctgtttt 15480

```
cttctatcat ttgttctgct tgtaatttac tgtgttcttt cagtttttgt tttcggacat  15540

caaaatgcaa atggatggat aagagttaat aaatgatatg gtccttttgt tcattctcaa  15600

attattatta tctgttgttt ttactttaat gggttgaatt taagtaagaa aggaactaac  15660

agtgtgatat taaggtgcaa tgttagacat ataaaacagt ctttcacctc tctttggtta  15720

tgtcttgaat tggtttgttt cttcacttat ctgtgtaatc aagtttacta tgagtctatg  15780

atcaagtaat tatgcaatca agttaagtac agtataggct tgagctccct aggcctgtta  15840

tccctaacaa gtttgtacaa aaaagcaggc tgagctcgac caagcccgtt attctgacag  15900

ttctggtgct caacacattt atatttatca aggagcacat tgttactcac tgctaggagg  15960

gaatcgaact aggaatattg atcagaggaa ctacgagaga gctgaagata actgccctct  16020

agctctcact gatctgggcg catagtgaga tgcagcccac gtgagttcag caacggtcta  16080

gcgctgggct tttaggcccg catgatcggg ctttgtcggg tggtcgacgt gttcacgatt  16140

ggggagagca acgcagcagt tcctcttagt ttagtcccac ctcgcctgtc cagcagagtt  16200

ctgaccggtt tataaactcg cttgctgcat cagacttgnn nnnnnnnnnn nnnnnnnngt  16260

tttagagcta gaaatagcaa gttaaaataa ggctagtccg ttatcaactt gaaaaagtgg  16320

caccgagtcg gtgctttttt tctagaccca gctttcttgt acaaagttgg cattaaccca  16380

gctttc                                                             16386
```

```
<210> SEQ ID NO 24
<211> LENGTH: 16792
<212> TYPE: DNA
<213> ORGANISM: Artificial Sequence
<220> FEATURE:
<223> OTHER INFORMATION: Vektor1_ZmU3
<220> FEATURE:
<221> NAME/KEY: misc_feature
<222> LOCATION: (16645)..(16664)
<223> OTHER INFORMATION: n is a, c, g, or t

<400> SEQUENCE: 24
```

```
ttgtacaaag tggttcgata attccgatcc agcctaggcc cgggcctgag gacgcgcctt     60

actagtggat cccttcaccg ccattgcaaa aattgtcaat aaatatttag agtgggtggc    120

atcagaaaaa catctctagt ggactctctt cctatcatag ctactcgggc tgtagataga    180

acgagggcac aagagttggg tggcgtaggt ttactcgtga cctcaactct tttggctgtg    240

tcttacgtct aagatgggtt tggcatgtga gaaacatagg tctaagcaat tcatgttagg    300

gctgttgcat tgttgttgca tcaaccaaat gtccagatag cagttcatgc tacatctagt    360

tgaaaaccct catcattagg cggaacatgt gttctttttt agcatagtca aagtcagatt    420

gcggcactcg ctcatccacg gaaagaattt tccctgtgca ggcatctcga tcaaaagacg    480

caaattaatt tttgaatagc gatataacaa tatctaatta acgtttcttg ttttctgcga    540

aatgtctttc atcataaaat gagtcatctc gatgagccca agtgacatag cccaacaccc    600

caccccacca ataaaagtga agaaaacatg ttgggaaaac tataccaagt aaaatacgag    660

ttgttctaaa gaaaaagtaa agtacgagtt agatcgcacc ctgtcctgga gtgtggcttg    720

atgatccaac tcctagcatt gtatccctgt ttttggatga tgtaactatt atttacaatg    780

aataaagagg tgttttacta gtaaaaaaat cttgagggga ggagaaaata atggaggtct    840

tttttcaaac cgatggacta ttatttttag tgaaagagaa taatattatt ggaaaaatta    900

ttctatccac ttattttata ttggcagaat acaaagaatg gtggggtcca cgcggaactt    960

gcggcccccg aaacctatcg agggcgcggt acccaagcaa ggaacggagg aaacttgcgg   1020
```

```
ggcccgaaac ctagtgataa aaggcatatc atccacacga tgaagatctg acggaccata   1080
tctcccacca cggaaagcca tcagacgagg atcagacggc caggaaggaa ccctagcgcc   1140
cgccggtgcc aatataaagc gccactctct ctcgtcttaa gccccagcct ctccattccc   1200
ctctccctct cgattacgag gtgtgttgtt catccgtccc gaatccatcc atcccctctt   1260
cagatgtgtt gttcatggct ctaatagctc tagatctgct tgtttgtgtt gtttagctct   1320
agatctactc gcgcgcgctt ctctctcgat ctcctgtaga acaattttgg ttggtttttt   1380
gtgcatatcc atggtaattt tgtctgcaat atggaggagg ctttctaagc tcctacgtag   1440
catcgatctt tagaattccc tcggtttctg tttatttctt cgcgagggct ctctgttatc   1500
tgtaggagta gctgtaagcg cggttcgtta cggattaatc gtcatgctta gttgaaccta   1560
tcggtcgaag gatttgtgtg ggttgtcgtg tagaattgac accatctact tactgtactg   1620
atatgccgat ctgtaggata ctcttcatta cttttgttta ctgctagttg tggtgtagat   1680
ttagcattct caaacccatg ctgtagcgtt tctaatattg ttacatagat ctaccggtgc   1740
ctgttaattg tattcgatcg ggcgtttcta catctgtccg cccacctagt tttatatgtg   1800
gtaatcaaaa ttgcgttgac ttcgtgatgc tgtctgtgta ctgtttttaa tcgctcttac   1860
ttagatgatc aacatggtga tggttacgat ttactgtttt ctaatccctg ttacttcgat   1920
gctgcagttt gattgatggg cccagaacga cgcccggccg acatccgccg tgccaccgag   1980
gcggacatgc cggcggtctg caccatcgtc aaccactaca tcgagacaag cacggtcaac   2040
ttccgtaccg agccgcagga accgcaggag tggacggacg acctcgtccg tctgcgggag   2100
cgctatccct ggctcgtcgc cgaggtggac ggcgaggtcg ccggcatcgc ctacgcgggc   2160
ccctggaagg cacgcaacgc ctacgactgg acggccgagt cgaccgtgta cgtctccccc   2220
cgccaccagc ggacgggact gggctccacg ctctacaccc acctgctgaa gtccctggag   2280
gcacagggct tcaagagcgt ggtcgctgtc atcgggctgc ccaacgaccc gagcgtgcgc   2340
atgcacgagg cgctcggata tgccccccgc ggcatgctgc gggcggccgg cttcaagcac   2400
gggaactggc atgacgtggg tttctggcag ctggacttca gcctgccggt accgccccgt   2460
ccggtcctgc ccgtcaccga gatctgaatg ccgaatttcc ccgatcgttc aaacatttgg   2520
caataaagtt tcttaagatt gaatcctgtt gccggtcttg cgatgattat catataattt   2580
ctgttgaatt acgttaagca tgtaataatt aacatgtaat gcatgacgtt atttatgaga   2640
tgggttttta tgattagagt cccgcaatta tacatttaat acgcgataga aaacaaaata   2700
tagcgcgcaa actaggataa attatcgcgc gcggtgtcat ctatgttact agatcgctcg   2760
aagatccccc gggctgcagg aattcaagct tggcactggc cgtcgtttta caacgtcgtg   2820
actgggaaaa ccctggcgtt acccaactta atcgccttgc agcacatccc cctttcgcca   2880
gctggcgtaa tagcgaagag gcccgcaccg atcgcccttc ccaacagttg cgcagcctga   2940
atggcgaatg agcttgagct tggatcagat tgtcgtttcc cgccttcagt ttaaactatc   3000
agtgtttgac aggatatatt ggcgggtaaa cctaagagaa aagagcgttt attagaataa   3060
cggatattta aaagggcgtg aaaaggttta tccgttcgtc catttgtatg tgcatgccaa   3120
ccacagggtt cccctcggga tcaaagtact ttgatccaac ccctccgctg ctatagtgca   3180
gtcggcttct gacgttcagt gcagccgtct tctgaaaacg acatgtcgca caagtcctaa   3240
gttacgcgac aggctgccgc cctgcccttt tcctggcgtt ttcttgtcgc gtgttttagt   3300
cgcataaagt agaatacttg cgactagaac cggagacatt acgccatgaa caagagcgcc   3360
```

-continued

```
gccgctggcc tgctgggcta tgcccgcgtc agcaccgacg accaggactt gaccaaccaa   3420
cgggccgaac tgcacgcggc cggctgcacc aagctgtttt ccgagaagat caccggcacc   3480
aggcgcgacc gcccggagct ggccaggatg cttgaccacc tacgccctgg cgacgttgtg   3540
acagtgacca ggctagaccg cctggcccgc agcacccgcg acctactgga cattgccgag   3600
cgcatccagg aggccggcgc gggcctgcgt agcctggcag agccgtgggc cgacaccacc   3660
acgccggccg gccgcatggt gttgaccgtg ttcgccggca ttgccgagtt cgagcgttcc   3720
ctaatcatcg accgcacccg gagcgggcgc gaggccgcca aggcccgagg cgtgaagttt   3780
ggcccccgcc ctaccctcac cccggcacag atcgcgcacg cccgcgagct gatcgaccag   3840
gaaggccgca ccgtgaaaga ggcggctgca ctgcttggcg tgcatcgctc gaccctgtac   3900
cgcgcacttg agcgcagcga ggaagtgacg cccaccgagg ccaggcggcg cggtgccttc   3960
cgtgaggacg cattgaccga ggccgacgcc ctggcggccg ccgagaatga acgccaagag   4020
gaacaagcat gaaaccgcac caggacggcc aggacgaacc gtttttcatt accgaagaga   4080
tcgaggcgga gatgatcgcg gccgggtacg tgttcgagcc gcccgcgcac gtctcaaccg   4140
tgcggctgca tgaaatcctg gccggtttgt ctgatgccaa gctggcggcc tggccggcca   4200
gcttggccgc tgaagaaacc gagcgccgcc gtctaaaaag gtgatgtgta tttgagtaaa   4260
acagcttgcg tcatgcggtc gctgcgtata tgatgcgatg agtaaataaa caaatacgca   4320
aggggaacgc atgaaggtta tcgctgtact taaccagaaa ggcgggtcag gcaagacgac   4380
catcgcaacc catctagccc gcgccctgca actcgccggg gccgatgttc tgttagtcga   4440
ttccgatccc cagggcagtg cccgcgattg ggcggccgtg cgggaagatc aaccgctaac   4500
cgttgtcggc atcgaccgcc cgacgattga ccgcgacgtg aaggccatcg gccggcgcga   4560
cttcgtagtg atcgacggag cgccccaggc ggcggacttg gctgtgtccg cgatcaaggc   4620
agccgacttc gtgctgattc cggtgcagcc aagcccttac gacatatggg ccaccgccga   4680
cctggtggag ctggttaagc agcgcattga ggtcacggat ggaaggctac aagcggcctt   4740
tgtcgtgtcg cgggcgatca aaggcacgcg catcggcggt gaggttgccg aggcgctggc   4800
cgggtacgag ctgcccattc ttgagtcccg tatcacgcag cgcgtgagct acccaggcac   4860
tgccgccgcc ggcacaaccg ttcttgaatc agaacccgag ggcgacgctg cccgcgaggt   4920
ccaggcgctg gccgctgaaa ttaaatcaaa actcatttga gttaatgagg taaagagaaa   4980
atgagcaaaa gcacaaacac gctaagtgcc ggccgtccga gcgcacgcag cagcaaggct   5040
gcaacgttgg ccagcctggc agacacgcca gccatgaagc gggtcaactt tcagttgccg   5100
gcggaggatc acaccaagct gaagatgtac gcggtacgcc aaggcaagac cattaccgag   5160
ctgctatctg aatacatcgc gcagctacca gagtaaatga gcaaatgaat aaatgagtag   5220
atgaatttta gcggctaaag gaggcggcat ggaaaatcaa gaacaaccag gcaccgacgc   5280
cgtggaatgc cccatgtgtg gaggaacggg cggttggcca ggcgtaagcg gctgggttgt   5340
ctgccggccc tgcaatggca ctggaacccc caagcccgag gaatcggcgt gacggtcgca   5400
aaccatccgg cccggtacaa atcggcgcgg cgctgggtga tgacctggtg gagaagttga   5460
aggccgcgca ggccgcccag cggcaacgca tcgaggcaga agcacgcccc ggtgaatcgt   5520
ggcaagcggc cgctgatcga atccgcaaag aatcccggca accgccggca gccggtgcgc   5580
cgtcgattag gaagccgccc aagggcgacg agcaaccaga tttttcgtt ccgatgctct   5640
atgacgtggg cacccgcgat agtcgcagca tcatggacgt ggccgttttc cgtctgtcga   5700
agcgtgaccg acgagctggc gaggtgatcc gctacgagct tccagacggg cacgtagagg   5760
```

tttccgcagg gccggccggc atggccagtg tgtgggatta cgacctggta ctgatggcgg 5820
tttcccatct aaccgaatcc atgaaccgat accgggaagg gaagggagac aagcccggcc 5880
gcgtgttccg tccacacgtt gcggacgtac tcaagttctg ccggcgagcc gatggcggaa 5940
agcagaaaga cgacctggta gaaacctgca ttcggttaaa caccacgcac gttgccatgc 6000
agcgtacgaa gaaggccaag aacggccgcc tggtgacggt atccgagggt gaagccttga 6060
ttagccgcta caagatcgta aagagcgaaa ccgggcggcc ggagtacatc gagatcgagc 6120
tagctgattg gatgtaccgc gagatcacag aaggcaagaa cccggacgtg ctgacggttc 6180
accccgatta ctttttgatc gatcccggca tcggccgttt tctctaccgc ctggcacgcc 6240
gcgccgcagg caaggcagaa gccagatggt tgttcaagac gatctacgaa cgcagtggca 6300
gcgccggaga gttcaagaag ttctgtttca ccgtgcgcaa gctgatcggg tcaaatgacc 6360
tgccggagta cgatttgaag gaggaggcgg ggcaggctgg cccgatccta gtcatgcgct 6420
accgcaacct gatcgagggc gaagcatccg ccggttccta atgtacggag cagatgctag 6480
ggcaaattgc cctagcaggg gaaaaaggtc gaaaaggtct ctttcctgtg gatagcacgt 6540
acattgggaa cccaaagccg tacattggga accggaaccc gtacattggg aacccaaagc 6600
cgtacattgg gaaccggtca cacatgtaag tgactgatat aaaagagaaa aaaggcgatt 6660
tttccgccta aaactcttta aaacttatta aaactcttaa aacccgcctg gcctgtgcat 6720
aactgtctgg ccagcgcaca gccgaagagc tgcaaaaagc gcctaccctt cggtcgctgc 6780
gctccctacg ccccgccgct tcgcgtcggc ctatcgcggc cgctggccgc tcaaaaatgg 6840
ctggcctacg gccaggcaat ctaccagggc gcggacaagc cgcgccgtcg ccactcgacc 6900
gccggcgccc acatcaaggc accctgcctc gcgcgtttcg gtgatgacgg tgaaaacctc 6960
tgacacatgc agctcccgga gacggtcaca gcttgtctgt aagcggatgc cgggagcaga 7020
caagcccgtc agggcgcgtc agcgggtgtt ggcgggtgtc ggggcgcagc catgacccag 7080
tcacgtagcg atagcggagt gtatactggc ttaactatgc ggcatcagag cagattgtac 7140
tgagagtgca ccatatgcgg tgtgaaatac cgcacagatg cgtaaggaga aaataccgca 7200
tcaggcgctc ttccgcttcc tcgctcactg actcgctgcg ctcggtcgtt cggctgcggc 7260
gagcggtatc agctcactca aaggcggtaa tacggttatc cacagaatca ggggataacg 7320
caggaaagaa catgtgagca aaaggccagc aaaaggccag gaaccgtaaa aaggccgcgt 7380
tgctggcgtt tttccatagg ctccgccccc ctgacgagca tcacaaaaat cgacgctcaa 7440
gtcagaggtg gcgaaacccg acaggactat aaagatacca ggcgtttccc cctggaagct 7500
ccctcgtgcg ctctcctgtt ccgaccctgc cgcttaccgg atacctgtcc gcctttctcc 7560
cttcgggaag cgtggcgctt tctcatagct cacgctgtag gtatctcagt tcggtgtagg 7620
tcgttcgctc caagctgggc tgtgtgcacg aaccccccgt tcagcccgac cgctgcgcct 7680
tatccggtaa ctatcgtctt gagtccaacc cggtaagaca cgacttatcg ccactggcag 7740
cagccactgg taacaggatt agcagagcga ggtatgtagg cggtgctaca gagttcttga 7800
agtggtggcc taactacggc tacactagaa ggacagtatt tggtatctgc gctctgctga 7860
agccagttac cttcggaaaa agagttggta gctcttgatc cggcaaacaa accaccgctg 7920
gtagcggtgg tttttttgtt tgcaagcagc agattacgcg cagaaaaaaa ggatctcaag 7980
aagatccttt gatcttttct acggggtctg acgctcagtg gaacgaaaac tcacgttaag 8040
ggattttggt catgcatgat atatctccca atttgtgtag ggcttattat gcacgcttaa 8100

-continued

```
aaataataaa agcagacttg acctgatagt ttggctgtga gcaattatgt gcttagtgca   8160
tctaatcgct tgagttaacg ccggcgaagc ggcgtcggct tgaacgaatt tctagctaga   8220
cattatttgc cgactacctt ggtgatctcg cctttcacgt agtggacaaa ttcttccaac   8280
tgatctgcgc gcgaggccaa gcgatcttct tcttgtccaa gataagcctg tctagcttca   8340
agtatgacgg gctgatactg ggccggcagg cgctccattg cccagtcggc agcgacatcc   8400
ttcggcgcga ttttgccggt tactgcgctg taccaaatgc gggacaacgt aagcactaca   8460
tttcgctcat cgccagccca gtcgggcggc gagttccata gcgttaaggt ttcatttagc   8520
gcctcaaata gatcctgttc aggaaccgga tcaaagagtt cctccgccgc tggacctacc   8580
aaggcaacgc tatgttctct tgcttttgtc agcaagatag ccagatcaat gtcgatcgtg   8640
gctggctcga agatacctgc aagaatgtca ttgcgctgcc attctccaaa ttgcagttcg   8700
cgcttagctg gataacgcca cggaatgatg tcgtcgtgca caacaatggt gacttctaca   8760
gcgcggagaa tctcgctctc tccaggggaa gccgaagttt ccaaaaggtc gttgatcaaa   8820
gctcgccgcg ttgtttcatc aagccttacg gtcaccgtaa ccagcaaatc aatatcactg   8880
tgtggcttca ggccgccatc cactgcggag ccgtacaaat gtacggccag caacgtcggt   8940
tcgagatggc gctcgatgac gccaactacc tctgatagtt gagtcgatac ttcggcgatc   9000
accgcttccc ccatgatgtt taactttgtt ttagggcgac tgccctgctg cgtaacatcg   9060
ttgctgctcc ataacatcaa acatcgaccc acggcgtaac gcgcttgctg cttggatgcc   9120
cgaggcatag actgtacccc aaaaaaacat gtcataacaa gaagccatga aaaccgccac   9180
tgcgccgtta ccaccgctgc gttcggtcaa ggttctggac cagttgcgtg acggcagtta   9240
cgctacttgc attacagctt acgaaccgaa cgaggcttat gtccactggg ttcgtgcccg   9300
aattgatcac aggcagcaac gctctgtcat cgttacaatc aacatgctac cctccgcgag   9360
atcatccgtg tttcaaaccc ggcagcttag ttgccgttct tccgaatagc atcggtaaca   9420
tgagcaaagt ctgccgcctt acaacggctc tcccgctgac gccgtcccgg actgatgggc   9480
tgcctgtatc gagtggtgat tttgtgccga gctgccggtc ggggagctgt tggctggctg   9540
gtggcaggat atattgtggt gtaaacaaat tgacgcttag acaacttaat aacacattgc   9600
ggacgttttt aatgtactga attaacgccg aattgctcta gccaatacgc aaaccgcctc   9660
tccccgcgcg ttggccgatt cattaattgc agcgtgaccc ggtcgtgccc ctctctagag   9720
ataatgagca ttgcatgtct aagttataaa aaattaccac atattttttt tgtcacactt   9780
gtttgaagtg cagtttatct atctttatac atatatttaa actttactct acgaataata   9840
taatctatag tactacaata atatcagtgt tttagagaat catataaatg aacagttaga   9900
catggtctaa aggacaattg agtattttga caacaggact ctacagtttt atcttttttag   9960
tgtgcatgtg ttctcctttt tttttgcaaa tagcttcacc tatataatac ttcatccatt  10020
ttattagtac atccatttag ggtttagggt taatggtttt tatagactaa ttttttttagt  10080
acatctattt tattctattt tagcctctaa attaagaaaa ctaaaactct attttagttt  10140
ttttatttaa taatttagat ataaaataga ataaaataaa gtgactaaaa attaaacaaa  10200
taccctttaa gaaattaaaa aaactaagga aacatttttc ttgtttcgag tagataatgc  10260
cagcctgtta aacgccgtcg atcgacgagt ctaacggaca ccaaccagcg aaccagcagc  10320
gtcgcgtcgg gccaagcgaa gcagacggca cggcatctct gtcgctgcct ctggacccct  10380
ctcgagagtt ccgctccacc gttggacttg ctccgctgtc ggcatccaga aattgcgtgg  10440
cggagcggca gacgtgagcc ggcacggcag gcggcctcct cctcctctca cggcaccggc  10500
```

agctacgggg gattcctttc ccaccgctcc ttcgctttcc cttcctcgcc cgccgtaata 10560
aatagacacc ccctccacac cctctttccc caacctcgtg ttgttcggag cgcacacaca 10620
cacaaccaga tctcccccaa atccacccgt cggcacctcc gcttcaaggt acgccgctcg 10680
tcctcccccc ccccccctct ctaccttctc tagatcggcg ttccggtcca tggttagggc 10740
ccggtagttc tacttctgtt catgtttgtg ttagatccgt gtttgtgtta gatccgtgct 10800
gctagcgttc gtacacggat gcgacctgta cgtcagacac gttctgattg ctaacttgcc 10860
agtgtttctc tttggggaat cctgggatgg ctctagccgt tccgcagacg ggatcgatct 10920
aggataggta tacatgttga tgtgggtttt actgatgcat atacatgatg gcatatgcag 10980
catctattca tatgctctaa ccttgagtac ctatctatta taataaacaa gtatgtttta 11040
taattatttt gatcttgata tacttggatg atggcatatg cagcagctat atgtggattt 11100
ttttagccct gccttcatac gctatttatt tgcttggtac tgtttctttt gtcgatgctc 11160
accctgttgt ttggtgttac ttctgcaggg gtaccgccat ggataagaag tactctatcg 11220
gactcgatat cggaactaac tctgtgggat gggctgtgat caccgatgag tacaaggtgc 11280
catctaagaa gttcaaggtt ctcggaaaca ccgataggca ctctatcaag aaaaacctta 11340
tcggtgctct cctcttcgat tctggtgaaa ctgctgaggc taccagactc aagagaaccg 11400
ctagaagaag gtacaccaga agaaagaaca ggatctgcta cctccaagag atcttctcta 11460
acgagatggc taaagtggat gattcattct tccacaggct cgaagagtca ttcctcgtgg 11520
aagaagataa gaagcacgag aggcacccta tcttcggaaa catcgttgat gaggtggcat 11580
accacgagaa gtaccctact atctaccacc tcagaaagaa gctcgttgat tctactgata 11640
aggctgatct caggctcatc tacctcgctc tcgctcacat gatcaagttc agaggacact 11700
tcctcatcga gggtgatctc aaccctgata actctgatgt ggataagttg ttcatccagc 11760
tcgtgcagac ctacaaccag cttttcgaag agaaccctat caacgcttca ggtgtggatg 11820
ctaaggctat cctctctgct aggctctcta agtcaagaag gcttgagaac ctcattgctc 11880
agctccctgg tgagaagaag aacggacttt tcggaaactt gatcgctctc tctctcggac 11940
tcacccctaa cttcaagtct aacttcgatc tcgctgagga tgcaaagctc cagctctcaa 12000
aggataccta cgatgatgat ctcgataacc tcctcgctca gatcggagat cagtacgctg 12060
atttgttcct cgctgctaag aacctctctg atgctatcct cctcagtgat atcctcagag 12120
tgaacaccga gatcaccaag gctccactct cagcttctat gatcaagaga tacgatgagc 12180
accaccagga tctcacactt ctcaaggctc ttgttagaca gcagctccca gagaagtaca 12240
aagagatttt cttcgatcag tctaagaacg gatacgctgg ttacatcgat ggtggtgcat 12300
ctcaagaaga gttctacaag ttcatcaagc ctatcctcga gaagatggat ggaaccgagg 12360
aactcctcgt gaagctcaat agagaggatc ttctcagaaa gcagaggacc ttcgataacg 12420
gatctatccc tcatcagatc cacctcggag agttgcacgc tatccttaga aggcaagagg 12480
atttctaccc attcctcaag gataacaggg aaaagattga gaagattctc accttcagaa 12540
tcccttacta cgtgggacct ctcgctagag gaaactcaag attcgcttgg atgaccagaa 12600
agtctgagga aaccatcacc ccttggaact tcgaagaggt ggtggataag ggtgctagtg 12660
ctcagtcttt catcgagagg atgaccaact tcgataagaa ccttccaaac gagaaggtgc 12720
tccctaagca ctctttgctc tacgagtact tcaccgtgta caacgagttg accaaggtta 12780
agtacgtgac cgagggaatg aggaagcctg ctttttttgtc aggtgagcaa aagaaggcta 12840

-continued

```
tcgttgatct cttgttcaag accaacagaa aggtgaccgt gaagcagctc aaagaggatt  12900
acttcaagaa aatcgagtgc ttcgattcag ttgagatttc tggtgttgag gataggttca  12960
acgcatctct cggaacctac cacgatctcc tcaagatcat taaggataag gatttcttgg  13020
ataacgagga aaacgaggat atcttggagg atatcgttct taccctcacc ctctttgaag  13080
atagagagat gattgaagaa aggctcaaga cctacgctca tctcttcgat gataaggtga  13140
tgaagcagtt gaagagaaga agatacactg gttggggaag gctctcaaga aagctcatta  13200
acggaatcag ggataagcag tctggaaaga caatccttga tttcctcaag tctgatggat  13260
tcgctaacag aaacttcatg cagctcatcc acgatgattc tctcaccttt aaagaggata  13320
tccagaaggc tcaggtttca ggacagggtg atagtctcca tgagcatatc gctaacctcg  13380
ctggatctcc tgcaatcaag aagggaatcc tccagactgt gaaggttgtg gatgagttgg  13440
tgaaggtgat gggaaggcat aagcctgaga acatcgtgat cgaaatggct agagagaacc  13500
agaccactca gaagggacag aagaactcta gggaaaggat gaagaggatc gaggaaggta  13560
tcaaagagct tggatctcag atcctcaaag agcaccctgt tgagaacact cagctccaga  13620
atgagaagct ctacctctac tacctccaga acggaaggga tatgtatgtg gatcaagagt  13680
tggatatcaa caggctctct gattacgatg ttgatcatat cgtgccacag tcattcttga  13740
aggatgattc tatcgataac aaggtgctca ccaggtctga taagaacagg ggtaagagtg  13800
ataacgtgcc aagtgaagag gttgtgaaga aaatgaagaa ctattggagg cagctcctca  13860
acgctaagct catcactcag agaaagttcg ataacttgac taaggctgag aggggaggac  13920
tctctgaatt ggataaggca ggattcatca agaggcagct tgtggaaacc aggcagatca  13980
ctaagcacgt tgcacagatc ctcgattcta ggatgaacac caagtacgat gagaacgata  14040
agttgatcag ggaagtgaag gttatcaccc tcaagtcaaa gctcgtgtct gatttcagaa  14100
aggatttcca attctacaag gtgagggaaa tcaacaacta ccaccacgct cacgatgctt  14160
accttaacgc tgttgttgga accgctctca tcaagaagta tcctaagctc gagtcagagt  14220
tcgtgtacgg tgattacaag gtgtacgatg tgaggaagat gatcgctaag tctgagcaag  14280
agatcggaaa ggctaccgct aagtatttct tctactctaa catcatgaat ttcttcaaga  14340
ccgagattac cctcgctaac ggtgagatca gaaagaggcc actcatcgag acaaacggtg  14400
aaacaggtga gatcgtgtgg gataagggaa gggatttcgc taccgttaga aaggtgctct  14460
ctatgccaca ggtgaacatc gttaagaaaa ccgaggtgca gaccggtgga ttctctaaag  14520
agtctatcct ccctaagagg aactctgata agctcattgc taggaagaag gattgggacc  14580
ctaagaaata cggtggtttc gattctccta ccgtggctta ctctgttctc gttgtggcta  14640
aggttgagaa gggaaagagt aagaagctca agtctgttaa ggaacttctc ggaatcacta  14700
tcatggaaag gtcatctttc gagaagaacc caatcgattt cctcgaggct aagggataca  14760
aagaggttaa gaaggatctc atcatcaagc tcccaaagta ctcactcttc gaactcgaga  14820
acggtagaaa gaggatgctc gcttctgctg gtgagcttca aaagggaaac gagcttgctc  14880
tcccatctaa gtacgttaac tttctttacc tcgcttctca ctacgagaag ttgaagggat  14940
ctccagaaga taacgagcag aagcaacttt tcgttgagca gcacaagcac tacttggatg  15000
agatcatcga gcagatctct gagttctcta aaagggtgat cctcgctgat gcaaacctcg  15060
ataaggtgtt gtctgcttac aacaagcaca gagataagcc tatcagggaa caggcagaga  15120
acatcatcca tctcttcacc cttaccaacc tcggtgctcc tgctgctttc aagtacttcg  15180
atacaaccat cgataggaag agatacacct ctaccaaaga agtgctcgat gctaccctca  15240
```

```
tccatcagtc tatcactgga ctctacgaga ctaggatcga tctctcacag ctcggtggtg  15300

attcaagggc tgatcctaag aagaagagga aggtttgagg cgcgccgagc tccaggcctc  15360

ccagctttcg tccgtatcat cggtttcgac aacgttcgtc aagttcaatg catcagtttc  15420

attgcccaca caccagaatc ctactaagtt tgagtattat ggcattggaa aagctgtttt  15480

cttctatcat ttgttctgct tgtaatttac tgtgttcttt cagtttttgt tttcggacat  15540

caaaatgcaa atggatggat aagagttaat aaatgatatg gtccttttgt tcattctcaa  15600

attattatta tctgttgttt ttactttaat gggttgaatt taagtaagaa aggaactaac  15660

agtgtgatat taaggtgcaa tgttagacat ataaaacagt ctttcacctc tctttggtta  15720

tgtcttgaat tggtttgttt cttcacttat ctgtgtaatc aagtttacta tgagtctatg  15780

atcaagtaat tatgcaatca agttaagtac agtataggct tgagctccct aggcctgtta  15840

tccctaacaa gtttgtacaa aaaagcaggc tgagctcgaa ttccatctaa gtatcttggt  15900

aaagcatgga ttaatttgga tgcccacttc aggtctatgc agctccggtg ccttgtgatt  15960

gtgagttgtg accgatgctc atgctattct gcatttctgc gatgtatgta gctagtagat  16020

cttcaaaact aacaccgcat gccatcatca tccactgctt gattttagtc tcaccgctgg  16080

ccaaaaatgt gatgatgcca gaaacctcaa ctaccttgaa tcaacacggg cccaacagtg  16140

tgatgacgac agaaacaaaa aaaaatgagc caatagttca gaaggaggca ctatgcagaa  16200

actacatttc tgaaggtgac taaaaggtga gcgtagagtg taattactag tagtttagcc  16260

accattaccc aaatgctttc gagcttgtat taagatttcc taagctgagc atcatcactg  16320

atctgcaggc caccctcgct tcgctgccaa gatcaacagc aaccatgtgg cggcaacatc  16380

cagcattgca catgggctaa agattgagct ttgtgcctcg tctagggatc agctgaggtt  16440

atcagtcttt cctttttttc atccaggtga ggcatcaagc tactactgcc tcgattggct  16500

ggacccgaag cccacatgta ggataccaga atgggccgac ccaggacgca gtatgttggc  16560

cagtcccacc ggttagtgcc atctcggttg ctcacatgcg tagaagccag cttaaaaatt  16620

tagctttggt gactcacagc attgnnnnnn nnnnnnnnnn nnnngtttta gagctagaaa  16680

tagcaagtta aaataaggct agtccgttat caacttgaaa aagtggcacc gagtcggtgc  16740

ttttttcta gacccagctt tcttgtacaa agttggcatt aacccagctt tc          16792
```

```
<210> SEQ ID NO 25
<211> LENGTH: 3256
<212> TYPE: DNA
<213> ORGANISM: Brome mosaic virus
<220> FEATURE:
<221> NAME/KEY: misc_feature
<222> LOCATION: (1)..(3256)
<223> OTHER INFORMATION: Fescue segment RNA1, complete sequence cDNA
      DQ530423

<400> SEQUENCE: 25

gagcgttaac gtagaccacg gaacgaggtt caatcccttg tcgaccacgg ttctactact     60

tgttctttgt ttttcaccaa caaaatgtca agttctatcg atttgctgaa gttgattgct    120

gagaagggtg ctgccagcca gagtgcccaa gacatcgtag acaatcaggt cgcgcaacag    180

ttatctgcgc agattgaata cgcgaaaagg tctaagaaaa tcaacgttcg caataagctc    240

tctattgagg aggctgacgc cttccgtgac cgttatggtg gtgcctttga tttaaatttg    300

actcagcagt atcatgcacc ccatagcctg gctggtgctc tgcgtgtagc ggagcattac    360

gactgtctcg acagttttcc ccctgaagac cccgttatag atttcggagg gtcttggtgg    420
```

```
catcactttt caagaaggga taaaagggtg cacagttgtt gtcctgtgtt gggtgttaga    480
gacgctgccc gacatgagga gaggatgtgc cgcatgcgga aaattttgca agaaagcgat    540
gatttcgatg aagtcccgaa cttttgtctt aaccgagctc aagattgtga tgtccaagct    600
gattgggcta tctgtatcca tggcggttat gatatgggct tccaaggtct gtgtgacgcc    660
atgcattcgc atggagtacg cgtactacgt ggtaccgtta tgttcgacgg cgccatgttg    720
tttgaccgcg agggttttct tcccttgctt aaatgtcact ggcaacgtga cgggtcaggc    780
gcggatgagg tgatcaaatt cgactttgaa aatgaaagca cattatctta catccatgga    840
tggcaagatt tgggctcctt tttcaccgag tcggtgcatt gcatcgatgg aaccacctat    900
ctgttggagc gcgaaatgct gaaatgtaac atcatgacct ataagatcat cgctacaaat    960
ttacgctgcc cccgggagac actacgtcac tgtgtatggt ttgaagacat atctaagtac   1020
gtgggagtct caatacctga agactggagt ctcaatcgct ggaaatgtgt gcgcgtcgcc   1080
aaaaccacag tgagagaggt agaggagata gctttcagat gtttcaagga aaataaagaa   1140
tggaccgaga acatgaaagc tgtcgcatct atcttatccg ccaagtcgtc gactgttatt   1200
attaacggtc aggctatcat ggctggtgag cgcttagaca ttgaagatta tcatctagtg   1260
gcctttgctt tgactttgaa tctgtatcaa aagtacgaaa agcttacggc cctccgcgat   1320
gggatggaat ggaaaggttg gtgccatcac ttcaaaacta ggttttggtg gggtggagat   1380
tcatccaggg cgaaagtagg atggctgaga acattggcta gcagatttcc cctactacgt   1440
ctggattctt atgcggacag ttttaagttt ctgactcgtc tctcaaacgt tgaagaattt   1500
gagcaagatt ctgtaccaat atcacgtttg agaacgtttt ggactgaaga ggacttattc   1560
gaccggctgg agcatgaagt gcagacagcc aagaccaagc gctcgaagaa gaaggcgata   1620
gtcccgccag ctgctgagat acctcaggag gagtttcatg atgcccctga gagttcgagc   1680
cctgagtccg tcagtgatga cgttaaaccg gtgactgatg tggtcccgga tgccgaggtg   1740
tctgttgagg taccaacgga ccctcgtggc atatctagac acggagccat gaaggaattt   1800
gtgcgttatt gtaagagatt acataacaac tccgagtcta atcttcgtca cctatgggac   1860
atttccggcg gtcgcggaag tgagatcgca aataagagca tcttcgagac ctaccatcgc   1920
atagacgata tggtgaatgt ccatttggcc aacggtaact ggttgtatcc taaaaaatac   1980
gattacaccg ttggatataa tgagcatggt ttaggtccga agcacgcaga tgaaacgtac   2040
attgttgata aaacatgtgc atgctctaac ttgagggaca ttgcagaagc tagcgccaaa   2100
gtttctgtcc ctacatgcga tatttccatg gttgatggag ttgcgggatg cggtaaaacc   2160
actgccataa aagatgcatt ccgtatggga gaggacctaa ttgtgacggc gaatcgtaaa   2220
tcggccgagg acgtcaggat ggctttattc cctgacactt ttaattccaa ggtagctttg   2280
gatgttgtgc gcaccgcgga ttctgcgatc atgcacggtg taccgtcctg tcataggctg   2340
cttgttgatg aggctggttt actacattac ggtcaactcc tggtggtggc tgctctgtct   2400
aaatgttcac aagttcttgc ctttggggac acagagcaga tttcgttcaa gtctcgtgac   2460
gcgggtttta aattgctcca cggtaatctg aaatatgatc gccgtgacgt tgttcacaag   2520
acttaccggt gtccgcaaga tgttatcgct gctgttaatc tgctgaagcg taaatgcggt   2580
aatagggaca cgaagtatca atcctggaca tctgagtcca aagtttctag aagtctcacg   2640
aagcgtcgta ttacttctgt tttgcaggtc actattgatc cgaacagaac gtatcttacg   2700
atgactcaag ctgataaagc ggcccttcaa acgagggcta aggactttcc cgtgagcaag   2760
```

gactggattg atggacatat aaaaacagta cacgaagcgc aagggatctc tgttgacaat 2820
gtcgctttgg ttcggcttaa gtcgaccaaa tgtgatttgt ttaaacatga ggagtactgt 2880
ttggttgcct taacacgaca caagaagtcc tttgagtatt gctttaacgg cgagctcgct 2940
ggtgatttga tctttaattg tgttaagtga tgcgcttgtc tctgtgtgag acctctgctc 3000
gaggagagcc ctgttccagg taggaacgtt gtggtctaac ttaagactag ctgaatcggt 3060
gctataaccg atagtcgtgg ttgacacgca gacctcttac aagagtgtct aggcgccttt 3120
gagagttact ctttgctctc ttcggaagaa cccctagggg ttcgtgcatg ggcttgcata 3180
gcaagtctta gaatgcgggt gccttacagt gttgaaaaac actgtaaatc tctaaaagag 3240
accattaatt aagctc 3256

<210> SEQ ID NO 26
<211> LENGTH: 2895
<212> TYPE: DNA
<213> ORGANISM: Brome mosaic virus
<220> FEATURE:
<221> NAME/KEY: misc_feature
<222> LOCATION: (1)..(2895)
<223> OTHER INFORMATION: Fescue segment RNA2, complete sequence cDNA DQ530424

<400> SEQUENCE: 26
gagcgttaac acgcgtgtaa accacggaac gaggttcaat cccttgtcga cccacggttt 60
gcgcaacaca catctaacct tgttgttgtt gtgttttgtt tctttctact atcaccaaga 120
tgtcttcgaa aacctgggat gatgatttcg ttcgccaggt cccgtctttc caatggatca 180
tagatcaatc cttagaagac gaggtggagg ctgctagcct tcaggtgcag gagccggcag 240
acggagttgc cattgacgga tctctcgcga gttttaaatt agctatagcg cccttggaga 300
taggaggggt gttcgatccc ccttttgacc gagtgcgctg gggctctatt tgcgataccg 360
tccagcaaat ggttcaacag ttcaccgata gaccactgat tcctcaggct gaaatggcac 420
ggatgttata tcttgacatt ccgggctctt ttgtgctcga agatgaaatc gatgactggt 480
atcctgagga tactagtgac ggttacggtg tatcgtttgc cgccgatgaa gatcatgcga 540
gcgatctaaa actcgccagt gattcctcga actgtgaaat tgaggaagtt cgtgttactg 600
gagatacccc caaggagctg acccttggag ataggtacat gggcattgac gaagagtttc 660
agactaccaa tactgattac gacatcactc ttcagatcat gaatcctatt gaacataggg 720
tttcgcgcgt tattgatacg cactgccatc cagataaccc tgacatctcc actgggccaa 780
tttatatgga gagagtcagc cttgctagaa cagaagcaac cagtcattcc atactgccaa 840
cccatgctta tttcgatgat tcgtaccatc aagcccttgt tgagaatggt gattattcca 900
tggactttga taggatcaga cttaagcaaa gtgatgtaga ctggtacagg gaccccgata 960
aatattttca accaaaaatg aatatcggga gtgctcagcg aagagttggt actcagaaag 1020
aagtcttaac cgcacttaaa aagcgaaacg cggatgttcc agaaatggga gacgcgatta 1080
acatgaagga aactgcgaag gctatagcaa agcgctttcg tagcacattc cttaatgttg 1140
acggtgaaga ctgtctgaga gcttctatgg atgtcatgac taagtgtctt gagtaccata 1200
agaagtgggg taagcacatg gacttacaag gtgtgaatgt ggcagcagag actgatttac 1260
gtcggtacca gcatatgctg aagtctgatg taaaacctgt tgtaactgac acccttcact 1320
tggaacgagc agtagcagct actataacat ttcatagtaa aggtgtgact agtaattttt 1380
cacccttttt cactgcttgt ttcgagaagt tatcattggc cctgaaatcc aggttcattg 1440

-continued

```
tgcctatcgg aaagatatcc tctctggagc ttaagaatgt ccgcttgaat aacagatact   1500
ttcttgaagc ggacctaagc aaatttgata aatctcaggg tgagctgcac ctagagtttc   1560
agagagagat acttcttgcg ctgggctttc cagcgccgct gacgaattgg tggtctgatt   1620
ttcatcgcga ttcttattta tcagaccctc atgccaaggt gggaatgtcc gtttccttcc   1680
aacgcagaac tggtgatgcg tttacatatt tcgggaatac tcttgtcact atggctatga   1740
ttgcatatgc ctctgatcta agtgactgtg actgtgcaat attctcagga gatgattctt   1800
taatcatttc taaagttaaa ccagtcttgg ataccgatat gttcacgtct ctctttaata   1860
tggagataaa agttatggac cctagtgtgc cctacgtttg tagtaagttt cttgttgaaa   1920
ctgaaatggg caattgggtg tctataccag accctatgag agagatccag cgcttagcta   1980
agcgaaagat tctgcgtgaa gaacagatgc tcagagcaca tttcgtttcc ttctgcgatc   2040
gaatgaagtt tattaatcaa cttgatgaga agatgattac gatgctctgt cattttgttt   2100
atctgaaata tgggaaagaa aaaccttgga ttttcgagga ggttagagct gctcttgcgg   2160
ctttttcttt atactccgag aatttcctga ggttctctga ttgctactgt accgaaggca   2220
tcagagttta tcagatgagc gatcctgtat gtaagttcaa acgcactatg gaagagcgta   2280
aaactgatgg tgactggttt cacaactgga agaatccaaa gtttcctggt gtgttagaca   2340
aagtctacag aacccttgga atttattcct cggactgtag tactaaggag ctccctgtca   2400
aacggatcgg acgtttacat gaggcccttg agcgtgagtc actcagatta gcgaatgatc   2460
gtaggaccac acaacgcttg aaaaagaagg tcgacgatta cgctaccggt agaggaggcc   2520
taacgtcagt tgatgctttg ctcttgaagt cccattgtga gacttttaag ccctctgatc   2580
tgagatgatc ggttctatat gatatatgaa cctaagctgt gagcagccct ttggttaagg   2640
ttaaaaactc ctggtcaggt agaccacttt ggctaagttt aaaagcttgt tgaatcagta   2700
caataactga tagtcgtggt tgacacgcag acctcttaca agagtgtcta ggtgcctttg   2760
agagttactc tttgctctct tcggaagaac ccttaggggt tcgtgcatgg gcttgcatag   2820
caagtcttag aatgcgggta ccgtacagtg ttgaaaaaca ctgtaaatct ctaaaagaga   2880
ccattaatta agctc                                                    2895
```

<210> SEQ ID NO 27
<211> LENGTH: 2148
<212> TYPE: DNA
<213> ORGANISM: Brome mosaic virus
<220> FEATURE:
<221> NAME/KEY: misc_feature
<222> LOCATION: (1)..(2148)
<223> OTHER INFORMATION: Fescue segment RNA3 T1025C cDNA

<400> SEQUENCE: 27

```
gagcccatgg gttaacgtaa aataccaact aattctcgtt cgattccggc gaacattcta     60
ttttaccaac atcggttttt tcagtagtga tactgttttt gttcccgatg tctaacatag    120
tttctccctt cagtggttcc tcacgaacta cgtctgacgt tggcaagcaa gcgggaggta    180
ctagcgacga gaagctcatt gagtcgctgt tctctgaaaa ggctgtgaaa gagatagctg    240
ccgagtgtaa actcggatgt tataactatc tgaagtctaa tgaaccccgc aactatatag    300
acctggtgcc aaagtcacac gtatctgctt ggctctcatg ggctacaccc aagtatgata    360
aaggagagtt accttccagg ggattcatga acgttccacg catcgtttgt tttctcgttc    420
gtaccacaga tagcgcagag tccggttcta taaccgtgag cctgtgcgat tctggtaagg    480
ctgctcgtgc tggagtactc gaagccattg ataatcagga ggccacaatt cagttgtcgg    540
```

ctttacctgc tttgatagct ttgacgccta gctatgattg tccgatggaa gtcatcggcg 600
gtgatagcgg taggaatcga tgttttggga tagcaaccca acttagcggt gtggtgggga 660
caacaggttc cgttgcagtt actcatgctt attggcaagc taatttcaaa gcgaagccca 720
acaactataa gttgcatggt cccgctacaa ttatggtaat gccatttgac agactgagac 780
aactcgataa gaaaagcctc aaaaattaca tcagaggtat ttctaaccag tctgtggatc 840
atgggtatct tctcggaaga ccgttacaat ctgttgatca ggttgcccag gaagatttgt 900
tagttgagga atccgagtct ccttccgctc tcggcagagg tgtgaaggat agtaagtctg 960
tatccgcgtc atctgtcgct ggacttcctg tgtccagtcc ttcgcttaga attaaatagg 1020
taaatccggt ctaacaagct cggtccattt cgtggagtta agcaagctgg ggagaccccc 1080
gacagccgtt tggatcagcg ctcgcgtctc gtttgggttc aattccctta ccttacaacg 1140
gcgtgttgag ataggtcctc gggggaggtt atccatgttt gtggatattc tatgttgtgt 1200
gtctgagtta ttaaaaaaaa aaaaaaaaaa aaaagatcta tgtcctaatt cagcgtatta 1260
ataatgtcga cttcaggaac tggtaagatg actcgcgcgc agcgtcgagc tgccgctcgt 1320
agaaatcgtc ggaccgctac ggtccaaccg gtaattgtcg aaccattcgc tgctggccaa 1380
ggcaaggcca ttaaagcgat tgcaggatac agcatatcaa agtgggaggc gtcttcggac 1440
gcgattacag cgaaagccac caatgccatg agtatcactc tgccccatga gctctcttct 1500
gaaaagaata aggagcttaa ggtcggcagg gtgctgcttt ggttgggact tcttcctagc 1560
gttgctggga ggattaaggc ttgtgttgct gagaaacagg cacaggccga ggccgctttt 1620
caagtagcct tggcggttgc tgactcctcg aaagaggtgg tcgcggccat gtatacggac 1680
gcctttcgag ggcgactctg gggggatttg cttaatctcc agatttatct gtatgcatct 1740
gaagcagtgc ctgctaaggc ggtcgttgta catctagaag ttgagcacgt aaggcctacg 1800
ttcgatgact tcttcacccc ggtttatagg tagtgcccct gctcggagag cccctgactg 1860
ggttaaagtc acaggcccct tgtctcaggt agagaccctg tccaggtagg acactttggc 1920
taaggttaaa agcttgttga atcagtacaa taactgatag tcgtggttga cacgcagacc 1980
tcttacaaga gtgtctaggt gcctttgaga gttactcttt gctctcttcg gaagaaccct 2040
taggggttcg tgcatgggct tgcatagcaa gtcttagaat gcgggtaccg tacagtgttg 2100
aaaaacactg taaatctcta aaagagacca ttaattaact gcaggctc 2148

<210> SEQ ID NO 28
<211> LENGTH: 2114
<212> TYPE: DNA
<213> ORGANISM: Brome mosaic virus
<220> FEATURE:
<221> NAME/KEY: misc_feature
<222> LOCATION: (1)..(2114)
<223> OTHER INFORMATION: Fescue segment RNA3 cDNA DQ530425

<400> SEQUENCE: 28
gtaaaatacc aactaattct cgttcgattc cggcgaacat tctattttac caacatcggt 60
tttttcagta gtgatactgt ttttgttccc gatgtctaac atagtttctc ccttcagtgg 120
ttcctcacga actacgtctg acgttggcaa gcaagcggga ggtactagcg acgagaagct 180
cattgagtcg ctgttctctg aaaaggctgt gaaagagata gctgccgagt gtaaactcgg 240
atgttataac tatctgaagt ctaatgaacc ccgcaactat atagacctgg tgccaaagtc 300
acacgtatct gcttggctct catgggctac acccaagtat gataaaggag agttaccttc 360

-continued

```
caggggattc atgaacgttc cacgcatcgt ttgttttctc gttcgtacca cagatagcgc    420

agagtccggt tctataaccg tgagcctgtg cgattctggt aaggctgctc gtgctggagt    480

actcgaagcc attgataatc aggaggccac aattcagttg tcggctttac ctgctttgat    540

agctttgacg cctagctatg attgtccgat ggaagtcatc ggcggtgata gcggtaggaa    600

tcgatgtttt gggatagcaa cccaacttag cggtgtggtg gggacaacag gttccgttgc    660

agttactcat gcttattggc aagctaattt caaagcgaag cccaacaact ataagttgca    720

tggtcccgct acaattatgg taatgccatt tgacagactg agacaactcg ataagaaaag    780

cctcaaaaat tacatcagag gtatttctaa ccagtctgtg gatcatgggt atcttctcgg    840

aagaccgtta caatctgttg atcaggttgc ccaggaagat ttgttagttg aggaatccga    900

gtctccttcc gctctcggca gaggtgtgaa ggatagtaag tctgtatccg cgtcatctgt    960

cgctggactt cctgtgtcca gtccttcgct tagaattaaa taggtaaatc cggtctaaca   1020

agcttggtcc atttcgtgga gttaagcaag ctggggagac cccgacagc cgtttggatc   1080

agcgctcgcg tctcgtttgg gttcaattcc cttaccttac aacggcgtgt tgagataggt   1140

cctcggggga ggttatccat gtttgtggat attctatgtt gtgtgtctga gttattaaaa   1200

aaaaaaaaaa aaaaaaaaga tctatgtcct aattcagcgt attaataatg tcgacttcag   1260

gaactggtaa gatgactcgc gcgcagcgtc gagctgccgc tcgtagaaat cgtcggaccg   1320

ctacggtcca accggtaatt gtcgaaccat tcgctgctgg ccaaggcaag gccattaaag   1380

cgattgcagg atacagcata tcaaagtggg aggcgtcttc ggacgcgatt acagcgaaag   1440

ccaccaatgc catgagtatc actctgcccc atgagctctc ttctgaaaag aataaggagc   1500

ttaaggtcgg cagggtgctg ctttggttgg gacttcttcc tagcgttgct gggaggatta   1560

aggcttgtgt tgctgagaaa caggcacagg ccgaggccgc ttttcaagta gccttggcgg   1620

ttgctgactc ctcgaaagag gtggtcgcgg ccatgtatac ggacgccttt cgaggggcga   1680

ctctggggga tttgcttaat ctccagattt atctgtatgc atctgaagca gtgcctgcta   1740

aggcggtcgt tgtacatcta gaagttgagc acgtaaggcc tacgttcgat gacttcttca   1800

ccccggttta taggtagtgc cctgctcgg agagccctg actgggttaa agtcacaggc   1860

cccttgtctc aggtagagac cctgtccagg taggacactt tggctaaggt taaaagcttg   1920

ttgaatcagt acaataactg atagtcgtgg ttgacacgca gacctcttac aagagtgtct   1980

aggtgccttt gagagttact ctttgctctc ttcggaagaa cccttagggg ttcgtgcatg   2040

ggcttgcata gcaagtctta gaatgcgggt accgtacagt gttgaaaaac actgtaaatc   2100

tctaaaagag acca                                                     2114
```

<210> SEQ ID NO 29
<211> LENGTH: 2145
<212> TYPE: DNA
<213> ORGANISM: Brome mosaic virus
<220> FEATURE:
<221> NAME/KEY: misc_feature
<222> LOCATION: (1)..(2145)
<223> OTHER INFORMATION: RNA3 R-BMV cDNA

<400> SEQUENCE: 29

```
gagcccatgg gttaacgtaa aataccaact aattctcgtt cgattccggc gaacattcta     60

ttttaccaac atcggttttt tcagtagtga tactgttttt gttcccgatg tctaacatag    120

tttctccctt cagtggttcc tcacgaacta cgtctgacgt tggcaagcaa gcgggaggta    180

ctagcgatga gaagctcatt gagtcgctgt tctctgaaaa ggctgtgaaa gagatagctg    240
```

```
ccgagtgtaa actcggatgt tataactatc tgaagtctaa tgaaccccgc aactatatag    300

acctggtgcc aaagtcacac gtatctgctt ggctctcatg ggctacatcc aagtatgata    360

aaggagagtt accttccagg ggattcatga acgttccacg catcgtttgt tttctcgttc    420

gtaccacaga tagcgcagag tccggttcta taaccgtgag cctgtgcgat tctggtaagg    480

ctgctcgtgc tggagtactc gaagccattg ataatcagga ggccacaatt cagttgtcgg    540

ctttacctgc tttgatagct ttgacgccta gctatgattg tccgatggaa gtcatcggcg    600

gtgatagcgg taggaatcga tgttttggga tagcaaccca acttagcggt gtggtgggga    660

caacaggttc cgttgcagtt actcatgcgt attggcaagc taatttcaaa gcgaagccca    720

acaactataa gttgcatggt cccgctacaa ttatggtaat gccatttgac agactgagac    780

aactcgataa gaaaagcctc aaaaattata ttagaggtat ttctaaccag tctgtggatc    840

atgggtatct tctcggaaga ccgttacaat ctgttgatca ggttgcccag gaagatttgt    900

tagttgagga atccgagtct ccttccgctc tcggcagagg tgtgaaggat agtaagtctg    960

tatccgcgtc atctgtcgct ggacttcctg tgtccagtcc tacgcttaga attaaatagg   1020

taaatccggt ctaacaagct cggtccattt cgtagagtta agcaagctgg ggagaccccc   1080

gacagccgtt tggatcagcg ctcgcgtctc gtttgggttc aattccctta ccttacaacg   1140

gcgtgttgag ataggtcctc gggggaggtt atccatgttt gtggatattc tatgttgtgt   1200

gtctgagtta ttattaaaaa aaaaaaaaaa agatctatgt cctaattcag cgtattaata   1260

atgtcgactt caggaactgg taagatgact cgcgcgcagc gtcgtgctgc cgctcgcaga   1320

aatcgttgga ccgctagggt ccaaccagta attgtcgaac cactcgctgc tggccaaggc   1380

aaggccatta aagcgattgc aggatacagc atatcaaagt gggaggcgtc ttcggacgcg   1440

attacagcga aagccaccaa tgccatgagt atcactctgc cccatgagct ctcttctgaa   1500

aagaataagg agcttaaggt cggcagggtg ctgctttggt tgggacttct tcctagcgtt   1560

gctgggagga ttaaggcttg tgttgctgag aaacaggcac aggccgaggc tgcttttcaa   1620

gtagccttgg cggttgcaga ctcctcgaaa gaggtggtcg cggccatgta tacggacgcc   1680

tttcgagggg cgactctggg ggatttgctt aatctccaga tttatctgta tgcatctgaa   1740

gcagtgcctg ctaaggcggt cgttgtacat ctagaagttg agcacgtaag gcctacgttc   1800

gatgacttct tcaccccggt ttataggtag tgcccctgct cggagagccc ctgactgggt   1860

taaagtcaca ggccccttgt ctcaggtaga gaccctgtcc aggtaggaca ctttggctaa   1920

ggttaaaagc ttgttgaatc agtacaataa ctgatagtcg tggttgacac gcagacctct   1980

tacaagagtg tctaggtgcc tttgagagtt actctttgct ctcttcggaa gaacccttag   2040

gggttcgtgc atgggcttgc atagcaagtc ttagaatgcg ggtaccgtac agtgttgaaa   2100

aacactgtaa atctctaaaa gagaccatta attaactgca ggctc                   2145
```

<210> SEQ ID NO 30
<211> LENGTH: 2111
<212> TYPE: DNA
<213> ORGANISM: Brome mosaic virus
<220> FEATURE:
<221> NAME/KEY: misc_feature
<222> LOCATION: (1)..(2111)
<223> OTHER INFORMATION: RNA3 gi|331498|gb|J02042.1|MBRCG3Z Brome mosaic virus 3a and coat protein genes, complete cds

<400> SEQUENCE: 30

```
gtaaaatacc aactaattct cgttcgattc cggcgaacat tctattttac caacatcggt     60
```

```
tttttcagta gtgatactgt ttttgttccc gatgtctaac atagtttctc ccttcagtgg    120
ttcctcacga actacgtctg acgttggcaa gcaagcggga ggtactagcg atgagaagct    180
cattgagtcg ctgttctctg aaaaggctgt gaaagagata gctgccgagt gtaaactcgg    240
atgttataac tatctgaagt ctaatgaacc ccgcaactat atagacctgg tgccaaagtc    300
acacgtatct gcttggctct catgggctac atccaagtat gataaaggag agttaccttc    360
caggggattc atgaacgttc cacgcatcgt ttgttttctc gttcgtacca cagatagcgc    420
agagtccggt tctataaccg tgagcctgtg cgattctggt aaggctgctc gtgctggagt    480
actcgaagcc attgataatc aggaggccac aattcagttg tcggctttac ctgctttgat    540
agctttgacg cctagctatg attgtccgat ggaagtcatc ggcggtgata gcggtaggaa    600
tcgatgtttt gggatagcaa cccaacttag cggtgtggtg gggacaacag gttccgttgc    660
agttactcat gcgtattggc aagctaattt caaagcgaag cccaacaact ataagttgca    720
tggtcccgct acaattatgg taatgccatt tgacagactg agacaactcg ataagaaaag    780
cctcaaaaat tatattagag gtatttctaa ccagtctgtg gatcatgggt atcttctcgg    840
aagaccgtta caatctgttg atcaggttgc ccaggaagat ttgttagttg aggaatccga    900
gtctccttcc gctctcggca gaggtgtgaa ggatagtaag tctgtatccg cgtcatctgt    960
cgctggactt cctgtgtcca gtcctacgct tagaattaaa taggtaaatc cggtctaaca   1020
agctcggtcc atttcgtaga gttaagcaag ctggggagac ccccgacagc cgtttggatc   1080
agcgctcgcg tctcgtttgg gttcaattcc cttaccttac aacggcgtgt tgagataggt   1140
cctcggggga ggttatccat gtttgtggat attctatgtt gtgtgtctga gttattatta   1200
aaaaaaaaaa aaaaagatct atgtcctaat tcagcgtatt aataatgtcg acttcaggaa   1260
ctggtaagat gactcgcgcg cagcgtcgtg ctgccgctcg cagaaatcgt tggaccgcta   1320
gggtccaacc agtaattgtc gaaccactcg ctgctggcca aggcaaggcc attaaagcga   1380
ttgcaggata cagcatatca aagtgggagg cgtcttcgga cgcgattaca gcgaaagcca   1440
ccaatgccat gagtatcact ctgccccatg agctctcttc tgaaaagaat aaggagctta   1500
aggtcggcag ggtgctgctt tggttgggac ttcttcctag cgttgctggg aggattaagg   1560
cttgtgttgc tgagaaacag gcacaggccg aggctgcttt tcaagtagcc ttggcggttg   1620
cagactcctc gaaagaggtg gtcgcggcca tgtatacgga cgcctttcga ggggcgactc   1680
tgggggattt gcttaatctc cagatttatc tgtatgcatc tgaagcagtg cctgctaagg   1740
cggtcgttgt acatctagaa gttgagcacg taaggcctac gttcgatgac ttcttcaccc   1800
cggtttatag gtagtgcccc tgctcggaga gcccctgact gggttaaagt cacaggcccc   1860
ttgtctcagg tagagaccct gtccaggtag gacactttgg ctaaggttaa aagcttgttg   1920
aatcagtaca ataactgata gtcgtggttg acacgcagac ctcttacaag agtgtctagg   1980
tgcctttgag agttactctt tgctctcttc ggaagaaccc ttaggggttc gtgcatgggc   2040
ttgcatagca agtcttagaa tgcgggtacc gtacagtgtt gaaaaacact gtaaatctct   2100
aaaagagacc a                                                         2111
```

<210> SEQ ID NO 31
<211> LENGTH: 2150
<212> TYPE: DNA
<213> ORGANISM: Brome mosaic virus C-BMVA/G

<400> SEQUENCE: 31

-continued

```
gagcccatgg gttaacgtaa aataccaact aattctcgtt cgattccggc gaacattcta     60
ttttaccaac atcggttttt tcagtagtga tactgttttt gttcccgatg tctaacatag    120
tttctccctt cagtggttcc tcacgaacta cgtctgacgt tggcaagcaa gcgggaggta    180
ctagcgacga gaagctcatt gagtcgctgt tctctgaaaa ggctgtgaaa gagatagctg    240
ccgagtgtaa actcggatgt tataactatc tgaagtctaa tgaaccccgc aactatatag    300
acctggtgcc aaagtcacac gtatctgctt ggctctcatg ggctacaccc aagtatgata    360
aaggagagtt accttccagg ggattcatga acgttccacg catcgtttgt tttctcgttc    420
gtaccacaga tagcgcagag tccggttcta taaccgtgag cctgtgcgat tctggtaagg    480
ctgctcgtgc tggagtactc gaagccattg ataatcagga ggccacaatt cagttgtcgg    540
ctttacctgc tttgatagct ttgacgccta gctatgattg tccgatggaa gtcatcggcg    600
gtgatagcgg taggaatcga tgttttggga tagcaaccca acttagcggt gtggtgggga    660
caacaggttc cgttgcagtt actcatgctt attggcaagc taatttcaaa gcgaagccca    720
acaactataa gttgcatggt cccgctacaa ttatggtaat gccatttgac agactgagac    780
aactcgataa gaaaagcctc aaaaattaca tcagaggtat ttctaaccag tctgtggatc    840
atgggtatct tctcggaaga ccgttacaat ctgttgatca ggttgcccag gaagatttgt    900
tagttgagga atccgagtct ccttccgctc tcggcagagg tgtgaaggat agtaagtctg    960
tatccgcgtc atctgtcgct ggacttcctg tgtccagtcc tacgcttaga attaaatagg   1020
taaatccggt ctaacaagct cggtccattt cgtagagtta agcaagctgg ggagaccccc   1080
gacagccgtt tggatcagcg ctcgcgtctc gtttgggttc aattccctta ccttacaacg   1140
gcgtgttgag ataggtcctc gggggaggtt atccatgttt gtggatattc tatgttgtgt   1200
gtctgagtta ttattaaaaa aaaaaaaaaa agatctatgt cctaattcag cgtattaatt   1260
taacaatgtc gacttcagga actggtaaga tgactcgcgc gcagcgtcga gctgccgctc   1320
gtagaaatcg tcggaccgct acggtccaac cggtaattgt cgaaccattc gctgctggcc   1380
aaggcaaggc cattaaagcg attgcaggat acagcatatc aaagtgggag gcgtcttcgg   1440
acgcgattac agcgaaagcc accaatgcca tgagtatcac tctgccccat gagctctctt   1500
ctgaaaagaa taaggagctt aaggtcggca gggtgctgct ttggttggga cttcttccta   1560
gcgttgctgg gaggattaag gcttgtgttg ctgagaaaca ggcacaggcc gaggccgctt   1620
ttcaagtagc cttggcggtt gctgactcct cgaaagaggt ggtcgcggcc atgtatacgg   1680
acgcctttcg aggggcgact ctgggggatt tgcttaatct ccagatttat ctgtatgcat   1740
ctgaagcagt gcctgctaag gcggtcgttg tacatctaga agttgagcac gtaaggccta   1800
cgttcgatga cttcttcacc ccggtttata ggtagtgccc ctgctcggag agcccctgac   1860
tgggttaaag tcacaggccc cttgtctcag gtagagaccc tgtccaggta ggacactttg   1920
gctaaggtta aaagcttgtt gaatcagtac aataactgat agtcgtggtt gacacgcaga   1980
cctcttacaa gagtgtctag gtgcctttga gagttactct ttgctctctt cggaagaacc   2040
cttaggggtt cgtgcatggg cttgcatagc aagtcttaga atgcgggtac cgtacagtgt   2100
tgaaaaacac tgtaaatctc taaaagagac cattaattaa ctgcaggctc               2150
```

<210> SEQ ID NO 32
<211> LENGTH: 3787
<212> TYPE: DNA
<213> ORGANISM: Barley stripe mosaic virus
<220> FEATURE:
<221> NAME/KEY: misc_feature

<222> LOCATION: (1)..(3787)
<223> OTHER INFORMATION: BSMV ND18 RNA1 U35767

<400> SEQUENCE: 32
gtatgtaagt tgcctttggg tgtaaaattt cttgcatgca cataatcgta atcgattctt 60
cttgatctct aaacaacact ttcccgttag catggctagc gatgagattg tccgcaatct 120
gatctcccgt gaggaggtga tgggtaattt gattagcaca gcttctagct cagtaaggtc 180
acccttacat gacgtactgt gctcgcacgt aaggaccatc gtcgattccg tggataagaa 240
agcggtcagt cgcaagcatg ttgatgtacg gcgcaacatc tcctctgaag agttacagat 300
gttgataaat gcatatcctg aatatgccgt ttcatcctca gcttgtgaat ctggtactca 360
tagcatggcg gcttgttttc gatttctgga gacagaatac ctcttagata tggttccaat 420
gaaagagact tttgtttatg acattggtgg taactggttt tctcatatga agtttcgtgc 480
tgatagagaa attcattgtt gctgtccgat cttatctatg agagattctg aaagactgga 540
aacacgcatg atggcaatgc aaaaatatat gcgtggatcg aaagacaaac cgttacgctt 600
gttaagccgt tatcaaaata tcctgcgtga acaagcggcg agaacaactg cctttatggc 660
aggtgaggtg aatgcgggtg ttctcgatgg agatgtgttt tgtgagaaca cttttcaaga 720
ctgtgtgaga caggtgcccg aaggtttttt gaagacagct atagcagttc atagcatcta 780
cgatatcaaa gtggaagaat ttgcgtctgc attgaaaaga aaaggtataa cacaggctta 840
tgggtgcttc ctgtttcctc ctgctgtatt gataggtcag aaggaaggta ttttaccttc 900
cgtggacggt cattacttgg tggagaatgg caggattaag ttcttctttg cgaatgatcc 960
gaatgccggt tactctcatg accttaagga ttatctgaag tatgtggaaa aaacctacgt 1020
ggatataaag gatggagtgt ttgctattga gctgatgcaa atgcgaggtg ataccatgtt 1080
ctttaagatc acggatgtca ccgcagcaat gtatcatatg aaatacagag gtatgaaacg 1140
tgatgaaaca ttcaaatgca ttccgttgct aaaaaaattca tccgttgtcg tacctctatt 1200
ttcgtgggac aaccgttctt taaagatcac aagtggttta ttaccacgaa ctttggtcga 1260
gcaaggtgcg gcgtttatta tgaaaaacaa ggagaaggac ttgaacgttg ctgtgttgaa 1320
gaactatctt tccgctgtga acaactcata cattttcaac ggatcccagg ttagagatgg 1380
tgtgaaaatt gccccggatt taatctccaa attggcagtg actctgtacc tgagagaaaa 1440
ggtctatcga caaagagaaa attcaatcat aagttatttc gagcaagaaa tgcttcacga 1500
tcccaacttg aaagccatgt ttggagactt tctgtggttt gttccaaata ctctctcgag 1560
tgtctggaag aacatgcgaa aatcactgat ggaatggttt ggctacgcag aatttgactt 1620
gactactttt gatatttgcg atcccgttct ctacgtagag atagtggatc ggtataagat 1680
cattcaaaaa gggcgaattc cacttggtga gttttttgat tgtcatgaag aatgcgagaa 1740
ttacgaactg cgtgagaagg agaaaaatga cctagcggtg aaaatggccc agaaggtaac 1800
agggacggtg accgaatgcg agaaggacct gggacctctt gttcaaccga taaaacagat 1860
attggttcaa cttgtgatgc ccaatttggt cagagcgctg tgtagacctc gtagcccaac 1920
gtctcctttg gacttaaata tcccagggtc aactccatca cactcaagtt cagattctga 1980
acaatctatg actgaagaag cgagctgcgc cattgcgggt agcgtaccaa catgggaaat 2040
tgcgactaag aaagatctaa cctttcagcg aattgatgaa gatatgtctc gacgaactgg 2100
tatgcctcca agaccaaaag taacttctag ttacaacatg aatgccagag ctgagtttct 2160
ctactatcaa ctgtgtagcg tgatttgtga aagggctcag attttgagtg tcatcgaaga 2220

```
ctttcgtcag aatttgatat tctcagataa agtggccgtt ccattgaacg ctagattcta   2280
cagttttcag tcattgcaac ccggatgggt gttcaagact ccatcgcata gtgaagtagg   2340
ccacagttat gcagtacatt ttgacttcaa gacagttgga accgatttgg aagagagcct   2400
agctttttgc cgaatggtac cgatttcatg ggataaaagc ggcaaataca tcgcgacaac   2460
tcctcatttt cccgagagac atggttacta cgtgatttgt gacaacacta aattgtgtaa   2520
caattggctt atttacaata agttagttga tgtctacgca cgagtggctg atagacctct   2580
gagatttgag ttgattgacg gagttcctgg ctgcggaaag tcaaccatga ttttaaacag   2640
ctgtgatatt cgacgcgaag ttgttgttgg tgaaggaagg aatgcaactg atgacttaag   2700
ggagaggttc aagcgtaaga aaaatttgaa tagtaagact gctaatcata gagttcgaac   2760
gcttgacagc ttattacttg ctgaaggacc ttgtgtaccg caagctgata ggtttcattt   2820
tgatgaagct ctaaaagttc attacggcgc cataatgttc tgtgctgata agcttggtgc   2880
ctcagaaatt ctcgctcagg gagatagggc tcaactgccg atgatctgtc gtgtagaagg   2940
tattgaactt caatttcaat ctcctgatta cacgaagacg atcataaatc ctaagctacg   3000
atcataccgt atccctggag atgttgcctt ctatttgagt gctaaggaat tttacaaagt   3060
taaaggaata cctcaaaagg ttacaacttc taacagtgtg aaacgttccc tgtacgctag   3120
aggcgaaaca actccggaaa gattcgtgag tttgcttgat gttccggtga gaaaaaacac   3180
ccattatcta accttcttac aagctgagaa ggaaagtttg atgagtcatt tgattccaaa   3240
gggtgtgaag aaagagtcta tttcaacgat tcatgaggcg cagggtggta cctatgaaaa   3300
tgtgattctg gtccgtttgc aacggacgcc caatgaaatt tatccgggtg gacctaggtc   3360
cgccccttac attgtggttg ggacttcaag gcatacaaaa actttcactt attgtagtgt   3420
tacggacgat aagttgcttt tagatatcgc cgacgtcggt ggtattgcac atacacctat   3480
tcgtactttt gaatctcata tagtttaaaa aaaaaaaaaa aaaaaaaaaa aaaaaaaaaa   3540
aaaaaaaaat gtttgatcag atcattcaaa tctgatggtg cccatcaacc atatgatggg   3600
agtgtttgca agtccactat aatcgaactt gaaaacgatg cctgaattgg aaaccatgaa   3660
tcttaacgga ttctggagag aaaatttagg aattggtatg taagctacaa cttccggtag   3720
ctgcgtcaca ctttaagagt gtgcatactg agccgaagct cagcttcggt cccccaaggg   3780
aagacca                                                             3787
```

<210> SEQ ID NO 33
<211> LENGTH: 3239
<212> TYPE: DNA
<213> ORGANISM: Barley stripe mosaic virus
<220> FEATURE:
<221> NAME/KEY: misc_feature
<222> LOCATION: (1)..(3239)
<223> OTHER INFORMATION: BSMV ND18 RNA2 U35770

<400> SEQUENCE: 33

```
gtaaaagaaa aggaacaacc ctgttgttgt tcgacgctat actaaatata tattatctta     60
ttagtgcatt tcttttacca cttcacagta tgccgaacgt ttctttgact gctaagggtg    120
gaggacacta caacgaggat caatgggata cacaagttgt ggaagccgga gtatttgacg    180
attggtgggt ccacgtagaa gcctggaata aatttctaga caatttacgt ggtatcaact    240
ttagcgttgc ttcctctcgg tcgcaagtcg ctgaatgctt agctgcgtta gatcgtgatc    300
tacctgctga tgtagacaga cggtttgcag gtgctagagg acaaattggt ttacccaatt    360
atcttcctgc gccaaaattc tttcgtctcg ataagcgaac tatcgctgaa ctgactagac    420
```

-continued

```
tctctcgtct tacggatcag ccgcacaaca atcgtgatat agagcttaac cgagcgaaaa    480
gagccacaac taacccatct cccccggcgc aggcaccgtc ggagaatctt actcttcgtg    540
atgttcaacc gttaaaggat agtgcgttgc attatcaata cgtgttgatt gacctacaga    600
gtgcgagact cccagtgtat accaggaaga ctttcgaacg tgaactcgct ttggaatgga    660
tcattccaga tgccgaggaa gcgtgacctg ctgttgaagc ggtaaaagga tgtacatatg    720
tatcttattt attttgttta tctattttct tttactttta gtttttgctt tttacgcgtt    780
aactagatgt attgacttta gccatggaca tgacgaaaac tgttgaggaa aagaaaacaa    840
atggaactga ttcagtgaaa ggtgtttttg aaaactcgac gattcccaaa gttccgactg    900
gacaggaaat gggtggtgac gattcttcta cttctaaatt aaaggaaact ctaaaagttg    960
ccgatcagac tccattgtcc gttgacaacg gtgccaaatc caaattggat tcttctgata   1020
gacaagttcc tggtcctaag ttggcaacaa ctgtggaaaa ggaacctgag ttgaaaccca   1080
acgttaagaa gtccaagaag aaaagaatcc aaaaacctgc tcaaccgagt aggcccaatg   1140
accttaaagg cgggactaag ggatcatctc aagtgggtga aaatgtgagt gagaactata   1200
ctgggatttc taaggaagca gctaagcaaa agcagaagac acccaagtct gtgaaaatgc   1260
aaagcaatct ggccgataag ttcaaagcga atgatactcg tagatcggaa ttaattaaca   1320
agtttcagca atttgtgcat gaaacctgtc ttaaatctga ttttgagtac actggtcgac   1380
agtatttcag agctagatca aatttctttg aaatgattaa gctcgcatcc ttgtatgaca   1440
aacatctaaa ggaatgtatg gcgcgagcct gcaccctaga acgagaacga ttgaagcgta   1500
agttactcct agtacgagct ttgaaaccag cagttgactt ccttacggga atcatctctg   1560
gagttcctgg ctcaggaaaa tcaaccattg tgcgtacttt gctcaaaggt gaatttccgg   1620
ctgtttgtgc tttggccaat cctgccttaa tgaacgacta ttctggtatt gaaggcgttt   1680
acgggttaga tgacctgttg ctttctgcag ttccgataac gtctgattta ttgatcatag   1740
atgaatatac acttgctgag agcgcggaaa tcctgttgtt acaacgaaga ctcagagcct   1800
ctatggtgtt gttagtcggg gatgtagctc aaggaaaagc caccactgct tccagtattg   1860
agtatttaac tctgccggtg atctacagat cagagacgac ttatcgtttg ggacaagaga   1920
ctgcttcgct ttgcagcaag cagggtaaca gaatggtttc aaagggtgga agggacacag   1980
tgatcattac tgattacgat ggcgaaacag atggaacgga gaaaaatatc gcttttactg   2040
tcgatacagt tcgagatgtg aaagattgcg ggtacgattg tgccctggca attgatgtgc   2100
aagggaaaga attcgattca gtgactttat tcctaaggaa cgaagaccgg aaagctttag   2160
cagataagca tttgcgttta gtcgctttga gcagacataa gtcgaagtta atcatcaggg   2220
ccgacgcgga aattcgtcaa gcattcctga caggtgatat tgacttgagc tctaaggcga   2280
gtaactctca tcgttattct gcaaaaccgg atgaagacca cagttggttc aaggccaaat   2340
aagtattggc caattgtcgc cggaatcggt gtcgttggat tgtttgcgta tttgatcttt   2400
tcaaatcaaa aacattctac ggaatccggc gataatattc acaaattcgc caacggaggt   2460
agttacaggg acgggtcaaa gagtataagt tataatcgta atcatccttt tgcctatggc   2520
aatgcctcat cccctggaat gttgttgccc gcaatgctta ccatcatcgg aatcatttcc   2580
tatttatggc gaacaagaga ttccgtgctc ggagactcag gcggaaacaa ttcctgcgga   2640
gaagactgtc agggcgaatg tcttaacgga cattctcgac gatcattact atgcgatatt   2700
ggctagtctt tttatcattg ctctatggtt attgtatata tatctaagca gtatacctac   2760
```

```
ggagactggt ccctacttct atcaagatct gaactctgtg aagatctatg gaataggggc   2820

tacgaatcca gaagttattg cggccatcca ccattggcag aagtaccctt ttggggaatc   2880

tccgatgtgg ggaggtttag tcagtgtttt gagcgttctt cttaaaccgc tgacgttagt   2940

ttttgcgtta agctttttc tcttactttc ttcaaaaagg taaaaaaaaa aaaaaaaaaa   3000

atgtttgatc agatcattca aatctgatgg tgcccatcaa ccatatgatg ggagtgtttg   3060

caagtccact ataatcgaac ttgaaaacga tgcctgaatt ggaaaccatg aatcttaacg   3120

gattctggag agaaaattta ggaattggta tgtaagctac aacttccggt agctgcgtca   3180

cactttaaga gtgtgcatac tgagccgaag ctcagcttcg gtcccccaag ggaagacca    3239
```

<210> SEQ ID NO 34
<211> LENGTH: 2790
<212> TYPE: DNA
<213> ORGANISM: Barley stripe mosaic virus
<220> FEATURE:
<221> NAME/KEY: misc_feature
<222> LOCATION: (1)..(2790)
<223> OTHER INFORMATION: BSMV ND18 RNA3 U13917

<400> SEQUENCE: 34

```
gtatagcttg agcattaccg tcgtgtaatt gcaacacttg gcttgccaaa taacgctaaa     60

gcgttcacga aacaaacaac acttcggcat ggatgttgtg aagaaattcg ccgtcatgtc    120

agtgactgta gtagcaggtc ccgtccttac gctttcatca cctgtggtgg tgacgtttgg    180

aacaggctta attgccgtat ctttggtgaa acggttgcta caggaacaac cccgtgtaat    240

tgctcacgat cacgaacatt acccaggtgg ttctgagagc agttctagct cttgtgctac    300

cgcgcctatt ttacgtaatc tttcgcgaga tcagtgcgat tcagagaata ttggatgcag    360

ttctagcgcc tgttctccgt ctgaaattgt gaaagttaca aggcaggtag tgggagttga    420

acgtggtctt taccgggaca tttttcagga caacgaaatc ccatcagtca tggaagagaa    480

actgcagaaa ctcctttact ctgagggtga gaagattcga agacgttgcc aatttgaagc    540

atcaacgatg cactcacgca aagtaaaggt tccggaggta ggtactatcc cagatatcca    600

aacttggttc gatgctacgt ttcctggtaa ctccgttagg ttttctgatt tcgacggtta    660

tactgttgct acggaggaca ttaacatgga tgttcaggat tgtagactta agttcgggaa    720

gacttttcga ccttatgaat ttaaggaatc actgaaacca gtactgagga cagcaatgcc    780

agaaaaacga cagggtagtt tgattgaaag tgtgctggcc tttcgtaaaa gaaatttggc    840

tgcgcccaga ttacaaggag ctttgaatga atggcacaca attgagaatg tgctaacgaa    900

ggcgttaaag gtattcttct ttgaagattt aattgatcga acggatcact gcacttacga    960

gtcagcgctc agatggtggg ataaacaatc agtgacagct cgagcgcagc tcgtggcgga   1020

tcagcggagg ttatgtgatg ttgacttcac gacttataac ttcatgataa aaaatgatgt   1080

aaagccgaag ttagatctaa cacctcaagt tgaatatgca gctttgcaga ctgttgtata   1140

tcctgataag atagtcaatg ctttctttgg tccgatcata aaggagatta atgaacggat   1200

catcagagcg cttagacctc atgtggtctt taattctcgt atgactgctg atgaactgaa   1260

tgaaacagct gcctttttga cacctcataa gtacagagcc ttagagattg atttttcaaa   1320

atttgataaa tcaaagactg ggcttcatat caaagctgtc attggactct ataagctctt   1380

tggcctagat ggcctgttaa aagtgctctg ggaaaaatcg caatatcaga cttacgtgaa   1440

agatagaaac ttcggtctcg aggcatatct attgtatcag caaaagtcag gaaattgtga   1500

cacttacggt tcgaacacct ggtctgccgc cttggcgttg ttagattgtc ttcctttgga   1560
```

```
agatgcacat ttctgtgtat ttggtggtga tgattcattg atattgtttg atcagggata   1620

cataatttcc gacccatgcc ggcaacttgc cggtacttgg aatcttgaat gtaaagtgtt   1680

cgacttcaag taccccgcat tttgtggtaa atttctgctg tgcatagatg gaaaatatca   1740

atttgttcca gatgcggcaa aatttatcac aaaattaggt agaactgatg tgagagatgt   1800

agaagttttg agtgagattt atatctctat caatgacaat tacaaatctt acaaagactt   1860

taaggtgctt gatgctttgg ataaggcttt agtggataga tatcgatccc cttatagtgc   1920

tatttctgct ttggtttctt tatgttatca tatctttgac tttaataagt ttaagttgct   1980

gtttaattgt gaagggaaat ttgtggataa gaagctgaga aaagacttcg agtggtgaac   2040

tctaggtcct gatgtttaaa tctactgtat ttaccttcgc atgatggcta ctttctcttg   2100

tgtgtgttgt ggtaccttaa ctacaagtac ttactgtggt aagagatgtg agcgaaagca   2160

tgtatattct gaaacaagaa ataagagatt ggaactttac aagaagtatc tattggaacc   2220

gcaaaaatgc gccctgaatg gaatcgttgg acacagttgt ggaatgccat gctccattgc   2280

ggaagaggct tgtgatcaac tgccaatcgt gagtaggttc tgtggccaaa agcatgcgga   2340

tctgtatgat tcacttctga aacgttctga acaggagtta cttcttgaat ttctccagaa   2400

gaagatgcag gagctgaaac tttctcatat cgtaaaaatg gctaagcttg aaagtgaggt   2460

taacgcaata cgtaagtccg tagcttcttc ttttgaagat tctgttggat gtgatgattc   2520

ttcttccgtt tctaagtaaa aaaaaaaaaa aatgtttgat cagatcattc aaatctgatg   2580

gtgcccatca accatatgat gggagtgttt gcaagtccac tataatcgaa cttgaaaacg   2640

atgcctgaat tggaaaccat gaatcttaac ggactctgga gagaaaattt aggaattggt   2700

atgtaagcta caacttccgg tagctgcgtc acactttaag agtgtgcata ctgagccgaa   2760

gctcagcttc ggtcccccaa gggaagacca                                     2790
```

<210> SEQ ID NO 35
<211> LENGTH: 3768
<212> TYPE: DNA
<213> ORGANISM: Barley stripe mosaic virus
<220> FEATURE:
<221> NAME/KEY: misc_feature
<222> LOCATION: (1)..(3768)
<223> OTHER INFORMATION: BSMV_RNA1_gi|19744917|ref|NC_003469.1|

<400> SEQUENCE: 35

```
gtatgtaagt tgcctttggg tgtaaaattt cttgcatgca cataatcgta atcgattctt     60

cttgatctct aaacaacact ttcccgttag catggctagc gatgagattg tccgcaatct    120

gatctcccgt gaggaggtga tgggtaattt gattagcaca gcttctagct cagtaaggtc    180

acccttacat gacgtactgt gctcgcacgt aaggaccatc gtcgattccg tggataagaa    240

agcggtcagt cgcaagcatg aagatgtacg gcgcaacatc tcctctgagg aattgcagat    300

gttgataaat gcatatcctg aatatgccgt ttcatcctca gcttgtgaat ctggtactca    360

tagcatggcg gcttgttttc gatttctgga gacagaatat ctcttagata tggttccaat    420

gaaagagact tttgtttatg acattggtgg caactggttt tctcatatga agtttcgtgc    480

tgatagagaa attcattgtt gctgtccgat cttatctatg agagattctg aaagactgga    540

aacacgcatg atggcaatgc aaaaatatat gcgtggatcg aaagacaaac cgttacgctt    600

gttaagccgt tatcaaaata tcctgcgtga acaagcggcg agaacaactg cctttatggc    660

aggtgaggtg aatgcgggtg ttctcgatgg agatgtgttt tgtgagaaca cttttcaaga    720
```

-continued

```
ctgtgtgaga cgagtgcccg aaggtttttt gaagacagct atagcagttc atagcatcta    780
cgatatcaaa gtggaggaat ttgcgtctgc attgaaaaga aaaggtataa cacaggctta    840
tgggtgtttc ctgtttcctc ctgctgtatt gataggtcag aaggaaggca ttttaccttc    900
cgtggacggt cattacttgg tggagaatgg caggattaag ttcttctttg cgaatgatcc    960
gaatgccggt tactctcatg accttaagga ttatctgaag tatgtggaaa agacctatgt   1020
ggatatagag gatggagtgt ttgctattga gctgatgcaa atgcgaggtg ataccatgtt   1080
ctttaagatc acggatgtca ccgcagcaat gtatcatatg aaatacagag gtatgaaacg   1140
cgatgaaaca ttcaaatgca ttccgttgct aaagaattca tctgttgtcg tacctctatt   1200
ttcgtgggac aaccgttctt taaagatcac aagtggttta ctaccacgaa ctttggtcga   1260
gcagggtgcg gcttttatta tgaaaaacaa ggagaaggac ttgaacgttg ctgtgttgaa   1320
gaactatctt tccgctgtga acaactcata cattttcaac ggatcccagg ttagagatgg   1380
cgtgaaaatt gccccggatt taatctccaa gttggcagtg actctgtacc tgagagaaaa   1440
agtctatcga caaagagaaa attcaatcat aagttatttc gagcaagaaa tgcttcacga   1500
tcccaacttg aaagccatgt ttggagactt tctgtggttt gttccaaata ctctctcgag   1560
tgtctggaag aacatgcgaa aatcactgat ggaatggttt ggctacgcag aatttgactt   1620
gactactttt gatatttgcg atcccgttct ctatgtagag atagtggatc ggtataagat   1680
cattcaaaaa gggcgaattc cacttggtga gttctttgat tgtcatgaag aatgcgagaa   1740
ttacgaactg cgtgagaagg agaaaaacga cctagcggtg aaaatggccc agaaggtaac   1800
agggacggtg accgaatgcg agaaggacct gggacctctt gttcaaccga taaaagagat   1860
attggttcaa cttgtgatgc ccaatttggt cagagcgctg tgtagacctc gtagcccaac   1920
gtctcctttg gacttaaaaa gtatcccagg gtcaactcca tcacactcaa gttcagattc   1980
tgaacactct atgactgaag aagcgagctg caccattgcg ggtagcgtac caacatggga   2040
aattgcgact aggaaagatc taacctttca gcgaattgat gaagatatgt ctcgacgaac   2100
tggtatgcct ccaagaccaa aagtaacttc tagttacaac atgaatgcca gagctgagtt   2160
tctctactat caactgtgta gcgtgatttg tgaaagggct cagattttga gtgtcatcga   2220
agactttcgt cagaatttga tattctcaga taaagtggcc gttccattga acgctagatt   2280
ctacagtttt cagtcattga gacccggatg ggtgttcaaa actccatcgc atagtgaagt   2340
aggccacagt tatgcagtac attttgactt caagacaatt ggaaccgatt tggaagagag   2400
cctagctttt tgccgaatgg taccgatttc atgggataaa agcggcaaat acatcgcgac   2460
aactcctcat tttcccgaga gacatggtta ctacgtgatt tgtgacaaca ctaaattgtg   2520
taacaattgg cttatttaca ataagttagt tgacgtctac gcactagtgg ctgatagacc   2580
tctgagattc gagttgattg acggagttcc tggctgcgga aagtcaacca tgattttaaa   2640
cagctgtgat attcgacgcg aagttgttgt tggtgaagga cggaatgcaa ctgatgactt   2700
aagggagagg ttcaagcgta agaaaaattt gaatagtaag actgctaatc acagagttcg   2760
aacgcttgac agcttattac ttgctgaagg accttgtgta ccgcaagctg ataggtttca   2820
ttttgatgaa gctctaaaag ttcattacgg cgccataatg ttctgtgctg ataagcttgg   2880
tgcctcagaa attctcgctc agggagatag ggctcaattg ccaatgatct gtcgtgtaga   2940
aggtattgaa cttcaatttc aatctcctga ttacacgaag acgatcataa atcctaagct   3000
acggtcatac cgtatccctg gagatgttgc cttctatttg agtgctaagg aattttacaa   3060
agttaaagga atacctcaaa aggttataac ttctaacagt gtgaaacgtt ccttgtacgc   3120
```

```
tagaggcgaa acgactccgg aaagattcgt gagtttgctt gatgttccgg tgagaaaaga   3180
cacccactat ctaaccttct tacaagctga gaaggaaagt ttgatgagtc atttgattcc   3240
aaagggtgtg aagaaagagt ctatttcaac gattcatgag gcgcagggtg gtacctatga   3300
aaatgtgatt ctggtccgtt tgcaacggac gcccaatgaa atttatccgg gtggacctag   3360
gtccgcccct tacattgtgg ttgggacttc aaggcataca aaaactttca cttattgtag   3420
tgttacggac gataagttgc ttttagatat cgccgacgtc ggtggtattg cacatacacc   3480
tattcgtact tttgaatctc atatagttta aaaaaaaaaa aaaaaaaaaa tgtttgatca   3540
gatcattcaa atctgatggt gcccatcaac catatgatgg gagtgtttgc aagtccacta   3600
taatcgaact tgaaaacgat gcctgaattg gaaaccatga atcttaacgg attctggaga   3660
gaaaatttag gaattggtat gtaagctaca acttccggta gctgcgtcac actttaagag   3720
tgtgcatact gagccgaagc tcagcttcgg tcccccaagg gaagacca                3768
```

<210> SEQ ID NO 36
<211> LENGTH: 3289
<212> TYPE: DNA
<213> ORGANISM: Barley stripe mosaic virus
<220> FEATURE:
<221> NAME/KEY: misc_feature
<222> LOCATION: (1)..(3289)
<223> OTHER INFORMATION: BSMV_RNA2_gi|19744922|ref|NC_003481.1|

<400> SEQUENCE: 36

```
gtaaaagaaa aggaacaacc ctgttgttgt tcgacgctat actaaatata tattatctta     60
ttagtgcatt tcttttaccg cttcacagta tgccgaacgt ttctttgact gctaagggtg    120
gaggacacta catcgaggat caatgggata cacaagttgt ggaagccgga gtatttgacg    180
attggtgggt ccacgtagaa gcctggaata aatttctaga caatttacgt ggtatcaact    240
ttagcgttgc ttcctctcgg tcgcaagtcg ctgaatactt agctgcgtta gatcgtgatc    300
tacctgctga tgtagacaga cggtttgcag gtgctagggg acaaattggt tcacccaatt    360
atcttcctgc gccaaaattc tttcgtctcg ataagcgaac tatcgctgaa ctgactagac    420
tctctcgtct tacggatcag ccgcacaaca atcgcgatat agaacttaac cgagcgaaaa    480
gagccacaac taacccatct cccccggcgc aggcaccgtc ggagaatctc actcttcgtg    540
atgttcaacc gttaaaggat agtgcgttgc attatcaata cgtgttgatt gacctacaga    600
gtgcgagact cccggtgtat accaggaaga ctttcgaacg tgaactcgct ttggaatgga    660
tcattccaga tgccgaggaa gcgtgacctg ctgtcgaagc ggtaaaagga tgtacatatg    720
tatcttattt attttgttta tctattttct tttgctttta gtttttgctt tttacgcatt    780
aactagatgt attgacttta gccatggaca tgacgaaaac tgttgaggaa aagaaaacaa    840
atggaactga ttcagtgaaa ggtgtttttg aaaactcgac gattcccaaa gttccgactg    900
gacaggaaat gggtggtgac ggttcttcta cttctaaatt aaaggaaact ctgaaagttg    960
ccgatcagac tccattgtcc gttgacaatg gtgccaaatc caaattggat tcctctgata   1020
gacaagttcc tggagttgcc gatcagactc cattgtccgt tgacaatggt gccaaatcca   1080
aattggattc ctctgataga caagttcctg gacctgagtt gaaacccaac gttaagaagt   1140
ccaagaagaa aagaatccaa aaacctgctc aaccgagtgg gcccaatgac cttaaaggcg   1200
ggactaaggg atcatctcaa gtgggtgaaa atgtgagtga gaactatact gggatttcta   1260
aggaagcagc taagcaaaag cagaagacgc ccaagtctgt gaaaatgcaa agcaatctgg   1320
```

-continued

```
ccgataagtt caaagcgaat gatactcgta gatcggaatt aattaacaag tttcagcaat   1380

ttgtgcatga aacctgtctt aaatctgatt ttgagtacac tggtcgacag tatttcagag   1440

ctagatcaaa tttctttgaa atgattaagc tcgcatcctt gtatgacaaa catctaaagg   1500

aatgtatggc gcgagcctgc accctagaac gtgaacgatt gaagcgtaag ttactcctag   1560

tacgagcttt gaaaccagca gttgacttcc ttacgggaat catctctgga gttcctggct   1620

caggaaaatc aaccattgtg cgtactttgc tcaaaggtga atttccggct gtttgtgctt   1680

tggccaatcc tgccttaatg aacgactatt ctggtattga aggcgtttac gggttagatg   1740

acctgttgct ttctgcagtt ccgataacgt ctgatttatt gatcatagat gaatatacac   1800

ttgctgagag cgcggaaatc ctgttgttac aacgaagact cagagcctct atggtgttgt   1860

tagtcgggga tgtagctcaa ggaaaagcca ccactgcttc cagtattgag tatttaactc   1920

tgccggtgat ctacagatca gagacgactt atcgtttggg acaagagact gcttcgcttt   1980

gcagcaagca gggtaacaga atggtttcaa agggtggaag ggacacagtg atcattactg   2040

attacgatgg cgaaacagat gaaacggaga aaaatatcgc ttttactgtc gatacagttc   2100

gagatgtgaa agattgcggg tacgattgtg ccctggcaat tgatgtgcaa gggaaagaat   2160

tcgattcagt gactttattc ctaaggaacg aagaccggaa agctttagca gataagcatt   2220

tgcgtttagt cgctttgagc agacataagt cgaagttaat catcagggcc gacgcggaaa   2280

ttcgtcaagc attcctgaca ggtgatattg acttgagctc taaggcgagt aactctcatc   2340

gttattctgc aaaaccggat gaagaccaca gttggttcaa ggccaaataa gtattggcca   2400

attgtcgccg gaatcggtgt cgttggattg tttgcgtatt tgatcttttc aaatcaaaaa   2460

cattctacgg aatccggtga taatattcac aaattcgcca acggaggtag ttacagagac   2520

gggtcaaaga gtataagtta taatcgtaat catccttttg cctatggcaa tgcctcatcc   2580

cctggaatgt tgttgcccgc aatgcttacc atcatcggaa tcatttccta tttatggcga   2640

acaagagatt ccgtgctcgg agactcaggc ggaaacaact cctgtggaga agactgtcag   2700

ggcgaatgtc ttaacggaca ttctcgacga tcattactat gcgatattgg ctagtctttt   2760

tatcattgct ctatggctat tgtatatata tctaagcagt atacctacgg agactggtcc   2820

ctacttctat caagatctga actctgtgaa gatctatgga ataggggcta cgaacccaga   2880

agttattgcg gccatccacc attggcagaa gtaccctttt ggggaatctc cgatgtgggg   2940

aggtttaatc agtgttttga gtattcttct taaaccgctg acattagttt ttgcgttaag   3000

ctttttttctc ttactttctt caaaaaggta aaaaaaaaaa aaaaaaaaaa atgtttgatc   3060

agatcattca aatctgatgg tgcccatcaa ccatatgatg ggagtgtttg caagtccact   3120

ataatcgaac ttgaaaacaa tgcctgaatt ggaaaccatg aatcttaacg gattctggag   3180

agaaaattta ggaattggta tgtaagctac aacttccggt agctgcgtca cactttaaga   3240

gtgtgcatac tgagccgaag ctcagcttcg gtcccccaag ggaagacca              3289
```

<210> SEQ ID NO 37
<211> LENGTH: 3164
<212> TYPE: DNA
<213> ORGANISM: Barley stripe mosaic virus
<220> FEATURE:
<221> NAME/KEY: misc_feature
<222> LOCATION: (1)..(3164)
<223> OTHER INFORMATION: BSMV_RNA3_gi|19744919|ref|NC_003478.1|

<400> SEQUENCE: 37

```
gtatagcttg agcattaccg tcgtgtaatt gcaacacttg gcttgccaaa taacgctaaa     60
```

```
gcgttcacga aacaaacaac aattcggcat ggatgttgtg aagaaattcg ccgtcatgtc    120
agtgactgta gtagcaggtc ccgtccttac gctttcatca cctgtggtgg tgacgtttgg    180
aacaagctta attgccgtat ctttggtgaa acggttgcta caggaacaac cccgtgtaat    240
tgctcacgat cacgaacatt acccaggtgg ttctgagagc agttctagct cttgtgctac    300
cgcgcctatt ttacgtaatc tttcgcgaga tcagtgcgat tcagagaata ttggatgcag    360
ttctagcgcc tgttctccgt ctgaaattgt gaaagttaca aggcaggtag tggaagttga    420
acgtggtctt taccgggaca aacaacaatt cggcatggat gttgtgaaga aattcgccgt    480
catgtcagtg actgtagtag caggtcccgt ccttacgctt tcatcacctg tggtggtgac    540
gtttggaaca agcttaattg ccgtatcttt ggtgaaacgg ttgctacagg aacaaccccg    600
tgtaattgct cacgatcacg aacattaccc aggtggttct gagagcagtt ctagctcttg    660
tgctaccgcg cctattttac gtaatctttc gcgagatcag tgcgattcag agaatattgg    720
atgcagttct agcgcctgtt ctccgtctga aattgtgaaa gttacaaggc aggtagtgga    780
agttgaacgt ggtctttacc gggacatttt tcaggacaac gaaatcccat cagtcatgga    840
agagaaactg cagaaactcc tttactctga gggtgagaag attcgaagac gttgccaatt    900
tgaagcatca acgatgcact cacgcaaagt aaaggttccg gaggtaggta ctatcccaga    960
tatccaaact tggttcgatg ctacgtttcc tggtaactcc gttaggtttt ctgatttcga   1020
cggttatact gttgctacgg aggacattaa catggatgtt caggattgta gacttaagtt   1080
cgggaagact tttcgacctt atgaatttaa ggaatcactg aaaccagtac tgaggacagc   1140
aatgccagaa aagcgacagg gtagtttgat tgaaagtgtg ctggcctttc gtaaaagaaa   1200
tttggctgcg cccagattac aaggggcttt gaatgaatgg cacacaattg agaatgtgct   1260
gaagaaggcg ttaaaggtat tcttctttga agatttaatt gatcgaacgg atcattgcac   1320
ttacgagtca gcgctcagat ggtgggataa acaatcagtg acggctcgag cgcagctcgt   1380
ggcggaccaa cggaggttat gtgatgttga cttcacgact tataacttca tgataaaaaa   1440
tgatgtaaaa ccgaagttag atctaacacc tcaagttgaa tatgcagctt tgcagactgt   1500
tgtgtatcct gataagatag tcaatgcttt ctttggtccg atcataaagg agattaatga   1560
acggatcatc agagcgctta gacctcatgt ggtctttaat tctcgtatga ctgctgatga   1620
actgaatgaa acagttgcct tttgacacc tcacaagtac agagccttag agattgactt    1680
ttcaaaattt gataaatcaa agactgggct tcatatcaaa gctgtcattg gactctataa   1740
gctctttggt ctagatggcc tgttaaaagt actctgggaa aaatcgcaat atcagactta   1800
cgtgaaagat agaaacttcg gtctcgaggc atatctatta tatcagcaaa agtcaggaaa   1860
ttgtgacact tacggttcga acacctggtc tgccgccttg gcgttgttag attgtcttcc   1920
tttggaagat gcacatttct gtgtatttgg tggtgatgat tcattgatat tgtttgatca   1980
gggatacata atttccgacc catgccggca acttgccggt acttggaatc ttgaatgtaa   2040
agtgttcgac ttcaagtacc ccgcattttg tggtaaattt ctgctgtgca tagatggaaa   2100
atatcagttt gttccagatg cggcaaaatt tatcacaaaa ttaggtagaa ctgatgtgag   2160
agatgtagaa gttttgagtg agatttatat ctctatcaat gacaattaca aatcttacaa   2220
agactttaag gtgcttgatg ctttggataa ggctttagtg gacagatatc gatcccctta   2280
tagtgctatt tctgctttgg tttctttatg ttatcatatc tttgacttta ataagtttaa   2340
gttgctgttt aattgtgaag ggaaatttgt ggataagaag ctgagaaagg acttcgagtg   2400
```

gtgaactctg ggtcctgatg tttaaatcta ctgtatttac cttcgcatga tggctacttt 2460
ctcttgtgtg tgttgtggta cctcaactac aagtacttac tgtggtaaga gatgtgagcg 2520
aaagcatgta tattctgaaa caagaaataa gagattggaa ctttacaaga agtatctatt 2580
ggaaccgcaa aaatgcgccc tgaatggaat cgttggacac agttgtggaa tgccatgctc 2640
cattgcggaa gaggcttgtg atcaactgcc aatcgtgagt aggttctgtg gccaaaagca 2700
tgcggatctg tatgattcac ttctgaaacg ttctgaacag gagttacttc ttgaatttct 2760
ccagaagaag atgcaggagc tgaaactttc tcatatcgta aaaatggcta agcttgaaag 2820
tgaggttaac gcaatacgta agtccgtagc ttcttctttt gaagattctg ttggatgtga 2880
tgattcttct tccgtttcta agttgtaaaa aaaaaaaaaa aaaaaatgtt tgatcagatc 2940
attcaaatct gatggtgccc atcaaccata tgatgggagt gtttgcaagt ccactataat 3000
cgaacttgaa aacgatgcct gaattggaaa ccatgaatct taacggattc tggagagaaa 3060
atttaggaat tggtatgtaa gctacaactt ccggtagctg cgtcacactt taagagtgtg 3120
catactgagc cgaagctcag cttcggtccc ccaagggaag acca 3164

<210> SEQ ID NO 38
<211> LENGTH: 2360
<212> TYPE: DNA
<213> ORGANISM: Maize stripe virus
<220> FEATURE:
<221> NAME/KEY: misc_feature
<222> LOCATION: (1)..(2360)
<223> OTHER INFORMATION: segment 3, complete sequence GenBank: AJ969410.1

<400> SEQUENCE: 38
acacaaagtc ctgggtaaaa aatattattt tttatcaata tatatattac ttctgtccat 60
cgaagcatga acttttacac atcatctgtt ggagtgcgac aatacgacca ctctttattg 120
gtcttgaatg atctcaccaa cattcatatc acttgtgagg atgtccactg ctctgcaaag 180
ctcctctgct acatatatga tatctacaag tctaggtacc catcaatgga tgagcattct 240
ttcttgcgct tgctaaaagg tccagatgat gctgagatac ttagcacctt tttgagaaca 300
atcatttgga tactgtctca tgacagagac ttcccagatg agttcaggat tccagctaca 360
gcacttgctt cagtttatat aaaatattac tctgaattga aaccaagagc tcctaccacc 420
aattgttgga catgcagaat gtccaaaaac aatctacctt tccaagtccc ctcaataaag 480
ggattccctg ctgaagcaga gctatatata gttccaatct ctgatcatga tggaaagaca 540
atagagtttt caggaatgaa aacactgtac aagtctccaa gcaagaagaa acacaattat 600
gtcatttcat cagatatgcc cccacttagt gctagataca ctgtctggga tggcaaatag 660
agtagtatct gtagaatccc ctttctagga gtgtacggat aatgtaacta agttacattt 720
taagaataaa aaagtgtgct aagcacacta tccgaatagc aatcggatga aggccttaac 780
ctaatttttt gttttttttgc tttttttgttt tttatttgtt tttttgtttt ttcatttttt 840
tggttttttt aatatattat aagattttga gcactctaaa agctcaattt attatacaca 900
ctatatgtac atatcaataa tagtgaacta aaaagcacaa gcactaaaat ataatagaag 960
caaaagcaaa gcataataaa catcataaac tataataaga taatattgtt aaaccataat 1020
aataatgaca cacaaacact caatactaat attatcatac tctcattcat acttgttttt 1080
gattttccat tttcccattt ttttgttttt ttgtataatc taatttttat ggttttcttg 1140 attttttga tttttttgtt tttttgttta aaacacacaa tacaataata taacacaaac 1200

```
aacacactta aatagaatat catgacacaa tgtgagcact tcccctgctc agtgccagac   1260

cgtcttatcc aacgcattct tccactttat gatgatatca tcatagtatg aggaactcac   1320

tcctcctcga agaactcaat gatcaatgcc ttcatctcat cctgagtctt tgagctgttg   1380

tctacaatgg ttttcatcaa gctgcactgt tctgccaaaa attgcttgac ctgagtacca   1440

taggagcaga caacattctt tccgaatgat gcaagcaagg ccaagaatga ctccttgaat   1500

ttctcattaa catagtatgg ctcacatact ttggtcctcc cagatttctt cttcgcttcg   1560

ttgaggtttt tggattgaca ggtgatgacc agcaaaccag tggtatactt tatcatgtct   1620

atgtctttga gcaatcctct ctccttcttt tttgtctctg gcattgtttt cttagtgacc   1680

aagaaagcat gaatcacatg aatgctgaaa agaatgtggt tgacactctt agttgtgcag   1740

tatggtgcag atgagctgtc aagtgtaata tattggggaa caaagtccca cagcagggaa   1800

tcagtcccag acatgctaag atcagatgaa tcaatagcca ttttcagacc agtgaactgt   1860

ttggtcacct cataggatac atttggaaag agttgagcta cccttcccag tgtaatagca   1920

tttgcgttgc tacccacaga tgaaactaat ccatagcggg caaccaatgc cgctgcttcc   1980

tcactgccag cagttgcctt ggttttctta gtgacatcct taacaaagcc agtccctcgg   2040

acatacctca tcacaatcat cttgacaaca tcttgagcaa gagttgcccc acccttgtct   2100

ttgagaatac caatcaaagt agccgcatca tagcctgcat accctatctg atcatgaaag   2160

gtggtcacag acgccttgtt atcagtgaga tacttcaaag catctttgga gatatcattg   2220

atagctttct ggagatcatt aagatttgca ggcttattag tggccatttt cttcaagggt   2280

attggtgcaa tggttatgat ttagaccttt ctttagttga tcaatacgaa atcgattaaa   2340

cgattaccca gactttgtgt                                                2360
```

<210> SEQ ID NO 39
<211> LENGTH: 1368
<212> TYPE: PRT
<213> ORGANISM: Streptococcus pyogenes

<400> SEQUENCE: 39

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
```

-continued

```
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590
```

-continued

```
Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005
```

-continued

```
Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 40
<211> LENGTH: 1880
<212> TYPE: DNA
<213> ORGANISM: Brachypodium distachyon

<400> SEQUENCE: 40

-continued

```
cttcaccgcc attgcaaaaa ttgtcaataa atatttagag tgggtggcat cagaaaaaca      60
tctctagtgg actctcttcc tatcatagct actcgggctg tagatagaac gagggcacaa     120
gagttgggtg gcgtaggttt actcgtgacc tcaactcttt tggctgtgtc ttacgtctaa     180
gatgggtttg gcatgtgaga aacataggtc taagcaattc atgttagggc tgttgcattg     240
ttgttgcatc aaccaaatgt ccagatagca gttcatgcta catctagttg aaaaccctca     300
tcattaggcg gaacatgtgt tcttttttag catagtcaaa gtcagattgc ggcactcgct     360
catccacgga aagaattttc cctgtgcagg catctcgatc aaaagacgca aattaatttt     420
tgaatagcga tataacaata tctaattaac gtttcttgtt ttctgcgaaa tgtctttcat     480
cataaaatga gtcatctcga tgagcccaag tgacatagcc caacacccca ccccaccaat     540
aaaagtgaag aaaacatgtt gggaaaacta taccaagtaa aatacgagtt gttctaaaga     600
aaaagtaaag tacgagttag atcgcaccct gtcctggagt gtggcttgat gatccaactc     660
ctagcattgt atccctgttt ttggatgatg taactattat ttacaatgaa taaagaggtg     720
ttttactagt aaaaaaatct tgaggggagg agaaaataat ggaggtcttt tttcaaaccg     780
atggactatt atttttagtg aaagagaata atattattgg aaaaattatt ctatccactt     840
attttatatt ggcagaatac aaagaatggt ggggtccacg cggaacttgc ggcccccgaa     900
acctatcgag ggcgcggtac ccaagcaagg aacggaggaa acttgcgggg cccgaaacct     960
agtgataaaa ggcatatcat ccacacgatg aagatctgac ggaccatatc tcccaccacg    1020
gaaagccatc agacgaggat cagacggcca ggaaggaacc ctagcgcccg ccggtgccaa    1080
tataaagcgc cactctctct cgtcttaagc cccagcctct ccattcccct ctccctctcg    1140
ccgccgccgt ctccttctcc tactcccttc gaggtgtgtt gttcatccgt cccgaatcca    1200
tccatcccct cttcagatgt gttgttcatg gctctaatag ctctagatct gcttgtttgt    1260
gttgtttagc tctagatcta ctcgcgcgcg cttctctctc gatctcctgt agaacaattt    1320
tggttggttt tttgtgcata tccatggtaa ttttgtctgc aatatggagg aggctttcta    1380
agctcctacg tagcatcgat ctttagaatt ccctcggttt ctgtttattt cttcgcgagg    1440
gctctctgtt atctgtagga gtagctgtaa gcgcggttcg ttacggatta atcgtcatgc    1500
ttagttgaac ctatcggtcg aaggatttgt gtgggttgtc gtgtagaatt gacaccatct    1560
acttactgta ctgatatgcc gatctgtagg atactcttca ttacttttgt ttactgctag    1620
ttgtggtgta gatttagcat tctcaaaccc atgctgtagc gtttctaata ttgttacata    1680
gatctaccgg tgcctgttaa ttgtattcga tcgggcgttt ctacatctgt ccgcccacct    1740
agttttatat gtggtaatca aaattgcgtt gacttcgtga tgctgtctgt gtactgtttt    1800
taatcgctct tacttagatg atcaacatgg tgatggttac gatttactgt tttctaatcc    1860
ctgttacttc gatgctgcag                                               1880
```

<210> SEQ ID NO 41
<211> LENGTH: 17
<212> TYPE: DNA
<213> ORGANISM: Artificial Sequence
<220> FEATURE:
<223> OTHER INFORMATION: Protospacer Region guide RNA 14

<400> SEQUENCE: 41

```
tggttctgcc tctggtc                                                    17
```

<210> SEQ ID NO 42

<211> LENGTH: 20
<212> TYPE: DNA
<213> ORGANISM: Artificial Sequence
<220> FEATURE:
<223> OTHER INFORMATION: Protospacer Region guide RNA 16

<400> SEQUENCE: 42
taacggatag cgctcctcgt 20

<210> SEQ ID NO 43
<211> LENGTH: 20
<212> TYPE: DNA
<213> ORGANISM: Artificial Sequence
<220> FEATURE:
<223> OTHER INFORMATION: Protospacer Region guide RNA 37

<400> SEQUENCE: 43
tggagcttac cgactcgctc 20

<210> SEQ ID NO 44
<211> LENGTH: 20
<212> TYPE: DNA
<213> ORGANISM: Artificial Sequence
<220> FEATURE:
<223> OTHER INFORMATION: Protospacer Region guide RNA 38

<400> SEQUENCE: 44
ggagcttacc gactcgctca 20

<210> SEQ ID NO 45
<211> LENGTH: 20
<212> TYPE: DNA
<213> ORGANISM: Artificial Sequence
<220> FEATURE:
<223> OTHER INFORMATION: Protospacer Region guide RNA 39

<400> SEQUENCE: 45
ggaaagctgc tggcgacagg 20

<210> SEQ ID NO 46
<211> LENGTH: 20
<212> TYPE: DNA
<213> ORGANISM: Artificial Sequence
<220> FEATURE:
<223> OTHER INFORMATION: Protospacer Region guide RNA 43

<400> SEQUENCE: 46
tcctggtcga acttttcagg 20

<210> SEQ ID NO 47
<211> LENGTH: 20
<212> TYPE: DNA
<213> ORGANISM: Artificial Sequence
<220> FEATURE:
<223> OTHER INFORMATION: Protospacer Region guide RNA 18

<400> SEQUENCE: 47
taattctagt acatggatat 20

<210> SEQ ID NO 48
<211> LENGTH: 20
<212> TYPE: DNA
<213> ORGANISM: Artificial Sequence
<220> FEATURE:
<223> OTHER INFORMATION: Protospacer Region guide RNA 52

<400> SEQUENCE: 48
cggtcataaa gcagctctca 20

<210> SEQ ID NO 49
<211> LENGTH: 9
<212> TYPE: PRT
<213> ORGANISM: Simian virus 40

<400> SEQUENCE: 49

Met Ala Pro Lys Lys Lys Arg Lys Val
1 5

<210> SEQ ID NO 50
<211> LENGTH: 18
<212> TYPE: PRT
<213> ORGANISM: Agrobacterium tumefaciens

<400> SEQUENCE: 50

Lys Arg Pro Arg Asp Arg His Asp Gly Glu Leu Gly Gly Arg Lys Arg
1 5 10 15

Ala Arg

<210> SEQ ID NO 51
<211> LENGTH: 18
<212> TYPE: PRT
<213> ORGANISM: Agrobacterium tumefaciens

<400> SEQUENCE: 51

Lys Arg Pro Arg Glu Asp Asp Asp Gly Glu Pro Ser Glu Arg Lys Arg
1 5 10 15

Glu Arg

<210> SEQ ID NO 52
<211> LENGTH: 17
<212> TYPE: PRT
<213> ORGANISM: Agrobacterium tumefaciens

<400> SEQUENCE: 52

Lys Leu Arg Pro Glu Asp Arg Tyr Val Gln Thr Glu Arg Tyr Gly Arg
1 5 10 15

Arg

<210> SEQ ID NO 53
<211> LENGTH: 17
<212> TYPE: PRT
<213> ORGANISM: Agrobacterium tumefaciens

<400> SEQUENCE: 53

Lys Leu Arg Pro Glu Asp Arg Tyr Ile Gln Thr Glu Lys Tyr Gly Arg
1 5 10 15

Arg

<210> SEQ ID NO 54
<211> LENGTH: 15
<212> TYPE: PRT
<213> ORGANISM: Agrobacterium tumefaciens

<400> SEQUENCE: 54

Lys Arg Arg Tyr Gly Gly Glu Thr Glu Ile Lys Leu Lys Ser Lys
1 5 10 15

<210> SEQ ID NO 55

<211> LENGTH: 15
<212> TYPE: PRT
<213> ORGANISM: Agrobacterium tumefaciens

<400> SEQUENCE: 55

Lys Thr Lys Tyr Gly Ser Asp Thr Glu Ile Lys Leu Lys Ser Lys
1 5 10 15

<210> SEQ ID NO 56
<211> LENGTH: 20
<212> TYPE: PRT
<213> ORGANISM: Agrobacterium rhizogenes

<400> SEQUENCE: 56

Lys Arg Lys Arg Ala Ala Ala Lys Glu Glu Ile Asp Ser Arg Lys Lys
1 5 10 15

Met Ala Arg His
20

<210> SEQ ID NO 57
<211> LENGTH: 20
<212> TYPE: PRT
<213> ORGANISM: Agrobacterium rhizogenes

<400> SEQUENCE: 57

Lys Arg Lys Arg Val Ala Thr Lys Glu Glu Ile Glu Pro His Lys Lys
1 5 10 15

Met Ala Arg Arg
20

<210> SEQ ID NO 58
<211> LENGTH: 18
<212> TYPE: PRT
<213> ORGANISM: Agrobacterium rhizogenes

<400> SEQUENCE: 58

Lys Arg Pro Arg Val Glu Asp Asp Gly Glu Pro Ser Glu Arg Lys Arg
1 5 10 15

Ala Arg

<210> SEQ ID NO 59
<211> LENGTH: 3738
<212> TYPE: DNA
<213> ORGANISM: Artificial Sequence
<220> FEATURE:
<223> OTHER INFORMATION: pEn Chimera Vector

<400> SEQUENCE: 59
gggcgaattg ggcccgacgt cgcatgctcc cggccgccat ggcggccgcg ggaattcgat 60
caaataatga ttttattttg actgatagtg acctgttcgt tgcaacaaat tgatgagcaa 120
tgctttttta taatgccaac tttgtacaaa aaagcaggct cttttttctt tcttcttcgt 180
tcatacagtt ttttttgtt tatcagctta catttcttg aaccgtagct ttcgttttct 240
tctttttaac tttccattcg gagtttttgt atcttgtttc atagtttgtc ccaggattag 300
aatgattagg catcgaacct tcaagaattt gattgaataa aacatcttca ttcttaagat 360
atgaagataa tcttcaaaag gcccctggga atctgaaaga agagaagcag gcccatttat 420
atgggaaaga acaatagtat ttcttatata ggcccattta agttgaaaac aatcttcaaa 480
agtcccacat cgcttagata agaaaacgaa gctgagttta tatacagcta gagtcgaagt 540
agtgattggg gtcttcgaga agacctgttt tagagctaga aatagcaagt taaaataagg 600

```
ctagtccgtt atcaacttga aaaagtggca ccgagtcggt gcttttttc tagacccagc    660
tttcttgtac aaagttggca ttaacccagc tttcttgtac aaagttggca ttataaaaaa    720
taattgctca tcaatttgtt gcaacgaaca ggtcactatc agtcaaaata aaatcattat    780
ttgatcacta gtgaattcgc ggccgcctgc aggtcgacca tatgggagag ctcccaacgc    840
gttggatgca tagcttgagt attctatagt gtcacctaaa tagcttggcg taatcatggt    900
catagctgtt tcctgtgtga aattgttatc cgctcacaat tccacacaac atacgagccg    960
gaagcataaa gtgtaaagcc tggggtgcct aatgagtgag ctaactcaca ttaattgcgt   1020
tgcgctcact gcccgctttc cagtcgggaa acctgtcgtg ccagctgcat taatgaatcg   1080
gccaacgcgc ggggagaggc ggtttgcgta ttgggcgctc ttccgcttcc tcgctcactg   1140
actcgctgcg ctcggtcgtt cggctgcggc gagcggtatc agctcactca aaggcggtaa   1200
tacggttatc cacagaatca ggggataacg caggaaagaa catgtgagca aaaggccagc   1260
aaaaggccag gaaccgtaaa aaggccgcgt tgctggcgtt tttccatagg ctccgccccc   1320
ctgacgagca tcacaaaaat cgacgctcaa gtcagaggtg gcgaaacccg acaggactat   1380
aaagatacca ggcgtttccc cctggaagct ccctcgtgcg ctctcctgtt ccgaccctgc   1440
cgcttaccgg atacctgtcc gcctttctcc cttcgggaag cgtggcgctt tctcatagct   1500
cacgctgtag gtatctcagt tcggtgtagg tcgttcgctc caagctgggc tgtgtgcacg   1560
aaccccccgt tcagcccgac cgctgcgcct tatccggtaa ctatcgtctt gagtccaacc   1620
cggtaagaca cgacttatcg ccactggcag cagccactgg taacaggatt agcagagcga   1680
ggtatgtagg cggtgctaca gagttcttga agtggtggcc taactacggc tacactagaa   1740
gaacagtatt tggtatctgc gctctgctga agccagttac cttcggaaaa agagttggta   1800
gctcttgatc cggcaaacaa accaccgctg gtagcggtgg tttttttgtt tgcaagcagc   1860
agattacgcg cagaaaaaaa ggatctcaag aagatccttt gatcttttct acggggtctg   1920
acgctcagtg gaacgaaaac tcacgttaag ggattttggt catgagatta tcaaaaagga   1980
tcttcaccta gatcctttta aattaaaaat gaagttttaa atcaatctaa agtatatatg   2040
agtaaacttg gtctgacagt taccaatgct taatcagtga ggcacctatc tcagcgatct   2100
gtctatttcg ttcatccata gttgcctgac tccccgtcgt gtagataact acgatacggg   2160
agggcttacc atctggcccc agtgctgcaa tgataccgcg agacccacgc tcaccggctc   2220
cagatttatc agcaataaac cagccagccg gaagggccga gcgcagaagt ggtcctgcaa   2280
ctttatccgc ctccatccag tctattaatt gttgccggga agctagagta agtagttcgc   2340
cagttaatag tttgcgcaac gttgttgcca ttgctacagg catcgtggtg tcacgctcgt   2400
cgtttggtat ggcttcattc agctccggtt cccaacgatc aaggcgagtt acatgatccc   2460
ccatgttgtg caaaaaagcg gttagctcct tcggtcctcc gatcgttgtc agaagtaagt   2520
tggccgcagt gttatcactc atggttatgg cagcactgca taattctctt actgtcatgc   2580
catccgtaag atgcttttct gtgactggtg agtactcaac caagtcattc tgagaatagt   2640
gtatgcggcg accgagttgc tcttgcccgg cgtcaatacg ggataatacc gcgccacata   2700
gcagaacttt aaaagtgctc atcattggaa aacgttcttc ggggcgaaaa ctctcaagga   2760
tcttaccgct gttgagatcc agttcgatgt aacccactcg tgcacccaac tgatcttcag   2820
catcttttac tttcaccagc gtttctgggt gagcaaaaac aggaaggcaa aatgccgcaa   2880
aaaagggaat aagggcgaca cggaaatgtt gaatactcat actcttcctt tttcaatatt   2940
```

-continued

```
attgaagcat ttatcagggt tattgtctca tgagcggata catatttgaa tgtatttaga   3000

aaaataaaca aataggggtt ccgcgcacat ttccccgaaa agtgccacct gatgcggtgt   3060

gaaataccgc acagatgcgt aaggagaaaa taccgcatca ggaaattgta agcgttaata   3120

ttttgttaaa attcgcgtta aatttttgtt aaatcagctc attttttaac caataggccg   3180

aaatcggcaa aatcccttat aaatcaaaag aatagaccga gatagggttg agtgttgttc   3240

cagtttggaa caagagtcca ctattaaaga acgtggactc caacgtcaaa gggcgaaaaa   3300

ccgtctatca gggcgatggc ccactacgtg aaccatcacc ctaatcaagt tttttggggt   3360

cgaggtgccg taaagcacta aatcggaacc ctaaagggag cccccgattt agagcttgac   3420

ggggaaagcc ggcgaacgtg gcgagaaagg aagggaagaa agcgaaagga gcgggcgcta   3480

gggcgctggc aagtgtagcg gtcacgctgc gcgtaaccac cacacccgcc gcgcttaatg   3540

cgccgctaca gggcgcgtcc attcgccatt caggctgcgc aactgttggg aagggcgatc   3600

ggtgcgggcc tcttcgctat tacgccagct ggcgaaaggg ggatgtgctg caaggcgatt   3660

aagttgggta acgccagggt tttcccagtc acgacgttgt aaaacgacgg ccagtgaatt   3720

gtaatacgac tcactata                                                 3738
```

<210> SEQ ID NO 60
<211> LENGTH: 1023
<212> TYPE: DNA
<213> ORGANISM: Zea mays

<400> SEQUENCE: 60

```
ctttgacttt tcccttaatg acgacttatt atttaattta ctcgtcacga ttcccctctc     60

ctggtcgaac ttttcaggtg gggaaagctg ctggcgacag gtggaaatcc ctgagcgagt    120

cggtaagctc catcttctgt actaaagtag tagttgattg gactagaaat ctcgtgctga    180

ttaattgttt tacgcgtgcg tttgtgtgga ttgtaggaca aggctcccta tgtagccaag    240

gctaacaagc tcaagctcga gtacaacaag gccatcgctg cctacaacaa gggcgaggta    300

gggaaactga tgcttcaatt gcgttgttac ttaatgtgta tatagactgc tcctgctggt    360

catttattca aatacgtatg cttactgaac catgtgttgt ttgttcagag cactgcagct    420

aagaaggctc ctgccaagga ggaagaggag gaagatgaag aggagtctga caagtccaag    480

tcggaggtca atgacgagga tgatgaagag ggtagtgagg aggtatacaa aatctattcc    540

tgtcttctcc atattttttc cttagacaaa ataccaatta atccaggata catagcatgt    600

tcatgcatta agcaagttgc taaatttatc ttcgaccaca atgtagacct agtagtattg    660

tattggattc catcaatgca aaacatatgc agatttgcat atgcaaccct cttttgcaag    720

tcctcaatat gagcatttgt ttggaacacg gtgcattggc cttaggaagt ctttaaaaat    780

atgtcttccc tctgcttgca ggatgaagat gatgacgagt gatggagctc ctcgagacaa    840

tggaccgtgc ttcatccaac aatggagcgg ctacacaagg ccccgtggcg atcacaaaaa    900

aggagcctat atccatgtac tagaattatt cagtttcact ccacatcgtg atgttttatt    960

tttacttttg tcgtgctata acggatagcg ctcctcgttg gcgccactgg cgggtggttc   1020

tgc                                                                 1023
```

<210> SEQ ID NO 61
<211> LENGTH: 210
<212> TYPE: DNA
<213> ORGANISM: Artificial Sequence
<220> FEATURE:
<223> OTHER INFORMATION: genome edited hmg13 gene -continued

<400> SEQUENCE: 61

```
ctttgacttt tcccttaatg acgacttatt atttaattta ctcgtcacga ttcccctctc     60
ctggtcgaac ttttcaggtg gggaaagctg ctggcgactc catgtactag aattattcag    120
tttcactcca catcgtgatg ttttattttt acttttgtcg tgctataacg gatagcgctc    180
ctcgttggcg ccactggcgg gtggttctgc                                     210
```

METHODS AND HYBRIDS FOR TARGETED NUCLEIC ACID EDITING IN PLANTS USING CRISPR/CAS SYSTEMS

CROSS-REFERENCE TO RELATED APPLICATIONS

This application is a U.S. National Phase of International Patent Application No. PCT/EP2016/061237, filed May 19, 2016, which claims priority to German Patent Application Nos. 102015006335.9, filed on May 19, 2015, and 102015014252.6, filed on Nov. 5, 2015, all of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Mar. 12, 2018, is named KWS0228PCT_newUS_20180312ST25.txt and is 197,096 bytes in size.

TECHNICAL FIELD

The present invention relates in particular to methods for the manufacture of a plant, a plant material or a plant cell, comprising providing and introducing at least one gRNA as well as a CRISPR nuclease or a catalytically active fragment thereof and/or an effector domain or at least one recombinant construct, comprising a gRNA as well as a CRISPR nuclease or a catalytically active fragment and/or an effector domain or the sequences coding therefor, as well as at least one regulatory sequence and/or a localization sequence, into a target plant structure comprising at least one meristematic cell, whereupon a plant, a plant material or a plant cell comprising a targeted modification of a nucleic acid in a target region, can be obtained directly, wherein the at least one recombinant construct is preferably not integrated chromosomally or extrachromosomally. In addition, appropriate recombinant constructs and vectors as well as methods for introducing these constructs and vectors into a target plant structure of interest are disclosed. Finally, the use of a recombinant construct for the specific modification of a target nucleic acid region in a plant cell is disclosed, as well as plants, plant material or a plant cell which can be obtained or is obtained by the method in accordance with the invention. Furthermore, an in vitro screening method is disclosed as a preliminary test, in order to readily determine, with a high output, the functionality of a gRNA or an encoding sequence for a gRNA with respect to the targeted modification of a specific nucleic acid target region in a plant cell, together with a CRISPR nuclease, comprising a Cas and/or Cpf1 nuclease, or variations or catalytically active fragments thereof, or a catalytically active fragment thereof. The methods disclosed herein are suitable in particular for the targeted introduction, modification, or elimination of a desired trait in a plant, in particular in the framework of the targeted trait development, in order to ensure a highly specific and efficient genome editing.

BACKGROUND OF THE INVENTION

Genome editing constitutes a molecular biological method by means of which specific modifications such as insertions, deletions or point mutations or combinations thereof can be introduced into the genome of a living organism. To this end, specific molecular instruments are required which firstly have nuclease activity, but above all can be guided to the target sequence to be modified with sufficient specificity to programme and carry out a specific and site-directed mutagenesis. In the past few years in plant biotechnology, specific genome editing has developed into an alternative to conventional cultivation and to transgenic strategies. However, tools which are currently available, such as zinc finger nucleases (ZFNs) or "transcription activator-like effector nucleases" (TALENs) are only used in plant biotechnology to a limited extent because of occasional low efficiency and also because of the complex and costly design of the constructs.

A further molecular tool which has been widely used in recent years for precise and site-directed genome modification is the CRISPR nuclease-based system. These nucleases, including inter alia Cas (CRISPR associated gene) nuclease or Cpf1 nucleases, form part of the system described now in the literature as "CRISPR" systems (clustered regularly interspaced short palindromic repeat). This system was originally identified in 1987 when the lap gene of *E. coli* was analysed, when naturally occurring repeat sequences in the bacterial genome were identified. Later on it was discovered that these palindromic DNA repeat sequences of 20 to 50 nucleotides followed a pattern. The acronym CRISPR was then adopted (Jansen, R. et al, "Identification of genes that are associated with DNA repeats in prokaryotes", *Mol. Microbiol.,* 2002, 43(6), 1565-1575), whereupon research focused even more closely upon bacteria. Finally, it was reported that the CRISPR locus constitutes a type of bacterial immune system and could confer immunity against phages (Barrangou et al "CRISPR provides acquired resistance against viruses in prokaryotes" *Science* 2007, 315: 1709.1712), wherein the invading phage DNA was initially installed as a protospacer into a CRISPR locus, the locus was then transcribed and finally the CRISPR-mediated silencing mechanism was activated.

Functional characterization gradually led to the system being exploited as a universal tool for genome modification of higher organisms. In the meantime, a large number of CRISPR/Cas systems have been described (see, for example Van der Oost et al "Unravelling the structural and mechanistic basis of CRISPR-Cas systems" *Nature* 2014, 482:331-338, Makarova et al., "An updated evolutionary classification of CRISPR-Cas systems", Nature Reviews Microbiology 13, 722-736); as yet, the analyses are still far from completed.

A further genome editing system with huge potential is now available thanks to the discovery and exploitation of the bacterial type II CRISPR system.

Five types (I-V) of CRISPR systems have been described so far (Barrangou et al., 2007, Science, 315(5819):1709-12; Bouns et al., 2008, Science, 321(5891): 960-4; Marraffini and Sontheimer, 2008, Science, 322(5909): 1843-5; Makarova et al., Nature Rev. Microbiol., 13, 722-736, 2015), wherein each system comprises a cluster of CRISPR-associated genes (Cas or others) and a CRISPR array belonging thereto. These characteristic CRISPR arrays are composed of repetitive sequences (direct repetitions, so-called repeats), in which short sections of non-repetitive sequences ("spacers") are embedded, wherein the spacers originate from short fragments of foreign genetic material (protospacers). The CRISPR arrays are subsequently transcribed into short CRISPR RNAs (crRNAs), wherein the crRNAs direct the Cas proteins or other effector nucleases of a CRISPR system to the respective target nucleic acid molecules, where cleavage occurs by means of Watson- Crick base pairing. The Type I and Type III CRISPR systems use complexes of Cas proteins and crRNAs for the recognition and subsequent cleaving of target nucleic acids (Wiedenheft et al., 2011, Nature, 477(7365):486-9). On the contrary, Type II CRISPR systems are recognized and cleaved in their natural form, their target DNA interacting with the RNA-directed nuclease Cas9 with two non-encoded RNAs, the crRNA, and a trans-activating RNA (tracrRNA) (Garneau et al., 2010; Sapranauskas et al., 2011, Nucleic Acids Res., 39(21); 9275-82; Deltcheva et al., 2011, Nature, 471(7340); 602-7). A possible Type IV CRISPR system has also been proposed (Makarova et al., Biol. Direct, 6(38), 2011).

The immune response mediated by CRISPR/Cas in natural systems requires CRISPR-RNA (crRNA), wherein the maturation of this guide RNA, which controls the specific activation of the Cas nuclease, varies significantly between the various CRISPR systems which have been characterized so far. Firstly, the invading DNA, also known as a spacer, is integrated between two adjacent repeat regions at the proximal end of the CRISPR locus. Type II CRISPR systems code for a Cas9 nuclease as a key enzyme for the interference step, which contains both a crRNA and also a trans-activating RNA (tracrRNA) as the guide motif. These hybridize and form double-stranded (ds) RNA regions which are recognized by RNAseIII and can be cleaved in order to form mature crRNAs. These then in turn associate with the Cas molecule in order to direct the nuclease specifically to the target nucleic acid region.

A recombinant CRISPR/Cas system, or in general, a CRISPR/nuclease system, enables a targeted DNA recognition and/or bonding through a small, individually tailored, non-encoding RNA (guide RNA or gRNA) in combination with a possibly modified nuclease, and the optional generation of a single- or double-strand break. Recombinant gRNA molecules can comprise both the variable DNA recognition region and also the nuclease interaction region and thus can be specifically designed, independently of the specific target nucleic acid and the desired nuclease (Jinek et. al., 2012, supra). As a further safety mechanism, PAMs (protospacer adjacent motifs) must be present in the target nucleic acid region; these are DNA sequences which in type II CRISPR system follow on directly from the Cas9/RNA complex-recognized DNA. The PAM sequence for the Cas9 from *Streptococcus pyogenes* is in fact "NGG" or "NAG" (Standard IUPAC nucleotide code) (Jinek et al, "A programmable dual-RNA-guided DNA endonuclease in adaptive bacterial immunity", Science 2012, 337: 816-821). The PAM sequence for Cas9 from *Staphylococcus aureus* is "NNGRRT" or "NNGRR(N)". Further variant CRISPR/Cas9 systems are known. Thus, a *Neisseria meningitidis* Cas9 cleaves at the PAM sequence NNNNGATT. A *Streptococcus thermophilus* Cas9 cleaves at the PAM sequence NNAGAAW. Furthermore, by using modified Cas polypeptides, specific single-stranded breaks can be obtained. The combined use of Cas nickases with various recombinant gRNAs can also induce highly specific DNA double-stranded breaks by means of double DNA nicking. By using two gRNAs, moreover, the specificity of the DNA binding and thus the DNA cleavage can be optimized.

In addition to the CRISPR/Cas system, so-called CRISPR/Cpf1 systems have also been described recently, which are suitable as tools for the targeted genome editing in a manner analogous to that with CRISPR/Cas systems (see Zetsche et al., "Cpf1 Is a Singel RNA-Guides Endonuclease of a Class 2 CRISPR-Cas System," Cell, 163, pp. 1-13, October 2015). The CRISPR/Cpf1 system is also referred to as a Type V CRISPR system (Makarova et al., Nature Rev. Microbiol., 2015, above). In differing from a Cas9 nuclease of a Type II CRISPR/Cas system, a Cpf1 nuclease requires no additional trans-activating tracr-RNAs. Cpf1 recognizes T-rich PAM sequences, and cleaves the target DNA, producing "sticky ends," i.e. overhangs, while in contrast, Cas9 leaves "blunt ends." As with Cas nucleases, Cpf1 nucleases contain an RuvC-like endonuclease domain, while in contrast, they lack a second HNH endonuclease domain (Makarova & Koonin, Methods Mol. Biol., 1311, 47-75, 2015). While Type I, II and IV CRISPR systems are currently referred to as Class 1 systems, Type II and Type V systems are regarded as Class 2 (cf. Makarova et al., Nature Rev. Microbiol., 2015, above).

A DNA double-strand break inside a plant cell is repaired, either by "non-homologous end joining" (NHEJ) or "homologous recombination ((HR), also referred to as "homology-directed repair" (HDR)). Furthermore, in plants, so-called alternative end joining (AEJ) pathways have been described (Charbonnel C, Allain E, Gallego M E, White C I (2011) Kinetic analysis of DNA double-strand break repair pathways in *Arabidopsis*. DNA Repair (Amst) 10: 611-619).

It is therefore proposed in US 2015/082478 A1 that a separate HDR DNA repair vector be used, in order to introduce a double-strand break, which was previously obtained through a recombinant CRISPR/Cas system. Apart from the genetic modification of bacterial genomes, the modification of complex eukaryotic genomes constitutes a huge challenge since, because of the complexity of this genome, molecular tools have to be provided which can effect a specific genome modification without unwanted off-target effects, i.e. unwanted mutations or modifications within the genome or the non-genomic DNA of the target cell.

U.S. Pat. No. 8,697,359 B1 discloses that using CRISPR/Cas technology, eukaryotic genomes, in particular mammalian genomes can be modified, preferably for therapeutic purposes. In this regard, the expression of a target gene by specific introduction of a Cas9 endonuclease as well as a guide RNA (gRNA) is suppressed in a programmable manner. This gRNA is an essential element of every Cas9 CRISPR system, since it in fact guides the actual Cas nuclease specifically to the (genomic) target DNA. To this end, in addition, a tracr (trans-activating CRISPR RNA) sequence and a tracr mate sequence are disclosed for Cas9-CRISPR systems which can be included in the gRNA, wherein the tracr sequences hybridize and can thus be recognized. The use of CRISPR technology to modify complex plant genomes and the molecular tools required for this were not disclosed, however.

WO 2015/026885 A1, on the other hand, is especially concerned with the application of CRISPR/Cas technology in plants. Here, however, only an overall strategy and appropriate molecular tools are disclosed which necessarily require the subculture, selection and regeneration of plant calluses following the successful introduction of the CRISPR/Cas tools and thus do not allow a plant or plant material containing the desired DNA modification and which contains the desired DNA modification to be obtained directly.

An overview of the actual status of the development of the use of CRISPR/Cas technology for genome editing of plant genomes can be found in Bortesi & Fischer ("*The CRISPR/Cas9 system for plant genome editing and beyond*", Biotechnology Advances, 33, pages 41-52, 20 Dec. 2014). This reports, inter alia, on the problems with providing specific gRNAs for targeting in maize. Further, the problems of the high off-target mutation rates are discussed; these are not only observed when using CRISPR/Cas in mammalian cells, but are also observed when using them in plant cells; here, the design of the individual CRISPR/Cas tools is decisive in order, in the respective target cell/respective target organism, to obtain a site-directed targeted modification without off-target effects. Further, Bortesi & Fischer recognise that the CRISPR/Cas system can also be used for epigenetic modification of DNA since the CRISPR/Cas system can also be used to cleave methylated DNA, but state that as yet, no applications in plants are known.

Furthermore, Guilinger et al describe FokI nucleases which are used in the manner of nickases, and thus produce a higher specificity (Guilinger et al; Fusion of catalytically inactive Cas9 to FokI nuclease improves the specificity of genome modification, doi:10.1038/nbt.2909). However, Guilinger et al only present data for human cells, and not for plant cells.

Mali et al 2013 are concerned with the use of the CRISPR/Cas system in human cells, wherein here, nuclease-zero variants of Cas9 or aptamer-coupled gRNAs are used which may be fused to transcriptional activator domains (Mali, P., et al (2013), "CAS9 transcriptional activators for target specificity screening and paired nickases for cooperative genome engineering). However, Mali et al do not mention how and to what extent a corresponding system could be used in plant cells.

In summary, many of the strategies used today are only temporary or transient in the plant field, meaning that mutations occur in already differentiated cells, for example in leaves, but these mutations cannot be inherited via the germ line. Further, there are strategies which require a stable integration of the coding sequences including the required regulatory sequences such as promoters and terminators into the genome, via which a stable mutation can then be produced which is inherited from generation to generation. However, the CRISPR/Cas tools are still contained in the genome of the plant and thus also in potential plant products such as fruit and seeds, which is undesirable having regard to the risk assessment of the corresponding products.

Accordingly, the CRISPR/Cas strategy in plant biotechnology is still of low efficiency, but is also characterized by a difficult and expensive design of the construct as well as the frequent appearance of off-target effects. In addition, many of the current strategies are based on either integrating the CRISPR/Cas tools into the genome of a plant cell in a stable manner or introducing the CRISPR/Cas tools into cells of a differentiated tissue, for example into leaves. As a consequence, with the stable strategy, the individual tools such as Cas9 and not just the specific DNA modifications effected by them are inherited by the descendants. Upon transformation into differentiated cells and tissue, the mutation introduced by the CRISPR/Cas tools is only effective in the relevant cells, but cannot be inherited further via the germ line. Specifically with regard to the targeted development of positive traits in plants, comprising resistances, in particular to pests and environmental effects, e.g. cold, drought, saline content, increased yield, or herbicide resistances, the creation of reliable methods for targeted activation and deactivation, or for modification, of genomic material, as well as for silencing RNA inside a plant cell, is of major economical interest.

Regarding the selection of suitable gRNAs, in silico tools already exist, which enable identification of suitable gRNAs, and the subsequent production thereof (see: www.dna20.com/eCommerce/cas9/input), but there are currently no specific tools that could be used in important crop plants, which always have complex genomes. Moreover, the available tools provide no information regarding the actual effectiveness of a gRNA determined in silico, in a subsequent test in vitro or in vivo inside a plant cell.

Thus, there is a continuing need for the establishment of transient and also optionally inducible methods and constructs based, inter alia, on gRNAs and CRISPR nucleases or gRNAs and other effector domains, in order to carry out a desired modification of a target sequence in a target plant cell, wherein only the modification of the target sequence but not the construct is passed on to descendants. In addition, there is a substantial need for a CRISPR-based method which offers the possibility of carrying out a germ line modification directly in a plant cell or a plant tissue, so that the modification can be inherited and seeds can be immediately harvested from the plant resulting from the modified plant cell or tissue which contain the specific genome modification without having to carry out difficult and expensive intermediate steps. Finally, there is a need for specifically broadening RNA-directed DNA modification systems which are provided by the CRISPR/Cas tools, in which not only genomic target structures but any nucleic acid as the target structure can not only be modified in a controlled manner in the genome of a cell but also indeed in the cytosol or in plastids. In this regard, there is currently also a desire for suitable insertion systems, which allow the targeted insertion of CRISPR/Cas tools and thus allow the targeted modification of a target region inside a plant target structure.

Furthermore, there is a desire for efficient in vitro screening methods, by means of which it is possible to check the effectiveness of a gRNA inside a plant cell in an in vitro assay with a high output, and make reliable predictions, in order to avoid costly and lengthy attempts with plant material.

The ultimate goal is to optimize the precision of a genome editing approach, in particular for the modification of larger eukaryotic genomes, comprising plant genomes and genomes from animal organisms, in order to obtain fewer off-target effects, and ideally, to obtain an optimal repair of a targeted, inserted, double strand break, by creating a repair matrix, together with the actual genome modification tools.

SUMMARY OF THE INVENTION

Thus, the object of the present invention is to provide methods and molecular tools which permit the transient transformation of plant tissue or plant cells, especially meristematic cells, and thus allow the controlled modification of any target nucleic acid region in any plant cellular compartment. Likewise, one object is to create suitable insertion methods for the molecular tools in accordance with the present disclosure. In addition, suitable in vitro screening assays or tests should be created, such that suitable functional gRNAs can be identified in vitro in advance, in order to be able to efficiently reduce the subsequent effort in planta or in vitro in plant tissue.

Combining the above advantages in one system with broad application in plant biotechnology is an aim of the invention.

In particular, tools are to be created, which facilitate plant cultivation, such that traits of interest can be inserted in a plant genome, or likewise removed therefrom or modified therein.

This object is accomplished by the method and constructs provided herein as claimed in the accompanying claims and as described in the description, the figures and the accompanying sequence listing. In particular, the object is accomplished by the provision of a method comprising the transformation or transfection of at least one meristematic cell. Furthermore, the aim is accomplished by the provision of recombinant constructs which comprise specifically modified CRISPR tools and/or further effector domains. Finally, the aim is accomplished by the provision of appropriate regulatory sequences and localization sequences which allow the recombinant construct of interest to be directed in a controlled manner into any discretionary compartment of a target plant structure of interest.

In this manner, at least one specific modification in any target nucleic acid region can be obtained in any compartment of a plant cell, in particular a meristematic plant cell. Since the thus modified at least one meristematic cell can pass on the specific modification in the target nucleic acid region by subsequent cell division and differentiation to its descendants and/or has the potential for a completely modified plant organism to mature from the meristematic cell, then a plant or plant material or a plant cell can be provided without having to carry out further complex culturing or crossing and selection steps (above all complex back-crossing procedures). Moreover, from the at least one meristematic target cell modified in this manner, a plant, plant material or a plant cell can be immediately and directly obtained. In this manner, it is possible to produce or provide or activate gRNA(s) and/or CRISPR nuclease(s) or one or more catalytically active fragment(s) thereof and/or other effector domain(s) only transiently in the meristems, whereupon these recombinant macromolecules are then preferably degraded, i.e. after the gRNA(s) and/or CRISPR nuclease(s) or catalytically active fragments thereof and/or other effector domain(s) have carried out their desired purpose, since no integration thereof occurs into the genome or endogenous extrachromosomal DNA; this may be of advantage as regards regulatory aspects and risk assessment of the plant product. The CRISPR nucleases or catalytically active fragments thereof used herein may also contain one or more mutation(s) in the catalytic domains responsible for DNA (double-stranded or single strand) cleavage. This results in a broad spectrum of application for the Cas nuclease and, in the case of Cas-based nickases, in a higher binding specificity, since two CRISPR/Cas constructs are used in order to cut both single strands of the DNA double-stranded at the desired site. Even Cas-zero variants are proposed herein, as well as their combined use with other effector domains to optimize a specific nucleic acid edit.

Furthermore, it was found that by exploiting the mechanism of action of the CRISPR tools, other effector domains such as DNA or RNA or histone-modifying or DNA or RNA or histone-binding polypeptides or nucleic acids comprising, for example, any type of monomeric, dimeric or multimeric nucleases, including nickases, transcription activators and suppressors, phosphatases, glycosylases or enzymes which can make epigenetic modifications such as methylases, acetylases, methyltransferases or histone deacetylases, aptamers, including single-stranded DNA or RNA sequences as well as peptides, fluorescent proteins, bioluminescence proteins, marker nucleic acid sequences or marker amino acid sequences and the like, and combinations thereof in accordance with the method provided herein, whereupon the spectrum of known specific genome editing can be broadened to general nucleic acid editing which is not per se limited to genomic DNA.

Regarding the aspect of editing genomic DNA disclosed herein, a DNA repair matrix or HDR matrices shall also be created, which can be inserted in a targeted manner, together with the CRISPR tools, into a target cell or target structure of interest, in order to dominate over an error-prone endogenous NHEJ repair system, and to furthermore be able to insert a desired nucleic acid at the location of a double strand break.

The present disclosure thus offers the possibility of using the CRISPR/Cas mechanism in a manner that allows not only the nucleolytic cleavage of DNA, but also any modification of genomic DNA, for example epigenetic modification, as well as RNA, in plant cells (for example mRNA).

By using other regulatory sequences comprising promoters, terminators, transcription factor binding sites or introns, and/or localization sequences comprising nuclear, mitochondrial and plastid localization sequences, the present disclosure also offers the possibility of modifying any target nucleic acid region of a target plant structure in a specific manner, whereupon mitochondrial and plastid DNA, for example, can also act as the target for editing. Furthermore, the possibility of specific modification of RNA, for example mRNA, is also raised, wherein here too, gRNA-directed sequence recognition which is the basis of the CRISPR/Cas system can be exploited and "reprogrammed" in accordance with the present disclosure in order to broaden the field of application of CRISPR/Cas technology.

Methods and constructs are also provided herein, by means of which gRNA and/or CRISPR nuclease or the catalytically active fragment thereof already linked to a further effector domain is/are provided on a recombinant construct.

Furthermore, a method is provided in which the at least one gRNA as well as the at least one CRISPR nuclease or the catalytically active fragment thereof and/or the at least one further effector domain are provided separately on different recombinant constructs. In accordance with this method, the gRNA component may be provided as DNA or RNA, the CRISPR nuclease or variant thereof or the catalytically active fragment thereof may be provided as DNA or RNA or as a polypeptide sequence and the effector domain may be provided as DNA or RNA.

An additional object is the possibility of providing specific constructs which may be inducible or tissue or organelle-specific, and of minimizing unwanted off-target effects by establishing plant-specific constructs and methods. Finally, in one aspect, methods and constructs are designed which not only offer the possibility of specific gene knock-ins but also, for example, offer the possibility of specific gene knock-outs, insertions of genetic fragments, specific epigenetic modifications, the introduction of point mutations, acetylations, methylations, phosphorylations, glycosylations, marking by resistance markers or fluorescent proteins, activation or repriming of transcription, specific cleavage of double-stranded or single-stranded nucleic acids, binding of nucleic acids and the like, so that the field of application in plant cultivation is broadened. From a cultivation and from a regulatory standpoint, it is desirable to have a stable inheritability of a feature effected by the modification over at least one generation with the simultaneous absence of the constructs of the CRISPR/Cas system required for it in the resulting plant or the resulting plant cells.

Lastly, one of the objects was to create an in vitro screening method for identifying a gRNA or an encoding sequence for a gRNA in an in vitro assay, to identify a gRNA or an encoding sequence for a gRNA, which, together with a CRISPR nuclease or catalytically active fragment thereof, is suitable for targeted modification of a nucleic acid target region in a plant cell.

Specific aspects and embodiments of the present invention will become apparent from the following detailed description and the examples, the figures, the sequence listing and in particular the accompanying patent claims.

BRIEF DESCRIPTION OF THE DRAWINGS

In FIG. 5 (A) a diagrammatic image of an embryo with the discoid meristem structure (highlighted by a double ring and an arrow) is shown. FIG. 5 (B) presents the fluorescence (white areas in the b/w image) after the test bombardment. For the test bombardment, a gene coding for a fluorescing protein was used. A clear expression of the protein in the meristematic regions (double ring) can be detected.

FIG. 7 (A) is a diagrammatic image of the meristem tissue of the maize tassel. FIG. 7 (B) shows fluorescence (white areas in the b/w image) after the test bombardment. For the test bombardment, a gene coding for a fluorescing protein was used. A clear expression of the protein in the meristematic regions can be detected.

FIG. 9(A) shows the bombardment with 1350 psi in six individual illustrations. FIG. 9(B) shows the bombardment with 1550 psi in the four individual illustrations. In comparison, significantly more fluorescence can be seen in the lower illustrations, indicated by the brighter regions in the black-and-white illustration. An increased fluorescence/brightness, i.e. an increased efficiency in the insertion, may however be accompanied by a reduced germination of the embryos.

FIG. 10 (A) shows the embryo, FIG. 10(B) shows a deeper layer in which the fluorescence can also be seen in the meristematic region (marked with stars). The images were recorded with a laser scanning microscope, the vector used for the bombardment was an expression vector, which encodes a fluorescent protein. The embryo layers have been dyed with a suitable pigment.

FIG. 11(A) shows a microscope recording of the prepared meristem in a side view. FIG. 11(B) shows the detected fluorescence in this side view (white dots). The embryo layers have been dyed with a suitable pigment.

FIG. 12(A) shows a microscope recording of the prepared meristem in a top view. FIG. 12(B) shows the detected fluorescence in this view (white dots). FIG. 12(C) shows the region where fluorescence has been detected, enlarged by a factor of 2. The embryo layers have been dyed with a suitable pigment.

FIG. 17A shows the use of two gRNAs, gRNA-1 and gRNA-2, which activate a region of the genomic DNA with the goal of excising the region lying between them from a genomic DNA region by means of a CRISPR nuclease, e.g. a Cas nuclease or any other CRISPR nuclease. (RE: restriction enzyme). FIG. 17B shows the results of the analysis of an editing event after using the 2-gRNA strategy on the genome of a maize plant. For this, the genomic DNA is isolated from maize plants, and the target gene, the hmg13 gene (HMG-transcription factor 13; GRMZM2G066528), is amplified with PCR. FIG. 17B shows the results of a separation in a 1% gel, with the standard parameter of 100 V and the subsequent visualization via fluorescence obtained with ethidium bromide. Column 5 contains the molecular size indicator (given in base pairs; GeneRuler 50 bp DNA Ladder (Thermo Fisher Scientific Inc., USA; SM0373) 1000, 900, 800, 700, 600, 500, 400, 300, 250, 200, 150, 100, 50 bp). Columns 1 and 2 each show the results for non-edited maize plants, and column 4 shows the results after a successful editing. The PCR product is smaller, because the region between the two gRNA target regions has been excised.

FIG. 19 shows the leaf inoculation of *N. benthamiana* with a red fluorescent protein construct (RFP) and a control construct, using expressions obtained from the tobacco rattle virus (TRV). The construct pZFN-tDT-nptII functions as a control, allowed expressly by the expression of the RFP in the inoculated leaves, but not in the distal leaves. In the black-and-white illustration in FIG. 19, light(er) regions correspond to the originally detected red fluorescence, while black regions indicate those regions in which no fluorescence could be detected.

FIGS. 20C (original in black-and-white) and D (counterpart to C, with contrast/exposure adjustment) show a flower bud. A pistil has been recorded in FIGS. 20E (original in black-and-white) and F (counterpart to E, with contrast/exposure adjustment). FIGS. 20G (original in black-and-white) and H (counterpart to G, with contrast/exposure adjustment) show a prepared pistil with exposed ovaries.

FIG. 25B shows the fluorescent development (white and light regions) on the first day after the bombardment. FIG. 25C shows a mature maize plant that was obtained from the embryos from FIGS. 25A and B, which was bombarded in this manner and subsequently raised to maturity.

FIG. 27 A: Immature grains of wheat after meristem transformation. FIG. 27B: corresponds to the fluorescent recording of FIG. 27A. The light regions correspond to the detected fluorescence (light/white regions in the black-and-white recording). After the meristem transformation, germinating wheat plants could be obtained directly from the treated grains of wheat (A and B).

DETAILED DESCRIPTION

Definitions

Figure 1:
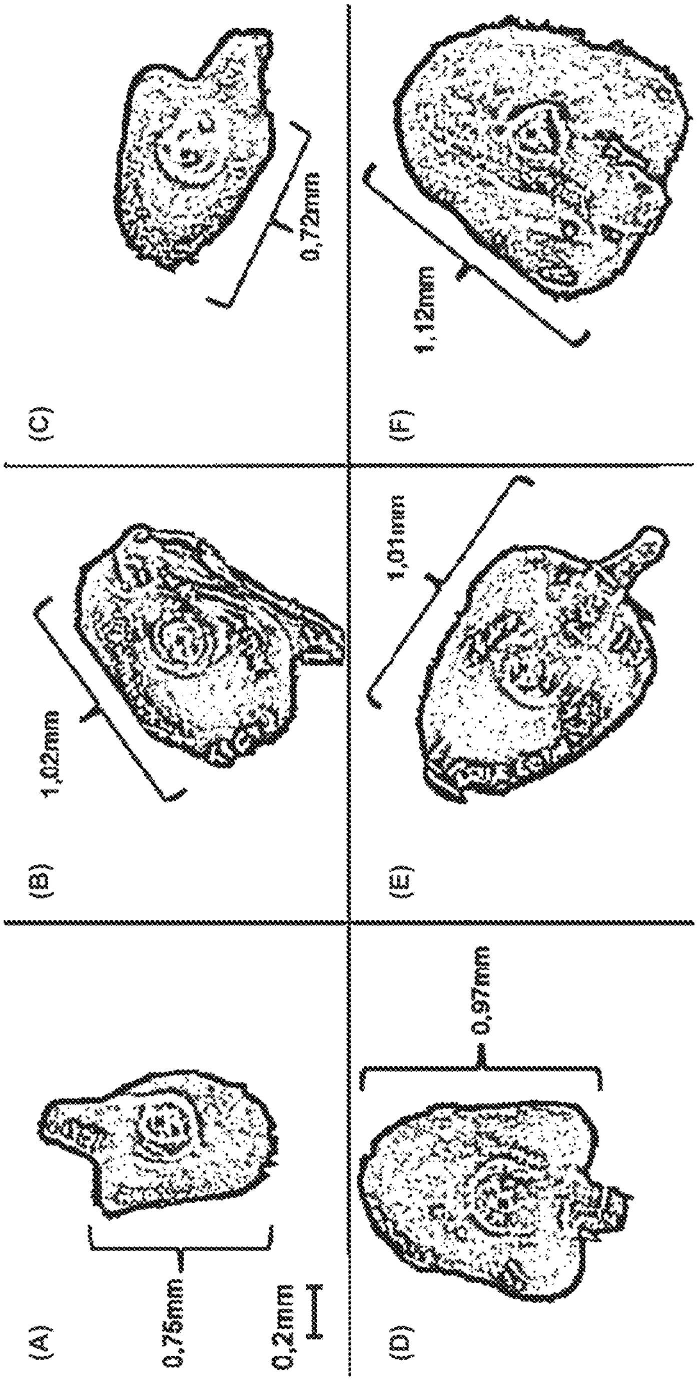
FIGS. 1 A-F (FIG. 1 A-F) show maize embryos of various sizes. In the embryos analysed here, the meristem can clearly be seen as the discoid structure in the centre of the embryo. Depending on the size and the stage of development of the embryos, the meristem is at different stages of development and easy or hard to detect. In addition, the meristem is also marked with an asterisk (*).

The term "plant" or "plant cell" as used herein refers to plant organisms, plant organs, differentiated and undifferentiated plant tissues, plant cells, seeds and their progeny or descendants. "Plant cells" includes, for example, cells of seeds, mature and immature embryos, meristematic tissues, seedlings, callus tissue, leaves, flowers, roots, plant buds, gametophytes, sporophytes, pollen and microspores, protoplasts, macroalgae and microalgae.

The term "fertile plants" as used herein refers to a fertile plant capable of reproduction, i.e. a fertile plant is a plant that can produce living male and female gametes. A male-sterile plant, accordingly, is a plant that cannot produce living male gametes, but which may be female-fertile. A female-sterile plant is a plant that cannot produce living female gametes, wherein the plant may still be male-fertile.

"Plant material" as used here means any material which can be obtained from a plant in any stage of development. The term thus encompasses plant cells, tissue and organs as well as formed plant structures as well as, if relevant, sub-cellular components such as nucleic acids, polypeptides, as well as all chemical plant substances which are present inside a plant cell and/or can be produced by it.

The term "chromosomally or extrachromosomally integrated" as used herein means the transient introduction and/or the formation of one or more recombinant construct/constructs of the present invention and thus to the subsequent fate of the one or more recombinant construct/constructs in a target plant structure, for example a cell, wherein both the one or more recombinant construct(s) and also the conditions for introduction thereof are maintained in a manner such that no integration of the at least one recombinant construct takes place in the endogenous nucleic acid material of a target plant structure comprising the genome or extrachromosomal nucleic acid of the target plant structure, for example a cell, so that the at least one recombinant construct is not chromosomally or extrachromosomally integrated into the endogenous DNA/RNA of the target cell and thus not passed on to the descendants of the cells. The one or more recombinant construct(s) or its transcription or translation products are thus only temporarily active in the target cell, i.e. transient, constitutive or inducible, but cannot be inherited by the descendants of the target cells, i.e. they are also not actively present in the descendants of a target cell.

The term, "homologous recombination," as used herein, indicates a process that takes place in all organisms. This requires homologous, double-strand DNA sections. "Homologous" therefore means that there is a large similarity in the nucleotide sequences of two sequences. With naturally occurring double-strand breaks, damage can be repaired through homologous recombination, in that the data on the intact chromatid in the genome of an organism can be used as a template. If a targeted and precise double-strand break is inserted in a nucleic acid target region of interest in the framework of the genome editing, in accordance with the present disclosure, homologous recombination can also be used here to repair the break, wherein, consequently, the targeted drafting of a DNA repair matrix may be used to obtain the targeted effect on the nucleic acid target regions of interest that are to be repaired. Different organism are differentiated with regard to the ratio of homologous to non-homologous recombinations, as occurs in nature (see above, NHEJ). In general, the length of the homologous region affects the frequency of homologous recombination events, i.e. a longer homologous region results in a greater frequency. The length of the homologous region used to obtain homologous recombination depends on the species. In some cases, it may be necessary to use at least five kilo-bases (kb) of homology, but homologous recombination has also been observed in a homologous region having only approximately 25 base pairs (bp).

"Homology directed repair" (HDR) refers to a cellular mechanism for repairing double-strand as well as single-strand DNA breaks. HDR thus comprises elements of homologous recombination, as well as the so-called single-strand annealing (SSA) (Lieber Michael et al., Annu. Rev. Bichem. 79: 181-211, 2010). The most frequent form of HDR in a cell is homologous recombination, wherein this type of repair also requires the highest sequence homology between donor and acceptor DNA. Other forms of HDR comprise single-strand annealing (SSA). SSA is non-conserving, and occurs naturally between direct repetitions of >30 bp, and results in deletions. HDR is obtained with nickings, i.e. with single-strand breaks, via a mechanism other than HDR with double-strand breaks (Davis and Maizels PNAS, 2014 E924-32). Because, in accordance with the present disclosure, CRISPR nucleases are proposed that induce both double-strand breaks as well as single-strand breaks, the term, "HDR," or homologous recombination, therefore refers to repairing a single-strand break or a double-strand break that has been inserted in a targeted manner, with the use of a suitable repair matrix.

"Herbicide resistance" and "herbicide tolerance," as used herein, refer to the resistance or tolerance capacity of a plant or a plant cell to the effects of a herbicide or pesticide. This property is normally obtained through at least one protein or one RNA, which has been either artificially inserted in a plant cell, e.g. as a transgene, or which may be acquired through (targeted) modification of an endogenous gene.

The term "progeny or descendants" as used herein means, in the context of a recombinant microorganism, a plant or a cell in accordance with the present disclosure, the descendants of such an organism or such a cell which derive from the original organism or the original cell from natural reproductive asexual cell division and differentiation processes. The skilled person in this field is aware that mutations in the genome of an organism can be introduced during cell division and differentiation in a natural manner, whereupon the progeny or descendant differs genomically from the parent organism, but can still be assigned to the same (sub)species. Even such progeny modified by natural processes which introduce modifications into other DNA regions in addition to the specifically introduced modification are thus comprised in the term "progeny or descendants" in the present invention.

The term, "CRISPR nuclease," as used herein, refers in general to a nuclease as it occurs in a naturally occurring CRISPR system, as well as to modifications, mutations, and catalytically active fragments thereof. In a naturally occurring CRISPR locus, the CRISPR nuclease is the molecule that forms the effector molecule, and can recognize and/or cleave a nucleic acid target structure through interaction with a crRNA and, optionally, a tracrRNA, or together with an artificial gRNA. CRISPR nucleases therefore comprise Cas nucleases, Cpf1 nucleases, or other CRISPR effector domains and/or nuclease domains, comprising Csf1 and combinations and variations thereof. Moreover, this term also comprises nucleases that have been modified in a targeted manner, each of which is converted to nicking enzymes for obtaining single-strand breaks, or nuclease-null variations that are converted for bonding and recognition purposes, but not for obtaining a double-strand break. Because the term "CRISPR/Cas has meanwhile become established as a synonym for all types of CRISPR systems in the relevant references, this term shall be used in accordance with the present disclosure for any CRISPR type I-V system, as well as the associated effector proteins, if not specifically indicated otherwise.

The term "vector" or "vector system" as used herein means a transport means which can introduce a recombinant construct, comprising nucleic acids or even polypeptides as well as further sequences such as regulatory sequences or localization sequences directly or indirectly into a desired target cell or target plant structure, into the desired cellular compartment. Direct introduction is carried out directly into a target plant cell or target plant structure which contains nucleic acids which are to be specifically modified in accordance with the present disclosure. The indirect introduction encompasses introducing into a structure cells of leaves or other plant organs and tissues, for example, which do not directly comprise the target plant cells of interest, but which ensure the systematic propagation and transport of the vector comprising a recombinant construct in accordance with the present disclosure into the target plant structure, i.e. meristematic tissues or cells or stem cells. The term "vector" or "vector system" as used herein in the context of transfection of amino acid sequences encompasses suitable agents for peptide or protein transfection such as, for example, ionic lipid mixtures or agents which are suitable for transfection of a nucleic acid such as, for example, carrier materials through which nucleic acid and amino acid sequences can be introduced into a cell by means of particle bombardment, for example using gold and tungsten particles. Furthermore, in particular when applying the method and constructs disclosed herein, this term also encompasses viral vectors, i.e. modified viruses such as, for example, those which derive from one of the following viruses: Maize Streak Virus (MSV), Barley Stripe Mosaic Virus (BSMV), Brome Mosaic virus (BMV, access numbers: X58456; RNA2: X58457; RNA3: X58458), Maize Stripe Virus (MSpV), Maize Rayado Fino virus (MYDV), Maize Yellow Dwarf Virus (MYDV), Maize Dwarf Mosaic Virus (MDMV), Positive strand RNA viruses of the Benyviridae family, e.g. Beet necrotic yellow vein virus (access numbers: RNA1: NC_003514; RNA2: NC_003515; RNA3: NC_003516; RNA4: NC_003517) or the Bromoviridae family, e.g. viruses of the Alfalfa mosaic virus genus (access numbers: RNA1: NC_001495; RNA2: NC_002024; RNA3: NC_002025) or the Bromovirus genus, e.g. BMV (see above), or the Cucumovirus genus, e.g. Cucumber mosaic virus (access numbers: RNA1: NC_002034; RNA2: NC_002035; RNA3: NC_001440), or the Oleavirus genus, dsDNA viruses of the Caulimoviridae family, in particular the Badnavirus or Caulimovirus families, e.g. various Banana streak viruses (see, e.g., access numbers: NC_007002, NC_015507, NC_006955 or NC_003381) or Cauliflower mosaic virus (access number: NC_001497), or viruses of the Cavemovirus, Petuvirus, Rosadnavirus, Solendovirus, Soymovirus or Tungrovirus genus, positive strand RNA viruses of the Closteroviridae family, e.g. the genus Ampelovirus, Crinivirus, e.g. Lettuce infectious yellows virus (access numbers: RNA1: NC_003617; RNA2: NC_003618) or Tomato chlorosis virus (access numbers: RNA1: NC_007340; RNA2: NC_007341), Closterovirus, e.g. Beet yellows virus (access number: NC_001598), or Velarivirus, single-strand DNA (+/−) viruses of the Geminiviridae family, e.g. viruses of the Becurtovirus, Begomovirus family, e.g. Bean golden yellow mosaic virus, Tobacco curly shoot virus, Tobacco mottle leaf curl virus, Tomato chlorotic mottle virus, Tomato dwarf leaf virus, Tomato golden mosaic virus, Tomato leaf curl virus, Tomato mottle virus, or Tomato yellow spot virus, or Geminiviridae of the Curtovirus genus, e.g. Beet curly top virus, or Geminiviridae of the genus Topocuvirus, Turncurtvirus or Mastrevirus, e.g. Maize streak virus (see above), Tobacco yellow dwarf virus, Wheat dwarf virus, positive strand RNA viruses of the Luteoviridae family, e.g. the genus Luteovirus, e.g. Barley yellow dwarf virus-PA V (access number: NC_004750), or the genus Polerovirus, e.g. Potato leafroll virus (access number: NC_001747), single-strand DNA viruses of the Nanoviridae family, comprising the genuses Nanovirus or Babuvirus, double-strand RNA viruses of the Partitiviridae family, comprising inter alia the families Alphapartitivirus, Betapartitivirus or Deltapartitivirus, viroids of the Pospiviroidae family, positive strand RNA viruses of the Potyviridae family, e.g. comprising the genuses Brambyvirus, Bymovirus, Ipomovirus, Macluravirus, Poacevirus, e.g. *Triticum* mosaic virus (access number: NC_012799), or Potyviridae of the genus Potyvirus, e.g. Beet mosaic virus (access number: NC_005304), Maize dwarf mosaic virus (access number: NC_003377), Potato virus Y (access number: NC_001616), or *Zea* mosaic virus (access number: NC_018833), or Potyviridae of the genus Tritimovirus, e.g. Brome streak mosaic virus (access number: NC_003501) or Wheat streak mosaic virus (access number: NC_001886), single-strand RNA viruses of the Pseudoviridae family, e.g. the genuses Pseudovirus, or Sirevirus, double-strand RNA viruses of the Reoviridae family, e.g. Rice dwarf virus (access numbers: RNA1: NC_003773; RNA2: NC_003774; RNA3: NC_003772; RNA4: NC_003761; RNA5: NC_003762; RNA6: NC_003763; RNA7: NC_003760; RNA8: NC_003764; RNA9: NC_003765; RNA10: NC_003766; RNA11: NC_003767; RNA12: NC_003768), positive strand RNA viruses of the Tombusviridae family, e.g. comprising the genuses Alphanecrovirus, Aureusvirus, Betanecrovirus, Carmovirus, Dianthovirus, Gallantivirus, Macanavirus, Machlomovirus, Panicovirus, Tombusvirus, Umbravirus or Zeavirus, e.g. Maize necrotic streak virus (access number: NC_007729), or positive strand RNA viruses of the Virgaviridae family, e.g. viruses of the genus Furovirus, Hordeivirus, e.g. Barley stripe mosaic virus (access numbers: RNA1: NC_003469; RNA2: NC_003481; RNA3: NC_003478), or the genus Pecluvirus, Pomovirus, Tobamovirus or Tobravirus, e.g. Tobacco rattle virus (access numbers: RNA1: NC_003805; RNA2: NC_003811), as well as negative strand RNA viruses of the order Mononegavirales, in particular the Rhabdoviridae family, e.g. Barley yellow striate mosaic virus (access number: KM213865) or Lettuce necrotic yellows virus (access number/specimen: NC_007642/AJ867584), positive strand RNA viruses of the order Picornavirales, in particular the Secoviridae family, e.g. the genuses Comovirus, Fabavirus, Nepovirus, Cheravirus, Sadwavirus, Sequivirus, Torradovirus, or Waikavirus, positive strand RNA viruses of the order Tymovirales, in particular the Alphaflexiviridae family, e.g. viruses of the genus Allexivirus, Lolavirus, Mandarivirus, or Potexvirus, Tymovirales, in particular of the Betaflexiviridae family, e.g. viruses of the genus Capillovirus, Carlavirus, Citrivirus, Foveavirus, Tepovirus, or Vitivirus, positive strand RNA viruses of the order Tymovirales, in particular the Tymoviridae family, e.g. viruses of the genus Maculavirus, Marafivirus, or Tymovirus, and bacterial vectors such as *Agrobacterium* spp., for example, with *Agrobacterium tumefaciens* being an example Finally, the term also encompasses suitable transport means for introducing linear nucleic acids (single-stranded or double-stranded) into a target cell. Knowing the constructs disclosed herein, the skilled person in this field will be aware of all further sequences which a vector must contain in order to be functional in a desired target cell. Conventional production, processing and use of vectors of this type is also known to the skilled person in this field.

The term "vector system" as used here denotes a system which consists of at least one or more vector(s) or contains it(them). Thus, a vector system may comprise a vector which contains/codes for two different recombinant constructs comprising nucleic acid and/or amino acid sequences. Furthermore, a vector system can also contain several vectors which in their turn contain/code for at least one nucleic acid or amino acid sequence in accordance with the present disclosure.

The terms, "quantitative trait locus" or "QTL," as used herein, refer to a DNA region that is associated with the differential expression of a quantitative phenotype trait in at least one defined genetic background, e.g. in at least one cultivation population. The QTL region comprises, or is closely linked to, the gene or genes that affect the trait in question. An allele of a QTL can therefore comprise numerous genes or other genetic factors inside a coherent genomic region, or a linkage group, e.g. a haplotype. An allele of a QTL can indicate a haplotype inside a defined window, wherein this window represents a coherent genomic region, which can be defined and (back)referenced with a set on one or more polymorphic markings. A haplotype can be defined by the unique fingerprints of alleles in each marking within the defined window.

As shall be explained in greater detail below, a number of methods are available to the person skilled in the art for identifying those plant target structures, comprising at least one meristematic cell, or an entire plant or a plant material or a plant cell thereof, which contribute to a targeted modification in their genomic DNA in or close to a nucleic acid target region, without the use of marker phenotypes that can be checked. Such methods are based on the direct analysis of a nucleic acid target region or target sequence of interest, in order to show an arbitrary modification in this nucleic acid region or sequence, and comprise, but are not limited to, PCR processes, sequencing processes, nuclease digestion, southern blots, northern blots, and any arbitrary combination thereof.

The term "nucleic acid" or "nucleic acid sequence" as used herein refers to both natural and synthetic deoxyribonucleic acids (DNA) and ribonucleic acids (RNA) which may also contain synthetic nucleotide analogues. The nucleic acids which are used in accordance with the present invention for the synthesis of a desired product such as protein or RNA or for specific control thereof, for example a CRISPR nuclease, including inter alia a Cas nuclease or a Cpf1 nuclease, or a gRNA, may if relevant be "adapted for use in a target plant structure". In one embodiment, said sequences may be codon-optimized, i.e. the codon use of a gene or a RNA is specifically adapted to the target cell/target organism. The skilled person in the field is familiar with the fact that a desired target gene which codes for a protein of interest can be modified without modification to the translated protein sequence in order to account for the specific species-dependent codon use. Thus, the nucleic acids of the present invention may specifically be adapted to or are adapted to the codon use of *Hordeum vulgare, Sorghum bicolor, Secale cereale, Triticale, Saccharum officinarium, Zea mays, Setaria italic, Oryza sativa, Oryza minuta, Oryza australiensis, Oryza alta, Triticum aestivum, Triticum durum, Hordeum bulbosum, Brachypodium distachyon, Hordeum marinum, Aegilops tauschii, Malus domestica, Beta vulgaris, Helianthus annuus, Daucus glochidiatus, Daucus pusillus, Daucus muricatus, Daucus carota, Eucalyptus grandis, Erythranthe guttata, Genlisea aurea, Nicotiana sylvestris, Nicotiana tabacum, Nicotiana tomentosiformis, Solanum lycopersicum, Solanum tuberosum, Coffea canephora, Vitis vinifera, Cucumis sativus, Morus notabilis, Arabidopsis thaliana, Arabidopsis lyrata, Arabidopsis arenosa, Crucihimalaya himalaica, Crucihimalaya wallichii, Cardamine flexuosa, Lepidium virginicum, Capsella bursa-pastoris, Olmarabidopsis pumila, Arabis hirsuta, Brassica napus, Brassica oleracea, Brassica rapa, Brassica juncacea, Brassica nigra, Raphanus sativus, Eruca vesicaria sativa, Citrus sinensis, Jatropha curcas, Glycine max, Gossypium* ssp. or *Populus trichocarpa*. Furthermore, in accordance with the present disclosure, the sequence of the gRNA or the sequence coding for the gRNA has to be adapted to the target nucleic acid region within a target plant structure. In a further embodiment, the gRNA or the sequence coding for the gRNA must additionally be adapted in the region which is responsible for interaction or coupling with a Cas nuclease and/or an effector domain.

The term "sequences" as used herein refers to nucleic acid sequences as well as to amino acid sequences wherein the respective sequence, in addition to natural nucleotides and amino acids, may also contain synthetic analogues or synthetic linkages as construction elements.

The terms "polypeptide", "polypeptide sequence", "protein sequence" and "amino acid sequence" are used interchangeably herein.

The term, "catalytically active fragment," as used herein, in particular in reference to CRISPR nucleases or variations thereof, refers to an amino acid nuclei sequence, derived from a given amino acid template sequence, with the condition that the resulting catalytically active fragment comprises all are part of the active centre of the template sequence, and therefore fulfils, as always, the same enzymatic function as the template sequence. These modifications, i.e. truncations, are well known to the skilled person in the field, and are particularly useful with sterically demanding enzymes, for creating multifaceted and more stable truncated enzymes, comprising the catalytically active fragment.

The term "regulatory sequence" as used herein refers to a nucleic acid or a protein sequence which can control cis or trans transcription and/or translation of a disclosed nucleic acid sequence.

The term "construct" or "recombinant construct" (used interchangeably herein) as used herein refers to a construct comprising, inter alia, plasmids or plasmid vectors, cosmids, yeast or bacterial artificial chromosomes (YACs and BACs), phagemid, bacteriophage vectors, an expression cassette, single-stranded or linear nucleic acid sequences or amino acid sequences, and viral vectors, i.e. modified viruses, which can be introduced into a target cell in accordance with the present disclosure. A recombinant construct in accordance with the invention may include CRISPR/Cas tools or parts thereof comprising at least one gRNA or at least one CRISPR nuclease variant and/or at least one further effector domain either in the form of a nucleic acid or an amino acid sequence. Furthermore, the recombinant construct may comprise regulatory sequences and/or localization sequences. The recombinant construct may be integrated into a plasmid vector and/or be isolated from a plasmid vector in the form of a polypeptide sequence or as a single-stranded or double-stranded nucleic acid not linked into a plasmid vector. After introduction, the construct is preferably extrachromosomal and not integrated into the genome and usually in the form of a double-stranded or single-stranded DNA, a double-stranded or single-stranded RNA or a polypeptide. "Plasmid vector," as used herein, relates to a construct that was originally obtained from a plasmid. These are normally circular, autonomous, replicating, extrachromosomal elements in the form of a double-strand nucleic acid sequence. In genetic engineering, these original plasmids are modified in a targeted manner, in that resistance genes, target nucleic acids, localization sequences, regulating sequences, etc. are inserted. The structural components of the original plasmid, such as the replication source, are maintained thereby. Numerous plasmid vectors for use in a target cell of interest are commercially available, and the modification thereof for specific cloning strategies is well known to the skilled person in the field. These known plasmid vectors are also referred to as standard vectors herein, wherein this is intended to imply that the basis vector is commercially available, and can be readily adapted to the needs of the respective experiment by a skilled person in the corresponding technological field.

The term, "enhancer" or "enhancer element," refers to a base/nucleotide sequence that has a characteristic sequence. An enhancer is one of the cis-regulatory elements, and can affect the bonding of a transcription complex on a promoter, and thus the transcription activity of a gene. A promoter, in turn, is a DNA sequence that can regulate the expression of an encoded sequence or a functional RNA. The promoter sequence is composed of both proximal as well as distal elements in relation to a regulated sequence, wherein the latter are frequently referred to as enhancers. Promoters may have a broad activity spectrum, and they may however also be active in tissues, or be development-specifically active, or activatable, e.g. in root cells, seeds, meristematic cells, etc. Likewise, there are constructively active as well as inducible promoters, wherein the induction can be stimulated through numerous environmental effects. There are strong promoters, which can activate a high level of transcription of the regulated sequence, as well as weak promoters. Promoters are frequently strongly regulated. A promoter in accordance with the present disclosure can be a promoter containing native endogens, or an artificial (synthetic/chimeric) or transgenic promoter, which has either been obtained from another species, or which is artificial or synthetic/chimeric, i.e. not present in this form in nature, or is comprised of various promoter elements.

The terms "3' non-encoding sequence," "transcription terminator," "terminator," or "terminator sequence," as used herein, refer to DNA sequences that are located upstream, i.e. in the 3'-direction of an encoding sequence, and comprise polyadenylation recognition sequences and other sequences that encode regulating sequences, which are capable of affecting the mRNA processing and/or the gene expression. The polyadenylation signal is normally characterized in that it causes poly-A-nucleotides to be added to the 3'-end of an mRNA precursor.

The term, "functionally linked," as used herein, refers to the bonding of nucleic acid sequences to a single nucleic acid fragment, such that the individual fragments of genes or regulating sequences, or other regions, are physically joined, and the individual sequences or segments can regulate, hybridize, or affect one another in a reciprocal manner. A promoter is then functionally linked to an encoding sequence, as long as it is capable of regulating the expression of this encoding sequence, i.e., the encoding sequence is then subject to the transcriptional regulation of the promoter in question. Moreover, encoding sequences can be functionally linked to regulating sequences, in either a clockwise or counter-clockwise orientation. Complementary RNA regions can basically be linked, directly or indirectly, at 5' with the target mRNA, or 3' with the target mRNA, or inside the target mRNA, or a first region of the complementarity is functionally linked at 5' and its complement is functionally linked at 3' to the target mRNA.

The terms, "stable transformation," or "stable integration," as used herein, refer to the insertion of a nucleic acid sequence of interest, e.g. in the form of a DNA repair matrix or a portion thereof, or a suitable vector, in the genome of a plant target structure of interest, wherein the genome comprises both the nucleic as well as the extra-nucleic genome, basically the genome of organelles, resulting in a genetically stable and thus inheritable modification of the genome. In contrast thereto, the terms, "transient transformation," or "transient insertion," or "transient integration," as used herein, refer to the insertion of a nucleic acid sequence of interest into a plant compartment of interest, comprising the nucleus, organelles or the cytoplasm, or a further compartment inside a plant cell, by means of which, either the transcription and/or translation, or, in the case of a direct-effector molecule (DNA, RNA, or protein), the inserted molecule or complexes, can deploy their effects inside the plant cell, but there is no stable integration in the genome of the cell, and thus no inheritance of the corresponding sequences and/or effector molecules.

The term, "genome," as used herein, relates to the totality of the genetic engineering material, comprising genes and non-encoding sequences present in a cell of an organism or a virus or an organelle, and therefore comprises both the nucleic (if present) as well as the extra-nucleic (if present) genome. Furthermore, the term, "genome," as used herein, relates to the entire set of chromosomes that are inherited as a (haploid) unit of an ancestor organism.

One incentive for developing new molecular markers in plant species is the potential for obtaining an increased efficiency in the targeted plant breeding through marker assisted selection (MAS). Gene technology marker-alleles, or alternatively, the quantitative trait loci (QTL) alleles mentioned above, are used for identifying plants or plant material, or a plant cell, which contain a desired genotype at a locus, or at numerous, unlinked or linked, loci, e.g. a haplotype, from which it can be assumed that they can pass on the desired genotype, together with a desired phenotype, to their descendants. With respect to the marker assisted selection, the term, "marker," as used herein, can therefore mean both marker and QTL loci. As soon as it has been determined for a desired phenotype and a polymorphic chromosomal locus, e.g. a marker locus or a QTL, that they segregate collectively, it is possible to use these polymorphic loci to select alleles that correspond to the desired phenotype. This approach is referred to as marker assisted selection (MAS). For this, a nucleic acid sequence corresponding to the marker nucleic acid is detected in a biological sample from a plant that is to be analysed. This can be demonstrated in the form of a hybridization of a nucleic acid probe on a marker, e.g. using allele-specific hybridization, southern blot analysis, northern blot analysis, in situ hybridization, hybridization of primers followed by PCR amplification of a region of the marker, or suchlike, or through any arbitrary combination thereof. Numerous methods for detecting markers are known to the skilled person in the field. After the presence or absence of a specific marker has been confirmed in the biological sample of interest, comprising at least one plant cell, preferably a meristematic cell, the plant is selected, and can be used subsequently for obtaining descendant plants through selective breeding. Likewise, the method according to the invention can be used for analysing an in planta meristematic cell, modified in a targeted manner, for the presence or absence of a specific marker. Preferably either female or male gametes or germ cells can be obtained from these meristematic cells, wherein in particular, the pollen of a plant modified in planta in this manner can be used directly for the subsequent selective breeding. Because there is a desire in classic plant breeding to insert traits of interest into a target plant, which encode a high yield and/or other desirable traits, in order to develop improved plants, there is a large interest in marker assisted selection, in order to reduce the time needed for elaborate and expensive testing of a large number of samples.

In accordance with the method of the present disclosure, phenotype markers can also be inserted in a plant target structure of interest in a targeted manner. A "phenotype marker," as used herein, refers to a marker that can be selected, which facilitates the checking and detectability of a plant cell or target structure of interest. Phenotype markers comprise, in general, either positive or negative selectable markers that can be used in a plant target structure of interest, such as visible markers or (antibiotic)resistant genes. Any type of plant marker that can be used in a plant target structure of interest, in particular a meristematic cell, can be used. Selectable or detectable markers normally comprise DNA segments that allow a cell, or a molecule marked with a "tag" inside a cell of interest, to be identified, often under specific conditions. Such markers can encode an activity, selected from, but not limited to, the production of RNA, peptides, or proteins, or the marker can provide a bonding site for RNA, peptides, proteins, inorganic and organic compounds or composites, etc. By way of example, selectable markers comprise, without being limited thereto, DNA segments that comprise restriction enzyme cleavage points, DNA segments comprising a fluorescent probe, DNA segments that encode products that provide resistance to otherwise toxic compounds, comprising antibiotics, e.g. spectinomycin, ampicillin, kanamycin, tetracycline, BASTA, neomycin-phosphotransferase II (NEO) and hygromycin-phosphotransferase (HPT), DNA segments that encode products that a plant target cell of interest would not have under natural conditions, e.g. tRNA genes, auxotrophic markers and the like, DNA segments that encode products that can be readily identified, in particular optically observable markers, e.g. phenotype markers such as β-galactosidases, GUS, fluorescent proteins, e.g. green fluorescent protein (GFP) and other fluorescent proteins, e.g. blue (CFP), yellow (YFP) or red (RFP) fluorescent proteins, and surface proteins, wherein those fluorescent proteins that exhibit a high fluorescence intensity are of particular interest, because these proteins can also be identified in deeper tissue layers if, instead of a single cell, a complex plant target structure or a plant material or a plant comprising numerous types of tissues or cells is to be analysed, new primer sites for PCR, the recording of DNA sequences that cannot be modified in accordance with the present disclosure by restriction endonucleases or other DNA modified enzymes or effector domains, DNA sequences that are used for specific modifications, e.g. epigenetic modifications, e.g. methylations, and DNA sequences that carry a PAM motif, which can be identified by a suitable CRISPR system in accordance with the present disclosure, and also DNA sequences that do not have a PAM motif, such as is naturally present in an endogenous plant genome sequence.

The methods according to the present invention can be used specifically for the breeding of plants, in order to insert a more transgenic trait in a plant, or the at least one plant target structure of interest, comprising at least one meristematic cell. Currently, transgenic traits are inserted randomly into the plant genome through transformation systems, wherein this takes place with physical/mechanical methods, or biologically, basically comprising the biolistic bombardment of plant material or the transformation with *Agrobacterium* and/or viral vectors. Over the last few years, specific protocols for the targeted insertion of transgenes into the genomes of plant cells have become increasingly more common. One important technology is basically site-specific integration (SSI), which allows for the targeted insertion of a transgene at the same site in a chromosome where a transgene has already been inserted. Moreover, over the last few years target-specific nuclease systems, drafted in a targeted manner, have become increasingly more common for facilitating the cleaving of a chromosomal target point through nucleases. The nucleases currently frequently used for genome editing in eukaryotic genomes comprise, e.g., mega-nucleases, zinc finger mega-nucleases, transcription activator-like effector nucleases (TALENs), and a constantly growing family of CRISPR nucleases, as well as variations that have been modified in a targeted manner and catalytically active fragments thereof. Specifically, CRISPR-based nuclease systems have proven to be extremely useful for high precision target-specific and programmable modification of nucleic acid target regions of interest. Because the CRISPR system is guided by a, frequently chimeric, gRNA, and does not allow purely protein-based targeting and target selection, this can result in a high level of reliability, and a reduction in undesired off-target effects. Moreover, the present disclosure offers further advantages for the CRISPR systems intrinsically composed of two components, specifically in that either a gRNA and/or a CRISPR nuclease, or a variation or catalytically active fragment thereof, can be provided with a further effector domain in a targeted manner, by means of which the variability and the range of use of the CRISPR system can be significantly expanded. Through a reprogramming of a CRISPR nuclease, a nuclease-null variation can be generated, which has lost its catalytic activity regarding the cleavage of DNA, but retained its DNA identification function. Through the combination of a molecule modified in this manner with an effector domain, in particular an effector domain that allows the epigenetic modulation of the genome of a target cell of interest, targeted epigenetic modifications, e.g. methylations, demethylations, acetylations, de-acetylations, phosphorylations, de-phosphorylations, or ubiquitinations, can be inserted in a histone protein, or another arbitrary protein inside a nucleosome in the cell nucleus of an eukaryotic cell of interest through the transient insertion of a CRISPR system, comprising at least one gRNA, at least one CRISPR nuclease, and at least one effector domain. As a result, targeted structural adaptations can be acquired in chromosomal regions to obtain modified states of the activation, even when the CRISPR system used for this is only inserted in a transient manner in a plant target structure of interest, and thus cannot be inherited, wherein these structural adaptations can then potentially be inherited.

The CRISPR systems disclosed herein, as well as the methods, in particular for targeted modification of at least one meristematic cell, are suited in particular for genome editing of plant cells or organisms, because off-target cleavage, which is frequently lethal for the target cells, or leads to undesired side effects, can be avoided through the high level of precision.

In one embodiment, the CRISPR nuclease components of the CRISPR system, or a variation, comprising nicking enzymes or nuclease null-variations, or an active fragment thereof, can be stably integrated in a plant genome. The expression of the CRISPR nuclease can be regulated by a plant-specific promoter, wherein the promoter is a constitutive promoter, a tissue-specific promoter, or an inducible promoter, e.g. a temperature, stress, development stage, or chemically, inducible promoter. Without a further essential component of the CRISPR system, i.e. a synthetic gRNA or a crRNA, the Cas nuclease is not capable of cleaving and/or identifying DNA, such that the mere presence of the Cas nuclease has little or no effect on the plant cell of interest and its metabolism. It is therefore an advantage of the method described herein for plant breeding and development, that cell lines or transgenic plant cells can be produced and propagated, which can express a Cas nuclease in a constitutive or inducible manner, or a variation or catalytically active fragment thereof, without having negative consequences for the cell integrity or viability. In order to acquire the activity of a CRISPR nuclease, whether it is stably integrated or provided in a transient manner, as described above, the presence of a gRNA or a crRNA is always necessary as a further reliability mechanism, which can be inserted into a plant target structure comprising at least one meristematic cell of interest in a stable or transient manner through a number of methods. The gRNA can be inserted in the cell as a transcribable DNA construct in the form of a genetic construct, such as a vector, wherein the gRNA transcribes, in either a constitutive or inducible manner, and can thus be provided in a functional manner. Alternatively, the gRNA can also be directly inserted in a plant target structure of interest as RNA. CRISPR nucleases and gRNA can thus be inserted simultaneously, or offset over time, wherein it is preferred that the gRNA and CRISPR nuclease are provided spatially and temporally such that the less stable RNA and the protein CRISPR nuclease can interact in the cell compartment of interest in a stoichiometrically ideal composition. If the target of the targeted modification is an RNA, then the compartment of interest is the cytoplasm of a target cell. If the nucleic acid target region of interest is genomic DNA or the nucleosome, then the compartment of interest is the cell nucleus of a plant target structure comprising at least one meristematic cell. In this configuration, it may be necessary that the gRNA and/or CRISPR nuclease are functionally linked to suitable nuclear localization sequences, in order that the CRISPR molecules, or the CRISPR complex composed of gRNA and CRISPR nucleases, as well as optional effector domains associated therewith, can reach their workplace. In another embodiment, if the nucleic acid target region is located in an organelle, in particular plastids, the presence of plastid localization sequences, e.g. mitochondrial localization sequences or chloroplast localization sequences, may be necessary for conducting the CRISPR tools to the workplace in accordance with the present disclosure.

A gRNA in accordance with the present disclosure can be a single molecule, or it may be used or present in the form of two separate RNAs, corresponding to crRNA and/or tracrRNA.

The term "recombinant" as used herein means a series of nucleic acids or amino acids, in particular not occurring naturally as a totality. Furthermore, the term, "recombinant" also comprises those nucleic acid or amino acid sequencings that occur naturally with regard to their nucleic acid or amino acid sequences, but can also be obtained through a targeted modification or synthesis, e.g. synthetically obtained nucleic acid or amino acid sequences, or through bio-engineering, e.g. nucleic acid or amino acid sequences that are obtained through a fermentative process, which may exist in nature, but can also be produced in a targeted manner in an organism other than the source organism.

The term, "epigenetics" or "epigenetic," as used herein, describes the structural adaptation of chromosomal regions in order to encode, signalize, conserve, and to potentially pass onto the descendants of a cell, modified states of the activation. Accordingly, potentially inheritable modifications are obtained via modifications that are not encoded in the genomic DNA itself.

When the present disclosure refers to the "sequence homologies" or "sequence identities" of nucleic acid sequences or protein sequences in the form of percentages, these refer to values as can be calculated using EMBOSS Water Pairwise Sequence Alignments (Nucleotide) www.ebi.ac.uk/Tools/psa/emboss_water/nucleotide.html) for nucleic acid sequences, or EMBOSS Water Pairwise Sequence Alignments (Protein) (www.ebi.ac.uk/Tools/psa/emboss_water) for amino acid sequences. Tools for local sequence alignments available from the European Molecular Biology Laboratory (EMBL) European Bioinformatics Institute (EBI) use a modified Smith-Waterman algorithm (see www.ebi.ac.uk/Tools/psa/and Smith, T. F. & Waterman, M. S. "Identification of common molecular subsequences" *Journal of Molecular Biology,* 1981 147 (1): 195-197). Furthermore, when carrying out the respective paired alignments of two sequences using the modified Smith-Waterman algorithm, the Default Parameters currently available from EMBL-EBI should be employed. These are as follows: (i) for amino acid sequences: Matrix=BLOSUM62, Gap open penalty=10 and Gap extend penalty=0.5 and (ii) for nucleic acid sequences: Matrix=DNAfull, Gap open penalty=10 and Gap extend penalty=0.5.

In the context of the present invention, the term "homologous sequences" or "homologues" or similar terms should be understood to be a reference to nucleic acid sequences which have the same phylogenetic origin. Preferably, proteins which are coded by these nucleic acid sequences have the same function. Homologous nucleic acid sequences exhibit at least 70%, preferably at least 75%, at least 80%, at least 85% or at least 90%, particularly preferably at least 95%, at least 96%, at least 97%, at least 98% or at least 99% sequence identity.

"Nucleic acid target regions" as used herein refer to any genomic as well as extrachromosomal DNA or RNA, in particular mRNA, of a target organism or a target cell which is to be modified and which can be modified by the method and constructs disclosed herein and is definitely not limited to gene regions, i.e. regions which carry the information for transcription of a mRNA region. These target regions are thus natural or endogenous target regions, wherein the terms, "endogenous" and "natural" are used interchangeably in this context. Moreover, the term, "nucleic acid target region," is not limited to an endogenous sequence. If an artificial nucleic acid target region has been previously inserted in a target cell of a target structure of interest, the term, "nucleic acid target region," can thus relate to an artificially inserted nucleic acid target region.

"Complementary" or "complementarity" as used herein describes the relationship between two DNA or RNA nucleic acid regions the nucleobases of which fit together like a lock and key and form hydrogen bonds between each other (hybridize). In this regard, Watson-Crick base pairing of the bases adenine and thymine/uracil or guanine and cytosine are considered to be complementary. Other pairings such as non-Watson-Crick pairing, reverse Watson-Crick, Hoogsteen, reverse Hoogsteen and wobble pairing are encompassed by the term "complementary" insofar as the corresponding base pairs form hydrogen bonds together, i.e. two different nucleic acid strands can hybridize together on the basis of their complementarity.

The term "hybridize" or "hybridization" should be understood to mean a procedure during which a single-stranded nucleic acid molecule is applied to by a maximally complementary nucleic acid strand, i.e. undergoes base pairing. Examples of standard methods for hybridization are described in Sambrook et al, 2001. Preferably, this should be understood to mean at least 65%, 70%, 75%, 80% or 85%, particularly preferably 90%, 91%, 92%, 93%, 94%, 95%, 96%, 97%, 98% or 99% of the bases of the nucleic acid sequence undergo base pairing with the maximally complementary nucleic acid strand. The possibility of such an application depends on the stringency of the hybridization conditions. The term "stringency" refers to the hybridization conditions. High stringency is then when a base pairing is made difficult and low stringency is when base pairing is facilitated. The stringency of the hybridization conditions depends, for example, on the concentration of salt or ionic strength and the temperature. In general, stringency can be increased by increasing the temperature and/or by reducing the salt content. The term "stringent hybridization conditions" should be understood to mean those conditions in which a hybridization primarily only occurs between homologous nucleic acid sequences. The term "hybridization conditions" then refers not only to the conditions prevailing during the actual application of the nucleic acids, but also on the conditions prevailing during the subsequent washing steps. Examples of stringent hybridization conditions are conditions in which overwhelmingly only those nucleic acids hybridize which exhibit at least 70%, preferably at least 75%, at least 80%, at least 85% or at least 90%, particularly preferably at least 95%, at least 96%, at least 97%, at least 98% or at least 99% sequence identity. Examples of stringent hybridization conditions are: hybridization 4×SSC at 65° C. and then washing in 0.1×SSC at 65° C. for a total of approximately 1 hour. The term "stringent hybridization conditions" used here can also mean: hybridization at 68° C. in 0.25 M sodium phosphate, pH 7.2, 7% SDS, 1 mM EDTA and 1% BSA for 16 hours and then washing twice using 2×SSC and 0.1% SDS at 68° C. Preferably, the hybridization is carried out under stringent conditions.

DETAILED DESCRIPTION

In one aspect, the present invention concerns a method for the production of a plant, a plant material or a plant cell, comprising the following steps: (i) providing a target plant structure which comprises at least one meristematic cell, wherein the at least one meristematic cell comprises at least one target nucleic acid region; (ii) providing at least one gRNA or providing one or more recombinant construct/constructs, wherein the recombinant construct(s) comprise at least one gRNA or a sequence coding for a gRNA, and optionally at least one regulatory sequence and/or a localization sequence, and optionally comprise the provision of at least one DNA repair template or HDR template, and the provision of at least one CRISPR nuclease or a catalytically active fragment thereof and/or an effector domain or providing one or more recombinant construct/constructs, wherein the recombinant construct(s) comprise(s) at least one CRISPR nuclease or a catalytically active fragment thereof or a sequence coding for a CRISPR nuclease or a catalytically active fragment thereof and/or at least one effector domain or a sequence coding for an effector domain, and optionally at least one regulatory sequence and/or a localization sequence, wherein the gRNA is both able to hybridize with a section of the target nucleic acid region and also to interact with the CRISPR nuclease or catalytically active fragment thereof and/or the effector domain; wherein, when the gRNA or the sequence coding for the gRNA and the CRISPR nuclease or the catalytically active fragment thereof or the sequence coding for the CRISPR nuclease or the catalytically active fragment thereof and/or the effector domain or the sequence coding for an effector domain is provided by one or more recombinant construct(s), the gRNA or the sequence coding for the gRNA and the CRISPR nuclease or the catalytically active fragment thereof or the sequence coding for the CRISPR nuclease or catalytically active fragment thereof and/or the effector domain or the sequence coding for an effector domain may be located on or in the same or on or in different recombinant constructs; optionally: wherein the gRNA or the sequence coding for the gRNA and/or the Cas nuclease or the sequence coding for the Cas nuclease and/or the effector domain or the sequence coding for an effector domain is adapted to use in a plant cell; (iii) optionally: providing at least one vector for introducing the recombinant construct/constructs; (iv) optionally: providing at least one further recombinant construct comprising a recombinant nucleic acid section for specific homology-directed repair of the target nucleic acid region in the target plant structure or insertion into the target nucleic acid region in the target plant structure preferably comprising at least one regulatory sequence and optionally at least one further vector for introducing the at least one further recombinant construct; (v) introducing the gRNA, the CRISPR nuclease or the catalytically active fragment thereof and/or the effector domain and/or the recombinant construct/constructs into the target plant structure; (vi) culturing the target plant structure under conditions which allow activation of the introduced gRNA, the CRISPR nuclease or catalytically active fragment thereof and/or the effector domain and/or the introduced recombinant construct/constructs and thus a specific modification of the target nucleic acid region in the target plant structure, in order to obtain a target plant structure comprising at least one meristematic cell which comprises the specific modification of the target nucleic acid region; (vii) obtaining a plant, a plant material or a plant cell from the specifically modified at least one meristematic cell; (viii) wherein the plant, the plant material or the plant cell is obtained directly by cell division and differentiation and optionally cross-fertilization or self-fertilization from the specifically modified at least one meristematic cell, and wherein the plant obtained, the plant material obtained or the plant cell obtained comprises the specific modification of the target nucleic acid region, wherein the recombinant construct(s) which comprise(s) at least one gRNA or a sequence coding for a gRNA, and/or at least one CRISPR nuclease or a catalytically active fragment thereof or a sequence coding for CRISPR nuclease or a catalytically active fragment thereof and/or at least one effector domain or a sequence coding for an effector domain is/are preferably not integrated chromosomally or extrachromosomally.

Meristematic cells belong to a tissue type in a plant which is described as the meristem or formation tissue. In the manner of stem cells in animal organisms, meristematic plant cells, because they are undifferentiated cells, have the ability (depending on environmental influences) of differentiating into any specialized cell type. Meristems in plant organisms are not only present during embryo development, but also throughout the life cycle, so that a specific modification of meristematic cells and tissue in accordance with the present invention is not limited to plant embryos or seedlings, but also in larger seedlings and mature plants, for example in meristems from which generative plant organs (for example in maize the tassel or the cob) can be generated.

In accordance with one embodiment, the meristematic cell is a mature or immature plant cell of a plant embryo or a seedling or a plant comprising at least one meristematic cell or meristematic tissue.

According to one embodiment of the method disclosed herein, the at least one recombinant construct, comprising at least one gRNA, one CRISPR nuclease, optionally at least one effector domain, and optionally at least one DNA repair matrix, can be inserted transiently into a target cell. In another embodiment, the at least one recombinant construct for obtaining at least one targeted modification of at least one nucleic acid target region can be stably inserted in a plant target structure of interest, comprising at least one meristematic cell. In another embodiment, at least one recombinant construct can be used to first stably insert a component of the CRISPR system, preferably a nuclease or a variant or catalytically active fragment thereof, and optionally an effector domain, in the genome of a plant target structure of interest. Subsequently, the other components, i.e. gRNA, are introduced onto at least one further recombinant construct, optionally in an effector domain, and optionally, a DNA repair matrix is inserted transiently into the plant target structure. In all of the embodiments, the individual components can be introduced onto the same of different constructs simultaneously or successively. In some embodiments of the transient introduction it may be advantageous to first insert the construct, which carries one or more product components of the system, i.e. CRISPR nucleases, variations or catalytically active fragments thereof, and optionally, an effector domain. Optionally, if this is a DNA construct, this at least one construct can then be first translated by the cell. The constructs that carry the gRNA and the optional further DNA repair matrices and/or effector domains can then be introduced in a temporally offset manner. As a result, it can be ensured that the less stable gRNA can interact directly with the CRISPR nuclease of interest, and that decomposition of the gRNA will not prevent an effective DNA editing.

In accordance with one embodiment, the meristematic cell is a cell of a monocotyledonous or dicotyledonous plant.

In accordance with the present invention, then, a special method is provided which can either directly or indirectly specifically control the small population of meristematic cells in a plant in all of its stages of development as a target plant structure. The at least one meristematic target cell may be controlled directly or indirectly, i.e. at least one recombinant construct in accordance with the present disclosure may be introduced directly into the at least one meristematic target cell or the at least one recombinant construct may be introduced into any plant cell or any plant tissue with the aid of a suitable vector, wherein the at least one recombinant construct can then be transported to the target plant structure. This is accomplished by means of the systemic propagation of at least one recombinant construct introduced into a plant cell or into a plant tissue by means of a vector.

The term "target plant structure" as used herein encompasses at least one meristematic plant cell which may be present as tissue, plant material, as a whole plant or as isolated cell, wherein the meristematic plant cell also contains at least one nucleic acid target region. The at least one target nucleic acid region contained in the target plant structure comprises DNA and RNA sequences and may be present in the target structure chromosomally or extrachromosomally. The targeted CRISPR-based methods for modifying a nucleic acid target region of interest can thus be used with the modification of genomic DNA, comprising the epigenetic modification of genomic DNA, or the modification of plastid or mitochondrial DNA, as with the modification of RNA in the form of silencing.

In one aspect of the present invention, which concerns the introduction of a specific nucleic acid modification into a non-chromosomal target structure, the term "target plant structure" as used herein encompasses at least one plant cell which may be present as tissue, plant material, as a whole plant or as isolated cells, wherein the plant cell additionally contains at least one target nucleic acid region comprising DNA and RNA.

In accordance with one aspect of the present invention, at least one target nucleic acid region in a meristematic plant cell as the target structure is modified by transiently introduced CRISPR/Cas tools and/or further effector domains if appropriate. Since the at least one meristematic cell modified in this manner can directly and immediately pass on the specific modification in the target nucleic acid region by subsequent cell division and differentiation to its descendants, the method of the present invention does not require any more crossing and selection steps in order to provide a plant, plant material or a plant cell with the desired target modification. Moreover, from embryonal or even from secondary meristems such as pollen or ovaries, for example, optionally with self-fertilization or cross-fertilization, plant organisms or target plant structures may be obtained which carry the specifically introduced modification.

In one embodiment, the method of the present invention has the further advantage that the CRISPR/Cas tools and/or any further effector domains are introduced into the target plant structure, preferably a meristematic cell or a meristematic tissue, in only a transient manner, so that no stable integration of the CRISPR/Cas tools such as CRISPR nuclease and gRNA and possible regulatory sequences as well as other effector domains occurs into the endogenous chromosomal or endogenous extrachromosomal nucleic acids of the target plant structure.

In accordance with the present disclosure it was found that, by exploiting the mechanism of action of RNA-directed DNA modification of the CRISPR/Cas tools, further effector domains in accordance with the method provided herein can be introduced, whereupon the spectrum of specific genome editing can be broadened. Either the CRISPR nuclease variant or the catalytically active fragment thereof or the gRNA or both may be linked with an effector domain.

An "effector domain" as used herein encompasses DNA- or RNA-modified or DNA- or RNA-binding polypeptides or nucleic acids, encompassing all types of monomeric, dimeric or multimeric nucleases, such as TALE nucleases, meganucleases, zinc finger nucleases, ribonucleases, deoxyribonucleases, exonucleases, endonucleases and restriction endonucleases of type I, II, III or IV and the like and including nickases, transcription activators and suppressors, phosphatases, glycosylases or enzymes which can cause epigenetic modifications, examples of which are acetylases, methylases, methyl transferases, proteins which can bind methylated DNA, or histone deacetylases, aptamers, comprising single-stranded DNA or RNA sequences as well as peptides, fluorescent proteins, marker nucleic acid sequences or marker amino acid sequences and the like, and combinations thereof. Concerning enzymes or polypeptides in general, the term "effector domain" also means a catalytic domain or nuclear domain of the respective enzyme or polypeptide, for example a binder protein, wherein the catalytic domain or nuclear domain is still capable of carrying out the enzymatic or binding function of the respective native enzyme or polypeptide. The design of such truncated domains and their adaptation to the desired function is known to the skilled person in this field.

In this regard, methods and constructs are provided in which gRNA and/or CRISPR nuclease or the catalytically active fragment thereof already linked to a further effector domain can be provided as or on a recombinant construct. The gRNA and/or the CRISPR nuclease, comprising at least one effector domain, are then introduced onto at least one recombinant construct in a target structure, in order to form a functional complex there, following transcription and, optionally, translation.

In a further embodiment, a method is provided in which the at least one gRNA or the at least one CRISPR nuclease or the catalytically active fragment thereof and/or at least one further effector domain is provided separately on different recombinant constructs. In accordance with this method, the gRNA component may be provided as DNA or RNA, the CRISPR nuclease or variant or the catalytically active fragment thereof may be provided as DNA or RNA or as a polypeptide sequence, and the effector domain may be provided as DNA or RNA or as a polypeptide sequence. The gRNA and the CRISPR nucleases, optionally comprising at least one effector domain, can thus be pre-assembled in vitro, and then inserted into a target structure.

According to one embodiment of the present invention, which comprises the simultaneous insertion of at least one gRNA and at least one CRISPR nuclease variation, or a catalytically active fragment thereof, together with at least one effector domain, the effector domain can be linked to the gRNA, or the CRISPR nuclease variation or the catalytically active fragment thereof, by a nucleic acid or amino acid linker, in order to ensure an ideal arrangement of the domains in relation to one another, and as a result, ensure their functionality through adequate flexibility of the domains in relation to one another. According to one embodiment, it is preferred that, in order to produce a plant, plant material, or a plant cell, optimized in a targeted manner, a DNA repair matrix is also provided, in addition to a gRNA and a CRISPR nuclease, a Cas or a Cpf1 nuclease, which can comprise independent effector domains. This embodiment is specifically preferred if a CRISPR nuclease, or a catalytically active fragment thereof, is used, which is capable of catalysing the introduction of a targeted DNA double-strand break in a nucleic acid target region of interest. The additional provision of a DNA repair matrix, either in the form of single-strand or double-strand DNA, can dominate over the natural and error-prone NHEJ repair mechanism of a plant cell, in order to bring about an even greater precision in the genome editing, as well as to provide the possibility of targeted introductions of insertions, mutations or deletions. The DNA repair matrix can be provided thereby in the form of a recombinant construct, either separately or on the same construct that is used for the introduction of the gRNA and/or the CRISPR nucleases. Alternatively, the DNA repair matrix can be inserted directly into a target cell or target structure of interest through transfection or transformation. Normally, a DNA repair matrix is designed such that it comprises left and right homology arms, which flank the position that is cleaved by a CRISPR nuclease. The two homology arms may exhibit a length of numerous hundreds of base pairs (bp), e.g. at least 100, at least 200, at least 300, at least 400, or at least 500 base pairs (bp), up to 1 kilobase (kb) or more. A homology region, i.e. a region where the sequences are aligned, can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1 100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases, so that the homology region contains enough homologies to permit a homologous recombination with the corresponding genomic region. "Sufficient homologies" in this context means that two polynucleotides exhibit sufficient structural similarity, and thus can serve as a substrate for a homologous recombination. Accordingly, the degree of homology of the respective homology arms of a DNA repair matrix may vary for the corresponding nucleic acid sequences. In general, with shorter homology regions, a higher degree of homology is needed in order to obtain an adequate accumulation of complementary nucleic acid sequences. The degree of homology, i.e. the sequence identity, can accordingly be at least approximately 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. In addition, the DNA repair matrix comprises a central construct, which carries a sequence, such as a transgene, that is to be introduced, or a modification that is to be introduced. The success of the introduction of a targeted modification in a nucleic acid target structure can be checked subsequently by (quantitative) PCR processes. Such a construct can be amplified via a PCR through primers that are specific for the two homology arms, the sequences of which can thus then be determined in order to establish whether the repair was made by the cells own NHEJ machinery, or by homologous recombination, assisted by the DNA repair matrix.

According to a further embodiment, first, at least one first plant, plant material, or plant cell is provided, which comprises at least one CRISPR nuclease, preferably a Cas nuclease or a Cpf1 nuclease, wherein the CRISPR nuclease is integrated in a stable or transient manner. This embodiment is specifically advantageous as long as the at least one first plant, plant material, or plant cell is later to be crossbred with at least one second plant, wherein the second plant, or at least one plant meristematic cell thereof, comprises a gRNA, with interacts with the Cas nuclease of the first plant, and can thus cause a targeted genome editing. The successful introduction of a targeted modification in a nucleic acid target region of interest in accordance with the present invention can be readily verified by a person skilled in the art using methods comprising polymerase chain reactions and the like, especially if nucleic acid target region of interest, and thus the region where the potential PCR primers can accumulate, is known, and is relevant for the design of a gRNA and/or a DNA repair matrix.

Activators and suppressors which may be used in accordance with the present invention preferably comprise SEQ ID NOs: 1-4 as well as sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences, which despite modification still carry out the same function as the sequences with the corresponding SEQ ID NOs.

A targeted modification according to the present disclosure can therefore comprise: (i) the exchange of at least one nucleotide of a nucleic acid target region; (ii) the deletion of at least one nucleotide in a nucleic acid target region; (iii) the insertion of at least one nucleotide in a nucleic acid target region; (iv) the targeted epigenetic modification of the region that regulates at least one nucleic acid target region; (v) the bonding and/or visualization to/of at least one nucleotide in a nucleic acid target region; or (vi) the interaction with and/or the cleavage of at least one RNA nucleic acid target region, or any combination of (i) through (vi). The methods according to the present invention can be used in particular for the precise and rapid trait development in a plant, plant material, or a plant cell.

In another embodiment of the first aspect of the present invention, a method is provided for producing a plant, plant material, or a plant cell, in which at least one plant target structure, comprising at least one meristematic cell, at least one gRNA, at least one CRISPR nuclease, or one catalytically active fragment thereof, and/or an effector domain, as well as at least one DNA repair matrix, is provided, wherein the targeted modification of the nucleic acid target region of interest comprises at least one heterologous sequence, i.e. a non-endogenous sequence, which comprises a gene selected from the group composed of a reporter gene, a selection marker, a gene that provides immunity to a disease, a herbicide resistance gene, a gene providing resistance to insects or nematodes, a gene involved in carbohydrate metabolism, a gene involved in fatty acid metabolism, a gene involved in amino acid metabolism, a gene participating in the plant development, a gene participating in the regulation of the plant growth, a gene participating in improving the yield of a plant material of interest, a gene participating in providing resistance to drought, a gene participating in providing heat resistance, a gene participating in providing resistance to a salt or salts, or a gene that is encoded by a functional RNA, wherein the functional RNA is selected from the group composed of an miRNA, a siRNA, or another RNA that can form an inverted repeat structure, e.g. a ddRNAi construct, that encodes both a clock-wise as well as a counter-clockwise strand, as well as a hairpin loop connecting the clockwise and the counter-clockwise strand, into which the genome of a plant target structure of interest, comprising at least one meristematic cell, is inserted.

Moreover, the methods according to the present disclosure are suitable for the formation of a complex trait locus. A complex trait locus is a chromosomal segment that has at least two modified nucleic acid regions and can be integrated in a nucleic acid target region according to the present disclosure in a single step, or sequentially, wherein the at least two modified nucleic acid regions are genetically linked to one another. The at least two modified nucleic acid regions both come from an endogenous plant locus, or the modification indicates a mutation or deletion of chromosomal DNA, or the at least two modified nucleic acid regions are transgenic sequences, or a combination thereof. Because the DNA repair matrix according to the present disclosure may have a central construct with a length of at least 1, 2, 3, 4, 5, 6, 7, 8, 9, 10, 20, 30, 40, 50, 60, 70, 80, 90, 100, 200, 300, 400, 500, 600, 700, 800, 1000, 2000, 3000, 4000 bp or more, the methods according to the present disclosure are suitable for introducing a complex trait locus in a plant target structure, comprising at least one meristematic cell, and a complex trait can be introduced with greater precision and efficiency, directly into a plant target structure, through the use of a CRISPR system and a DNA repair matrix. Because at least one plant, at least one plant material, or at least one plant cell can be obtained directly according to the methods of the present invention, there is the possibility of obtaining plant cells, plant material, or plants in a short period of time that have been modified in a targeted manner and are suitable for further crossbreeding, breeding, or further targeted modifications. In one embodiment, a first fertile plant, which has a first targeted modification in its genome, can be crossbred with a second plant, which has a second targeted modification in its genome, such that the targeted modifications can be physically linked, i.e. become part of the same nucleic acid molecule, wherein at least the first or the second, or both, plants are obtained according to the methods of the present disclosure. Artificial recognition sites in the form of a modified nucleic acid target region can be inserted in a locus through the intrinsic properties of the CRISPR system and knowledge of PAM motifs, as well as the interaction of an artificial gRNA with a CRISPR nuclease, in order to subsequently generate a nested complex locus, which comprises more than one targeted modification.

In another embodiment, a complex trait locus can also be directly inserted in a single step into a plant target structure comprising at least one meristematic cell. Because the CRISPR system according to the present disclosure can be scaled, in that it comprises numerous CRISPR nucleases, numerous gRNAs, optionally aligned with the CRISPR nucleases and/or a nucleic acid target region of interest, as well as at least one DNA repair matrix, which comprises at least one trait of interest that is to be integrated in the genome of a plant target structure, in addition to suitable homology arms, it is therefore not the case that just one trait can be affected in a targeted manner through the methods disclosed herein. Instead, it is possible to introduce a complex genotype trait in a plant target structure of interest in a stable manner that suppresses at least one phenotype trait.

In one embodiment according to the methods in the present disclosure, a process for producing a complex trait locus in a plant, plant material, or plant cell is therefore disclosed, wherein the method comprises the following steps: (a) selection of a genomic nucleic acid target region of interest in a plant, wherein the genomic nucleic acid target region comprises at least one first and one second nucleic acid target sequence; (b) bringing of at least one plant target structure, comprising at least one meristematic cell in contact with at least one first gRNA, one second gRNA, and optionally, at least one DNA repair matrix, and at lest one CRISPR nuclease or a catalytically active fragment thereof, wherein the first and the second gRNAs, and the at least one CRISPR nuclease or the catalytically active fragment thereof, can form a complex, which allows at least one CRISPR nuclease to introduce a double strand break, or a single strand break in the case of a nicking enzyme, in at least one first and one second nucleic acid target region, wherein, optionally, the at least one gRNA or the at least one CRISPR nuclease also comprises an effector domain, or can be associated with at least one effector domain; (c) identification of a cell from step (b), which comprises at least one first targeted modification on the first nucleic acid target sequence, and one second modification on a second nucleic acid target sequence; and optionally, (d) acquiring a first fertile plant from the at least one meristematic cell from step (c), wherein the fertile plant comprises the first targeted nucleic acid modification and the second targeted nucleic acid modification, wherein the first targeted nucleic acid modification and the second targeted nucleic acid modification are physically linked, i.e. located on the same nucleic acid strand.

In another embodiment, the method comprises a process for producing a complex trait locus in which at least two modified nucleic acid target sequences in a genomic nucleic acid target region of interest are modified in a plant, plant material, or plant cell, comprising the following steps: (a) selection of a genomic target region in a plant, plant material, or plant cell, comprising at least one meristematic cell, wherein the genomic target region comprises a first nucleic acid target sequence and a second nucleic acid target sequence; (b) bringing the at least one plant cell, comprising at least one meristematic cell, in contact with a first gRNA, a CRISPR nuclease, or a catalytically active fragment thereof, and optionally, a first donor DNA in the form of a DNA repair matrix, wherein the first gRNA, and the first CRISPR nuclease or the catalytically active fragment thereof, can form a complex that allows the CRISPR nuclease to insert a double strand break in the first nucleic acid target region, wherein the gRNA and/or the CRISPR nuclease can optionally comprise an effector domain, or be associated with an effector domain; (c) identification of the at least one meristematic cell from (b), which comprises the first targeted modification in the first nucleic acid target sequence; (d) acquiring a first fertile plant from the cell from step (c), wherein the first fertile plant comprises the first targeted modification; (e) bringing at least one plant, plant material, or plant cell, comprising at least one meristematic cell, in contact with a second gRNA, a second CRISPR nuclease or a catalytically active fragment thereof, and optionally, a second donor DNA in the form of a DNA repair matrix; (f) identification of a cell from step (e), wherein the cell comprises at least one second targeted modification in a second nucleic acid target sequence; (g) acquiring a second fertile plant from the cell from step (f), wherein the second fertile plant comprises the second targeted modification; and (h) obtaining fertile descendants from the second fertile plant from step (g), wherein the fertile descendant plants comprise both the first and the second targeted modification in a nucleic acid target region of interest, wherein the first targeted modification and the second targeted modification are physically linked.

The tools and methods disclosed herein are therefore valuable tools for targeted and efficient genome editing in higher plant life through the use of CRISPR tools, as well as the targeted homologous recombination, as a repair mechanism. In particular, through the method disclosed herein it is possible to circumvent the natural, error-prone, DNA repair mechanism, "non-homologous end joining" (NHEJ), which repair mechanism frequently leads to mutations or chromosomal deletions.

Selected traits, which, according to the present disclosure, are inserted into a plant, or can be triggered in a plant in the form a targeted modification through genome editing, comprise, without being limited thereto, resistances, comprising resistances to herbicides and pests, comprising prokaryotic and eukaryotic pests and viruses, e.g. bacteria, fungi, protozoa, plant pathogenic viruses, nematodes, insects or other animal organisms, obtaining higher yields, wherein the yields can relate to any desired plant product, e.g. an increased seed, fruit, carbohydrate, protein, or fat yield, or other plant metabolism products, comprising further primary metabolites or secondary metabolites, etc. One aim of the genome editing can be the endogenous 5-enolpyruvylshikimate-3-phosphate (EPSP) synthase gene. EPSP synthase naturally catalyses the conversion of phosphoenolpyruvate (PEP) and 3-phospho-shikimate into phosphate and 5-enolpyruvylshikimate-3-phosphate, and through the introduction of targeted mutations in this endogenous gene, a mutated EPSP synthase encoding gene can be obtained, which displays resistance to the herbicide N-(Phosphonomethyl)glycine, or a salt thereof.

Moreover, the methods according to the present disclosure can be used to introduce traits into a plant or to modify undesired traits in a targeted manner. There thus exists a greater desire for foodstuffs, or food products, that contain a low portion of acrylamide. Acrylamide, which has been categorized as carcinogenic, is an undesired by-product of the Maillard reaction of the amino acids asparagine and glutamine when they react with reduced sugars such as aldoses (e.g. glucose) or acyloines at temperatures above ca. 170° C. In starchy plant products such as potato products, there is therefore a large interest in reducing the content of potential educts that form acrylamides, such as asparagine, in order to create safe foodstuffs. Therefore, a potato plant can be created in a targeted manner through the method disclosed herein, which can be modified in a targeted manner such that the gene is affected in a targeted manner with respect to asparagine metabolism, by influencing an asparagine synthetase gene, or some other gene that is involved in asparagine metabolism.

Another endogenous target gene of interest in the genome of a plant cell, which can be modified such that it exhibits herbicide tolerance or resistance, is the acetohydroxy acid synthase (AHAS) gene. AHAS inhibitor herbicides are important herbicides in agriculture throughout the world. By modifying at least one allele of an endogenous AHAS gene with the method disclosed herein, a herbicide-tolerant, or resistant, plant cell can be generated, from which a fertile plant, plant material, or plant cell can therefore be obtained within a short period of time from the approach disclosed herein for targeting a meristematic cell.

Plants, in particular crop plants for energy and food production that are resistant to various environmental effects, have also become increasingly important. These environmental effects include heat, drought, cold, the condition of the ground and the associated salinity, etc., of the nutrient supply. Consequently, there is a high interest in creating plants that can thrive in changing, and frequently less than optimal, environmental conditions. These traits also include properties, which can be introduced into a plant, in particular a crop plant, in a targeted manner according to the methods of the present invention, or can be induced in at least one plant target structure of interest through the targeted modification of at least one nucleic acid target region.

Specifically with regard to the optimization of traits that are agronomically relevant in a plant, it may also be of interest to modify the endogenous sequences, thus controlling the sequences that function as regulatory sequences, comprising promoters, in a targeted manner.

In one embodiment according to the present invention, a method is therefore proposed for producing a plant, plant material, or a plant cell, which comprises at least one targeted modification in at least one meristematic cell of interest, wherein the targeted modification is the modification of an endogenous promoter. The targeted modification of the promoter can comprise the replacement of the promoter, or a fragment thereof, with another promoter, or a fragment thereof, wherein the promoter exchange results in some arbitrary combination of the following: an increased promoter activity, an increased promoter tissue specificity, an increased pathogen-induced promoter activity, a reduced promoter activity, a reduced promoter tissue specificity, a reduced pathogen-induced promoter activity, a new promoter activity, an inducible promoter activity, a pathogen-induced promoter activity, an expanded spectrum of possible gene expression, which is controlled by the promoter, a modification of the temporal, spatial, or developmental stage gene expression of a nucleic acid target region, in this case a plant gene of interest, by means of which active promoters that are only active in a specific development stage can likewise be active in another development stage, or, regarded spatially, can be active in another tissue, or a mutation of DNA bonding elements, and/or the deletion or addition of DNA bonding elements. The promoter, or the fragment thereof, which is to be modified according to the method of the present disclosure, can be a promoter or fragment thereof, which is endogenous in the plant cell of interest, but it can likewise be an artificial promoter or a transgenic promoter that is present in a plant target structure of interest, which comprises at least one meristematic cell. The promoter or fragment thereof that is to be modified is preferably integrated in the chromosomal or extrachromosomal genome of a plant target structure of interest comprising at least one meristematic cell. The promoter that is to be modified, or the fragment thereof, may also be present on an extrachromosomal, not genomically integrated construct, e.g. a plasmid.

These endogenous genes exhibit further interesting traits that encode relevant metabolism, information, and/or signal transduction proteins, e.g. kinases, transcription factors, zinc finger proteins or heat shock proteins. A targeted modification of these genes, and thus the encoded protein, makes it possible to intervene in numerous physiological processes, and thus provides the possibility of controlling metabolism processes in a targeted manner.

Furthermore, these genes, and the associated regulatory DNA elements and the regions that encode regulatory proteins, are nucleic acid target regions of interest that are responsible for the fertility and/or sterility of a plant.

Further biotic and abiotic factors, the reaction possibilities, on the basis of which a target plant of interest can be modified according to the method of the present disclosure through targeted modification, comprise nutrient shortages, reactions to exposure to toxic metals, trace elements, quality, in particular the quality of the seeds or grain, optimized nutrient content, starch quality and quantity, the size of the seeds or grains, the overall carbohydrate content, comprising starch, sucrose, and other mono-, di-, and polysaccharides, nitrogen fixation and use, fatty acid and/or oil content and/or the composition of the fat/oil, comprising saturated and unsaturated fats, an increase in the lysine content, or other amino acids, or sulphur in a plant product, or a combination of the aforementioned traits. Exemplary genes that can increase the grain yield include ammonia induced glutamate-dehydrogenases. Genes that affect the amino acid biosynthesis are, e.g. anthranilate synthases (EC 4.1.3.27).

In another embodiment, the nucleic acid target region that is to be modified in a targeted manner can be a promoter, wherein the targeted modification comprises the replacement of a native EPSPS1 promoter with a plant ubiquitin promoter.

In another embodiment, the nucleic acid target region that is to be used in a targeted manner can be a promoter, wherein the targeted modification of the promoter comprises replacement of an endogenous NPK1 promoter from maize with a stress-induced RAB17 maize promoter.

In one embodiment according to the present disclosure, the nucleic acid target region of interest can be a promoter, wherein the promoter that is to be modified in a targeted manner, is selected from the group comprising *Zea mays* PEPC1 promoters (Kausch et al. Plant Molecular Biology, 45:1-15, 2001), a *Zea mays* ubiquitin promoter (UBI1ZM PRO, see Christensen et al., Plant Molecular Biology 18:675-689, 1992), a *Zea mays* root met 2 promoter, an actin promoter from rice (US-ACTIN PRO, McElroy et al. The Plant Cell, Issue 2, 163-171, February 1990), a millet RCC3 promoter, a *Zea mays* GOS2 promoter, a *Zea mays* ACO2 promoter, or an oleosin promoter from *Zea mays*.

Because the methods disclosed herein, as outlined above, are also suitable for introducing targeted insertions into a nucleic acid target region of interest through the combination of a CRISPR system, in particular the combination of at least one specific CRISPR nuclease, or a variation or active fragment thereof, with a specific gRNA and a DNA repair matrix, and a further embodiment of the present disclosure pertains to the creation of a method for inserting a promoter or a promoter element in a genomic nucleic acid target region of interest in a plant target structure, comprising at least one meristematic cell, wherein the promoter insertion may result in any of the following phenotype modifications: an increased promoter activity, i.e., an increased promoter strength, an increased promoter tissue specificity, a new promoter activity, an inducible promoter activity, an expanded spectrum of gene expression for the gene that is regulated by the promoter, or that is set through the introduction of an exogenous promoter under the control of the newly introduced promoter, a modification of the temporal, spatial or developmental stage gene expression, a mutation of DNA bonding elements, and/or the addition of DNA bonding elements. Selected promoter elements that can be introduced according to the method of the present invention into a plant target structure comprising at least one meristematic cell of interest comprise, without being limited thereto, promoter nuclear elements, e.g. a CAAT-box, CCAAT box, Pribnow box, a bonding element that promotes pathogen inducibility, such as a W-box, S-box, or D-box, and/or a TATA box, regulatory sequences that can affect the translation, and/or a repressor system for obtaining an inducible expression, e.g. a Tet-operator/repressor/inducer element, or a sulfonylurea repressor/operator/inducer element. Further promoter/operator systems that can be regulated, which can be introduced into a plant target structure of interest for the purposes of the present disclosure, are known to the skilled person in the field. An exemplary promoter, which can be introduced as an exogenous promoter into a plant target structure of interest is the DRE promoter. This promoter was originally described by Yamaguchi-Shinozaki and Shinozaki (1994), Plant Cell 6, 251-265, as a cis-operating promoter element in promoters of the drought resistance gene, rd29A, which contains a conserved nuclear sequence comprising new base pairs, TACCGACAT. The introduction of a DRE promoter into an endogenous promoter of an arbitrary plant gene can therefore produce the inducible expression of the gene regulated by this promoter following a drought/aridity stimulus. A further example comprises ABA responsive elements, which contain a (c/T) ACGTGGC consensus sequence, and are found in numerous ABA and/or stress-regulated genes (Busk & Pages (1998), Plant Mol. Biol. 37:425-435). The insertion of 35 S enhancer or MMV enhancer into an endogenous promoter region in a plant cell can likewise increase the expression of the regulated gene. Therefore, through the targeted and precise modification of a promoter, or a portion thereof, in accordance with the present disclosure, the expression of a gene regulated by the promoter can be affected in a targeted manner, and the targeted modification introduced in this manner can be passed down directly to descendants, because the primary target cell is a meristematic cell, in accordance with the present invention, such that a fertile plant or plant material, or a plant cell therefrom, can be obtained, which has the desired promoter modification in its genome, and furthermore has a desired phenotype trait, which is the result of the gene regulated by the promoter through the modified expression.

In another embodiment according to the present disclosure, a method is provided, which relates to the targeted modification of a terminator, using the method disclosed herein. Accordingly, the nucleic acid target region of interest in a plant target structure comprising at least one meristematic cell can be a terminator, wherein the modification comprises the replacement of the terminator, or a fragment thereof, with another terminator, or a fragment thereof, wherein the terminator exchange may involve one or more of the following trait modifications: an increased terminator activity, an increase tissue specificity of the terminator, a reduced terminator activity, a reduced tissue specificity of the terminator, a mutation of DNA bonding elements and/or a deletion or addition of DNA bonding elements. The terminator (or the fragment thereof) that is to be modified in a targeted manner can be a terminator (or fragment thereof) of an endogenous gene, but it can likewise be an artificial, or chimeric or synthetic terminator, or a transgenic terminator. Likewise, the replacement terminator, thus the terminator, or fragment thereof, that is to be introduced through the method disclosed herein into the genome of a plant target structure of interest, can also be an endogenous terminator, an artificial terminator comprising a chimeric terminator, or a transgenic terminator. Exemplary terminators can be selected from the group composed of a maize ARGOS 8 or SRTF18 terminator, a tomato-PIN-II terminator, a millet-actin terminator, a millet-SB-GKAF terminator, a rice T28 terminator, an AT-T9 terminator, or a GZ-W64-A terminator. According to a preferred embodiment of the present invention, the terminator element that is to be replaced is used by the combination of at least one gRNA, aligned with at least one CRISPR nuclease and a nucleic acid target region of interest, together with a DNA repair matrix, wherein the central element of the DNA repair matrix serves as a donor sequence for the insertion of a terminator or terminator element of interest into a genomic nucleic acid target region of a plant target structure comprising at least one meristematic cell. In another embodiment, the gRNA/CRISPR nuclease/DNA repair matrix system disclosed herein is used in a meristematic cell to specifically delete a terminator, or a terminator element, that is genomically anchored in a plant target structure of interest.

In addition to promoters and terminators, other regulatory sequences exist in the genomes of eukaryotic cells that are important for regulating gene or functional RNA transcription. In one embodiment according to the present disclosure, the CRISPR system disclosed herein is used to modify or replace these regulatory sequences in a targeted manner in order to anchor these targeted modifications or replacements in a stable manner in the genome of a plant target structure of interest, to pass them on to the descendants via the initially modified meristematic cell, and thus be able to observe a targeted phenotype modification in the plant material or plant cells thereof obtained in this manner. Exemplary regulatory sequences according to the present disclosure comprise, without being limited thereto, 3'UTR (not translated) regions, 5'UTR regions, transcriptional activators, transcriptional enhancers or repressors, translation repressors, splicing factors, miRNAs, siRNAs, artificial miRNAs, incRNAs, promoter elements, CaMV 35S enhancers, MMV enhancer elements, SECIS elements, polyadenylation signals, and polyubiquitination sites.

In some embodiments, the genome editing, i.e. the targeted modification of a nucleic acid target region, comprises the targeted modification of replacement of regulatory elements, resulting in one or more of the following effects and/or phenotype expressions: modified protein translation, RNA cleavage, RNA splicing, and transcription or post-translational modification terminations. In one embodiment, the nucleic acid target region of interest, which is to be modified in a meristematic cell in a targeted manner, is a polyubiquitination site, wherein the targeted modification of the polyubiquitination site results in a modified protein degradation rate for a target protein of interest. The ubiquitin tag marks proteins, so that these can subsequently be reduced to proteasomes, or broken down through a process called autophagy. Proteasome inhibitors are known for being able to cause protein overproduction. The targeted modification of a nucleic acid target region of interest that encodes a protein of interest can therefore also lead to at least one amino acid modification of the protein of interest, wherein the modification allows for the subsequent polyubiquitination of the protein, i.e. a post-translational modification, which leads to a modification of the protein degradation, or the rate of protein degradation in the protein of interest.

In one embodiment, the genomic sequence of interest that is to be modified is a polyubiquitination site in a maize EPSP synthase gene, wherein the targeted modification of the polyubiquitination site results in an increased protein content, because the relevant protein is broken down at a lower rate.

In another embodiment, the genomic nucleic acid target sequence inside a meristematic cell that is to be modified in a targeted manner according to the method of the present invention is an intron site, wherein the targeted modification comprises the introduction of an intron-promoting motif into the intron, resulting in a modulation (increase/decrease) of the transcription activity of that gene comprising this intron.

In another embodiment, the nucleic acid target region of interest inside the genome of a plant target structure that is to be modified in a targeted manner is an intron site, wherein the targeted modification comprises the replacement of a specific intron, e.g. a soya bean EPSP synthase 1 intron, with another intron, e.g. a soya bean ubiquitin intron 1.

In one embodiment according to the present disclosure, the nucleic acid target sequence of interest that is to be modified in the genome of a meristematic cell of a plant of interest in a targeted manner is an intron or UTR site, wherein the targeted modification comprises the insertion of at least one micro RNA into this intron or UTR site, by means of which the expression of the gene that comprises the intron or UTR site also leads to the expression of this inserted micro RNA, which leads in turn to each target gene of interest being able to be "silenced" by the micro RNA that has been transcribed in this manner, whether it is an endogenous plant gene or the gene of a plant pest, without affecting the gene expression of the gene that carries the intron. Gene silencing or gene shutdown is a process in which the gene expression is reduced or shut off. The gene regulation in this case comprises the inhibition of the transfer of genetic information from the DNA to the mRNA, or the subsequent translation of the information stored on the mRNA into a protein. The processes that first take place after the transcription of the genetic information from the DNA onto the transferring mRNA are referred to as post-transcriptional gene silencing. These phenomena are frequently referred to as RNA interference or RNAi, which are regulatory processes in which specific RNA molecules participate, such as micro RNAs and siRNA or artificial ddRNAi hairpin constructs. The post transcriptional gene silencing can result in a concentrated degradation of a target mRNA of interest, impairing the formation of the gene products (protein). As a result, both endogenous as well as foreign products can be silenced or translated at a significantly lower frequency by means of a process called host-induced gene silencing (HIGS).

In one embodiment, the method disclosed herein is used for the targeted modification of a nucleic acid target region inside a plant target structure comprising at least one meristematic cell, using the combination of a CRISPR nuclease and a gRNA, and optionally, at least one effector domain, for the targeted modification of a transcription factor, i.e. to mutate or delete a transcription factor, or to insert a transcription factor into a nucleic acid target region of interest, using a suitable donor construct in the form of a DNa repair matrix. Exemplary transcription factors are the zinc finger transcription factor or the tapetal development and function factor (TDF; DE 10 2015 004 187 A1). The insertion of a single base pair into the encoding sequence of a transcription factor can result in a frameshift mutation, which in turn produces a new protein, which still displays DNA bonding activity, but has nevertheless lost its transcription activation capacity. Accordingly, the mutated zinc finger transcription factor protein, for example, competes to bond on cytokinin-oxidase gene promoters, and blocks the expression of cytokinin-oxidase. The reduction of the cytokinin-oxidase expression can increase the cytokinin level in rice plants, and promote panicle growth, whereas the ear growth in maize can be increased, and in general, the yield of a plant product of interest can be increased in numerous plants. The mutated TDF, on the other hand, can lead to male sterility in wheat, which can be implemented advantageously for the generation of hybrid wheat plants.

In another embodiment, the methods according to the present disclosure can be used for the targeted modification of splices in a genomic nucleic acid target region of interest in a plant target structure comprising at least one meristematic cell, or alternatively, to introduce splices into the genomic nucleic acid target region of interest. In eukaryotic cells, mRNA that is obtained from pre-mRNA molecules and subsequently subjected to a maturation process is used for the synthesis or expression of proteins. The pre-mRNA molecules are capped, spliced and subsequently stabilized by the addition of a poly-A strand. Eukaryotic cells have developed a complex process for the so-called splicing, which results in alternative variations of an original pre-mRNA molecule. In maize cells, the splicing process can be affected by splicings at the exon-intron bonding sites. One example of a canonical splicing site is AGGT. Sequences that encode genes may contain numerous alternative splicing sites, which can affect the overall efficiency of the pre-mRNA maturation process, and thus decisively limit the protein accumulation in cells. The gRNA/CRISPR nuclease pairs disclosed herein can be used, together with effector domains and a DNA repair matrix, which can be used to introduce a specific modification template into a plant target structure of interest, to modify a genomic nucleic acid target region of interest, such that a canonical splicing site is inserted or created at a specific position with high precision. In one embodiment, a plant EPSP synthase gene can be affected, for example, wherein the targeted modification of the gene comprises the modification of alternative splicing sites such that this targeted genome editing results in an increased production of functional gene transcriptions and gene products.

If the method disclosed herein has an endogenous plant gene as the nucleic acid target region, one or more of the following effects can be obtained through the targeted modification: an increased protein/enzyme activity, an increased functionality of a protein of interest, a reduced protein activity, a reduced protein functionality, a site-directed mutation, the replacement of a protein domain, a protein knock-out, a new protein functionality, or a modified protein functionality.

In one embodiment, the protein knock-out can comprise the introduction of a stop codon into the encoding sequence of interest.

In another embodiment, the protein knock-out can comprise the deletion of a start codon in an encoding sequence of interest.

In a further embodiment according to the present disclosure, the method disclosed herein can be used for the targeted silencing of a gene of interest.

In one embodiment, the aim is gene silencing of an endogenous plant gene, and in another embodiment, the target gene in which the expression is to be modified is not an endogenous plant gene, but instead, the gene of a plant pathogen, comprising a bacterial gene, a eukaryotic gene, comprising genes from protozoa, nematodes, fungi, insects, or other animal predators or plant pathogens, or a viral gene. The process referred to as RNAi for silencing genes takes place in the cytoplasm of a target structure of interest, because this is where the proteins and protein complexes needed for this are present in their functional form. The methods disclosed herein can thus be used in two different embodiments: (1) inverted gene fragments can be inserted into a nucleic acid target region of interest in a targeted manner through the method disclosed herein. These gene fragments can be subsequently transcribed, resulting in a double-strand RNA structure, e.g. an RNA hairpin structure, which can subsequently silence an endogenous or exogenous gene. Alternatively, in accordance with this first embodiment, as stated above, a nucleic acid sequence can also be introduced into a genomic nucleic acid target region in a targeted manner, which is encoded as functional RNA for an miRNA or a siRNA, wherein the siRNA or miRNA construct subsequently mediates the gene silencing or gene shut-down; (2) In a second embodiment, the CRISPR nucleases disclosed herein, and the associated gRNAs can be modified such that the artificial CRISPR system is specific to RNA as a nucleic acid target structure. For this, further effector domains can be associated with either the gRNA and/or the modified CRISPR nucleases of interest. This approach is advantageous in particular, when, instead of the targeted modification of a genomic target region, RNA is to be modified directly in the framework of a gene silencing approach.

In another embodiment, the methods disclosed herein are suitable for facilitating the trait mapping in the course of plant breeding. Regarding qualitative traits, the method disclosed herein can be used for the targeted elimination of candidate genes in the identified chromosomal region, in order to determine, on the basis of this, whether or not the deletion of a gene has an effect on the expression of a trait of interest. With quantitative traits, the expression of a trait of interest is controlled by multiple quantitative trait loci ("quantitative trait loci" (QTL)) of different and strongly varying sizes, complexities and statistical significance, which can also be located over numerous chromosomes scattered in the genome of a plant. A QTL is therefore a portion of a chromosome, or a portion of numerous chromosomes, that has an effect on the expression of a specific quantitative phenotype trait of interest. In differing from discrete traits, e.g. blossom colours in plants that are present in numerous different, differentiated states, quantitative or consistent traits can be measured without gradation on a continuous scale. In the case of a negative effect on QTL regions that define a complex trait, the methods described herein can thus be used in one embodiment in order to eliminate entire chromosomal regions inside a plant target structure comprising at least one meristematic cell of interest through marker assisted mapping, in order to mark specific regions for selective deletion, or redistribution.

In another embodiment of the present disclosure, the methods disclosed herein can be used to modify a genomic region of interest, which is flanked by two different nucleic acid target regions, according to the present disclosure, by two independent gRNA/CRISPR nuclease pairs, optionally using a DNA repair matrix. These modifications can take place simultaneously or successively. The removal preferably takes place simultaneously, and the resulting deletion can be subsequently repaired, optionally using a DNA repair matrix, by linking the two chromosomal ends without the deleted nucleic acid target region of interest.

In an alternative embodiment, a target region of interest can be modified through inversions, mutations in the cleavage sites, or duplication of a region of interest.

Exemplary herbicide resistant proteins or genes according to the present disclosure comprise acetolactate synthase (ALS) inhibitors, in particular if the herbicide is of a sulfonylurea type, and genes that encode a resistance to herbicides that inhibit the effects of glutamine synthases, e.g. phosphinothricin or BASTA, glyphosate, e.g. EPSP synthase genes and GAT genes, HPPD inhibitors, e.g. HPPD genes and suchlike. Thus, the bar gene encodes resistances to the herbicide BASTA, whereas the nptII gene provides resistances to the antibiotics kanamycin and geneticin (G418) and ALS gene mutants encode or provide resistance to the herbicide chlorsulfuron.

Exemplary genes according to the present disclosure that provide resistance to diseases or plant pathogens can provide resistance to plant pests such as the corn rootworm, *Bromius obscurus*, or the larva thereof, the European corn borer, etc. Disease resistance genes and/or insect resistance genes, comprise genes such as lysozymes or cecropins for protecting against microorganisms, or proteins such as defensins, glucanases or chitinases, for protecting against fungi pathogens, or *Bacillus thuringiensis* endotoxins, protease inhibitors, collagenases, lectins or glycosidases for controlling nematodes or insects.

Moreover, the methods according to the present disclosure, as indicated above, can be used for generating male- or female-sterile plants. The creation of male-sterile maize plants is advantageous because such a plant does not require the manual or mechanical removal of the tassel, i.e. the male inflorescence that produces pollen, which may be time consuming and expensive. Exemplary male sterility genes are, e.g. MS26, MS45, or MSCA1. Maize plants can be cultivated through both self-pollination as well as cross-pollination techniques. The maize plant has male flowers located on the tassel, and female flowers located on the ear, wherein the same plant has both male and female flowers. As a result, a maize plant can be reproduced through both self-pollination and cross-pollination. Breeding programs combine desirable traits of two or more strains, or from different sources in so-called breeding pools, from which new inbreeding strains or DH (double-haploid) strains are obtained, which are developed through selfing and subsequent selection of desired phenotypes. A hybrid maize type is a cross between two such inbreeding or DH strains, wherein each of the two parental inbreeding or DH strains carries one or more desirable characteristics that are lacking in the other parental strain, or that can complement the other strain. The new inbreeds or DHs are then crossed with other inbred or DH strains, and the hybrids thereof are examined in order to identify those plants of potential economical and agronomical interest. The hybrid descendants of the first generation (as well as descendants of the first generation in general) are labelled F1. The F1 hybrid is stronger and more robust than its parents. This effect, also referred to as heterosis, can express itself in a variety of ways, such as an increased vegetative growth or an increased yield. Hybrid maize seeds can be generated using a male-sterilization system for manual or mechanical tassel removal. By removing the male tassel, the female flowers of an inbreeding strain can only be pollinated with pollen from a male inbreeding strain of interest. The resulting seeds are therefore hybrids (F1) and produce hybrid plants. It is, however, frequently difficult to prevent self-pollination in female plants, particularly in field tests. As a result, seeds of a female inbreeding strain are then harvested together with hybrid seeds. As explained above, the seeds of a female inbreeding strain or DH strain are not as economically interesting as the F1 seeds, because no heterosis effect occurs. As a result, there is a high demand in plant breeding for male-sterile plants, which can be produced for the production of hybrid seeds for plants of agronomic interest, e.g. maize or wheat, which can be obtained ideally with low labour and production costs. Mutations that cause male-sterility in maize plants or wheat, for example, were obtained in the prior art through numerous methods, e.g. using X-rays or UV radiation, chemical treatment, or through the insertion of transposable elements (Chaubal et al., 2000 AM. J. Bot. 87:1193-1201). There is nevertheless still a strong demand for new genes that affect the male fertility in a plant of interest, and reliable methods for inserting precisely this gene, or a targeted modification of interest, into the genome of a plant of interest. Exemplary genes that are responsible for male sterility comprise the aborted microspores (AMS) gene from *Arabidopsis*, the *Arabidopsis* MS1 gene, the NEF1 gene, the *Arabidopsis* AtGPAT1 gene, the *Arabidopsis* dde2-2-mutation, the *Arabidopsis* faceless pollen-1 gene (flp1), the *Arabidopsis* male meiocyte death 1 gene, the tapetum-specific zinc finger gene (TAZ1), the tapetum determinant 1 gene, and the tapetal development and function (TDF) gene.

Because the methods disclosed herein are suitable for both stable as well as transient integration of a targeted modification in a nucleic acid target region of a plant target structure comprising at least one meristematic cell, a male- or female-sterile plant or plant material can be obtained directly, for example, because the targeted modification, which can be introduced in accordance with the method of the present invention into a meristematic cell, is passed on directly to the descendants of this cell. Using the technologies disclosed herein in vivo, a male- or female-sterile plant, in particular a maize plant, can therefore be obtained without further crossbreeding.

In one embodiment according to the present disclosure, a process is provided that is suitable for selecting or defining a plant, plant material, or a plant cell that comprises the at least one targeted modification in a nucleic acid target region, comprising a genomic target region or an RNA target region, wherein the method comprises the following steps:

a) Obtaining a first plant that comprises at least one CRISPR nuclease, or a variation or catalytically active fragment thereof in at least one meristematic cell, wherein the CRISPR nuclease is capable of inserting a double- or single-strand break in a genomic target region, or RNA nucleic acid target region, of interest;
b) Obtaining a second plant that comprises at least one gRNA, which is capable of forming a complex with the CRISPR nuclease, the variation, or the catalytically active fragment thereof, from step a);
c) Crossbreeding the first plant, from step a), with the second plant, from step b);
d) Checking the descendants from step c), or the cells thereof, for modifications in a nucleic acid target region of interest; and
e) Selection of a descendant plant, a plant material or a plant cell, which comprises the desired targeted modification in at least one nucleic acid target region of interest.

In a further embodiment of this selection process according to the present disclosure, the gRNA and/or the CRISPR nuclease also comprises at least one effector domain, which is associated with, or can be associated with, the gRNA and/or the CRISPR nuclease, and/or, if the gRNA and/or the CRISPR nuclease, as well as the at least one effector domain, are provided on a recombinant construct, an encoding sequence for an effector domain. The effector domain can be associated or linked in a covalent or non-covalent manner to the gRNA and/or the CRISPR nuclease.

In another embodiment according to the present disclosure, a process for selecting a plant, plant material, or a plant cell of interest is provided, which comprises a nucleic acid target region that has been modified in a targeted manner, either in its genome or in its transcriptome, i.e. the entirety of all of the transcribed genes or functional RNAs in a cell at a specific point in time, wherein the process comprises the following steps:

(a) Obtaining a first plant that comprises at least one CRISPR nuclease, or a variation or catalytically active fragment thereof, that is capable of causing a double-strand break, single-strand break, and/or specific DNA bond in a nucleic acid target region;
(b) Obtaining a second plant that comprises a gRNA, wherein the gRNA is capable of forming a complex with the CRISPR nuclease, or the variation or catalytically active fragment thereof, wherein the Cas nuclease, the variation, or the catalytically active fragment thereof, as well as the gRNA, are provided directly, or in the form of at least one recombinant construct, and wherein the gRNA and/or the CRISPR nuclease, or the variation or catalytically active fragment thereof, are associated with or can be associated with at least one effector domain or one encoding sequence for an effector domain; and wherein the first plant, from (a), or the second plant, from (b), also comprises a DNA repair matrix, which comprises at least one donor DNA as a central component thereof, wherein the DNA repair matrix is introduced directly, through transformation or transfection, or in a recombinant manner, in the form of at least one recombinant construct, into the first or second plant, plant material, of the plant cell;
(c) Crossbreeding the first plant, from step (a), with the second plant, from step (b) and optionally providing at least one gRNA and/or one DNA repair matrix, as long as this is not stably integrated in the genome of the first and/or second plant;
(d) Assessment of the descendants of the plant from step (c), or the plant cells thereof, with regard to whether a targeted modification can be observed in the at least one nucleic acid target region of interest; and
(e) Selection of a descendant plant, or a plant material or plant cell thereof, which comprises the desired insertion introduced into the at least one nucleic acid region of interest, wherein the insertion is introduced via the donor DNA as part of the DNA repair matrix.

The methods disclosed herein are therefore suitable for obtaining a high precision gene targeting of a transgene of interest, and/or also producing complex transgene trait loci, because, as explained above, according to the method of the present disclosure, multiple transgenes can also be inserted, either simultaneously or successively, into a plant target structure of interest comprising at least one meristematic cell. A more complex transgenic trait locus is a genomic locus that carries numerous transgenes that are genetically linked to one another. By inserting independent transgenes within 0.1, 0.2, 0.3, 0.4, 0.5, 1, 2, or even up to 5 centimorgans (cM) of one another, the transgenes can be configured as individual genetic loci (see, e.g., US 2013/0263324 A1). A centimorgan indicates the distance between two linked genes, markers, nucleic acid target regions, or loci, or an arbitrary pair thereof, wherein 1% of the meiosis products are recombinant. Therefore, 1 centimorgan is equivalent to a distance corresponding to 1% of the mean recombination frequency between the two linked genes, markers, nucleic acid target regions, loci, or an arbitrary pair thereof. After selecting the plant, plant material, or plant cell of interest, which comprises the transgene of interest, those plants that contain at least one transgene can then be crossbred, in order to produce an F1 plant, plant material, or plant cell, that contains both transgenes. One in five hundred of the descendants of these F1 plants would then comprise the two different transgenes, recombined on the same chromosome. The complex locus can then be used for further breeding as the only genetic locus having both transgenic traits. The process can be repeated as often as desired in accordance with the method disclosed herein, in order to collect as many traits as possible, or desired, in a complex locus. Subsequently, the chromosomal intervals that correlate with a phenotype or trait of interest can be identified. There are numerous methods available to the skilled person in this field for identifying chromosomal intervals. The boundaries of such chromosomal intervals are drawn such that they comprise markers that are linked to the gene that controls the trait of interest. In other words, the chromosomal intervals are drawn or defined such that each arbitrary marker lying within an interval, including the terminal markers that define the boundaries of the interval, can be used as a marker. In one embodiment, the chromosomal interval can comprise at least one QTL or more than one QTL. A strongly expressed proximity of the multiple QTLs in the same interval can however obscure the correlation of a specific marker with a specific QTL in the diagnostics, because a marker may indicate a link with more than one QTL. Conversely, it is sometimes unclear, if two markers that are close together display a segregation from the desired phenotype trait, whether each of these markers identifies the same QTL, or two different QTLs.

Furthermore, a plant, plant material, or a plant cell is disclosed, which is or can be obtained in accordance with one of the methods described above, in accordance with the first aspect of the present invention.

Methods for breeding and cultivating microorganisms and viruses which can be used in accordance with the present disclosure as vectors, are known to the skilled person in this field.

In one embodiment, the recombinant construct of the present invention is introduced into the target plant structure with the aid of at least one vector or vector system.

In another embodiment, the recombinant construct of the present invention is introduced into the target cell directly without an additional vector, preferably by mechanical methods, by transfection or by using endocytosis.

One embodiment of the present invention also envisages the introduction of at least one recombinant construct into a target plant structure.

Vectors and vector systems of the present invention encompass those which are selected from the group consisting of SEQ ID NOs:12-15 and 25-38, as well as sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences which, despite modification, still carry out the same function as the respective unmodified vector or vector system with the corresponding SEQ ID NO. The cited vectors and vector systems may include codon optimized or truncated recombinant constructs, or they may contain specific point mutations in order to ensure their activity in different target cells. The sequence of SEQ ID NO: 31 is a hybrid sequence with which the region between the BclI and the BssHII cleavage sites of the Fescue segment RNA3 of the Brom Mosaic Virus (see NCBI: DQ530425) is replaced with the corresponding section of the R_BMV_RNA3_SI13'A/G (Hema & Kao 2004, Journal of Virology) fragment. Further, in accordance with the present invention, an *Agrobacterium* spp. may be envisaged as a vector and may be used alone or in combination with other introduction means or vectors. In accordance with one embodiment, the vectors and vector systems cited above with SEQ ID NOs: 12-15 and 25-38 or sequences with the sequence homology cited above may be used for this purpose as a framework structure in order to introduce the recombinant constructs of the invention comprising at least one gRNA as well as at least one CRISPR nuclease and/or at least one effector domain into a target plant structure. The molecular biological methods and procedures required in this regard are familiar to the skilled person in this field.

Recombinant constructs of the present invention include those which are selected from the group consisting of SEQ ID NOs: 23 and 24 as well as sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences which, despite modification, still fulfil the same function as the respective unmodified recombinant construct with the corresponding SEQ ID NO. The cited recombinant constructs may comprise codon-optimized or truncated sequences or they may comprise specific point mutations in order to ensure or modify their activity or binding properties in various target cells. In SEQ ID NO:23, positions 16239-16258 correspond to the position for the respective gRNA of interest which can be modified depending on the target nucleic acid sequence. In SEQ ID NO:24 positions 16645-16664 correspond to the position of the respective gRNA of interest which can and must be modified depending on the target nucleic acid sequence.

In one aspect, the present invention concerns a method for the production of a plant, a plant material or a plant cell, wherein the recombinant construct is selected from SEQ ID NOs: 23 and 24, as well as sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences.

In a further aspect, the present invention concerns a plant, a plant material or a plant cell which can be obtained or is obtained by a method comprising introducing a recombinant construct in accordance with SEQ ID NOs: 23 and 24, as well as sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences, into a target plant structure which comprises at least one meristematic cell.

In a yet still further aspect, the present invention concerns the use of at least one recombinant construct in accordance with SEQ ID NOs: 23 and 24, as well as sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences, for the specific modification of at least one target nucleic acid region in a plant cell.

All Cas-polypeptide sequences as well as Cas-coding nucleic acid sequences which have been specially optimized for use in a plant cell or for which their coding constructs carry suitable regulatory sequences which can permit adequate transcription and/or translation in a plant cell in the cellular compartment provided therefor, including the cell nucleus, the cytosol, a mitochondrion, a plastid, including a chloroplast, are suitable for use in the present invention. Furthermore, in one embodiment the respective CRISPR nucleases must have their intrinsic nuclease function. Therefore, a catalytically active fragment derived from a native CRISPR nuclease can also be used as the CRISPR nuclease according to the present disclosure, as long as the catalytically active fragment still fulfils the same enzymatic catalytic function as the native enzyme from which it is derived.

Alternatively in an aspect of the present disclosure, Cas nickases or catalytically active fragments thereof may be used, i.e. Cas polypeptides which are modified such that they only cleave one DNA and do not produce a DNA double-stranded break, as in a native CRISPR nuclease. This means that firstly there is the possibility of an increased specificity, since in order to carry out a double-stranded break, two recombinant constructs including a Cas nickase have to be used. On the other hand, there is the possibility that a specifically offset double-stranded break can be introduced instead of a blunt cut.

Finally, in accordance with one aspect of the present disclosure, Cas-zero nucleases or catalytically active fragments thereof, i.e. variants which no longer have any nuclease activity, may also be used. In this regard, it raises the possibility that the CRISPR nuclease together with a further effector domain in accordance with the present disclosure, i.e. a further DNA- or RNA-modifying or DNA- or RNA-binding polypeptide or nucleic acids in accordance with the present invention may be used, whereupon the spectrum for introducing specific modifications into a target plant structure is broadened.

The skilled person in the field is aware that specific mutations in the catalytic domains of a CRISPR nuclease are of interest in order to "reprogram" these to a nickase or also a endonuclease-zero variant.

Examples of CRISPR nucleases or catalytically active fragments thereof or sequences coding CRISPR nucleases or catalytically active fragments thereof for application in the present disclosure are disclosed in SEQ ID NOs 16-22 and in UniProtKB/Swiss-Prot database accession no Q99ZW2.1 (SEQ ID NO: 39) and also comprise those sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences which, despite modification, still carry out the same function as the respective unmodified sequences with the corresponding SEQ ID NO or which are accessible under the said database accession number.

In a still further aspect of the present invention, the CRISPR/Cas system at the basis of the mechanism of activity of the RNA-controlled DNA modification is used so that an effector domain instead of or together with the CRISPR nuclease is directed by a specific adapted gRNA to the desired position of a target nucleic acid region in a target plant structure, so that the effector domain can be specifically placed in order to carry out the desired nucleic acid edit.

In one embodiment of this aspect, the target nucleic acid region is a genomic DNA.

In a further embodiment of this aspect, the target nucleic acid region is a mitochondrial or plastid DNA, wherein the recombinant construct comprises a localization sequence which comprises the localization of the recombinant construct in the corresponding target compartment, for example in a mitochondrion or a chloroplast.

In one embodiment, the CRISPR nuclease or catalytically active fragments thereof or the sequence coding for the CRISPR nuclease or catalytically active fragments thereof, and/or the effector domain or the sequence coding for the effector domain additionally comprises a sequence selected from a nuclear localization sequence, a plastid localization sequence, preferably a mitochondrial localization sequence and a chloroplast localization sequence. A nuclear localization process can be selected from SEQ ID NO: 49-58, which discloses the following sequences: simian virus 40 (SV40) monopartite: MAPKKKRKV; *A. tumefaciens* VirD2 (pTiA6): KRPRDRHDGELGGRKRAR; *A. tumefaciens* VirD2 (pTiC58): KRPREDDDGEPSERKRER; *A tumefaciens* VirE2 (pTiA6) #1: KLRPEDRYVQTERGRR; *A. tumefaciens* VirE2 (pTiC58) #1: KLRPEDRYIQTEKYGRR; *A. tumefaciens* VirE2 (pTiA6) #2: KRRYGGETEIKLKSK; *A. Tumefaciens* (PtiC58) #2: KTKYGSDTEIKLKSK; *A. rhizogenes* GALLS (pRiI 724): KRKRAAAKEEIDSRKKMARH; *A. rhizogenes* GALLS (pRiA4): KRKRVATKEEIEPHKKMARR; *A. Rhizogenes* GALLS VirD2 (pRiA4): KRPRVEDDGEPSERKRAR.

One or more nuclear localization sequences can be combined with an effector domain, which are preferably united on a plasmid vector.

In a further embodiment, the gRNA or the sequence coding for gRNA additionally comprises a sequence selected from a nuclear localization sequence, a plastid localization sequence, preferably a mitochondrial localization sequence and a chloroplast localization sequence.

In a yet still further embodiment of this aspect, the target nucleic acid region is a ribonucleic acid (RNS) in any plant compartment, for example the cytosol. In accordance with this embodiment, a specifically modified gRNA may be provided which is capable of interacting with a target RNA structure. The gRNA may in addition comprise a further effector domain, for example an aptamer.

The skilled person in the field will be aware that the design of the corresponding at least one gRNA which is used together with at least one CRISPR nuclease and/or with at least one effector domain, is dependent on the specificity and in particular the binding and recognition properties of the CRISPR nuclease and/or the effector domain as well as the target nucleic acid region which is to be specifically modified.

Wild type CRISPR nucleases, in particular of type Cas9, produce a blunt double-stranded break in the target DNA sequence, i.e. without a single-stranded DNA overhang. Moreover, these nucleases can also leave single nucleotide overhangs behind, resulting from offset cleavage of the two individual strands of a DNA double-strand. To this end, the endogenous DNA repair mechanisms of the target cell are activated comprising the so-called non-homologous end joining, NHEJ. This mechanism is prone to errors, however, in particular since hereby insertions and deletions (INDELs) can be introduced at the location of the double strand break. Thus mutations may be established at the sites where the individual DNA strands are re-joined. By means of NHEJ, single or plural gene knock-outs may be mediated, wherein after the specific DNA break, the DNA strands are brought together with a modified sequence that was obtained in a frameshift or another mutation, which can prevent the functional expression of one or more genes of interest, again by endogenous mechanisms. A further repair mechanism is homology-directed repair (HDR) or homologous recombination (HR). These mechanisms use homologous DNA as a template or matrix, from which the sequence information can be copied in order to repair a DNA break. At least one precise editing, insertion, or gene exchange can take place through the targeted provision of a DNA repair matrix, which is homologous over a specific length to a genomic DNA region in which a DNA break is to be induced inside a target cell of interest. The precise modifications obtained in this manner comprise no undesired or uncontrollable mutations, as is always desirable in any gene editing approach. Both repair mechanisms, NHEJ and HDR/HR, constitute naturally occurring mechanisms for DNA repair which are present in every cell disclosed herein.

In one embodiment according to all of the aspects of the present disclosure, a DNA repair matrix, or a repair template, is provided, which repairs a single-strand or double-strand break in a site oriented and precise manner, which was previously inserted by a CRISPR nuclease, or a variation or catalytically active fragment thereof, and/or an effector domain in a nucleic acid region of interest.

What is decisive for the site-directed introduction of the modification of a target nucleic acid region is, in accordance with the above mechanism of the type II CRISPR/Cas system, the specific selection and the specific design of the gRNA sequences in order to avoid cleavage of off-target regions other than the target region. The identification of suitable PAM motifs as a function of the CRISPR/Cas tools used and optional further effector domains and the use of this information for the design of suitable recombinant constructs is known to the skilled person in this field.

In accordance with one embodiment of the present disclosure, the genome or the extrachromosomal target nucleic acid region of a cell is thus initially investigated for suitable PAM sequences in order to be able to specifically design a suitable gRNA.

The term "guide RNA" or "gRNA" as used herein denotes a single stranded or double stranded or partially double stranded nucleic acid molecule which may consist of natural or synthetic RNA and/or of natural or synthetic DNA and has the function of being capable of building a complex with a CRISPR nuclease or a catalytically active fragment thereof, whereupon the CRISPR nuclease or the catalytically active fragment thereof is rendered capable of recognizing a target nucleic acid region. In addition, in addition to the CRISPR nuclease interaction domain, a gRNA functions as a recognition domain for specific hybridization to a complementary target nucleic acid molecule of interest. Thus, a gRNA comprises a crRNA and optionally, a tracrRNA, as explained above. The gRNA can thus be a synthetic dual molecule that unites numerous functionalities, or the gRNA can comprise only one functionality. The length of the crRNA and/or the tracrRNA can lie in a range of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more nucleotides. Consequently, gRNAs may form an intrinsic hairpin region by complementary base pairing, whereupon the natural tracrRNA/crRNA hairpin structure is imitated (see Jinek et al, 2012, above) and in addition, depending on the desired target structure, comprises a suitable recognition domain. If a Cpf1 nuclease is selected as a CRISPR nuclease, the gRNA can be a crRNA that does not comprise a structure used by tracrRNA (see Zetsche et al., 2015, above). Accordingly, a gRNA according to the present disclosure, can comprise one or more spacer regions, which do not interact with a bonding partner or target molecule, but instead are used for the correct folding and orientation of the gRNA or for the linking of a crRNA and a tracrRNA. These spacers can be composed of DNA and/or RNA, and exhibit a length of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides. A gRNA according to the present invention comprises at least one sub-region composed of RNA, wherein the RNA can be formed by natural or synthetic nucleotides. If desired, a gRNA of interest, preferably at its 5' or 3' ends, may carry a modification, wherein the modification is selected from the addition of a group composed of acridine, amine, biotin, Cascade Blue, cholesterol, Cy3 ®, Cy5 ®, Cy5.5® daboyl, digoxigenin, dinitrophenyl, EDANS, 6-FAM, fluorescein, or derivatives therefrom, 3'-glyceryl, HEX, IRD-700, IRD-800, JOE, phosphate, psoralen, rhodamine, ROX, Thiol (SH), spacers, TAMRA, TET, AMCA-S", SE, BODIPY<0>, Marina Blue®, Pacific Blue®, Oregon Green®, Rhodamine Green®, Rhodamine Red®, Rhodol Green® und Texas Red®, a locked nucleic acid (LNA), 5-methyl dC, 2,6-Diaminopurin, 2'-Fluor A, 2'-Fluor U, 2'-O-Methyl RNA, one or more phosphorothioate(s) as a spine, a polyethyleneglycol link, or a covalent 5'-3' link, resulting in the circularization, or combinations thereof. For specific embodiments, it may be of interest to reduce the length of the gRNA in a targeted manner, in order to design gRNAs comprising fewer than 100 nucleotides, fewer than 95 nucleotides, fewer than 90 nucleotides, fewer than 85 nucleotides, fewer than 80 nucleotides, fewer than 75 nucleotides, fewer than 70 nucleotides, fewer than 65 nucleotides, fewer than 60 nucleotides, fewer than 55 nucleotides, fewer than 50 nucleotides, fewer than 45 nucleotides, fewer than 40 nucleotides, fewer than 35 nucleotides, or fewer than 30 nucleotides, in order to obtain a higher specificity of the CRISPR nuclease through the shortening. In other embodiments, the gRNA according to the present invention can comprise at least one effector domain, e.g. an aptamer, or a DNA or RNA modified molecule, or a bonding site for a protein or peptide, in order to thus expand the functionality of the gRNA molecule.

In another embodiment according to the present disclosure, the at least one gRNA can also be associated with at least one nucleic acid molecule, in vitro or in vivo, which serves for the specific DNA repair after a double-strand break has been induced by a CRISPR nuclease. This (DNA) repair matrix, or HDR matrix, can be inserted, as a single-stranded and/or double-stranded DNA, directly, or in the form of a recombinant construct, into a target structure of interest. The repair matrix thus allows the targeted homologous recombination, by means of which the specificity, as well as the application range, of the genome editing can be significantly expanded.

In accordance with the present disclosure, gRNAs may be used which are specially adapted for use in a plant cell.

In accordance with the present invention, in addition, any gRNA as described herein may additionally be introduced to at least one effector domain, such as an aptamer, coupled with or together with the effector domain so that the functionality of the gRNA is broadened. The recombinant construct comprising a gRNA and at least one effector domain may be introduced into the target plant structure as DNA- or RNA-construct using a suitable recombinant construct and/or vector. The effector domain may in addition not only consist of a nucleic acid, but also be a polypeptide or a sequence coding for it.

In one embodiment, the gRNA coupled with the CRISPR nuclease or catalytically active fragments thereof and/or the effector domain, for example the DNA- or RNA-modifying or the DNA- or RNA-binding polypeptide or nucleic acid, is introduced into the target plant structure.

In a further embodiment, the gRNA is introduced into the target plant structure as a separate recombinant construct independently of the CRISPR nuclease and/or the effector domain, for example the DNA- or RNA-modifying or DNA- or RNA-binding polypeptide or nucleic acid.

The gRNA may be introduced into the target plant structure as a DNA- or RNA molecule. Thus, in one embodiment the gRNAs may be introduced directly in the form of a synthetic nucleic acid, for example as RNA, or optionally also in a complex with a CRISPR nuclease or a catalytically active fragment thereof, or in another embodiment into the target cell in the form of an activatable and transcribable recombinant DNA construct. Furthermore, in accordance with the present disclosure, an individual gRNA may be used or dual or multiple gRNAs in one or more recombinant construct(s) may be introduced into a cell simultaneously, wherein the gRNAs have the same or individual regulatory sequence(s). The selection of suitable gRNAs for insertion in a target cell can take place according to the aspect explained in greater detail below, in accordance with the invention, wherein this aspect provides an in vitro screening process for identifying a gRNA or an encoding sequence for a gRNA.

Since the interaction domain of a conventional CRISPR/Cas gRNA always interacts with the same CRISPR nuclease, individual gRNAs which carry a different recognition sequence as a further component, may be used in a multiplexing strategy, i.e. the specific modification of several target regions in one strategy. In this regard, it may always be necessary for a PAM sequence to be located adjacent to or within the target region. The design of a suitable gRNA may be determined in silico by a skilled person in the field who knows the CRISPR nuclease used, the nucleic acid target region, the type of the desired nucleic acid modification selected from mutation, insertion or deletion, as well as the desired target cell. The effectiveness of these gRNAs in vivo as well as possible off-target effects must, however, be evaluated separately for each gRNA. In addition, for unestablished systems, such as the transient transformation of meristematic plant cells, suitable vectors and methods have to be established for introducing at least one gRNA together with at least one suitable Cas nuclease and/or at least one effector domain, for example a DNA- or RNA-modifying or a DNA- or RNA-binding polypeptide or nucleic acid, so that the concerted activity of both molecules in the target cell can be ensured. In addition to the pure designing and synthesis or provision of the gRNA, the fact that, specifically, plant genomes are very complex, is a further difficulty, and so far no reliable method exists for pre-testing that would allow for a conclusion to be drawn regarding whether a selected gRNA, interacting with the desired CRISPR nuclease or the catalytically active fragment thereof, can actually effectively modify a nucleic acid target region in a plant cell.

In one embodiment of the present invention, the methods of the invention and thus the plants, plant materials or cells produced thereby are based on the naturally occurring DNA repair mechanisms in the target cell.

In another embodiment according to the aspects of the present disclosure, the repair of a single-stranded or double-stranded DNA break which was previously mediated by a CRISPR nuclease or a catalytically active fragment thereof and/or a further effector domain, is repaired by one or more HDR matrix(ces) as DNA repair template which are not naturally present but has/have been introduced into the target cell.

In the context of the present disclosure, then, in one embodiment a DNA repair matrix is disclosed which can optionally be introduced into the target cell together with or at a separate time to the CRISPR constructs and/or a further at least one effector domain, in order to induce a specific HDR mechanism and thus specific nucleic acid sequences at the site of the double-stranded break. In this regard, targeted genome editings comprising both knock-ins and also the specific repair of the DNA lesion to prevent an unwanted mutation at the site of the DNA break may be carried out. A knock-in can mean the specific insertion of at least one nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 15 nucleotides, at least 20 nucleotides, at least 50 nucleotides, at least 100 nucleotides, at least 200 nucleotides, at least 500 nucleotides or at least 1.000 nucleotides into the target nucleic acid in the plant cell. Moreover, a knock-in can also mean the introduction of an entire gene expression cassette, which may comprise up to 10,000 nucleotides. A genome editing can also mean the targeted replacement of at least one nucleotide with another nucleotide. Further, a knock-in may also be obtained by two, three, four or more exchanges or a combination of insertions and exchanges. "Insertions" means the specific insertion of at least one nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 15 nucleotides, at least 20 nucleotides, at least 50 nucleotides, at least 100 nucleotides, at least 200 nucleotides, at least 500 nucleotides, at least 1000 nucleotides, at least 2000 nucleotides, at least 5000 nucleotides, at least 10000 nucleotides or at least 15000 nucleotides into the target nucleic acid of the plant cell. A nucleic acid sequence as an insertion may be a sequence, or a part thereof, of a transcription factor binder site, a regulatory sequence, a polypeptide-coding sequence, an intron sequence, a sequence coding for a non-coding RNA (for example IncRNA), an expression cassette, a non-encoding sequence, for use as a marker, in particular a selecting marker, e.g. a marker for marker assisted selection in the framework of the breeding, or a RNAi construct. Furthermore, a knock-in may also be brought about by a deletion of sequence sections which perturb the functionality of a gene (for example the deletion of transposon insertions). The DNA repair matrix may be introduced into the target plant structure of interest as a single-stranded or as a double-stranded nucleic acid.

In one embodiment, a target nucleic acid may be specifically switched off (knock-out), i.e. the transcription and optional translation of the nucleic acid is inhibited. This may be carried out by specific insertion, mutation or deletion of a regulatory sequence such as a promoter or terminator sequence of a target nucleic acid or by specific mutation or deletion of the target nucleic acid itself or parts thereof. Furthermore, specific mutation or deletion which changes the reading frame of a target nucleic acid or specific mutation or deletion of potential splice signals may bring about a knock-out. In one embodiment, this knock-out is carried out without the insertion of an HDR matrix via the NHEJ pathway; in another embodiment, in addition to the CRISPR constructs and/or a further effector domain, an HDR matrix or DNA repair matrix is introduced into the target cell. A specific mutation is, for example, an exchange of at least one nucleotide for another nucleotide, preferably with the consequence that the codon concerned then codes for another amino acid. A specific knocked-out target nucleic acid in a plant cell has at least one specific mutation or deletion, but may also comprise two, three, four or more specific mutations and/or deletions.

In embodiments according to which a Cas or a Cpf1 gene, or another effector nuclease in the form of DNA, can be introduced onto a corresponding construct in a target cell of interest, the gene that encodes the nuclease can comprise a suitable promoter that is functionally linked to the sequence encoding the nuclease in order to improve its transcription. The promoters can be constitutively active, or they can be inducible promoters, which are first activated after an appropriate stimulus has been added thereto, or has acted thereon (chemical or physical, comprising light, temperature, etc.). Likewise, a construct that encodes a gRNA can comprise a suitable promoter. Suitable promoters for plant cells, in accordance with the present disclosure, can be selected from a group composed of: a maize-ubi-intron promoter (SEQ ID NO: 7), a maize U3 promoter (SEQ ID NO: 10), a plant U6 polymerase III promoter, e.g. a wheat U6 promoter (SEQ ID NO: 8), a U6 promoter derived from rice (see Mikami et al., Plant Mol. Biol. 2015, 88(6), 561-572), or a U6-26 promoter derived from *Arabidopsis thaliana*, a rice U3 promoter (SEQ ID NO: 9), and a *Brachypodium* EF1 promoter (SEQ ID NO: 40), or a simple or double 35S promoter derived from the cauliflower mosaic virus, comprising, among other items, a 35SPPDK promoter (see Yoo et al. Nature Protocols 2, 1565-1572 (2007)), but the promoters are not limited thereto, because the promoters are selected according to the respective plant cell of interest.

In yet another embodiment, the natural NHEJ mechanism of a plant cell can be deliberately suppressed by adding an appropriate inhibitor or by an targeted knock out or knock down of an endogenous nucleic acid sequence involved in the NHEJ process, whereupon the introduction of a targeted modification in the desired nucleic acid sequence is facilitated, because hereby the NHEJ mechanism of a cell can be reprimed. In one embodiment of the present invention, in which the target plant structure is an isolated meristematic cell of a seedling/plant or a plant embryo or exposed meristematic cells of a plant in a later stage of development, the target plant structures comprising meristematic cells before, during and after introduction of the at least one recombinant construct in accordance with the present disclosure are cultured in a manner such that an oxidation of the isolated structures is prevented. In one embodiment, this involves adding an antioxidant.

Table 1 below shows suitable media for culturing various target plant structures which comprise meristematic cells. Other suitable reaction conditions such as buffers, additives, temperature and pH conditions as well as any required additives can readily be determined by the skilled person in the field knowing the method and construct disclosed herein, in accordance with any aspect of the present disclosure.

*tachyon, Hordeum marinum, Aegilops tauschii*. Examples of dicotyledons are *Malus domestica, Beta vulgaris, Helianthus annuus, Daucus glochidiatus, Daucus pusillus, Daucus muricatus, Daucus carota, Eucalyptus grandis, Erythranthe guttata, Genlisea aurea, Nicotiana sylvestris, Nicotiana tabacum, Nicotiana tomentosiformis, Solanum lycopersicum, Solanum tuberosum, Coffea canephora, Vitis vinifera, Cucumis sativus, Morus notabilis, Arabidopsis thaliana, Arabidopsis lyrata, Arabidopsis arenosa, Crucihimalaya himalaica, Crucihimalaya wallichii, Cardamine flexuosa, Lepidium virginicum, Capsella bursa-pastoris, Olmarabidopsis pumila, Arabis hirsuta, Brassica napus, Brassica oleracea, Brassica rapa, Brassica juncacea, Brassica nigra, Raphanus sativus, Eruca vesicaria sativa, Citrus sinensis, Jatropha curcas, Glycine max, Gossypium* ssp. or *Populus trichocarpa*.

In one embodiment, the nucleic acid sequence which is used for the specific modification of a target nucleic acid region comprises at least one or more regulatory sequences.

In one embodiment, the nucleic acid sequence used for specific modification of a target nucleic acid region comprises, as a regulatory sequence, at least one or more

TABLE 1

Medium compositions for culturing various target plant structures with meristematic cells (MS Medium = Murashige Skoog medium; MS Salt = Murashige Skoog salt (Toshio Murashige, Folke Skoog: A Revised Medium for Rapid Growth and Bio Assays with Tobacco Tissue Cultures. In: Physiologia Plantarum, issue 15 (1962), Vol 3, p. 473-497, ISSN 0031-9317, doi: 10.1111/j.1399-3054.1962.tb08052.x).

| Embryo | Embryo | Embryo bombardment | Embryo bombardment | Agro-embryo | Agro-embryo | Plant meristem exposure |
|---|---|---|---|---|---|---|
| MM1 (MM = maturation medium) 1 | MM2-maturation medium 2 | MM1OSM (osmoticum) | MM1MOD (MOD = modified) | MM1Tim (Tim = timentin) | MM1ACE | Meristem peeling - antioxidant |
| MS salt<br>30.8 g/l sucrose | MS medium<br>3.4 g/l sucrose | MS salt<br>30.8 g/l sucrose<br>36.4 g/l sorbitol<br>36.4 g/l mannitol<br>95 mg L-cysteine<br>4.25 mg/l L-silver nitrate | MS salt<br>30.8 g/l sucrose<br>95 mg/l L-cysteine<br>4.25 mg/l silver nitrate | MS salt<br>30.8 g/l sucrose<br>150 mg/l Timentin | MS salt<br>30.8 g/l sucrose<br>19.62 g/l ACE | MS salt<br>95 mg/L cysteine<br>100 mg/L ascorbic acid |

The transient introduction of the construct disclosed herein into meristematic cells or tissue has the advantage that they develop from these reproductive tissues, via which the specific modification can then be stably passed on to the next generation, whereby the next generation is free from the constructs which had previously been introduced. The methods and constructs disclosed herein also mean that seeds can be harvested directly from the plant which has been modified in this manner, which carry the stable DNA modification without requiring an intermediate step of cell culture in the form of callus production and regeneration, whereupon also, the necessary selection and regeneration steps and the media and additives required therefor can be dispensed with.

The methods disclosed herein are suitable for the production of specific DNA modifications both in monocotyledonous and also in dicotyledonous plants. Examples of monocotyledons are grasses and cereals such as *Hordeum vulgare, Sorghum bicolor, Secale cereale, Triticale, Saccharum officinarium, Zea mays, Setaria italic, Oryza sativa, Oryza minuta, Oryza australiensis, Oryza alta, Triticum aestivum, Triticum durum, Hordeum bulbosum, Brachypodium dis-* promoter(s), optionally a plant and tissue-specific, a phenotypical, a constitutive or inducible promoter, which is suitable for induction of transcription in a desired target cell. A promoter is a nucleic acid region which is involved in the recognition and also binding of RNA polymerases as well as other proteins in order to control transcription. Suitable promoters for either the gRNAs or the CRISPR nucleases or the sequence coding the catalytically active fragment thereof are well known to the skilled person in the field. Induction of an inducible promoter may be carried out by stimuli such as temperature, chemicals, pH, light, endogenous plant signals for example which are emitted after injuring the plant, and the like. Exemplary promoters are selected from the group consisting of SEQ ID NOs:5-11, and also includes such sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences which, despite modification, still carry out the same function as the respective unmodified sequences with the corresponding SEQ ID NO. Further advantageous promoters are selected from the group consisting of promoters of the Wall-Associated Kinases (WAKs) 1 and 2 (see, for example, Wagner T A, Kohorn B D. Wall-Associated Kinases Are Expressed Throughout Plant Development and Are Required for Cell Expansion. The Plant Cell. 2001; 13(2):303-318 as well as, for example NCBI records: NCBI Reference Sequence: NC_003070.9), a promoter for the SCARECROW1 (scr1) gene (see, for example, Tissue Specificity and Evolution of Meristematic WOX3 Function; Rena Shimizu, Jiabing Ji, Eric Kelsey, Kazuhiro Ohtsu, Patrick S. Schnable and Michael J. Scanlon, Plant Physiology February 2009 vol. 149 no. 2 841-850 as well as, for example NCBI records: NCBI Reference Sequence: NC_003070.9), a promoter for the FAF2– and FAF4– gene (see, for example, the FANTASTIC FOUR proteins influence shoot meristem size in *Arabidopsis thaliana*, Vanessa Wahl, Luise H Brand, Ya-Long Guo, Markus Schmid Wahl et al, BMC Plant Biology 2010, 10:285 www.biomedcentral.com/1471-2229/10/285 as well as, for example, NCBI records: NCBI Reference Sequence: NC_003070.9), a promoter of the OSH1 gene (see, for example, Sato et al (1996) Proc. Natl. Acad. Sci. USA, 93: 8117-8122 as well as, for example, Genbank records: GenBank: CP002688.1 or GenBank: AP008209.2) or a promoter of a metalloprotein gene, for example from rice (for example GenBank: BAD87835.1). The promoters of the present invention may be naturally occurring, synthetic or chimeric promoters or a combination thereof. A preferred promoter in accordance with the present disclosure is a promoter which is active in a meristematic plant cell or a promoter which is active in plastids of a plant cell. In one embodiment, the nucleic acid sequence which is used for specific modification of a target nucleic acid region also comprises at least one terminator as a regulatory sequence.

In one embodiment, the nucleic acid or amino acid sequence which is used for specific modification of a target nucleic acid region, comprising a gRNA and a CRISPR nuclease or a catalytically active fragment thereof, or a sequence coding for it, comprises one or more nuclear localization sequence(s) (NLS), which brings about nuclear localization of the nucleic acid and polypeptides used for specific modification of a target nucleic acid region.

In one embodiment, the recombinant construct comprising a nucleic acid or amino acid sequence which is used for specific modification of a target nucleic acid region, a gRNA and a CRISPR nuclease or a catalytically active fragment thereof or a sequence coding therefor, comprises one or more plastid localization sequence(s) (PLS), for example a mitochondrial or chloroplast localization sequence (MLS or CLS), which brings about the localization of the specific modification of a target nucleic acid region used nucleic acid and polypeptide in the corresponding plant plastids.

In one embodiment, the nucleic acid sequence which codes for a CRISPR nuclease or a catalytically active fragment thereof disclosed herein or a CRISPR nuclease or a catalytically active fragment thereof disclosed herein also contains a tag sequence. A tag sequence is a nucleic acid or section of protein which may be located upstream and/or downstream and/or within the sequence with respect to the CRISPR nuclease or the gRNA or the nucleic acid sequence coding for the CRISPR nuclease or the gRNA in order optionally, inter alia, to allow its localization and visualization within a target cell. Particularly preferred tag sequences are selected from the following list: polyhistidine(His)-tag, glutathione-S-transferase (GST) tag, thioredoxin tag, FLAG tag, a tag with fluorescent properties selected from the green fluorescing protein tag (GFP), a DsRed tag, a mCherry tag and the like, a streptavidin or strep tag, maltose binder protein (MBP) tag, chloroplast transit peptide, mitochondrial transit peptide, a snap tag and/or a secretion tag.

In another embodiment, fusion constructs are suggested that may be used in the method according to the present invention. These fusion constructs comprise fusion proteins as well as fusion nucleic acids. Fusion proteins can be composed of a CRISPR nuclease, a variation or catalytically active fragment thereof, or the sequence that encodes the CRISPR nuclease or the variation or catalytically active fragment thereof, as an element, as well as, optionally, one of the aforementioned tags and an effector domain, or one of the nucleic acid sequences that encodes the effector domain. As a result, it is possible to introduce the effector domain disclosed herein and/or one or more identical or different CRISPR nucleases, or variations or catalytically active fragments thereof, as a physically linked unit in a plant target structure of interest, or to express them in a plant target structure of interest.

Preferably, the effector domain optionally comprises a left-hand amino acid sequence fused to the N- or C-terminus of the CRISPR nuclease, or the variation or catalytically active fragment thereof. The optionally present left-hand amino acid sequence, or the nucleic acid sequence that encodes this left-hand sequence, allows both the CRISPR nuclease as well as the effector domain to be positioned ideally, without affecting one another sterically, such that both the effector domain as well as the CRISPR nuclease can deploy their activities. A left-hand amino acid sequence can comprise 1, 2, 3, 4, 5, 6, 7, 8, 9, 10, 11, 12, 13, 14, 15, 16, 17, 18, 19, 20, or more, up to 50 or 100 amino acids, and in some cases, it can be even longer. Moreover, fusion nucleic acids are also disclosed, wherein a gRNA of interest is linked in a covalent manner to an effector domain of interest. Moreover, non-covalent fusion nucleic acids are also disclosed, which comprise a gRNA as well as an effector domain and/or DNA repair matrix, wherein the non-covalent link can take place in an association of the respective components through hybridization, i.e. through base pairing of complementary regions. Moreover, fusion constructs are disclosed, in which gRNA and/or a CRISPR nuclease of interest are chemically linked, in vitro/ex vivo, to an effector domain of interest, and subsequently introduced into a plant target structure of interest comprising at least one meristematic cell, whereby these effector molecules are already linked, thus increasing the availability in a plant cell of interest, by means of which the efficiency of the method disclosed herein can be increased. Moreover, the association of a gRNA to an effector molecule and/or a DNA repair matrix can lead to not only the effector domain and/or the DNA repair matrix fulfilling their function in the framework of the genome editing, but also an increase in the stability of a gRNA. Specifically in embodiments in which the gRNA is inserted directly into a plant target structure of interest comprising at least one meristematic target cell through transformation or transfection, this can significantly increase the breakdown of a gRNA by cellular RNAs, before it can exercise its function.

As with the gRNA and/or the CRISPR nuclease, comprising, among other things, a Cas nuclease or a Cpf1 nuclease, the fusion constructs described above, comprising fusion proteins and fusion nucleic acids, and/or mixed fusion proteins, comprising nucleic acids and proteins, can be introduced into a plant target structure of interest in a stable or transient manner, as recombinant constructs, or at least one of the molecules can be directly introduced, as RNA, DNA, or protein, into a plant target structure of interest, comprising at least one meristematic cell. By way of example, a gene that encodes for a CRISPR nuclease of interest can first be codon-optimized. This gene can then be introduced, in a stable or transient manner, in the form of a recombinant construct, into a plant target structure of interest. Alternatively, the CRISPR nuclease can also be translated in vitro, and subsequently introduced directly into a plant target structure of interest as a protein. In one embodiment, a gRNA can then be inserted directly into a plant target structure of interest as RNA. This can take place, as described in greater detail below, through particle bombardment or other transfection processes that are known to the skilled person in the field. Likewise, the function constructs described above are consequently inserted as either recombinant constructs or inserted directly into a nucleic acid target region of interest.

In one embodiment according to the method of the present invention, a transient expression of the CRISPR system disclosed herein, comprising at least one gRNA, one CRISPR nuclease, preferably also at least one effector domain, and optionally one DNA repair matrix, can be introduced in a transient manner, through particle bombardment, into a plant target structure of interest comprising at least one meristematic cell. For this, gold or tungsten particles, for example, can be coated with polyethylenimine (PEI). For this, the gold particles are first washed, and re-suspended in ethanol after centrifuging and optional washing, and stored at −20° C. In order to coat the particles with PEI (Sigma #P3143), the washed mixture of gold particles is centrifuged in ethanol, and the ethanol is discarded. The particles are then washed once in $ddH_2O$ in order to remove alcohol residue, and then added to 250 μl of a 0.25 mM PEI solution, followed by a pulsed ultrasonic treatment, in order to suspend the particles. The sealed containers are then snap-frozen in a dry ice/ethanol mixture, and the suspension is then lyophilised overnight. At this point, the dried, coated gold particles can be stored for at least three weeks at 80° C. Prior to further use, the particles are rinsed three times, in each case with 250 μl of 2.5 mM HEPES buffer, pH 7.1, followed by a pulsed ultrasonic treatment, and then briefly vortexed, before being centrifuged. The particles are then suspended in a final volume of 250 μl HEPES buffer. A 25 μl aliquot of particles is transferred into a clean reaction vessel, before the DNA bonding takes place. In order to bond uncoated DNA to the gold particles, the particles are subjected to a pulsed ultrasonic treatment, and one microgram of DNA (in 5 μl nuclease-free water) is then added, and the mixture is carefully pipetted a few times, before incubation for 10 minutes at room temperature. The particles are spun briefly, normally for 10 seconds, the precipitation is removed, and 60 μl fresh ethanol is added. The particles, which contain DNA precipitated with PEI, are washed twice in 60 μl ethanol. The particles are then centrifuged and the precipitation is discarded, after which the particles are re-suspended in 45 μl water. To bond a second DNA (DNA-2) thereto, a precipitation is used, making use of a water-soluble cationic lipid transfection reagent. 45 μl of the particle-DNA suspension, corresponding to the gold particles to which the first DNA was bonded, are briefly subjected to an ultrasonic treatment, and 5 μl of a 10 nanogram/microliter DNA-2, and 2.5 μl of the water-soluble cationic lipid transfection reagent are then added. The solution is incubated on an orbital shaker for 10 minutes, and subsequently centrifuged at 10,000 g for one minute. Subsequently, the precipitation is removed, and the particles are re-suspended in 60 μl ethanol. The solution can then be transferred to macro-carriers, and the gold particles, to which the first and second DNA were sequentially bonded, are then transfected into a meristematic cell of interest, using a standard protocol for particle bombardment with a PDS-1000 apparatus. Standard protocols for a PDS-1000 apparatus can be obtained from the manufacturer (Bio-Rad).

In one embodiment in accordance with the present invention, the method for the production of a plant, a plant material or a plant cell also comprises a screening step. In this step, by carrying out a method for the analysis of the nucleic acid sequence, a target region is examined, for example by means of a polymerase chain reaction or probes, as to whether the insertion, activation and subsequent reaction of the at least one recombinant construct of the present disclosure has resulted in the desired specific modification of a target nucleic acid region. Methods for carrying out this screening are known to the skilled person in the field in respect of any and all target plant structures and also target nucleic acid regions. There are however, currently no standard methods that would allow the effective interaction of a gRNA, a CRISPR nuclease, or a catalytically active fragment thereof, and a nucleic acid target region of interest for checking the actual efficacy of a gRNA of interest for a specific nucleic acid target region, in particular a nucleic acid target region within a plant cell, in an in vitro screening process, in order to thus monitor the time expenditures and costs with the use of CRISPR/Cas constructs, particularly in a high output process. In addition, most of the available in silico tools (see www.dna20.com/eCommerce/cas9/input), are specialised for *E. Coli*, yeast, or animal genomes or model plants, but not for important monocotyledons like dicotyledonous crop plants, which frequently differ significantly from model plants, specifically with regard to the PAM distribution in genomic regions.

In one aspect of the present invention, an in vitro screening method is therefore provided, for identifying a gRNA or an encoding sequence for a gRNA, in an in vitro assay for identifying a gRNA or an encoding sequence for a gRNA, that, together with a CRISPR nuclease or a catalytically active fragment thereof, is suitable for the targeted modification of a nucleic acid target region in a plant cell, comprising the following steps: (i) provision of one or more nucleic acid target region(s) of a plant, plant material, or a plant cell; (ii) insertion of the one or more nucleic acid target region(s) into at least one vector; (iii) provision of at least one gRNA; (iv) provision of at least one CRISPR nuclease or a catalytically active fragment thereof; (v) bringing the at least one CRISPR nuclease or a catalytically active fragment thereof in contact with the at least one vector in vitro, under suitable reaction conditions, which allows the interaction of a gRNA with a CRISPR nuclease and thereby the catalytic activity of the CRISPR nuclease or the catalytically active fragment thereof, wherein the at least one vector is brought into contact, in each case, with exactly one gRNA and exactly one CRISPR nuclease or a catalytically active fragment thereof, in a separate reaction preparation; (vi) analysis of the reaction products from step (v); and (vii) identification of a gRNA or an encoding sequence for a gRNA, which is capable, together with a specific CRISPR nuclease or a catalytically active fragment thereof, of the targeted modification of a nucleic acid target region in a plant cell.

According to this aspect of the present invention, the term in vitro is to be understood such that the at least one nucleic acid target region is not in its natural environment, i.e. a plant cell, but instead is first transferred into a suitable vector for the purpose of the in vitro screenings. Numerous results can then be generated from this pre-screening within a short time, which indicate the suitability of at least one gRNA, in interacting with the corresponding CRISPR nuclease or catalytically active fragment thereof, for the targeted modification of a nucleic acid target region in an intact plant cell. The candidates that have been established in this manner can then be used with a significantly higher success rate, both in vitro as well as in vivo, comprising in planta.

In one embodiment, the PCR amplifier of the nucleic acid target region is derived in accordance with this aspect from genomic DNA, wherein the genomic DNA also comprises, in addition to the nuclear genome, the genomes from plastids, such as mitochondria and chloroplasts. In another embodiment, the PCR amplifier of the nucleic acid target region is derived in accordance with this aspect from plant RNA.

The at least one vector according to this aspect of the present invention is preferably a plasmid vector, although any of the other vectors disclosed herein, that are suitable for the cloning and stable preservation of a PCR amplifier in a nucleic acid target region of interest, can also be used. The cloning of one or more nucleic acid target region(s) in at least one vector is known to the skilled person in the field. The vector can ideally comprise more than one target region of interest, such that numerous target regions of interest can be analysed. Alternatively, numerous vectors that comprise at least one nucleic acid target region of interest could also be provided.

The gRNA for use according to this aspect must be applied in an active ribonucleic acid form, i.e. the gRNA can be created synthetically, and optionally also modified. Alternatively, the gRNA can also be produced in a recombinant manner, i.e. through in vitro or in vivo transcription, and optionally through a purification step.

The CRISPR nuclease or the catalytically active fragment thereof is provided as an amino acid sequence. A commercially available CRISPR nuclease or a variation thereof can be used for this. Alternatively, the CRISPR nuclease or the active fragment thereof can be produced in another embodiment in a recombinant manner, and optionally isolated and/or purified, before it is used in the in vitro screening process according to the present invention.

In another embodiment, the CRISPR nuclease or the active fragment thereof that has been provided is coupled to at least one effector domain. Regarding the possible effector domains and their potential advantages and fields of application, the corresponding earlier statements in this disclosure apply accordingly. By already including the effector domains/Cas constructs in an in vitro screening process, there is the advantage that possible undesired positive or synergistic effects of the respective effector domains, which have a steric as well as chemical/physical effect on the Cas or Cpf1 constructs, can already be analysed in the pre-testing phase. This also relates to one possible effect of the at least one effector domain on the gRNA-Cas interaction, as well as the subsequent bonding to and modification of the nucleic acid target region of interest, in addition, or alternatively, to the actual field of application for the respective effector domain.

Bringing the at least one gRNA and the at least one CRISPR nuclease, or the catalytically active fragment thereof, in contact with the at least one vector in vitro takes place under suitable reaction conditions. In this context, these conditions are to be understood as those that allow both the bonding of the gRNA to the respective CRISPR nuclease or the catalytically active fragment thereof, as well as the interaction of the gRNA/Cas complex with the target region of interest and the catalytic activity of the CRISPR nuclease, or catalytically active fragment thereof. Suitable reaction conditions such as buffers, additives, and special cofactors that are needed, including temperature and pH conditions, as well as, if applicable, further additives, can be easily determined by the skilled person in the field with knowledge of a method disclosed herein and a construct disclosed herein, in accordance with any aspect of the present disclosure.

According to one embodiment, the reaction products are analysed in a qualitative manner in accordance with the in vitro screening process. According to another embodiment, the reaction products are analysed in a quantitative manner in accordance with the in vitro screening process. According to yet another embodiment, the reaction products are analysed in both a qualitative as well as quantitative manner in accordance with the in vitro screening process.

In one embodiment of this aspect, the in vitro screening process is a high output process, i.e. numerous gRNAs and/or numerous CRISPR nucleases or catalytically active fragments thereof, and/or numerous nucleic acid target regions on one or more vectors in separate reaction vessels can be tested simultaneously. This upscaling is of particular advantage for quickly acquiring a plurality of data regarding suitable gRNA/Cas candidate pairs for the respective at least one nucleic acid target region of interest. Alternatively, the question of which gRNA/Cas candidate pairs interact particularly efficiently can be analysed as a variable, particularly when the use of new CRISPR nucleases or catalytically active fragments thereof are examined. As a further problem, it is possible to check whether the addition of an effector domain to a CRISPR nuclease or catalytically active fragment thereof has an effect on the gRNA/Cas interaction, or the subsequent catalytic activity of the CRISPR nuclease or catalytically active fragment thereof.

In accordance with the present disclosure, the vectors and/or recombinant constructs may be used for the specific modification of a target nucleic acid region in a plant cell by mechanical methods, including particle bombardment, microinjection and electroporation, or by induced endocytosis, suitable vectors, direct transfection and the like. In one embodiment of the present disclosure, the vectors and/or the recombinant constructs are introduced into the target zones or target plant structure by particle bombardment. To this end, the vectors are initially precipitated onto gold or tungsten particles, for example, and the target cell/target plant structure is then bombarded with the particles obtained thereby or with further processed particles using suitable equipment. In a further embodiment of the present disclosure, the vectors and/or recombinant constructs are introduced directly or indirectly into the target cell or target plant structure by microinjection. In another embodiment of the present disclosure, the vectors and/or recombinant constructs are introduced by spraying with subsequent take-up, for example during a viral infection, or infiltration into the target cell or target plant structure.

In accordance with one embodiment, the vectors and/or recombinant constructs are introduced into a meristematic cell by particle bombardment. This method is suitable both for introducing recombinant constructs comprising double-stranded plasmid DNA, linear single-stranded or double-stranded DNA, single-stranded or double-stranded RNA and polypeptides, as well as combinations thereof in all types of plant meristems in different stages of the development of a plant. Gold and tungsten may, inter alia, be used as the carrier material for the recombinant constructs.

In a further embodiment of the present disclosure, the vectors of the invention and/or the recombinant constructs are introduced directly into the target cell or the desired compartment of a target cell by microinjection.

In accordance with this further embodiment, the vectors and/or recombinant constructs are introduced into a meristematic cell by microinjection. This type of introduction is suitable for all types of meristems (see Example 2 below). In addition, introduction using this embodiment is suitable both for introducing recombinant constructs comprising double-stranded plasmid DNA, linear single-stranded or double-stranded DNA, single-stranded or double-stranded RNA and polypeptides as well as combinations thereof.

In a still further embodiment of the present disclosure, the vectors of the invention are introduced by means of electroporation using high voltage pulses.

In a still further embodiment of the present disclosure, the vectors of the invention are introduced by endocytosis, i.e. an endogenous mechanism by means of which exogenous material can be taken up into the cell.

In one embodiment, the vector is a viral vector which comprises the at least one recombinant construct. Introduction using a viral vector means that the vector and its included at least one recombinant construct can propagate. Suitable viral vectors which may be used or modified for application in accordance with the present disclosure are selected from the group comprising but not limited to SEQ ID NOs: 12-15 and 25-38 and also include sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences. The skilled person in this field is aware that the sequence of a naturally occurring virus which might be used as the viral vector, corresponding to the desired recombinant construct to be introduced, as well as the target plant structure of interest, have to be adapted.

In a further embodiment, the recombinant construct is introduced by *Agrobacterium* spp.-mediated transformation, in particular *Agrobacterium tumefaciens*- or *Agrobacterium rhizogenes*-mediated transformation, into a target plant structure. This type of introduction is well known to the skilled person in the field for various target plants as well as various target plant structures thereof.

The skilled person in the field knows that the choice of introduction type may, inter alia, depend on the appropriate target plant cell as well as on the construct to be introduced; thus, depending on the target cell, a different mode of introduction might be necessary.

In a further embodiment of the present disclosure, the vectors of the invention and/or recombinant constructs are introduced by means of a combination of the introduction methods mentioned above. Thus, for example, a viral vector which contains the at least one recombinant construct of interest may be introduced into the target plant structure by means of *Agrobacterium tumefaciens* as the further vector, or indeed by particle bombardment or microinjection.

In one aspect of the present invention, special methods for introducing vectors and/or recombinant constructs in accordance with the present invention into meristematic plant cells and tissues are disclosed. For the transformation or transfection of meristematic cells and tissue, accessibility to them is a deciding factor, wherein the accessibility of the various plant meristem types in the various stages of development in a plant differ widely.

In one embodiment in accordance with the present invention, then, a method for providing a target plant structure is proposed, comprising at least one meristematic cell, wherein at least one recombinant construct in accordance with the present disclosure may be introduced into the target plant structure. The method of this embodiment comprises, as a vital step, ensuring that a meristematic structure of interest which does not yet comprise differentiated meristematic cells is rendered accessible. If the target plant structure is a meristem in embryo, then it is essential to select a plant embryo of the right size and to direct the at least one recombinant construct in accordance with the present invention towards the deeper, i.e. inwardmost-lying meristematic cells as a target for transformation or transfection therewith, since the meristematic cells in the outer layers may already have reached a certain degree of differentiation and thus are no longer in accordance with the present invention. Preferably, the plant embryos are selected for their size such that they are provided with an exposed meristem. For maize embryos, this means that embryos of less than a 1.5 mm maximum diameter, preferably less than 1 mm as a maximum diameter, particularly preferably less than 0.7 mm as a maximum diameter and more particularly preferably less than 0.5 as a maximum diameter may advantageously be used in accordance with the invention. A meristematic cell in the context of the present invention is thus a meristematic cell the degree of differentiation of which still allows it to produce from the cells, after specific modification of a nucleic acid region of interest, all desired types of plant cells, in particular those types from which a fertile plant can be regenerated either directly or indirectly.

In a further embodiment, a method for preparing a target plant structure comprising at least one meristematic cell is disclosed, into which at least one recombinant construct in accordance with the present disclosure may be introduced, wherein the meristematic cell is a cell of a seedling or an older plant.

In accordance with this embodiment, the meristem must be completely or almost completely dissected out. In addition, care must be taken that the deeper lying, i.e. innermost-lying meristematic cells are targeted for a transformation or transfection with at least one recombinant construct in accordance with the present invention, since the meristematic cells in the outer layers may already have reached a certain degree of differentiation and thus are no longer suitable for use in the present invention. In accordance with this embodiment, the exposed meristem undergoes an oxidation. In order to avoid damage to the meristematic cells, then, preferably, suitable antioxidizing protective measures are employed such as, for example, the use of an anti-oxidation agent or further protective measures to ensure further development of the target plant structure comprising at least one meristematic cell.

Sequence Listing—Free Text

The following details show the translation into German of the details provided in the sequence listing as the free text (numerical identification <223>), respectively supplied for the corresponding sequence identification number. All sequences contain under the numerical identification <213> the information about an ‘artificial sequence’.

SEQ ID NO:1

<223> VP16 Activator-comprising sequence

SEQ ID NO:2

<223> VP16 Activator

SEQ ID NO:3

<223> VP64 Activator with glycine serine spacers

SEQ ID NO:23

<223> Vector1 TaU6

SEQ ID NO:24

<223> Vector1 ZmU3

SEQ ID NOS: 41 to 48

Protospacer region guide RNA 14, protospacer region guide RNA 16, protospacer region guide RNA 37, protospacer region guide RNA 38, protospacer region guide RNA 39, protospacer region guide RNA 43, protospacer region guide RNA 18 or protospacer region guide RNA 52.

EXAMPLES

The present invention will now be explained in more detail with the aid of the following examples, which are not limiting in any way.

Example 1: Production of CRISPR/Cas Constructs

The constructs were produced on the basis of the publication by Mali et al, 2013. The promoters were specifically used against specific plant promoters and adapted to the gRNA of the respective target genes.

Constructs for Monocotyledonous Plants:

The promoters used were, inter alia, the maize-Ubi-Intron promoter (SEQ ID NO:7), the maize U3 promoter (SEQ ID NO:10), the wheat U6 promoter (SEQ ID NO:8), the rice U3 promoter (SEQ ID NO: 9) and the *Brachipodium* EF1 promoter (SEQ ID NO: 40). An exemplary construct had SEQ ID NO: 23 (vector1_TaU6 standard).

Constructs for Dicotyledonous Plants:

Here, a parsley-Ubi4 (SEQ ID NO:5) and an *Arabidopsis* U6 promoter (SEQ ID NO:6) were used. An exemplary construct had SEQ ID NO:24 (Vector 1_ZmU3 standard).

The various gRNAs were determined specifically for the respective target genes and cloned into the corresponding position in the vectors mentioned above. The position of the gRNA sequence corresponded to the nucleotides denoted "n" in SEQ ID NOs: 23 and 24.

In order to reduce the number of gRNAs that must be inserted into the plant to obtain a genome editing, an in vitro assay was established for testing the candidate gRNAs, so that only the most suitable candidates are inserted in the plants.

For this, potentially suitable gRNAs are first defined by in silico analysis. This definition depends on the nucleic acid target region of interest, due to the dual function of the gRNA, as explained in the introductory part of the description, particularly a PAM motif, as well as the desired CRISPR nuclease or the catalytically active fragment thereof, which are to be used.

In order to test the different gRNAs for different genes, in a first step, the nucleic acid target region of interest, or sub-regions thereof, are amplified by means of PCR and cloned in standard vectors. "Standard vectors" in this sense indicates commercially available vectors or vector systems, which can be readily adapted to the requirements of the desired assay through means known to the person skilled in the art, in particular in that they function as a backbone for the cloning of nucleic acids of interest. Exemplary vectors can be selected from: pJet (Thermo Fisher Scientific, Inc., USA), pGEM-T (Promega BioSciences, LLC, USA) or pBluescript (Addgene, USA). These vectors serve as a substrate in the newly developed in vitro assay. In a second step, the various gRNAs are produced by means of in vitro transcription (Invitrogen MAXIscript T7 Kit; Cat. No. AM1312M).

Figure 14:
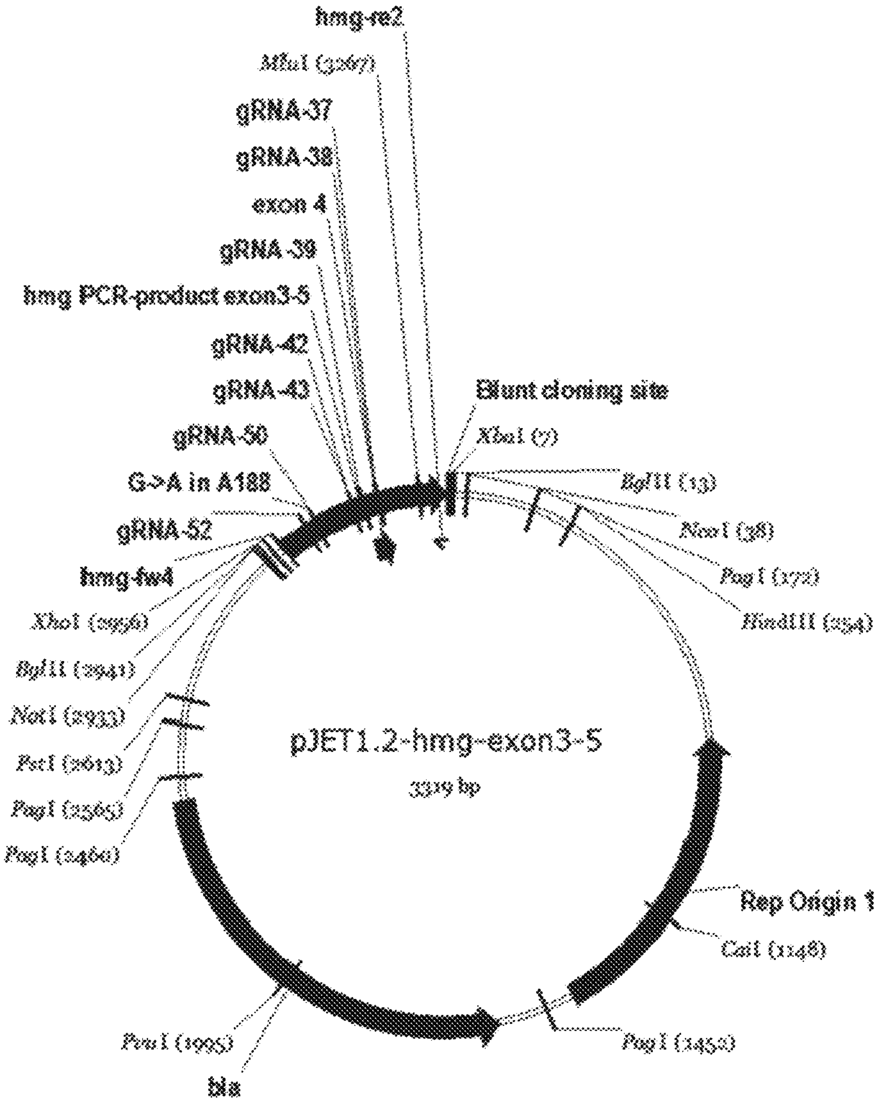
FIG. 14 shows an exemplary vector map of the plasmid pJET1.2-hmg-exon3-5 in accordance with example 1.
Figure 15:
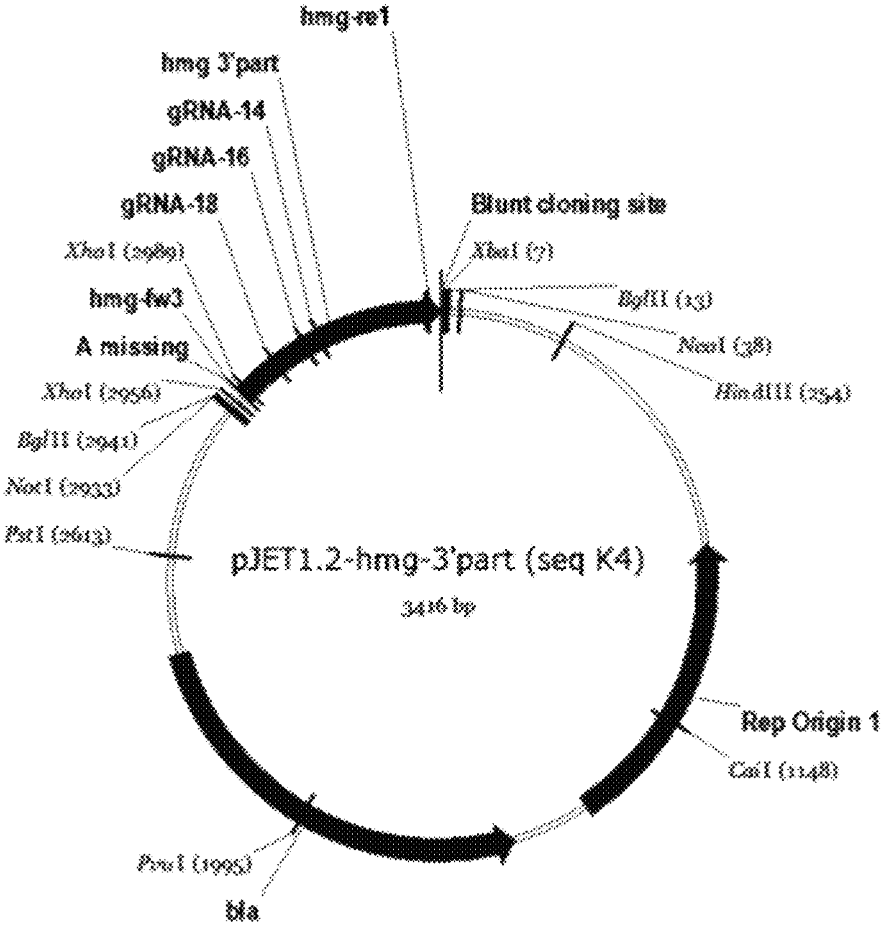
FIG. 15 shows an exemplary vector map of the plasmid pJET1.2-hmg-3'part/part in accordance with example 1.
Figure 16:
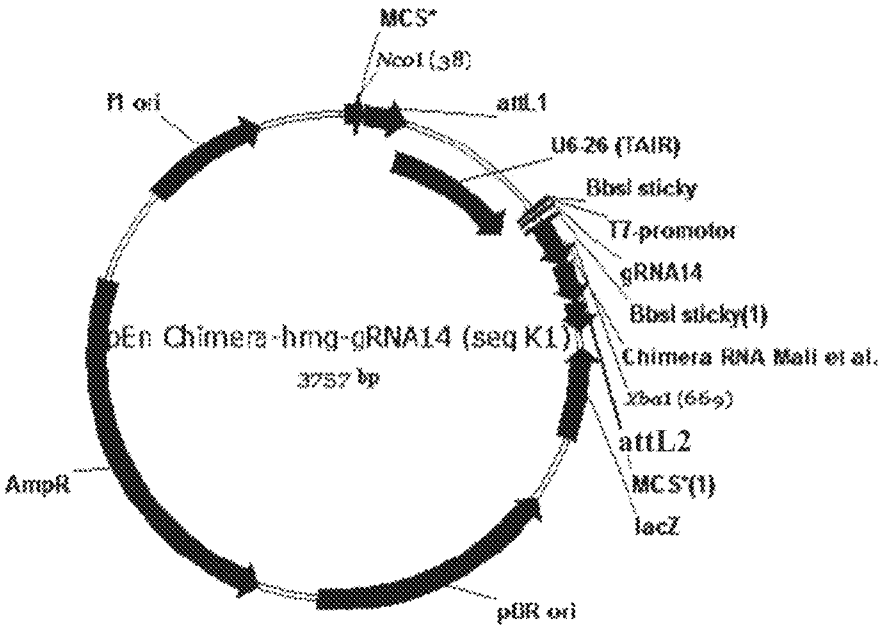
FIG. 16 shows an exemplary vector map of the plasmid pEn Chimera-hmg-gRNA14, in accordance with example 1.

The gRNAs were subsequently tested in an in vitro assay, and the potentially best candidates were selected and used for the further in planta tests. For this, among others, a maize plant A188 hmg13 gene was used as an exemplary nucleic acid region of interest (HMG transcription factor 13; see gene GRMZM2G066528 from EnsemblePlants or the maize genome data base). These were amplified by means of PCR, and cloned in the multiple cloning site from pJET1.2 accordingly, firstly the part comprising Exon 3-5 (hmg-fw4 and hmg-432, see FIG. 14), and secondly the hmg-3'part (hmg-fw3 and hmg-re1, see FIG. 15). After this, the plasmids were linearized through digestion with PvuI, and in order to prevent the recirculation, the vector backbone was dephosphorylated. The resulting product was applied to a preparative gel. Subsequently, the concentration of the resulting, linearized vectors was measured. For a typical assay, ca. 3 μl of a 30 nM vector were used as a substrate for the Cas digestion, carried out in each case at least three times. The gRNAs variations that were to be tested were cloned in the vector pEn-chimera (see, by way of example, FIG. 16 regarding the gRNA14). The cloning in this vector was carried out in accordance with standard methods in molecular biology, as shall be explained below by way of example. The sequence from pEn-chimera was located in SEQ ID NO: 59. An RNA chimera was located thereon, which could be specified relatively easily via BbsI+Oligo. Subsequently, it can be transferred into the pDe-CAS9 via a gateway LR reaction. The RNA chimera is controlled by the promoter AtU6-26. The resulting vector was then digested with NcoI and XbaI, wherein the resulting fragment comprises the gRNA of interest. The desired fragment comprising the gRNA was gel-separated, extracted and cleaned by typical methods. For the assays, ca. 1 μg of the resulting fragment was used as a template for the in vitro transcription (Invitrogen MAXIscript T7 Kit; Cat. No. AM1312M). An exemplary preparation comprises: 10 μl template (1 μg); 2 μl 10× transcription factor (Invitrogen); 1 μl 10 mM ATP; 1 μl 10 mM CTP; 1 μl 10 mM GTP; 1 μl 10 mM UTP; 2 μl T7-RNA polymerase (Invitrogen); 4 μl $H_2O$. The preparation is normally incubated for 2 hours at 37° C. $H_2O$ is added to obtain a volume of 100 μl, and the RNA is purified according to the manufacturer's instructions (Qiagen RNeasy Kit). Following elution (two times with 50 μl $H_2O$), the exact volume and the concentration of the resulting RNA is determined. For the further assays, ca. 15 ng/μl of the in vitro transcription was used, so that with an RNA that is 140 nucleotides long, 300 nM were needed. Subsequently, an in vitro digestion was carried out as follows: the reaction preparation was typically in a volume of 30 μl. In order to ensure an optimal cleavage efficiency, it was important to maintain a molar ratio of Cas9 and gRNA to the respective nucleic acid target region of 10:10:1 or higher. First, 300 nM of the respected gRNA that is to be tested was provided. In addition, 30 nM of substrate DNA, comprising in each case a single nucleic acid target region, was provided for each case. The reaction preparation was combined in the following order:

| Components | 30 μl preparation |
|---|---|
| Nuclease-free water | 20 μl |
| 10X Cas9 Nuclease reaction buffer (NEB) | 3 μl |
| 300 nM gRNA (~15 ng/μl) | 3 μl (30 nM final) |
| 1 μM Cas9 nuclease | 1 μl (~30 nM final) |
| reaction volume | 27 μl |
| pre-incubation for 10 min, at 37° C. | |
| 30 nM Substrate DNA | 3 μl (3 nM final) |
| Total-reaction volume | 30 μl |

This was then carefully mixed and briefly spun before the preparation was incubated for another hour at 37° C. Optionally, a treatment with proteinase K may then take place by adding 1 μl enzyme and incubating for 15-30 minutes at 37° C. At this point, the fragment analysis can then take place.

Figure 8:
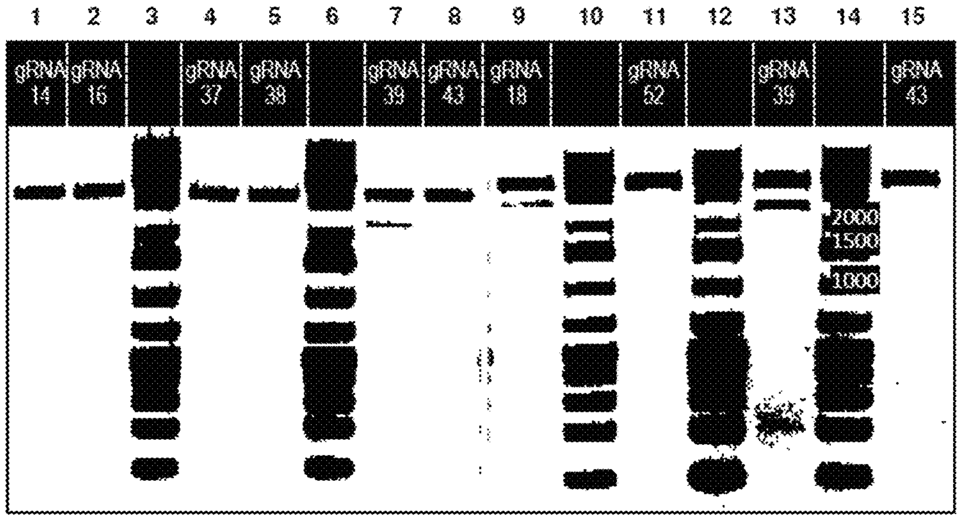
FIG. 8 shows the results of an in vitro assay for assessing the efficiency of a gRNA of interest. The starting plant here is a maize plant, the target gene is the hmg13 gene (HMG transcription factor 13; GRMZM2G066528). The figure shows the results of a separation in a 1% gel with the default parameter of 100 V and visualization via fluorescence provided by ethidium bromide. The molecular size markers (given in base pairs; GeneRuler 1 kb plus DNA ladder (Thermo Fisher Scientific Inc., USA; SM1331) 20000, 10000, 7000, 5000, 4000, 3000, 2000, 1500, 1000, 700, 500, 400, 300, 200, 75 bp) are located in columns 3, 6, 10, 12, and 14. The results for the gRNA 14 (SEQ ID NO: 41), gRNA 16 (SEQ ID NO: 42), molecular marker, gRNA 37 (SEQ ID NO: 43), gRNA 38 (SEQ ID NO: 44), molecular marker, gRNA 39 (SEQ ID NO: 45), gRNA 43 (SEQ ID NO: 46), gRNA 18 (SEQ ID NO: 47), molecular marker, gRNA 52 (SEQ ID NO: 48), molecular marker, gRNA 39 (SEQ ID NO: 45) and gRNA 43 (SEQ ID NO: 46) are shown from left to right in the other columns. The given SEQ ID NOS indicate the respective individual, different protospacer regions in the gRNAs, and the remaining regions of the gRNA are identical in all of the gRNAs used herein.

The results for 10 selected gRNAs, here, by way of example, in interaction with a Cas9 nuclease, are listed in FIG. 8. It is clear from these results that there are qualitative as well as quantitative differences in the efficiencies of the respective gRNAs and partner CRISPR nucleases regarding the cleavage efficiency of a nucleic acid target region of interest.

Further experiments (data not shown) were carried out with CRISPR nucleases from sources other than *S. Pyogenes*, and with Cas nucleases that carry at least one point mutation, e.g.: a Cas nicking enzyme, in order to test in vitro the efficiency of these other Cas nucleases on a plant nucleic acid target region of interest in interaction with the respective gRNA.

Moreover, first successful in vitro experiments were carried out, which showed that Cas nuclease gRNA pairs of interest that have been identified in a pre-screening are also suitable for the targeted modification of an RNA as well as plant mitochondrial or plastid DNA, as is proven by the broad application spectrum of the present assay.

In order to test the broad applicability of the method for further important crop plants, the novel in vitro screening process was likewise carried out using nucleic acid target regions derived from other crop plants, such as *Beta vulgaris, Brassica napus* and *Sorghum bicolour.*

For this, due to the specificity of the plant genome, it was necessary to carry out new in silico analyses, in order to be able to define suitable target regions, and thus suitable gRNAs. In addition, in the framework of the development of the process, other Cas nucleases, nicking enzymes, Cpf endonucleases and enzymatically active fragments derived therefrom were employed, which additionally carry an effector domain. Furthermore, alternative Cas proteins, or Cas proteins with point mutations, for example, could also be used in the assay in order to test the efficiencies of the different Cas proteins. In particular, also in direct interaction with the tested gRNAs.

This was intended to resolve numerous questions: (1) which gRNAs display particularly high activity?; (2) what are the effects of the modifications in the gRNA, such as different lengths of protospacers or mismatches?; (3) which Cas proteins integrate best with which gRNAs?; (4) which CRISPR nucleases have an effect on the enzymatic effects of the enzyme?; and (5) does the coupling of an effector domain, and thus the creation of a sterically more demanding Cas construct, affect the interaction with the gRNA in question and thus the efficiency of the targeted modification of a nucleic acid region of interest? In the course of this further series of experiments, it has so far been determined that particularly the reduction of a CRISPR nuclease on a catalytically active minimum fragment thereof is advantageous regarding the targeted cleavage efficiency. Moreover, it has been discovered that it is possible for effector domains to bond to the CRISPR nuclease, or the gRNA. Particularly here, the in vitro screening was indispensible, because the efficiency of these modified CRISPR nucleases or gRNAs was lower due to the larger steric demands by the effector domain, resulting in the interaction of the Cas and gRNA being more difficult for the pairs that were tested. Nevertheless, effective Cas-gRNA effector domain pairs were still identified.

Surprisingly, it was discovered that the results of the in vitro pre-testing, i.e. the screenings, also correlate with their efficacy in subsequent tests.

In a further test, all of the gRNAs shown in FIG. 8 were tested with regard to their efficiency in the actual, site oriented modification in a plant meristem. As a result, the in vitro assay proved to be ideal for assessing the efficiency of the gRNA that was used, because not all of the gRNAs that were used resulted in an in vivo or in vitro cleavage in the template. Specifically with the Cas-gRNA pairs, which have proven to be particularly efficient in in vitro screening assays, this efficiency was also confirmed in the subsequent testes in which plant material was employed, either in vitro or in vivo. A maize plant functioned as the starting plant for these subsequent studies, and the target gene hmg13 functioned specifically as the target.

Example 2: Introduction of CRISPR/Cas Constructs

The constructs described above in Example 1 were introduced into the meristems using various methods. The basis for this was accessibility to the meristems; the material used determined the various methods used (see Example 4).

Figure 5:
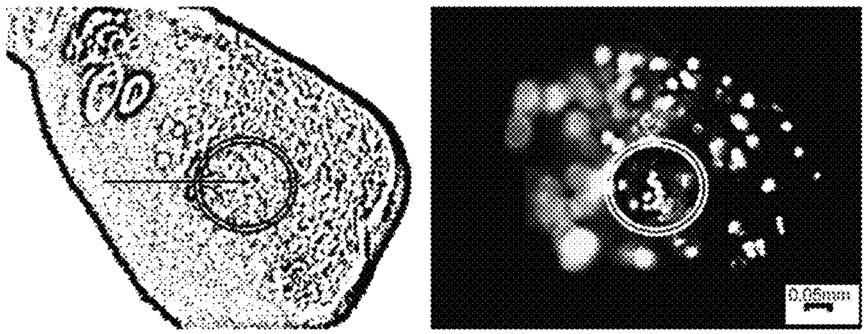
FIGS. 5 A and B (FIGS. 5 A and B) shows the biolistic test bombardment for the maize embryo meristems.
Figure 7:
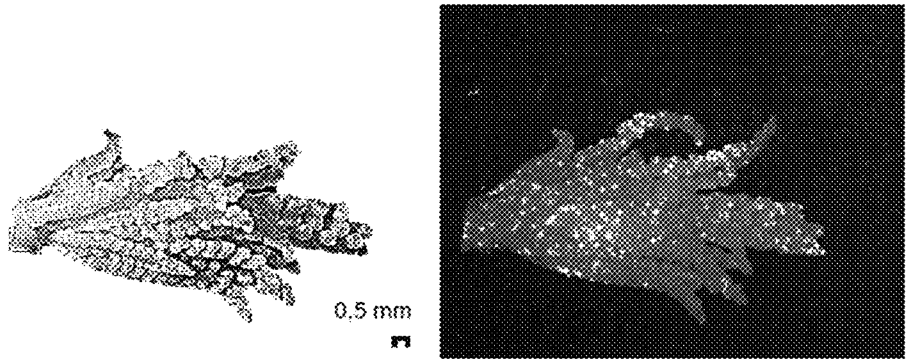
FIGS. 7 A and B (FIGS. 7 A and B) shows the biolistic test bombardment of an exposed tassel meristem from maize.
Figure 9:
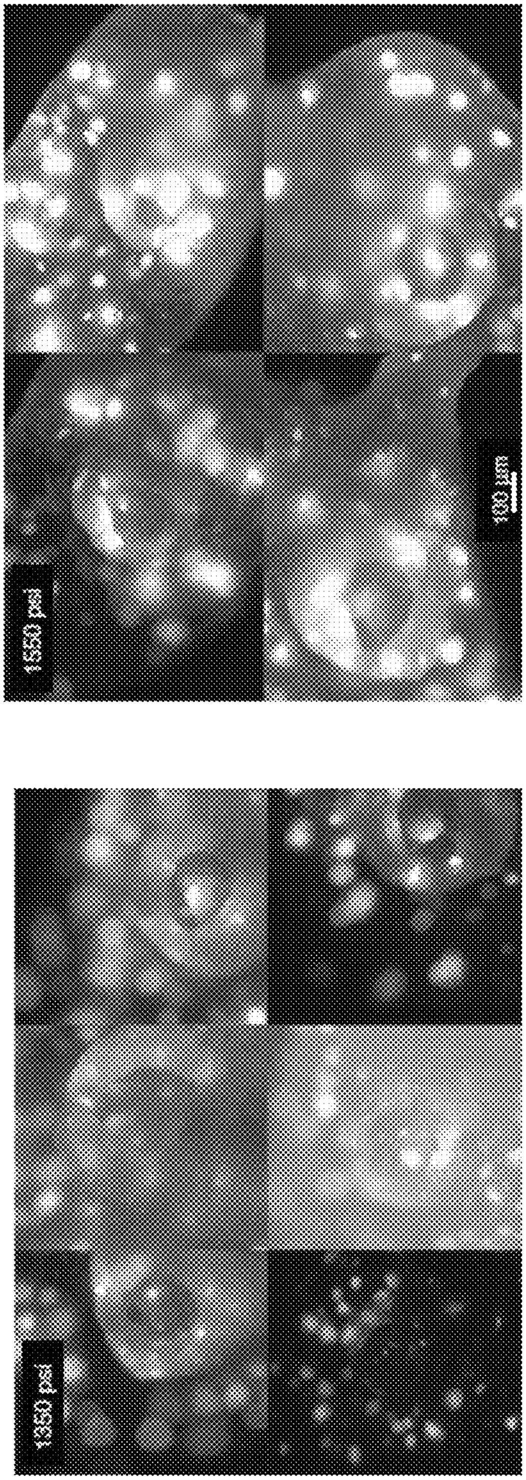
FIGS. 9 A and B (FIGS. 9 A and B) show the results of a test bombardment of maize embryos at different pressures (given in psi: pounds per square inch). The maize embryos were fired at 7-10 days after pollination, and 2 days later, the microscopic analysis was carried out. An expression vector was used as the plasmid, which encodes, among other things, a fluorescent marker.

The following methods were employed:

Particle bombardment:

Particle bombardment can be used in all of the meristems employed. Bombardment was carried out with dsplasmid DNA, linear dsDNA, RNA and protein as well as virus particles. For instances, Gold and tungsten could be used as the carrier material. Test bombardments of embryo meristems (FIG. 5) and tassel meristems (FIG. 7) were carried out with the aid of the red fluorescing protein; it was shown that it was possible to introduce DNA into these cells by particle bombardment. The important thing to observe thereby is that the suitable bombardment settings were used, depending on the respective materials. Thus, a higher bombardment may lead to an increased transient transfection (see FIG. 9 for images in this regard), but, e.g., also strongly damage the embryos, making germination and development impossible. Therefore, certain preliminary work was necessary, depending on the plant material of interest, which served as the target structure, in order to adjust suitable conditions of the particle bombardment to the respective requirements of the experiment.

Establishing suitable bombardment methods for the plant material that is used, as well as the desired effect (transient versus stable insertion) without damaging the plant tissue, or destroying the construct that is to be inserted, was therefore indispensible.

Microinjection:

Microinjection can be carried out for all meristems, preferably using a microscope with a micromanipulator. Because of the size of certain meristem structures such as prepared tassel and ear meristems, the microinjection could also be carried out with microscopic monitoring. The injection could be carried out using various methods and, as discussed above for particle bombardment (Example 1), with different molecules. On the one hand, dsplasmid DNA, linear dsDNA, RNA and proteins in liquid solution were injected into the meristematic cells through a micro- or nano-canula, and on the other hand dsplasmid DNA, linear dsDNA, RNA and protein, also virus particles, was applied to micro or nano needles and transferred to the meristematic cells by stabbing with the needles.

A further development of this technology comprises the use of a combination of silicon carbide (SiC) whiskers (e.g. Silar® silicon carbide whisker) and microinjections. A dsplasmid DNA, linear DNA, RNA, protein or virus particle is precipitated on the silicon carbide thereby, and injected into the meristems by means of microinjection cannulas.

This offers the advantage that not only one meristematic cell can transfect, but instead, through the distribution of the whiskers, there is the possibility of penetrating numerous cells in parallel. Because it is not necessary to penetrate the cell with the cannula, and the whiskers are significantly smaller, there is less damage to the cells.

Vascular Puncture Infection/Inoculation (VPI):

"Vascular puncture infection" or inoculation, is a method described in Benavente, 2012 (Virus-Induced Gene Silencing in the Diverse Maize Lines Using the Brome Mosaic Virus-based silencing vector) and Louie, 1995 (Louie R, 1995. Vascular puncture of maize kernels for the mechanical transmission of maize white line mosaic virus and other viruses of maize. Phytopathology 85: 139-143), which is used to introduce viruses, virus particles, agrobacteria, and naked DNA into intact maize kernels. This technique enables targeted insertion in the proximity of the embryo and the meristematic tissue. It offers the advantage that no preparatory steps are necessary, and the germinated seeds can be used immediately. This results in minimal damage to the tissue and only minor disruption of the plant development. This method has been modified and implemented as follows: seeds containing a nucleic acid target region of interest are soaked in water for 4 hours at 30° C. The seeds are then incubated overnight in moist towels at room temperature. Subsequently, a plasmid or plasmid mixture, or a virus of interest, is pipetted onto the side of the seed kernel carrying the embryo. Normally, a 100 μl plasmid mixture is prepared in a concentration of 37.5 μg/100 μl, or 1.5 μg/4 μl for each plasmid. Using a notching tool, the inoculum is moved 1-2 mm in the scutellum along the embryo, toward the vascular bundle.

Retaining pins are inserted at an angle of 45° to the surface of the kernel that is to be treated. Two inoculations are carried out at a distance of 1 mm to the embryo, in order to avoid injuring the embryo. The drops are then left on the kernel.

Figure 2:
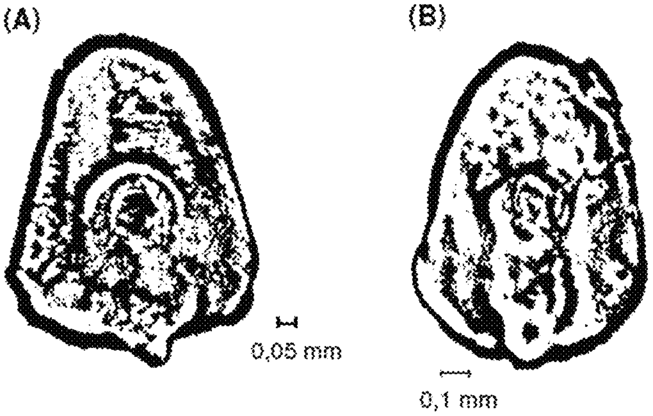
FIGS. 2 A and B (FIGS. 2 A and B) show a direct comparison of the meristems of a 0.5 mm (A) and a 1 mm maize embryo (B). In both cases, the meristem can be seen as the discoid structure in the centre of the embryo, but in the 1 mm embryo, the meristem is already surrounded by a great deal of leaf tissue. This makes access to the meristem more difficult, so that smaller embryos with an exposed meristem are preferred.
Figure 10:
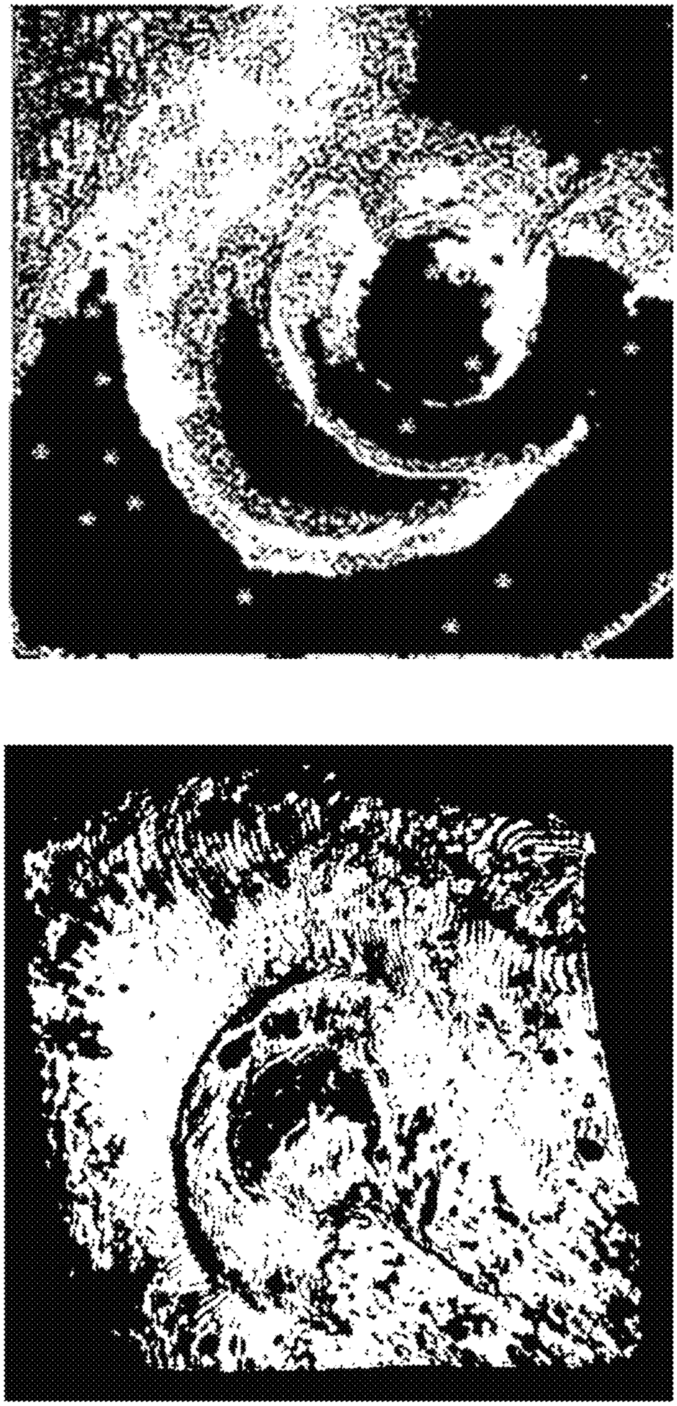
FIGS. 10 A and B (FIGS. 10 A and B) show two views of a maize embryo, as well as localized meristematic tissue. Initially, these data were indicated by a fluorescent marker. The accumulation of fluorescence in the original assay is indicated with stars in FIGS. 10 (A) and (B).
Figure 11:
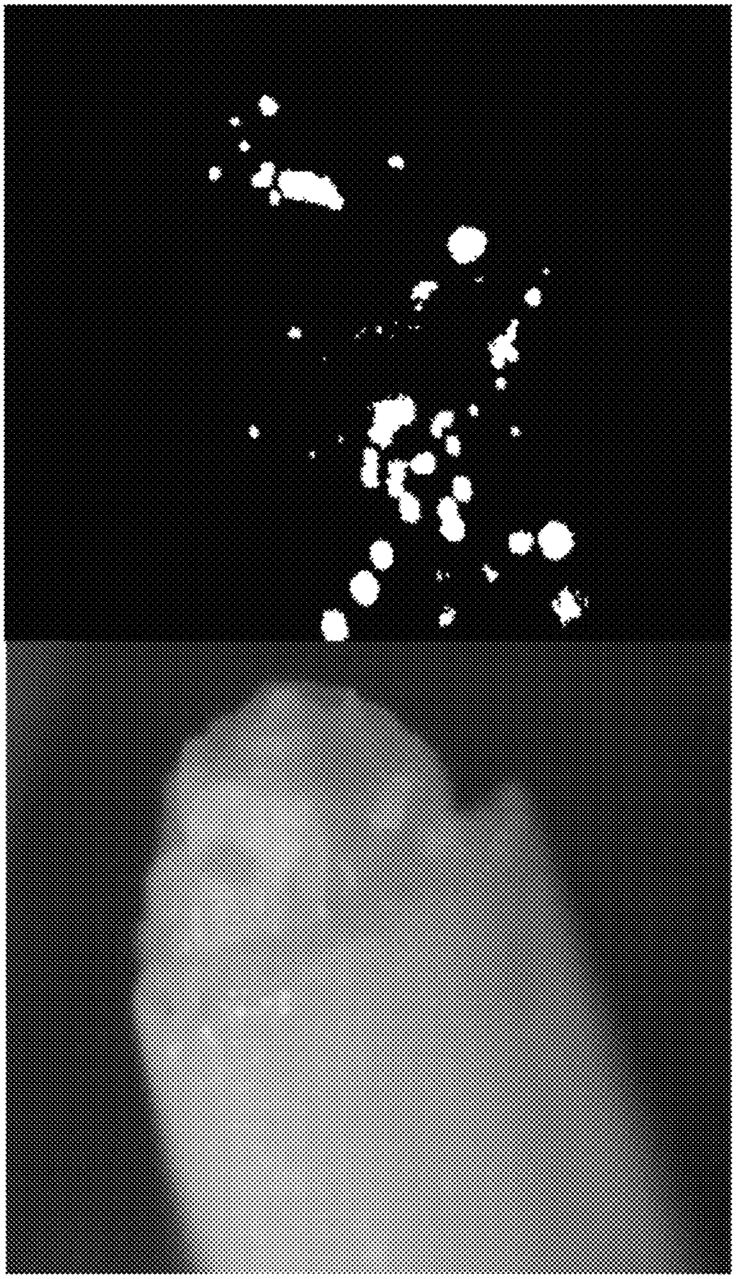
FIGS. 11 A and B (FIGS. 11 A and B) show the horizontal bombardment of the exposed meristems in older maize plants (5-10 day old seedlings) in accordance with example 3. Because the meristem in older plants, as in seedlings, is completely surrounded by leaves, it must be prepared in advance, in order to be accessible for bombardment, etc. For this, all of the outer leaves are removed. The images were recorded one day after the bombardment, with a laser scanning microscope, the vector used for the bombardment was a fluorescent protein-encoding expression vector.

Example 3: Transient Meristematic Transformation of Maize Seedlings and/or Embryos/Inventive Treatment of Meristem Tissue Accessibility to the meristem in the individual stages varies widely. Thus, in the embryo (FIGS. 1 and 2), the meristem is relatively easily accessible, provided that embryos of the right size are used. What is important is that the deeper-located cells of the meristem are transformed, since the upper cells have already undergone a certain amount of differentiation and are no longer suitable. FIGS. 10 and 11 show two views of a maize embryo, as well as the locations of meristematic tissue, indicated by stars. Initially, these data were made visible through a fluorescent marker. It is clear from this that the targeting of plant meristematic cells and tissue is made possible through the provision of the novel method. As a result, a novel method is obtained for inserting nucleic acid structures, e.g. vectors, as well as, in particular, RNAs and amino acids, into a plant target cell. The application of spectrum comprises numerous possible constructs thereby for the targeted genetic engineering modification of a plant cell, such as a CRISPR/Cas construct, viral vectors, RNAi constructs, etc., in order to obtain targeted knock-ins, knock-outs, or targeted point mutations in the nucleic acid target region of the plant cell.

Figure 3:
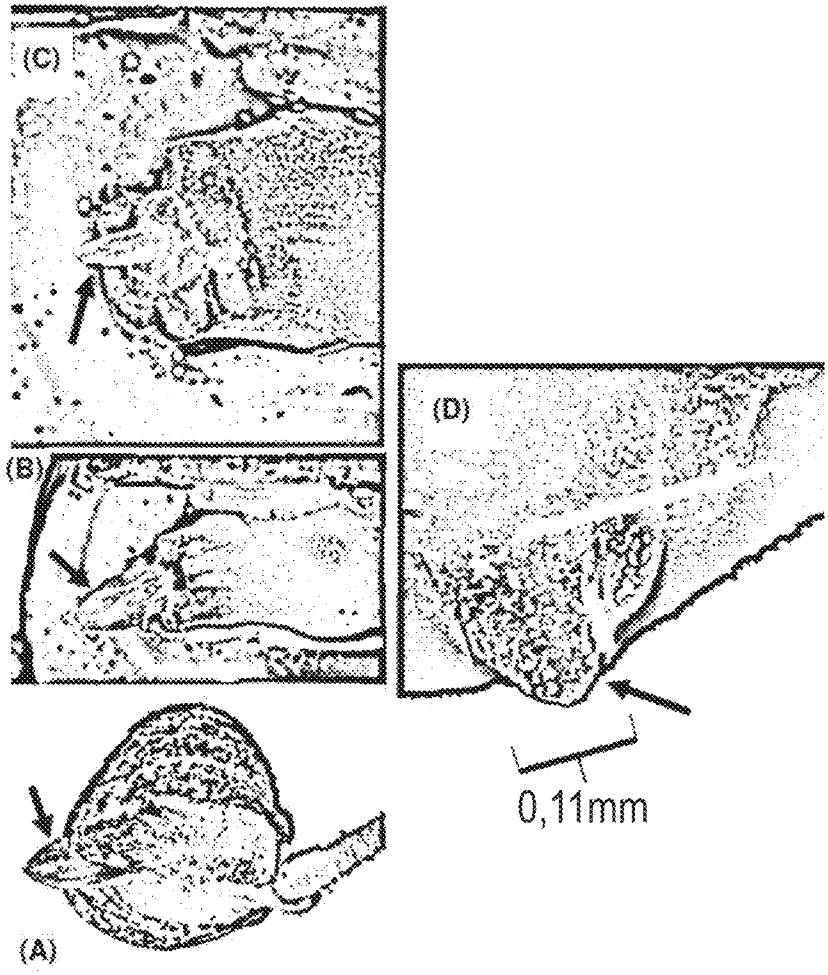
FIGS. 3 A-D (FIG. 3 A-D) show prepared meristems in maize seedlings. Since the meristem in seedlings is completely surrounded by leaves, it has to be dissected out in order to be accessible for bombardment, microinjection etc. To this end, the outer tissue structures are completely removed so that the meristem (arrows) is exposed.
Figure 4:
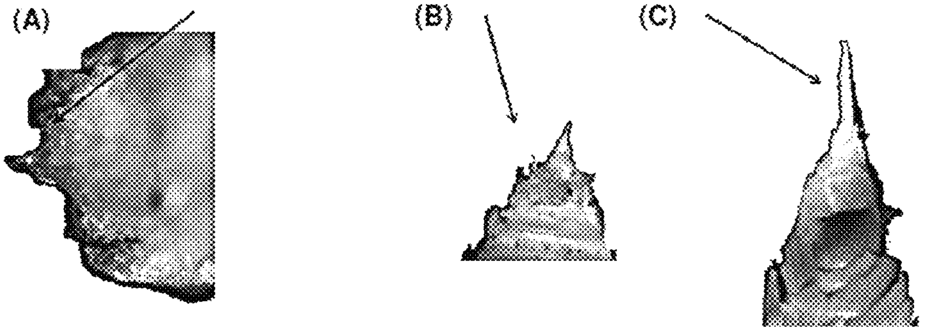
FIGS. 4 A-C (FIG. 4 A-C) show prepared meristems in older maize plants. Since the meristem in older plants as well as in seedlings is completely surrounded by leaves, it has to be prepared in order to be accessible for bombardment, microinjection etc. To this end, the outer tissue structures are completely removed so that the meristem (arrows) is exposed.
Figure 12:
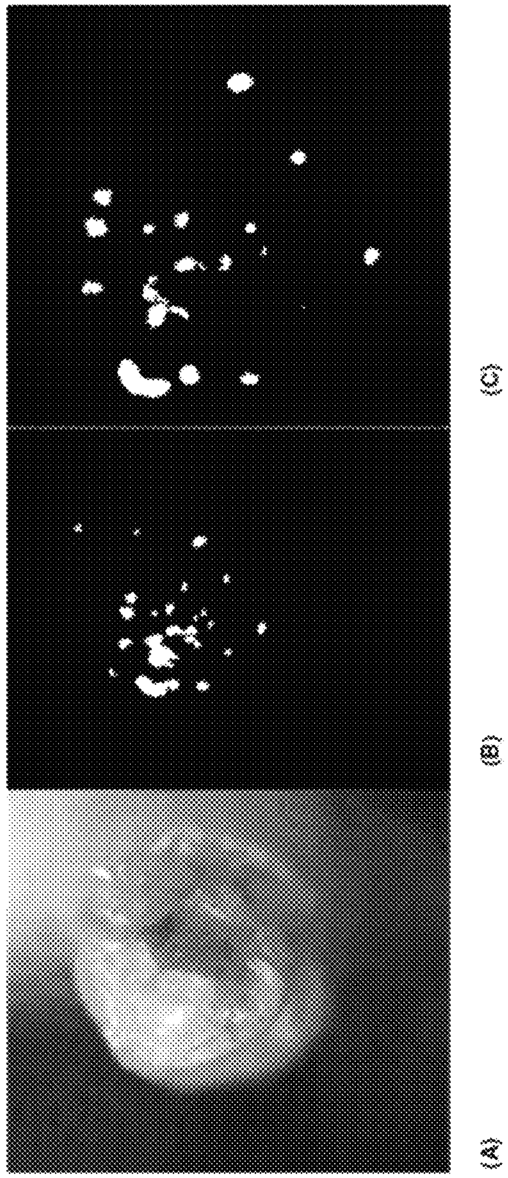
FIGS. 12 A-C (FIGS. 12 A-C) show the vertical bombardment of the exposed meristems in older maize plants (5-10 day old seedlings) in accordance with example 3. Because the meristem in older plants, as in seedlings, is entirely surrounded by leaves, it must be prepared in order to be accessible for a bombardment. For this, the outer leaves are removed entirely. The images were recorded one day after the bombardment, with a laser scanning microscope, the vector used for the bombardment was a fluorescence protein encoding expression vector.
Figure 13:
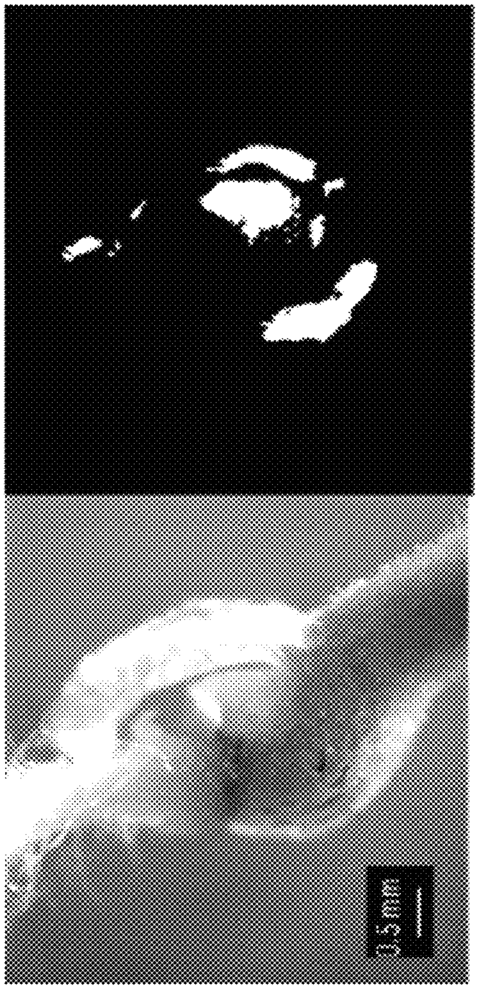
FIGS. 13 A and B (FIGS. 13 A and B) show a germinating embryo which also has transient fluorescence in the meristematic regions. The embryonic target structure can be seen in FIG. 13(A), and the same target structure is shown in FIG. 14(B) with the fluorescence of the inserted marking made visible by means of a fluorescence microscope. The fluorescence is obtained here by insertion of a suitable fluorescent marker. In the black-and-white image, the white regions in FIG. 13(B) correspond to the regions in which fluorescence has been detected.

Meristems in seedlings and older plants must be completely dissected out since they are already surrounded by so many layers of tissue that they are not accessible to bombardment or a microinjection. FIGS. 3 and 4 show the prepared meristems which may be used for the transformation. Here again, as for the embryo meristems, the upper cells have already undergone a certain amount of differentiation and are no longer suitable. Thus, the cells further inside in the meristems have to be transformed. The exposed meristems can be bombarded horizontally as well as vertically. In detailed studies it has been discovered that through the vertical bombardment, the hit-rate in the suitable meristematic regions is increased significantly (see FIGS. 11 and 12). This shows once again that although particle bombardment is a known and established method, its effective application nevertheless requires optimization of various parameters (construct to be inserted, shape and stage of the material to be transformed, pressure, orientation, etc.) for a specific problem in the transformation of specific plant tissues.

Since the isolated meristems are free and thus are exposed to a great deal of oxidation and resulting dying off, they were treated with antioxidant in order to allow the seedling to develop into a plant.

Figure 6:
FIG. 6 shows the preparation of tassel meristems in adult maize plants. The meristems (arrow) are partially exposed through a window-like aperture. The recombinant constructs can then be introduced, for example by bombardment or microinjection and the like. The advantage is that the plant is not badly damaged and the meristems are not completely exposed (about 1-2 days later, the tassel meristem can no longer be seen in the opening, since it is moved further up), and thus oxidation and further damage is reduced.

In order to make the tassel meristem accessible, a method was developed which damaged the plant and meristem as little as possible. To this end, at the level of the tassel meristem, a kind of window was cut through the leaves (FIG. 6). This ensured that the leaves would not die off and that the plant could develop further completely normally and that the meristem would still be protected from the remaining leaves. In addition, the meristem very quickly (within a few hours/days) moved upwards so that it was then once more completely protected. This reduced the probability of the meristem oxidizing and therefore dying. It is possible with this method to ensure a nearly normal flower development, and to obtain pollen for selfing or pollination. This offers the advantage, in turn, that reproductive cells modified in a targeted manner can already be obtained from the plant, making tedious in vitro cultivation steps unnecessary.

The transfection then took place using the methods described above (see Example 2).

The embryos germinated and plants were cultivated to self-fertilization and harvest. Similar results have been achieved with the seedlings and the adult plants, there was no germination.

Example 4: Detection of Successful Specific Genetic Modification

Detection is possible using various methods and at various times:

The presence of the desired specific modification of a target nucleic acid region can be analysed in the early phases of the seedling, the developing plant and the pollen so that indications of successful mutations can be obtained. A clear result is only obtained, however, when the descendants of the self-fertilization are analysed, as these provide the proof of an inherited mutation.

Enrichment PCR:

This method is of application when a restriction enzyme site is destroyed by the specific mutation. In this case, the isolated genomic or extrachromosomal DNA is digested with the enzyme which cuts at this site so that wild type DNA is cleaved. Next, a PCR is carried out with primers which lie upstream or downstream of the restriction enzyme site on the genome. In the ideal case, only one product is then obtained when a mutation has taken place and the DNA was not cut at this site. Since as a rule, digestion of the genomic or extrachromosomal DNA is not 100%, the PCR amplification material obtained is then digested anew with the enzyme in order to establish that a mutation has occurred and the restriction enzyme site has been mutated. The undigested fragments are then cloned and sequenced in order to carry out a precise analysis of the mutation. If the nucleic acid target region is an RNA, then it can first be transcribed into DNA using a method which is known to the skilled person before an enrichment PCR is carried out.

Sequencing:

If enrichment PCR is not possible, a Next Generation Sequencing (NGS) strategy is used to sequence the specific region and the sequences obtained are examined for their mutations Whole genome sequencing (WGS) to identify off-target effects:

In order to exclude the possibility of unwanted mutations, a WGS is carried out on the candidates with the desired mutations.

Additional analyses are constituted by absence detection of the constructs and viruses used using specific PCR and qPCR systems.

Example 5: Viral Vectors

Viruses offer the advantage that they can be introduced into a target plant structure as whole viral particles and also as DNA or RNA. The insertion of the viruses is achieved via the delivery methods listed in Example 2. By these means, a targeted insertion into the respective meristematic target regions of interest is obtained.

In addition, viruses offer the possibility of propagation in the cells. Prerequisite for that is, that this function has not been destroyed by modification to their RNA/DNA sequence. This has the advantage that firstly, the meristem does not have to be directly infected, or it is sufficient to infect only a few cells and notwithstanding this, propagation into several cell or tissue types occurs.

With this application, there are other possibilities, in addition to the delivery methods described in Example 2, for inserting viruses or virus particles.

Virus particles, in vitro transcripts of the viruses, or *Agrobacterium* that carry an encoding T-DNA for the viruses, are inserted by rubbing them into the leaves, or via infiltration (with and without a vacuum), in order to generate primary infections. The respective target cells and target tissues are then infected through a systematic spreading.

In addition, plant sap that has a high titre of plant viruses is used for the infection. For this, either tobacco or spinach is infected with the viruses, and subsequently, the plant sap containing the viruses is isolated and used for infecting the maize plants.

Aside from the broad spectrum of infection possibilities, and the spreading capabilities, DNA viruses offer the advantage of providing DNA templates for homologous recombination (HR).

In this case, a large quantity of templates is provided by the replication of the virus inside one or more cells for homologous recombination after the double-strand break has been introduced. As a result, homologous recombination and incorporation of the template fragment occur with greater frequency.

In one series of tests, different BMVs (see SEQ ID NOS: 25-31 or DSMZ filing number: BMV Virus-Inoculum: PV-0945; reference for BMV plasmids (C13/F1+F2 & C13/F3-13m): Benavente et al., Maydica, Vol. 57, No. 3(2012): "Virus-Induced Gene Silencing in Diverse Maize Lines Using the Brome Mosaic Virus-based silencing vector.") and BSMVs (comprising at least one sequence selected from the SEQ ID NOS: 32-37 or DSMZ filing number: BSMV Virus-Inoculum: PV-0330; Reference for BSMV plasmids (pCaBS-α & pCaBS-β & pCa-γbLIC): Yuan, C., et al., (2011). PLoS One 6(10): e26468: "A high throughput barley stripe mosaic virus vector for virus induced gene silencing in monocots and dicots."), virus particles, plasmids, or plasmid mixtures, were therefore inserted into a plant or plant cell of interest. Among others, *Nicotiana benthamiana*, maize A188, maize Va35, and *Spinacia oleracea* are infected with corresponding viruses, plasmids or a plasmid mixture. A rubbing inoculation, vascular puncture infection/inoculation, or transformations conveyed by agrobacteria were used.

For the rubbing inoculation, a DNA plasmid coating containing similar concentrations of different plasmids is prepared for the primary inoculation. By way of example, each plasmid is used in a concentration of 6 μg/μl. The different plasmids of the same concentration are then mixed in the same volume ratios. For each leaf, 6 μl plasmid mix was applied in drops to the surface of the leaves, on which the carborundum has already been distributed. The plasmid mixture was then rubbed into the surface of the leaves with one's fingers. Alternatively, a plant sap infected with a virus can be used as the starting material. For the second inoculation, fresh or frozen plant leaves infected with a virus were ground in a homogeniser, and the resulting powder/product was dissolved in a 3-4 ml inoculation buffer (0.2406 g $KH_2PO_4$+0.543 g $Na_2HPO_4$ in 500 ml deionized water). At this point, a small quantity of carborundum was added to the plasmid mixture or plant sap. The plasmid mixture or plant sap was introduced into the upper and lower surfaces of the leaf through rubbing, wherein this is achieved by submerging one or more fingers into the inoculum and then carefully applying the inoculum to at least one leaf by hand, wherein the leaf is preferably supported by the other hand. The rubbing inoculation can also be combined with a prior injury (incision) to a plant leaf, wherein an incision is first made in the leaf with a scalpel, and the rubbing inoculation then takes place directly in the injured leaf.

For the transformation conveyed by the Agrobacteria (Ab), Ab cultures were first cultivated overnight at 28° C. in 30 ml liquid Luria broth, comprising a suitable antibiotic, 10 mM MES, and 200 μm ACE. The next day, the overnight cultures were centrifuged at 4,400 rpm for 15 minutes. The precipitation was discarded, and the pellet was then centrifuged again at 4,400 rpm for 2 minutes. The remaining precipitation was discarded, and the pellet was re-suspended in a re-suspension medium (5 ml $H_2O$, 10 mM MES, 10 mM $MgCl_2$+20 μM ACE). The optical density $OD_{600}$ of the suspension was adjusted to 1.5 using the re-suspension medium. The diluted Ab suspension was then incubated for 4 hours at room temperature. The infiltration of the Ab suspension then preferably takes place on the undersurface of a leaf of interest, e.g. a leave from *Nicotiana benthamiana*, wherein, normally, 2 leaves from each plant are inoculated.

The following Table 2 shows exemplary results for selected viruses and plant species, using different transformation methods:

TABLE 2

| Overview of virus infection experiments (WpI: weeks post infection) | | | |
|---|---|---|---|
| Virus Material | Infected Plant Species | Methods | Results |
| BMV - Virus particle DSMZ | *N. benthamiana* | Rub + Carborundum | 2 WpI: 2/2 Plants with systemic BMV infection |
| BMV - Virus particle DSMZ | Maize A188 | Rub + Carborundum | 2 WpI: 2/2 Plants with local BMV infection |
| BMV - Tobacco sap infected with virus particles DSMZ | *N. benthamiana* | Rub + Carborundum | 2 WpI: 4/6 Plants with systemic BMV infection |
| BMV - Tobacco sap infected with virus particles DSMZ | Maize A188 | Rub + Carborundum | 2 WpI: 3/4 Plants with local BMV infection |
| BMV - Tobacco sap infected with virus particles DSMZ | Maize Va35 | Rub + Carborundum | 2 WpI: 1/6 Plants with local BMV infection |
| BMV - Tobacco sap infected with virus particles DSMZ | Maize Va35 | Sheet-Incision + Rub + Carborundum | 2 WpI: 1/2 Plants with systemic BMV infection |
| BMV - Plasmids C13/F1 + F2 und C13/ F3-13m | *N. benthamiana* | After Infiltration | 1 WpI: 12/12 Plants with systemic BMV infection |
| BMV - Plasmids C13/F1 + F2 und C13/F3-13m-GFP | *N. benthamiana* | After Infiltration | 5 WpI: 12/12 Plants with systemic BMV infection |
| BMV - Tobacco sap infected with plasmids C13/F1 + F2 & C13/F3-13m | Maize Va35 | Rub + Carborundum | 4 WpI: 1/2 Plants with systemic BMV infection |
| BMV - Tobacco sap infected with plasmids C13/F1 + F2 & C13/F3-13m-GFP | Maize Va35 | Rub + Carborundum | 4 WpI: 3/4 Plants with systemic BMV infection |
| BMV - Virus particle DSMZ | *Spinacia oleracea* | Rub + Carborundum | 2 WpI: 5/5 Plants with local BSMV infection; 3 thereof also systemic |
| BMV - Virus particle DSMZ | Maize A188 | Rub + Carborundum | 2 WpI: 4/6 Plants with local BSMV infection |
| BMV - Spinach sap infected with virus particles DSMZ | *Spinacia oleracea* | Rub + Carborundum | 2 WpI: 5/ Plants with systemic BSMV infection |
| BSMV - Plasmids pCaBS-α & pCaBS-β pCa-γLIC | *Spinacia oleracea* | Rub Plasmid mix + Carborundum | 2 WpI: 11/11 Plants with local BSMV infection |
| BSMV - Plasmids pCaBS-α & pCaBS-β & pCa-γLIC | *N. benthamiana* | After Infiltration | 2 WpI: 14/14 Plants with systemic BSMV infection |
| BSMV - Plasmids pCaBS-α & pCaBS-β & pCa-γLIC | Maize A188 | Vascular Puncture inoculation | 2 WpI: 1/15 Plants with systemic BSMV infection |
| BMV - Virus particles DSMZ | Maize A188 | Vascular Puncture inoculation | 2 WpI: 1/12 plants with systemic BSMV infection |

The white background in table 2 indicates that for this experiment, a systemic infection could be obtained. A light grey background indicates a local infection, while a dark grey background indicates a low infection rate.

Proof of a successful infection is obtained from either an ELISA or by means of an RT-PCR.

Example 6: 2-gRNA Strategy

Figure 17:
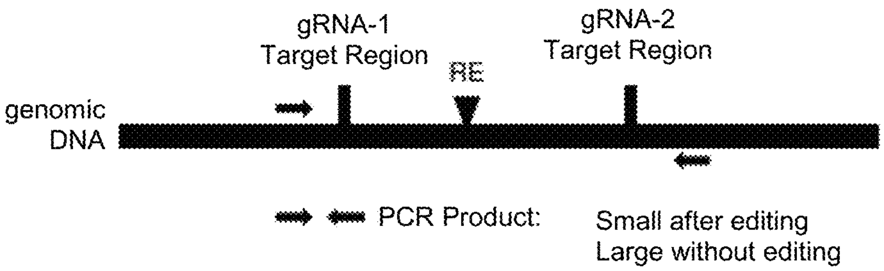
FIGS. 17 A and B (FIGS. 17 A and B) show the 2-gRNA strategy used for the method disclosed herein.
Figure 17:
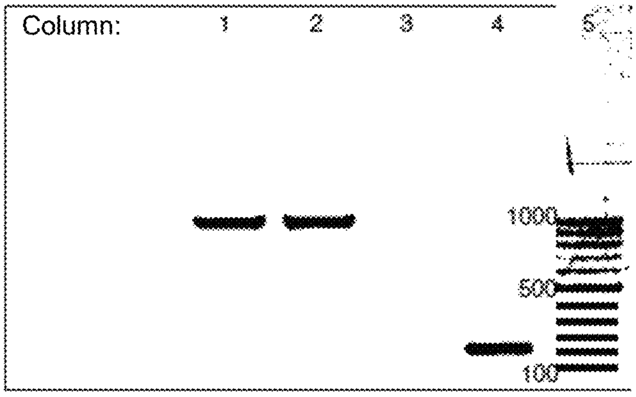

For the targeted spreading of genomic DNA and to specifically excise a nucleic acid target region of interest from the genome through the use of a CRISPR nuclease, a so-called 2-gRNA strategy was established (cf. FIGS. 17 A and B). As is shown in FIG. 17 A, genomic DNA is first isolated for this, and digested by a restriction enzyme (RE) of interest, the cleavage site of which lies within the PCR product of interest. Any RE can be used that can cleave between the two gRNA target regions. In this manner, an accumulation of potentially edited DNA takes place, because the region between the gRNA target regions no longer exists there, and the selected restriction enzyme cannot cleave this DNA. Subsequently, a PCR amplification takes place with primers that bond upstream and downstream of the two gRNA target regions, i.e. they can accumulate under suitable reaction conditions through hybridization. If necessary, a renewed re-PCR can be carried out with a nested primer set. After the successful editing, the resulting PCR product is smaller than the product from a non-edited DNA (see FIG. 17 B). The illustration in FIG. 17 B shows the results of the analysis of an editing after use of the 2-gRNA strategy with genomic DNA of a maize plant. The genomic DNA was isolated from maize plants and the target gene hmg13-gene (HMG-transcription factor 13; GRMZM2G066528) was amplified with PCR. The sequence for the HMG-transcription factor 13 gene without an editing is shown in SEQ ID NO: 60.

The nucleotide positions 1-98 of the SEQ ID NO: 60 and the nucleotide positions 912-1023 of the SEQ ID NO: 60 correspond to the region of the hmg gene that remains after a successful editing. Nucleotide positions 82-101 of the SEQ ID NO: 60 and nucleotide positions 909-928 of the SEQ ID NO: 60 are each gRNA target regions.

FIG. 17 B shows the results of a separation in a 1% gel with the standard parameter of 100 V and visualization via fluorescence obtained with ethidium bromide, with different contrast levels. Columns 1 and 2 show the results for non-edited maize plants, and column 4 shows the results after successful editing. The PCR product is smaller because the region between the two gRNA target regions has been excised. This approach thus represents a quick and efficient strategy for experimentally confirming a successful genome editing.

SEQ ID NO: 61 shows the results of the sequencing of the small PCR product after hmg13 editing with the 2-gRNA strategy. The deletion has taken place through a targeted editing between the two bases, C and T, at positions 98 and 99 of the SEQ ID NO: 61.

Example 7: Genome Editing in Tobacco

NbTTG1 was selected as the target gene in *Nicotiana benthamiana* for the genome editing work, the orthologous gene of which results in a trichome phenotype in *Arabidopsis thaliana* when dysfunctional. Mutants are described for the corresponding *Arabidopsis* gene AtTTG1 (AT5G24520):

- ttg1 (EMS-mutants): no trichomes on the leaf surfaces and stem.

yellow seeds resulting from the absence of brown pigments.

ttg1-13 (fast neutron mutants): no trichomes, transparent seed casings, increased number of root hairs.

Figure 18:
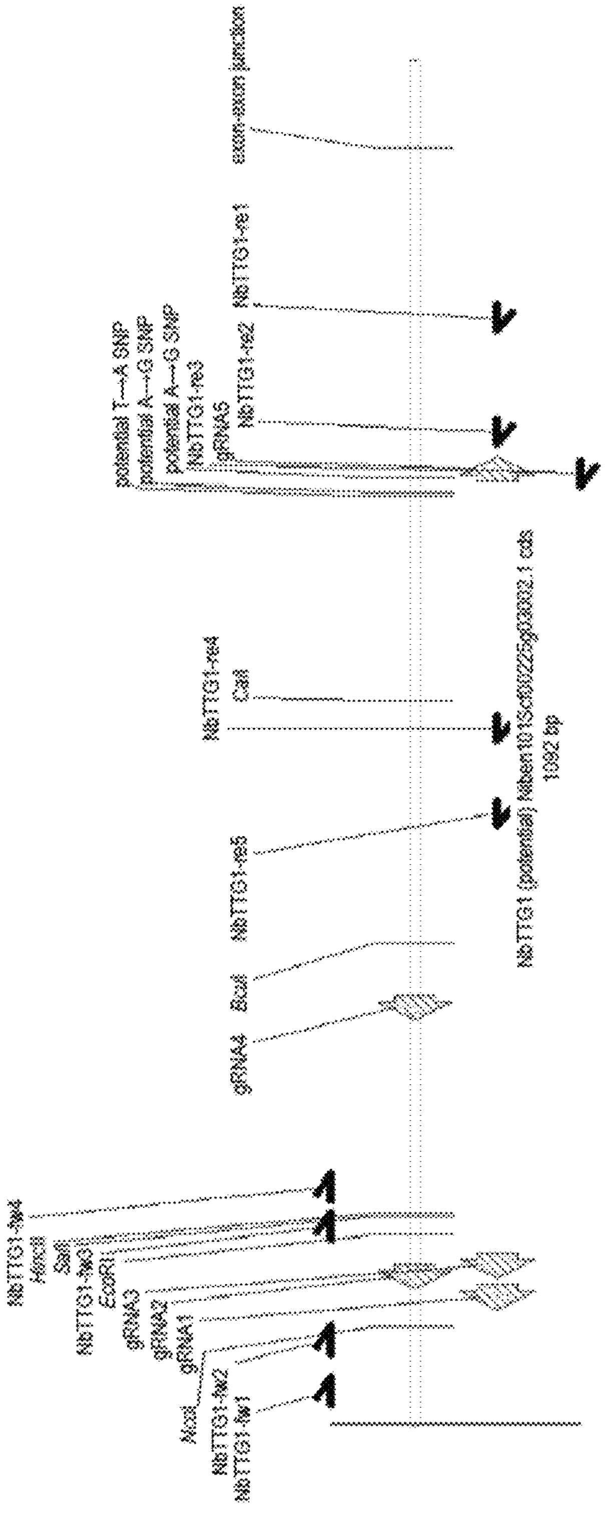
FIG. 18 shows a portion of *Nicotiana benthamiana* NbTTG1 Gene. The gRNA target regions are indicated by shaded arrows, and primer bonding sites (fw: forward, re: reverse) are indicated by black arrows. Moreover, cleavage points for restriction enzymes are indicated, which are used in the framework of the analysis of an editing result.

The orthologous gene in *Nicotiana benthamiana* was identified via sequence comparisons and the genomic locus was amplified via PCR. The section in question is shown in FIG. 18. Appropriate gRNAs were selected on the basis of this sequence, as described above. The components for the genome editing were introduced into the plant via TRV (tobacco rattle virus) (see example 8, below). The 2-gRNA strategy outlined above in example 6 was also used here for analysing a successful editing.

As can be seen in table 3 below, different sized deletions could be generated in the NbTTG1 gene through various combinations of two gRNAs. A Cas9 nuclease was used for this test, although the approach can be used for any of the CRISPR nucleases.

TABLE 3

| gRNAs | Deletion |
|---|---|
| gRNA1 + gRNA4 | 232 bp |
| gRNA2 + gRNA4 | 216 bp |
| gRNA3 + gRNA4 | 206 bp |
| gRNA4 + gRNA5 | 446 bp |
| gRNA1 + gRNA3 | 25 bp |

Example 8: Expressions of CRISPR-Cas in *Nicotiana benthamiana* Conveyed by Tobacco Rattle Virus (TRV)

Figure 19:
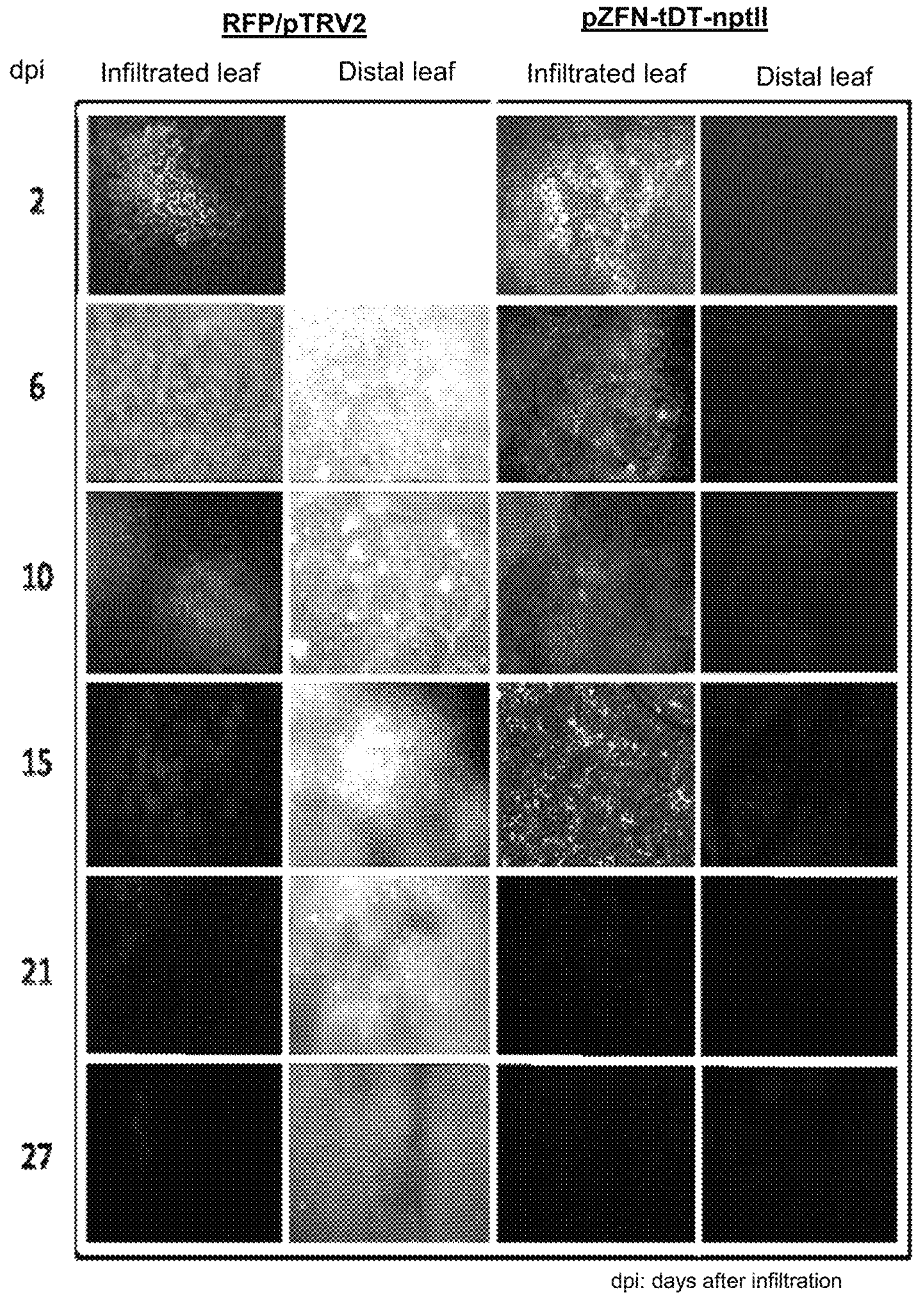
FIG. 19: TRV obtained in un-inoculated distal *Nicotiana benthamiana*, leaf tissue.

For the leaf inoculation of tobacco, first *Agrobacterium* (Ab) cultures were cultivated overnight at 28° C. in 30 ml liquid Luria broth (LB) medium, which contains a selective antibiotic. The next day, the overnight cultures were centrifuged at 4,400 rpm for 15 minutes. The precipitation was discarded and the pellet was again centrifuged at 4,400 rpm for 2 minutes. The remaining precipitation was discarded, and the pellet was re-suspended in 5 ml re-suspension medium (10 mM MES, 10 mM $MgCl_2$, 20 μM ACE). The optical density at 600 nm ($OD_{600}$) of the suspension was adjusted to 0.8 using the re-suspension medium. The diluted Ab suspension was then incubated for 4 hours at room temperature. The Ab suspension was subsequently infiltrated with a syringe or cannula on the undersurface of a leaf of interest, e.g. a leaf from *Nicotiana benthamiana*, wherein 3 leafs of each plant were normally inoculated. In order to make the systemic spreading efficiency of TRV visible, the leaves were inoculated with an RFP/pTRV2 (red fluorescent marker+TRV as a viral vector) and with pZFN-tDT-nptII as a control. As can be seen in FIG. 19, a clear RFP fluorescence can be detected in the directly inoculated leaves, as well as in the non-inoculated distal leaves (originally red fluorescence is indicated by the light and/or white regions in FIG. 19). The construct pZFN-tDT-nptII functions as a control, which only allows the expression of the RFP in the inoculated leaves, but not in the distal leaves.

Figure 20:
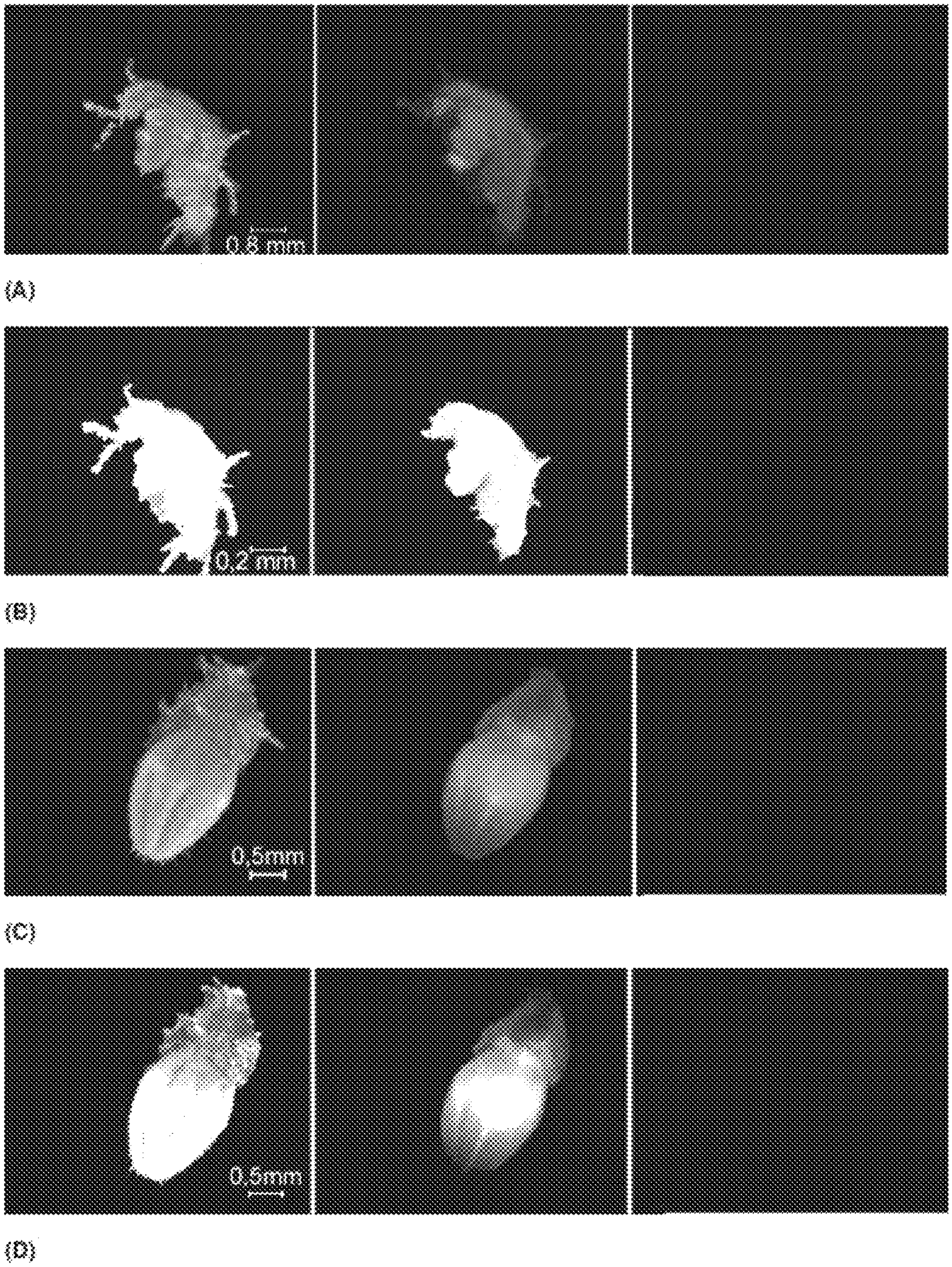
FIGS. 20 A-H (FIGS. 20 A-H) show fluorescence microscope recordings of various blossom structures that have been infected with TRV, which can express a red fluorescent protein. All of the figures A to H show a light-field recording on the left, a recording with a red filter in the middle, and a recording with a green (GPF) filter on the right. The latter serves as a control for autofluorescence. A blossom meristem is shown in FIG. 20A (original recording in black-and-white) and B (counterpart to A with contrast/exposure adjustment).
Figure 20:
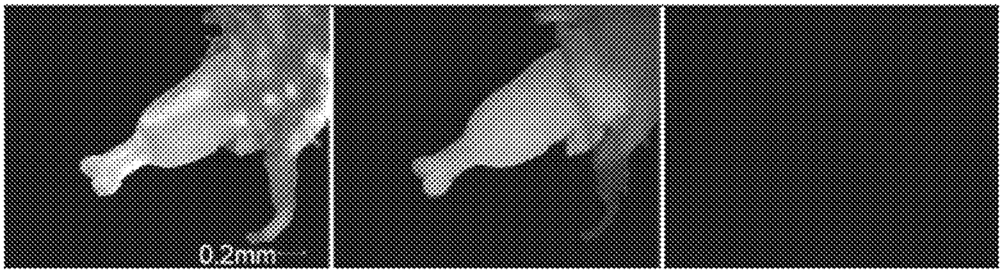
Figure 20:
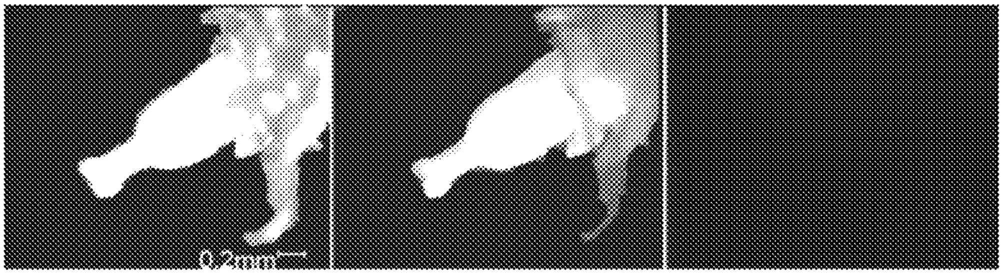
Figure 20:
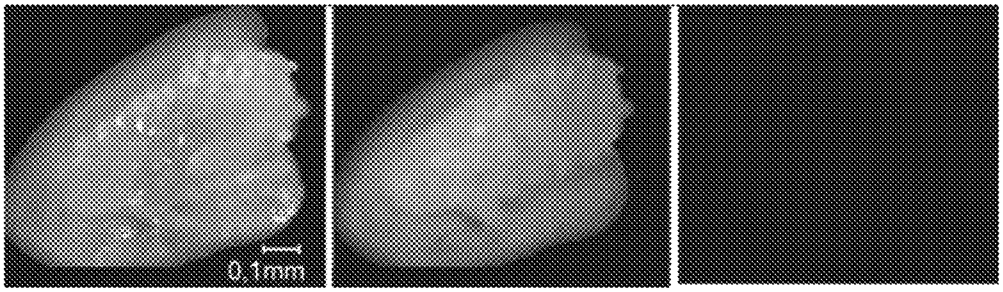
Figure 20:
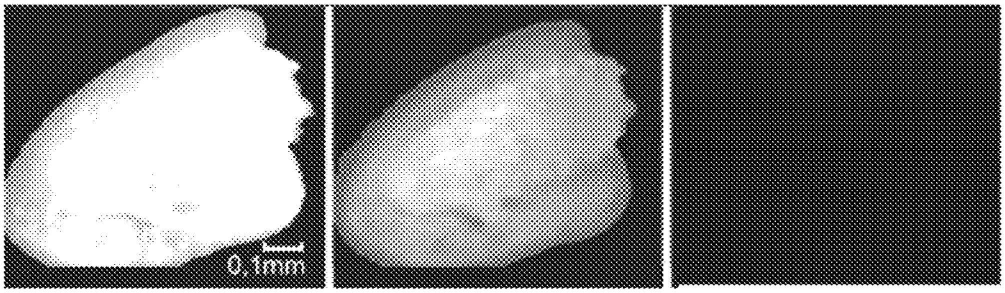

Moreover, it has been confirmed that even meristematic tissue can be activated through these TRV methods, allowing for a targeted modification of this type of tissue through the specific CRISPR methods. For this, *Nicotiana benthamiana* plants were infected with TRV, wherein the construct comprises a gene that encodes a red fluorescent protein, e.g. tdT or the like. Through detection of the red fluorescence with appropriate means (fluorescence microscope, binocular), it was possible to determine where the TRV is in the plant. It may be advantageous here to use fluorescent markers with a high intensity, because these can also be readily detected in deeper tissue layers. FIGS. 20 A to H show images of recordings of a flower meristem, a flower bud, a pistil, or a prepared pistil with exposed ovaries. All of the images demonstrate the successful expression of the fluorescent marker in the respective plant meristematic cells, or tissues as a target structure, and thus the efficiency of the selected insertion method.

Figure 21:
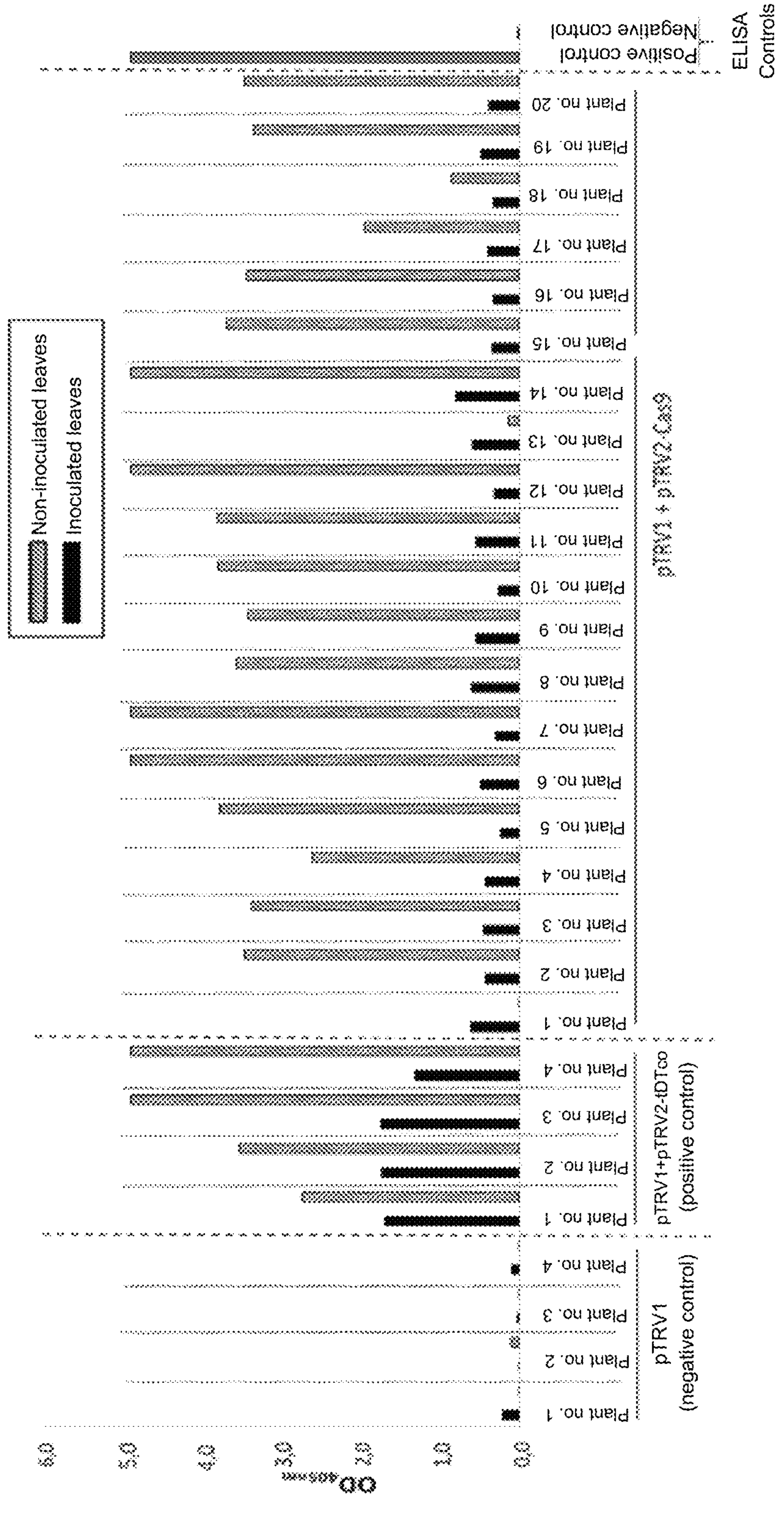
FIG. 21 shows the quantifying of TRV titres in *N. benthamiana* inoculated with pTRV1 (=Negative control), pTRV1+pTRV2-tDTco (=Positive control) and pTRV1+pTRV2-Cas9 10 dpl.

Lastly, TRV titres were quantified in the inoculated and non-inoculated tobacco leaves by means of a standard double antibody sandwich (DAS) ELISA. For this, 10-12 dpl leaf material was harvested from each plant that was to be analysed as the starting material for the ELISA, wherein for each plant, the following mixture samples were created: (i) mixture samples, each from two TRV inoculated leaves; (ii) mixture samples, each from two non-inoculated leaves. The harvested leaf material was pressed and the collected plant sap was used at a dilution of 1:50 in the DAS-ELISA. The DAS-ELISA was carried out using a polyclonal antiserum from rabbits. The antiserum was obtained from the company Loewe®, and labelled "Tobacco Rattle Tobravirus BroadRange TRV" (catalogue no. 07152S). The evaluation of the ELISAs takes place 60 minutes after application to the substrate 4-nitrophenylphosphate, through photometric measurement of the $OD_{405}$. In this manner, the TRV titres were quantified in *N. Benthamiana* inoculated with (i) pTRV1 (=negative control); (ii) pTRV1+pTRV2-tDTco (=positive control) and (iii) pTRV1+pTRV2-Cas9. The results are shown in FIG. 21.

Example 9: Quantification of CRISPR Tools

By way of example, Cas9 transcripts were detected by means of RT-PCR. For this, 10-12 dpl leaf material was harvested from each plant that was to be analysed as the starting material for the ELISA, wherein the following mixture samples were created for each plant: (i) mixture samples, each from two TRV inoculated leaves; (ii) mixture samples, each from two non-inoculated leaves (see example 8). First, RNA was extracted from the harvested leaf material, using an RNeasy Mini Kit (Qiagen). In each case, 500 ng RNA was subsequently transcribed into cDNA using the REvertAid H Minus First Strand cDNA Synthesis Kit (Thermo Fisher Scientific). The cDNA served as a template in a subsequent PCR for detecting Cas9. Cas9-specific primers were used.

Figure 22:
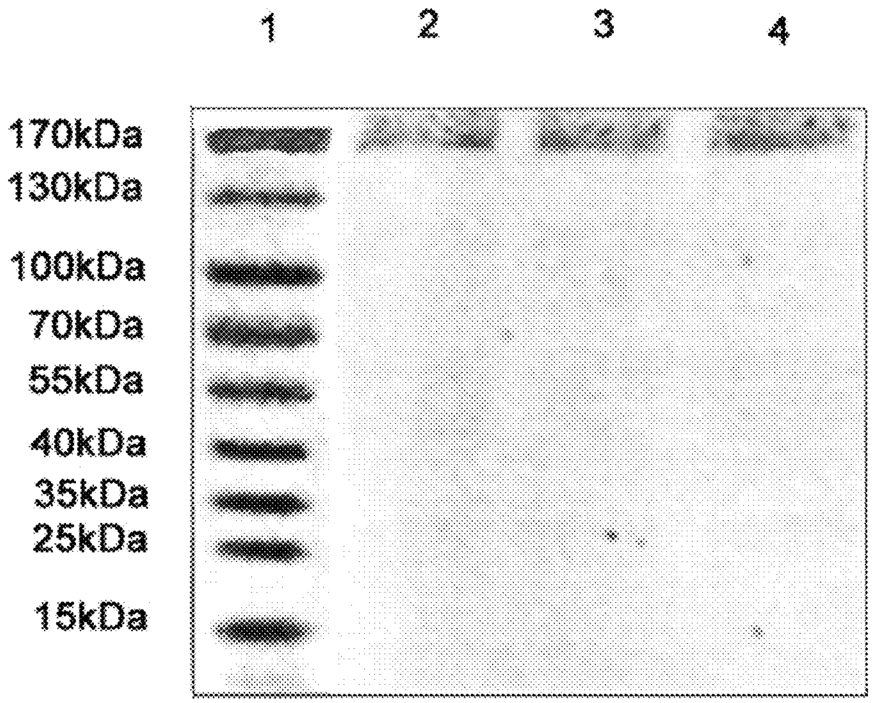
FIG. 22 shows the protein indication in Cas9 (160 kDa) expressed in and subsequently isolated from leaf material of transgenic maize plants. The PageRuler Prestained Protein Ladder (10-170 kDa; from top to bottom 170, 130, 100, 70, 55, 40, 35, 25, 15, 10 kDa) was used for the size standard. Exposure time was 30 minutes. Column 1: pre-dyed protein marker; column 2: 10 μg protein from maize expressing Cas9; column 3: 15 μg protein from maize expressing Cas9; column 4: 20 μg Protein from maize expressing Cas9.

Protein extracts were produced from leaf material of transgenic maize plants, and separated on a 4%-20% SDS-PAGE gradient gel. The detection of the 160 kDa Cas9 took place with a monoclonal antibody from ActiveMotif (catalogue no. 61577). The documentation of this detection system is shown in FIG. 22.

Figure 23:
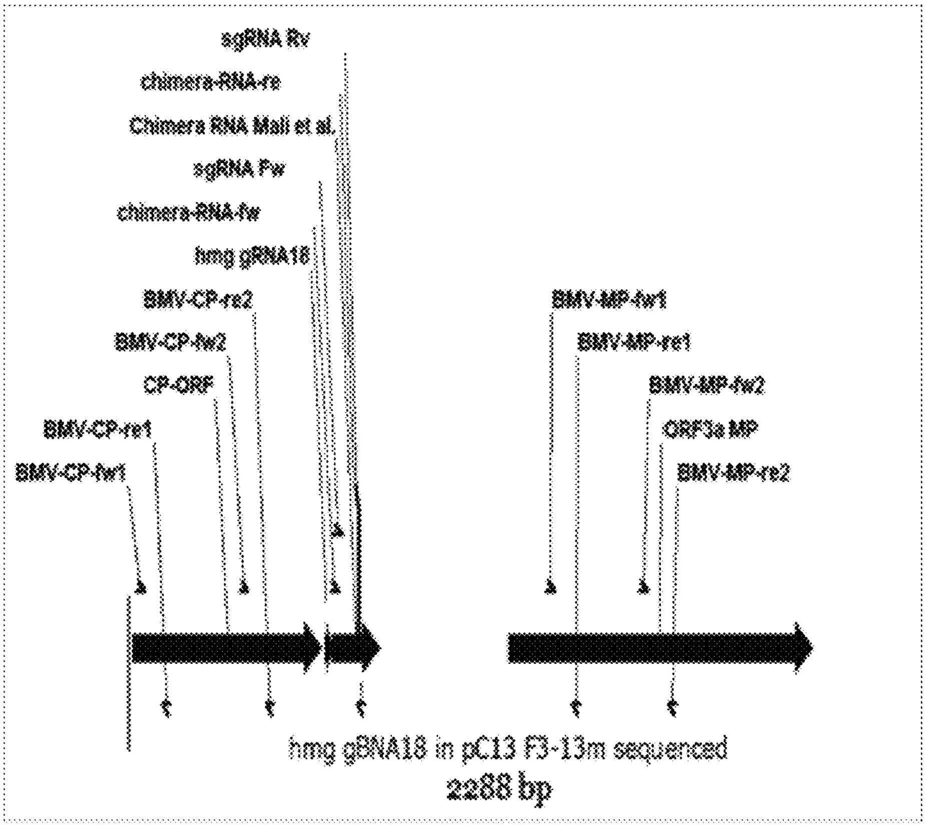
FIG. 23 shows an exemplary virus sequence (BMV). The various primer combinations used for the quantifying system of the gRNA are indicated by arrows. "Fw" indicates forward primers, and "re" indicates reverse primers, flanking a sequence of interest. A specific gRNA for the HMG transcription factor gene integrated in the construct of interest that is to be analysed is indicated by "hmg gRNA." The illustrated chimera RNA ("Chimera RNA Mali et al.") describes a chimeric, artificial RNA construct, supported by the disclosure of Mali et al., 2013 above, wherein the gRNAs described therein have been specifically adapted for use in plant cells, as explained in the example.

In order to quantify RNAs and to determine whether or not an expression by the gRNAs, conveyed through a sub-genomic promoter, takes place, quantitative RT-PCR systems on the basis of SYBR green were established. When amplified with the same PCR efficiency, a quantification could be conducted through a comparison of the gRNA quantity with the transcription level a viral proteins. This system is shown in FIG. 23, using the brome mosaic virus (BMV) by way of example.

Example 10: Viral Expression Systems

In addition to the viral vectors described above, the CRISPR tools and methods of this invention can likewise be virally introduced in other plant systems. Different methods may be used, depending on the target plant of interest, and the type of transformation, and the target tissue that is to be infected.

The system from Ugaki et al. (1991, Nucleic Acids Res., Replication of a geminivirus derived shuttle vector in maize endosperm cells) is suitable for maize endosperm cells serving as the primary target structure. Using the wheat dwarf virus (WDV) as a vector, an infected culture can thus be obtained through protoplast transformation of maize endosperm cultures. For this, a modified virus is used, which carries a neomycin phosphotransferase gene II (nptII) in place of the coat protein (CP). A transient replication system with the wheat dwarf virus as cargo, in accordance with Matzeit et al. (1991, Nucleic Acid Res., 19(2), 371-377) can be used for *Triticum* target plants. Protoplasts derived from *Triticum* suspension cultures are transfected thereby. The CP gene of the virus is again replaced by a marker gene of interest.

Moreover, systems on the basis of the Maize Streak Virus can be used, which are known to the skilled person in the field, and described in Palmer & Rybicki (2000, Archives of Virology, 146(6), 1089-1104). Three day old seedlings are infected at coleoptile nodes, and a transient expression of a recombinant construct of interest can be obtained. By exchanging the viral CP and MP genes, a systematic spreading of the virus can be prevented, such that only the first two or three leaves are infected.

As explained above, the barley stripe mosaic virus (BSMV) is also suitable as a viral vector. The BSMV genome is intensively transformed in order to establish a known plant protoplast vector (cf. Joshi et al., 1991, EMBO J., 9(9), 2663-2669). This vector, which carries a luciferase (luc) reporter gene according to Joshi et al., 1990, is suitable for protoplast transfection of maize and tobacco protoplasts.

BSMV (see Manning et al., 2010, New Phytologist, 187 (4), 1034-1047), WDV, Wheat Strike Mosaic Virus (WSMV) (Choi et al., 2000, Plant J., 23(4), 547-55), Tomato Yellow Leaf Curl Virus (TYLCV) (Peretz et al., 2007, Plant Physiol., 145 (4), 12514-1263) and Brome Mosaic Virus (BMV) (French et al., 1986, Science 231(4743), 1294-7) are also suitable as systems for transfection of protoplasts, seedlings, petioles and other plant cells or tissues in wheat, as well as barley and tobacco, as is comprehensively described in the references. In particular, BSMV vectors (see Manning et al., 2000, above) are suitable in a modified form as vectors for virus-induced gene silencing. For this, the BSMV genome is modified through site oriented mutagenesis by suppressing the expression of the viral coat protein. TYLCV (see Peretz et al., above, or EP 2 436 769 A1)) is attenuated in this regard, and made available for use as a viral shuttle vector for plants, as well as *E. Coli*, which have been deleted in the viral coat protein of a sequence comprising 60 base pairs in the proximity of the N-terminus of the gene.

Specific approaches for sugar beet transformation on the basis of viral vectors are likewise known. For this, in particular, the beat curly top virus (BCTV) (Kim et al., Plant Mol. Biol., 2007, 64(1-2):103-12), the beet yellows virus (BYV) (Prokhnevsky et al., Molecular Biotechnology, 57 (2), 101-110, 2015), the beet soil-borne mosaic virus (BSBMV) (Dach et al., 2015 ASSBT proceedings conference transcript, $47^{th}$ annual meeting of the work group, Virus Diseases of Plants", Section C), or the beet necrotic yellow vein virus (BNYVV) (Hamza et al., 2015, ASSBT proceedings) are suitable. These vectors are not only suitable as vectors for sugar beets, but also for other dicotyledons, e.g. spinach.

Numerous methods are likewise available for tobacco as the model plant, for transformation thereof by means of viral vectors. Many of these methods are based on *Agrobacterium* infiltration. Suitable viruses comprise the tobacco mosaic virus (TMV), potato virus X (PVX), cowpea mosaic virus (CPMV), bean yellow dwarf virus (BeYDV), plum pox virus (PPV) (see Gleba et al., 2014, or Slazar-Gonzalez et al., 2015, Plant Mol. Biol., 87:203-217). Moreover, diverse other systems have been described, that use, e.g., cabbage leaf curl virus (CaLCuV) (Yin et al., 2015, Nature Scientific Reports, 5:14926, 2015), tobacco rattle virus (TRV) (Ali et al., 2015, Genome Biology, 16:238), or tobacco yellow dwarf Gemini virus (TYDV) (Dugdale et al., 2014, Nat. Protoc., 9(5), 1010-27) as a virus.

All of the vectors above contain cloning sites for introducing target genes of interest. Specific cleavage sites can also be introduced easily into a viral genome of interest through available mutagenesis methods.

Example 11: Optimized Methods for Windowing Plants

To further optimize the targeted introduction of CRISPR constructs, and thus the effect of the genome editing, the method outlined in example 3, above, was further improved. The original method comprises the closing of the artificially inserted window with a closure, such as a special tissue paper. This may, however, be associated with the disadvantage, depending on the exposition, that the injured and exposed plant tissue can be more easily infected with fungi, or that a portion of the exposed tassel, the bombarded portion, comes in too much contact with air, which may result in a drying out of the exposed tassel structures, or immature flowers, and thus the individual tassel branching. For this reason, the exposed tassel tissue, transformed as described above, was covered with a moistened cotton pad or tissue in a first step. As a result, the drying could be significantly reduced, although this method is still prone to fungi infections. In order to address this problem, waxes or Vaseline-like substances were applied to the injured site (after transformation). Diverse substances were tested, comprising Vaseline, mixtures of natural waxes with Vaseline and other commercially available products, which are offered for healing wounds, specifically for trees. This approach is well known to the person skilled in the art, specifically in the field of grafting. In addition, the injured site was wrapped with a special grafting tape, which significantly improves the closing of the wound, and thus the protection against fungi infection, such that the transformed meristematic tissue can fully ripen to maturity. With this strategy, a majority of the tassels in their transformed form could ripen to maturity. Success rates of 75% and more, i.e. events in which the exposed and transformed tassel tissue could ripen to full maturity in planta, were obtained therewith.

Example 12: *Agrobacterium* Injection

Figure 24:
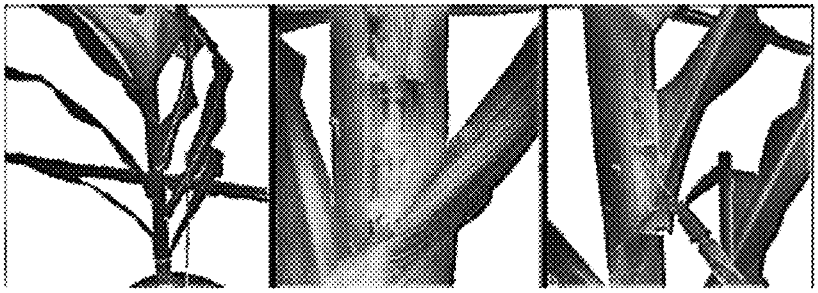
FIG. 24 shows a maize plant of the genotype A188 in the V7 stage (left-hand image), the same plant after insertion of an artificial window in the region protecting the tassel tissue (middle image), and the subsequent injection of an *Agrobacterium* solution in the region of the exposed tassel (right-hand image).

In order to further expand the breadth of the possible field of application, the method outlined in example 3 was carried out, modified such that instead of the particle bombardment, transformations caused by *Agrobacterium* (Ab) were used. In a preliminary test, the susceptibility to immature tassel tissue was first tested for Ab. For this, a red fluorescent protein was transformed in vitro in immature tassel tissue, which was previously isolated from the plant. At the time of the isolation, the plants were in the V6-V7 stage, and the tassels were ca. 2-3 cm long. Ab was set to an OD600 of 1.0, and the tassels were incubated for 10 minutes with the Ab suspension. The red fluorescence was observed two days after the infection. Numerous red fluorescent points dots were observed in the tassels, confirming the suitability of Ab infiltration for the transformation of tassel tissue. In a next step, plants in the V6-V7 stage were used, and the plants were windowed, as described above, in the region of the immature tassel tissue. Ab, which contain a red fluorescent expression construct, was injected directly into the tassel tissue in an OD of 0.7. Approximately 100-200 μl of the Ab suspension was injected into each tassel. The windowing sequence as well as the Ab injection sequence are shown in FIG. 24.

At this point, the tassels were covered with Vaseline/paraffin, as described above, and the development of red fluorescence was monitored two days after the injection. In order to suppress an excessive growth of Ab, an antibiotic solution was applied to the infected tissue 2 to 7 days after the initial injection. The treated tassels were able to ripen to maturity, and self-pollination was carried out. Molecular analyses in the T1 generation confirm the successful transformation. It is thus confirmed that an in planta method is suitable for transforming meristematic cells in planta, without impairing the further development of the tassels, such that the resulting pollen can be obtained directly from the plant, without lengthy (in vitro) cultivation processes, and can be used directly for pollination.

Example 13: Applicability to Different Maize Genotypes

The tassel transformation experiments outlined above were tested for different maize genotypes, specifically A188, Va35 and A632. For each genotype, the vegetation stage in which the tassel tissue can be transformed is naturally different. This can, however, be easily determined. In A188, the stage is V6-V7, by way of example, while A632 was targeted in stages V7 to V9. It was possible in all of these genotypes to expose the tassels in a suitable manner, i.e. it was possible to window the plants without damaging them or the tassel tissue, and to obtain mature, pollen-producing anthers.

Example 14: Embryo Meristem Bombardment

Figure 25:
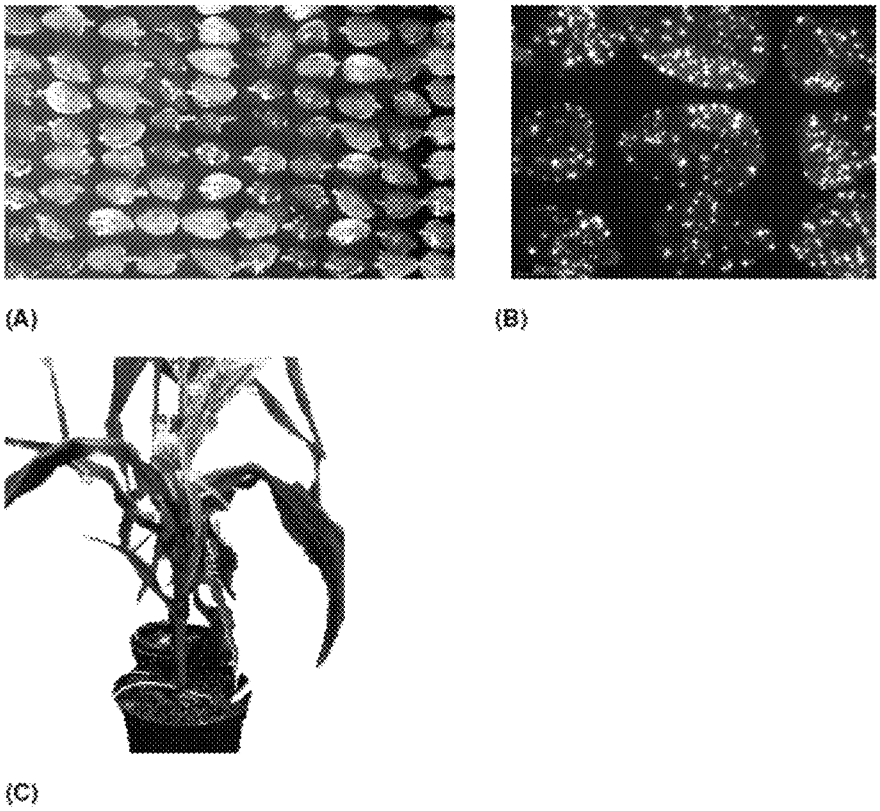
FIGS. 25 A-C (FIGS. 25 A-C) shows immature embryos (FIG. 25A) of a maize plant, which was isolated and subsequently bombarded with a particle bombardment comprising a CRISPR/Cas 9 construct, and a plasmid expressing a red fluorescent protein.

In order to further optimize the methods described herein, a so-called embryo meristem bombardment was established, which allows for plants to be efficiently obtained directly from immature embryos, without a time consuming and contamination-prone cell culture as an intermediate step. For this, the particle bombardment of meristem regions of embryos was carried out in the pipeline mode for the genotypes A188 and A632. Approximately 100 embryos (FIG. 25 A) were bombarded with CRISPR/Cas9 constructs, together with a plasmid expressing a red fluorescent protein. Fluorescent development was observed one day after the bombardment (FIG. 25 B). Numerous embryos demonstrated fluorescence, and thus the successful and functional introduction of the CRISPR construct. Work was continued with the successfully transformed embryos. After germination, 25% of the plants were analysed on the molecular level. All of the other fluorescent-positive plants were allowed to ripen to maturity in a greenhouse. As soon as the plants reached the reproductive stage, a sample was removed from the tassels, as well as the ears, and examined for CRISPR/Cas9 activity. When a successful result was identified, by means of PCR, for example, the plants were used for self-pollination, and the resulting descendants were likewise analysed.

The plants produced in this manner produced seeds for both genotypes, and were fertile. The plants displayed a slower growth rate and a slightly curved growth (FIG. 25 C), although fertile plants could be produced through this method without difficulty, the pollen of which could be used directly in further experiments. This type of transformation is thus also a highly efficient method for quickly and effectively introducing CRISPR constructs, or the genome editing obtained therefrom, in a meristematic tissue or a cell of interest, and to then be able to directly obtain and further use reproductive tissue from this tissue.

Example 15: Meristem Access in Different Types of Plants

As specified above, it is desirable to create an in planta transformation for numerous different plants, and to combine this with the methods disclosed herein, such that a targeted modification of numerous meristematic target structures can be obtained through the CRISPR systems. Specifically, the transient insertion of CRISPR constructs of interest into a plant meristematic target structure is of great interest, because this would allow for a targeted modification of a nucleic acid target region of interest, and this modification, but not the CRISPR construct itself, would then be passed on to further generations.

The tissues that can develop in planta to reproductive organs are limited. The most important thereof is the shoot meristem. This meristem is defined by the group of cells that can differentiate into all vegetative organs and cells, as well as reproductive organs and cells that are above ground. It is composed of a limited number of cells that can be (re) programmed, in order differentiate themselves into all of the organs of a plant. This meristem normally has the shape of a dome. The outer lines of the cells, called the L1 layer, form the basis for all epidermal tissue. The inner layers (L2 and L3) of the meristem form the rest of the organs, and are thus interesting targets for the purposes of the present invention. The meristem is formed very early in the development of the embryo. After the vegetative growth, the meristem develops in the flower meristem in order to generate the reproductive organs of the plant. The tissues that can produce the modified reproductive organs are: (1) the shoot meristem of the embryo, (2) the shoot meristem of plantlets or plants in the vegetative stage, and (3) the flower meristems or the inflorescences.

When the genetic information of this tissue is modified by non-viral approaches (gene guns, microinjections, *Agrobacterium*, etc.) it may be the case that not all of the cells of these meristems are modified in a targeted manner. Consequently, some of the differentiating plant organs are modified, and some retain the wild genotype. Chimeras are obtained in this manner.

One alternative for the targeted manipulation of numerous different grain plants is to transform microspores (immature pollen) or pollen grains. These tissues can then be used to pollinate further plants and obtain modified descendants. There are only a few examples in the reference sources, most of which are in the context of bombardment and transient expression analysis of the inserted genes (Twell et al., 1989, Obert et al., 2008). Nevertheless, the technology has been further developed for allowing microspores or pollen to ripen in a targeted manner, and to obtain modified descendants through subsequent pollination. The methods for these technologies are very similar for various crop plants. Microspores can be targeted directly into immature anthers, or by releasing microspores into a culture medium. This targeting can take place, for example, through bombardment or microinjections. This technique has been used successfully for producing transgenic tobacco plants (Touraev et al., 1997) and cotton (Gounaris et al., 2005). As with the targeting of mature pollen, recently obtained pollen can be treated through bombardment, or sonically (Eapen (2011)), and used immediately for the pollination of, e.g., maize ears (Horikawa et al., 1997). The descendants can then be analysed for the presence of transgenes or genomic events introduced in a targeted manner.

*Beta vulgaris:*

Figure 26:
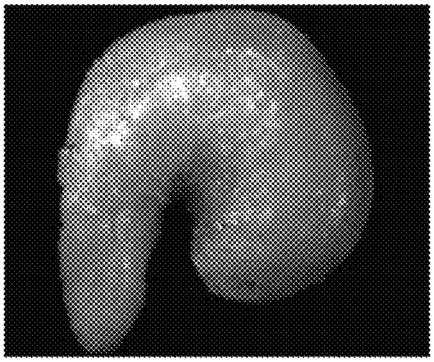
FIG. 26 shows an immature *Beta vulgaris* embryo, obtained according to the method described in detail below.

Immature embryos may be obtained, as described in Zhang et al. (2008), for the transformation of meristematic tissues in sugar beets. Flower spikes were obtained from plants grown in a greenhouse, 14 days after anthesis. They were sterilized in a 30% bleaching agent for 30 minutes. Immature embryos (IEs) were isolated, and subsequently cultivated for 4 weeks on a solid MS medium that has various plant growth regulators. An image of such an immature embryo is shown in FIG. 26. The apical shoot meristems can be treated in a targeted manner, directly in these immature embryos, wherein a targeted activation of the meristem regions can be obtained with the aid of a microscope. Alternatively, random targeting technologies, such as bombardment, can be implemented.

The plants continue to mature after the targeting. This embryo maturation takes place in an incubator, in the dark, at a temperature of ca. 20°-30° C. The maturation period lasts approximately 1 to 4 weeks. As soon as the embryo has reached maturity and begins to germinate, it is transferred to a solid MS medium and exposed to light, so that the plantlet can develop. When these plantlets are robust enough, they are transferred into soil, after an acclimation phase of ca. 1 to 4 weeks. These plants are then cultivated and the descendants are analysed.

The targeting of mature embryos from sugar beets requires the removal of the hard seed involucre (Hermann et al., 2007). The embryo is located in the middle and the apical shoot meristem is accessible. Prior to removal of the pericarp, the seed must be sterilized by bleaching in ethanol. The pericarp can then be removed with scalpels or other sharp tools, and the embryo is exposed. This embryo is then placed in a suitable medium for the specific methods for the transformation of interest. The meristem of the mature embryo, or the entire embryo, can then be subjected directly, with the use of a microscope, to a transformation that randomly activates meristem regions. After a resting phase of ca. 1 to 10 days in an incubator, in the dark, at 20°-30° C., the embryo germinates, and the plantlets can be planted. The sugar beet plants are then grown to maturity, and the descendants are analysed.

The shoot meristems in sugar beet shoots can be targeted through targeted incisions in meristem regions (Artschwager, 1926). For this, these types of shoot meristems were already targeted, e.g., through particle bombardment. Particle penetration tests were carried out prior to checking the gene expression. Transient GUS expressions were detected in the first and second cell layers of the meristem. Dividing cells with GUS activity showed that the cells survived the bombardment (Mahn et al., 1995). It was also proposed that meristems with attenuated *Agrobacterium* strains could be used for *Beta vulgaris* transformation (Kerns et al., 1988). Different methods (microinjection, *Agrobacterium*) and different plant tissues in different development stages could be used thereby. For the purposes of the present invention, a bombardment of meristematic tissues from seedlings that reproduced in vitro was carried out. The leaf material was removed, until the meristematic tissue was exposed. Vertical incisions were then made in the meristematic regions, or the regions were provided vertically, without an incision. After the bombardment with a gene cannon, the explants were left in vitro. One day after the bombardment of the cells, it was shown that the cells displayed beta-glucuronidase activity, which was introduced as a marker into the cells, confirming that meristematic regions of sugar beets are suitable for particle bombardment and thus for the insertion of genome editing tools, e.g. CRISPR tools.

In addition, the inflorescence of sugar beets can also be modified in a targeted manner, during maturation, either prior to flowering, or directly in the immature flowers. The flowers can then continue to mature, and after pollination, the seeds are harvested, and the descendants are analysed. In *Beta vulgaris*, the inflorescence is composed of an open main axis that has numerous closed, dichasial and sympodial branched inflorescences. The end flower of each inflorescence unit, and lateral flowers, merge at a later developmental stage. The five stamen primordial come from one another, and they occur in the course of flower development through the formation of an (intra)staminal ring from an annular intercalating meristem (Olvera et al., 2008).

*Triticum aestivum:*

Figure 27:
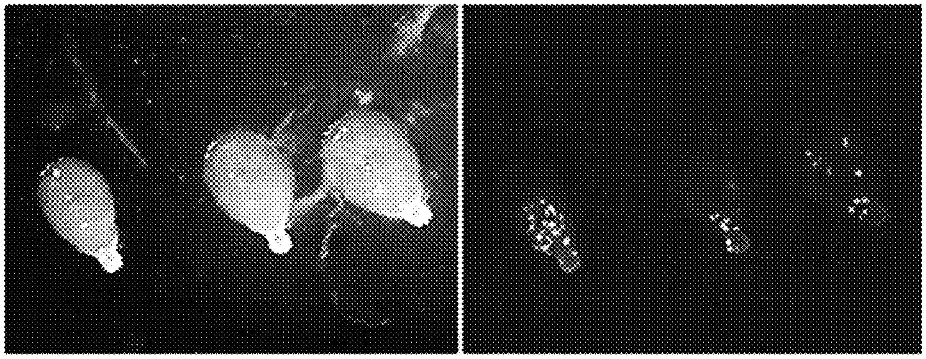
FIGS. 27 A und B (FIGS. 27 A und B)

Another approach has been developed for wheat used as the target plant. For this, immature kernels from immature spikes were collected 5 to 20 days after flowering. These kernels were sterilized through surface treatments with bleaching agents and ethanol. The immature embryos were then extracted with a scalpel under a microscope. These embryos displayed meristems exposed to different extents. These meristems were then subjected to various transformation methods, such as described in Sautter et al. (1995). FIGS. 27 A and B show images thereof. After the embryos were treated thus, they were further cultivated, specifically in an embryo cultivation medium, as described in Matthys-Rochon et al. (1998). The germinating plantlets (FIG. 27 C) were then transferred to the greenhouse, after acclimation. The plants were cultivated in the normal manner, and the descendants were subsequently analysed.

The shoot meristem in wheat can likewise be targeted for modification, as described in Sautter et al., 1995. For this, seeds were sterilized and washed for the production of vegetative shoot apical meristems through soaking in 70% ethanol for 2 minutes, followed by a sodium hypochlorite treatment and four rinsings in water. The sterile seeds were then sown in test tubes on an MS medium, supplemented with 100 mg/l cefotaxime, 2% sucrose, and 0.8% Difco agar. Shoot apical meristems from 6-10 day old plants were subsequently exposed through the removal of the coleoptiles and the first three to five leaves. Roots were then trimmed to approximately 5 mm. The explants were then supplemented with different sucrose concentrations (optimum: 10%) and placed on an MS base medium (0.8% agarose). Following particle bombardment, the explants were then transferred to a further culture on MS agarose.

Figure 28:
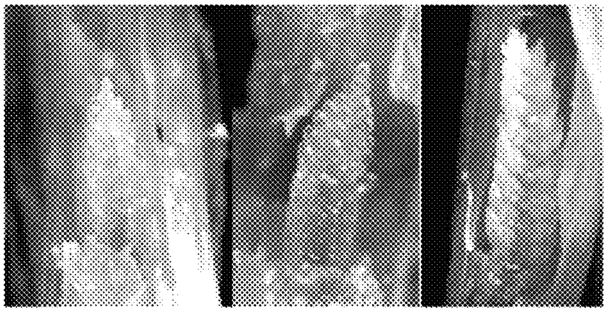
FIG. 28 shows the localization of the immature florescence in wheat in the left-hand image. The middle image and the right-hand image show the further development, from left to right, of the meristematic tissue that has been transformed, as described below.

Moreover, the flower organs can also be targeted in wheat. The shoot meristem differentiates itself very early in the development to immature spikes, or shoots, a few weeks after seeding. These immature spikes can be found on the bottom of the shaft (see FIG. 28, left-hand image). A window is formed in these immature spikes through an incision in the shoot. The meristematic tissues can be reached through this window with various transformation techniques. After the transformation, the wound is closed, and the transformed system is further cultivated until the seeds reach maturity (see FIG. 28, middle, left- and right-hand image), and the descendants are subsequently analysed. Alternatively, the immature spikelets are removed from the inflorescence, sterilized in vitro, and detached in a targeted manner. The maturation and seed production can then be carried out in vitro, on the basis of Barnabas et al., 1992.

It has furthermore been shown for wheat that it is possible to target immature inflorescence using a gene gun (Leduc et al., 1994, Sautter et al., 1995). It has been shown that after the bombardment, the cells in the tissue treated in this manner express inserted reporter genes, and can continue to divide.

*Brassica napus:*

It has also been shown for rapeseed that the shoot apical meristem has already developed in the so-called "heart stage." A transformation process for rapeseed in this stage that can also be used with the method disclosed herein is described in Huang et al., 2009.

Moreover, when rapeseed is used as the target plant, the shoot meristem can be transformed in a targeted manner after germination, or when the plants have reached the 2-8 leaf stage. For this, the leaf primordials covering the meristem are carefully removed with a scalpel. The exposed meristems are then preferably treated with an antioxidant for their protection. Subsequently, the meristematic regions can be transformed by means of various transformation techniques. Here as well, the plants can subsequently be cultivated until the reproductive organs have reached maturity, and the descendants thereof can be analysed for the presence of the modification that has been introduced in a targeted manner.

Rapeseed flowers can also be targeted. The flowers in a rapeseed inflorescence are produced continuously. New flowers are produced on the tips of the flower clusters. Two approaches can be taken for the transformation of rapeseed flower organs. In the first approach, immature flowers can be opened in situ, and the reproductive tissues can be activated in a targeted manner. After the treatment, untreated inflorescence and husks are removed, and the inflorescence is then covered, in order to promote self-pollination. The seeds are harvested, and the descendants are analysed. In the second approach, all of the differentiated flowers are carefully removed from the flower clusters/panicles, and the flower meristem is left exposed. These meristems are then treated with various types of transformations. The meristems are then covered, in order to allow the normal development to continue. All of the husks/pods are harvested, and the descendants are tested in terms of their molecular biology and their phenotypes.

*Glycine max:*

For soya bean transformation, meristematic regions can likewise be activated in a targeted manner.

The shoot meristem from an embryo is exposed to light and transformed, as described in McCabe (McCabe et al., 1988). For this, mature soya seeds (BR-16, Doko RC, BR-91 and Conquista) are subjected to a surface sterilization in 70% ethanol for 1 minute, followed by immersion in 1% sodium hypochlorite for 20 minutes, and then three rinsings in sterilized distilled water. The seeds are soaked in distilled water for 18-20 hours. The embryonic axes are cut out of the seeds, and the apical meristems are exposed by removing the primary leaves. The embryonic axes are placed in a bombardment medium (BM: MS (Murashige and Skoog, 1962) simple salt, 3% sucrose, and 0.8% Phytagel™ sigma, pH 5.7), the apical is oriented upward in 5 cm culture dishes with 12 ml culture medium. As soon as the shoots derived from the embryonic axes have reached a length of 2-3 cm, a 1 mm long section from the base of each leaf is removed for the GUS analysis (beta-blucuronidase) (McCabe et al., 1988). The shoots, or sprouts, that express the exogenous DNA are transferred individually into a plastic pot containing 0.2 l autoclaved, fertilized soil (vermiculite (1:1)), and then kept covered in a sealed manner with a plastic bag and rubber band in the greenhouse. The rubber band is removed after 1 week. After another week, the plastic bag is likewise removed. As soon as the acclimated plantlets have reached a length of about 10 cm, they are transferred into pots with 5 l of fertilized soil, until seeds start to develop (McCabe et al., 1988). As soon at the plantlets have grown, leaf samples are removed for analysis. The plants are then grown to maturity, in order to analyse the descendants thereof for targeted modification.

Alternatively, the meristems of the immature embryos are activated for a targeted transformation. For this, the pods are harvested 5 to 20 days after flowering, and the embryos are extracted with a scalpel and gripping tool between the heart and cotyledon stages. These embryos are placed on an embryo growth medium, and the shoot apical meristem is transformed in a targeted manner with various delivery/transformation methods. The embryos are then grown in the dark for 1 to 10 weeks, until reaching full maturity, as described in Buchheim et al. (1989), and exposed to light for embryo germination. The plantlets grown in this manner are cultivated to maturity in a greenhouse. The seeds are harvested, and the descendants are analysed. The targeted introduction of recombinant constructs in the shoot meristems of the germinating soya bean plantlets is carried out as described in Chee et al., 1989. Seeds from *Glycine max* L. Merr (Cv A0949) are sterilized by immersion for 15 minutes in a 15% Clorox solution, followed by numerous rinsings with sterilized distilled water. Seeds are place for 18 to 24 hours on sterilized, moistened paper towels in Petri dishes for germination, at 26° C. in darkness. The seed coverings are removed, and one of the two cotyledons of each germinated seed is removed, and the half-seeds, together with the shoot bud of the seedling (*Plumula*), the cotyledon nodes, and the neighbouring cotyledon tissue, are inoculated overnight with liquid cultures of an avirulent *Agrobacterium* line, C58Z707, which contains the binary plasmid pGA482G. *Agrobacterium* transformation can also be replaced by other introduction or transformation methods. Another approach is described in Chowrira et al., 1995. The terminal buds of plantlets (7-10 days old) are exposed through removal of the surrounding leaf tissue. Foreign DNA is injected with a syringe, also containing lipofectin as a transfection agent, and the meristem is subsequently electroporated. The plants are grown to maturity without selection, and chimeric plants can subsequently be obtained in this manner. The descendants thereof are then analysed.

Access to the scars of the pollinated soya bean flowers is obtained as described in Shou et al. (2002). In brief, all of the experiments were carried out in the late afternoon, with flowers that were naturally pollinated that same morning. Two petals and one keel petal were removed, in order to expose the stigmas/scars of soya bean flowers to light. Stigmas were severed at the border between the ovary and the stigma, and plasmid DNA (concentrations of 25, 80, 100 or 150 μg/ml) was applied to the exposed scar. The treated flowers were tagged, and untreated flowers and buds on the same node were removed. The shoots that form on the treated flowers were harvested individually. Alternatively, the soya bean inflorescence flower meristem could be transformed in a targeted manner, before it reached the end stage, in that the primordial were removed when the flowers start to develop further. This exposition is obtained through excision of the primordial with a scalpel. The flower meristem is covered as soon as it is transformed. After inflorescence can develop, and self-pollination has begun, the shoots of the treated plants can be harvested, the seeds processed, and the descendants can be tested for the targeted genomic modification.

*Gossypium* sp.:

Experiments according to the present invention for inserting a targeted modification of interest could be carried out for cotton, in that the meristems from embryos were treated as described in Aragão et al. (2005). For this, seeds (variation 7mH, CD-401, Antares and ITA94) were harvested by hand, and fibrous material is removed with an acid treatment. Concentrated sulphuric acid was added, and the seeds (3 ml/g seeds) were stirred thoroughly for 1 minute with a glass rod. The seeds were then transferred immediately into 5 l water, rinsed three times with distilled water, and dried on a paper towel. Mature seeds were surface-sterilized with 70% ethanol for 10 minutes, followed by 1 minute treatment in 2.5% calcium hypochlorite, and rinsed three times in sterilized distilled water. The seeds were then soaked in distilled water for 24 hours, upon which the seeds were able to germinate for 16 hours at room temperature in darkness. Embryonic axes were cut out of seeds, and apical meristems were exposed by removal of the cotyledons. Explants were transferred to an MS medium, containing 3% glucose (5 mg/l benzylaminopurine (BAP), 0.8% Phytagel (Sigma)). The pH value was set to 5.7 for the autoclaving. Embryonic axes were produced as described above, and positioned in a bombardment medium (MS simple salt medium, 3% glucose, 5 mg/l BAP, and 0.8% Phytagel Sigma, pH 5.7), apical at the top, in 5 cm culture dishes with 12 ml culture medium. At this point, the meristems could be transformed or transfected. The treated apical meristems were cultivated in darkness. The meristems exhibiting growth were transferred to a growth chamber. The plantlets were then transferred to a greenhouse and cultivated to maturity. The descendants were then analysed.

Alternatively, embryo meristems are transformed, as described in Rajasekaran (2013).

In another approach, immature embryo meristems were targeted in vitro, according to the protocol described by Mauney (1961). The culture medium that was used was composed of White's nutrient mixture, with all of its ingredients, plus five times the normal concentration of supplements (40 mg/l adenine sulphate, 250 mg/l casein hydrolysate, 150 ml/l coconut milk, and 7 g/l NaCl). The medium was stiffened with 8 g/l bacto-agar, and 20 g/l sucrose as a carbohydrate source. The most important feature of this medium for the success of the cultivation method was the adjustment of the osmotic pressure to a high level, which can be achieved through the addition of 7 g/l NaCl. After the embryos grew on this medium for 3-4 weeks, they were transferred to a medium with a medium osmotic pressure (3 g/l NaCl, instead of the 7 g/l), and then into a medium without NaCl after a further growth period of 2 weeks. The successfully cultivated embryos in the last medium germinated, and were planted in soil.

In order to transform shoot meristems in cotton plantlets, meristems were transformed in a first approach described in Zapata et al. (1999). Seeds were surface-sterilized with concentrated sulphuric acid (1 hour) at 50 rpm in a rotational shaker (50% Clorox (1 hour)), and rinsed at least three times with sterilized, doubly-distilled water. The seeds were then placed on a medium solidified with 0.15% (mass/volume) Gelrite, pH 5.7, which contains the inorganic salt from Murashige and Skoog (MS) (Murashige and Skoog, 1962), and 2% sucrose, for germination. The seeds were incubated for about 3-4 days at 28° C., in the dark. The shoot tips were isolated, and then transferred into MS inorganic salts (Murashige and Skoog, 1962), with 100 mg/l myo-inositol, 0.5 mg/l thiamine/HCl, 0.5 mg/l nicotinic acid, 0.5 mg/l pyridoxine/HCl, 3% sucrose, and 0.15% (mass/volume) Gelrite, at pH 5.7. After isolation, the delivery of a recombinant construct of interest could be carried out, and the plant material could subsequently be transferred to a new medium. The vital transformed apices were transferred to a fresh medium. The surviving apices were then transferred to the same medium, but without kanamycin. As soon as roots started to develop, the plants with roots (T0) were transferred to soil, and allowed to grow to maturity in a greenhouse. The descendants could then be analysed.

Alternatively, the cotton meristems were transformed as described in Keshamma et al. (2008). For this, seeds from a strain, viz. NC-71, were soaked overnight in distilled water, and the surface was sterilized, first with 1% Bavistin for 10 minutes, and then with 0.1% $HgCl_2$ for a few seconds, and subsequently washed thoroughly with distilled water. The seeds were able to germinate later at 30° C. in darkness on Petri dishes. Two day old seedlings were used as explants. The seedlings with straight *plumula*/shoot buds were infected, in that they were separated from the cotyledons, without damaging them, such that the meristem was visible. A transfection or transformation method of interest could then be used. The seedlings were subsequently transferred to autoclaved Soilrite (Vermiculite equivalent), watered, and covered for germination under aseptic conditions in a growth chamber, 5 seedlings per pot. After 5 to 6 days, the seedlings were transferred into pots with Soilrite, and allowed to grow for at least 10 days before they were transferred to the greenhouse. The mature plants could then be analysed.

In another approach, cotton meristems were transformed according to the protocol described in McCabe et al. (1993).

In yet another approach, cotton flowers could be transformed in a targeted manner according to the method from Gounaris et al. (2005). For this, cotton plants of the Christina type were used for the transformation. Flowers that were to be used as pollen receptors had to be separated from male plants two days prior to the expected dehiscence. On the morning of the pollination day, donor flowers with intact stamina were collected 1-2 hours after blooming. Each donor flower could then be treated with a transformation or transfection method of interest. These inflorescences were used for further pollination of receptor flowers (after prior removal of the male germ cell). The pollinated flowers could continue to develop and produce seeds. The descendants could then be analysed in terms of molecular biology. In another approach, flower meristems or immature flowers could be genetically modified in a targeted manner. For this, the meristem forming the flowering branch, the flower bud, and the immature flower were exposed by removing the primordials and floral bracts. A delivery method (transformation/transfection, biological, chemical or mechanical) of interest could then be used according to the present disclosure. Subsequently the treated zones were covered, and allowed to continue to grow. The flowers were then harvested. The descendants could be analysed with regard to their molecular biology, as well as their phenotypes.

*Oryza sativa:*

If the target plant of interest is rice, the following methods could be used for introducing a targeted genomic modification in a meristematic target structure.

According to the methods from Naseri et al., 2014, rice seeds (*O. sativa*, Hashimi) were sterilized through soaking in 90% ethanol (1 minute), and washed three times with water. Sterile seeds were placed on wet cotton for two days at 22° C. The inoculation with *A. tumefaciens* took place in embryonic apical meristems of the saturated seeds, on the surface of the seed where a shoot would later develop. The surface was penetrated to a depth of approximately 1 to 1.5 mm with a needle (Ø0.7 mm, previously immersed in *A. tumefaciens* inoculum) The inoculated seeds were then covered with aluminium foil in bottles, placed on filter paper on wet perlite, and incubated for nine days at 23° C. in darkness. 70% to 75% of the inoculated seeds germinated. In order to kill off *A. tumefaciens*, the seedlings were immersed at room temperature in an aqueous solution (1000 ppm) of cefotaxime for 1 hour. For root formation, the seedlings were placed in a Yoshida solution. Lastly, the seedlings were planted in pots, and grown to maturity (T0) under unsterilized conditions. This enabled self-pollination, and thus the production of a T1 generation.

In another approach, the meristems of immature embryos were activated for a targeted modification with the CRISPR tools disclosed herein. Immature seeds were harvested 3-12 days after pollination. The immature embryos were placed in a maturation medium (Ko et al., 1983), and the transformation/transfection methods of interest could then be used. The embryos were raised to maturity, as described in Ko et al. (1983). The seeds were harvested, and the descendants analysed in terms of their molecular biology.

Meristems from rice plants were treated as described in Muniz de Pèadua et al. (2001). For this, rice seeds were surface sterilized and brought to germination in vitro. After ca. 4 days, the shoot apices were excised from the distal part of the first internode of the epicotyl, and the coleoptile. After exposition, a delivery system of interest could be used. This enabled root formation. The plants were then transferred to the greenhouse, and further cultivated, and the descendants were subsequently analysed.

Immature rice spikes were treated for the targeting of flower organs as described in Rodin et al. (2014). The inflorescence were used in stage 51 (start of panicle development: tips of the inflorescence protrude out of the pod) in accordance with the BBCH scale (Lancashire et al., 1991), and could then be treated, and the descendants could be subsequently analysed. Moreover, the flower meristems could be activated. For this, the meristems had to be exposed by removing the surrounding tissue, and subsequently transformed and further cultivated, and the descendants were subsequently analysed. Furthermore, the immature spikes could be treated, either before differentiation, or after the surrounding primordials were removed, through transformation or transfection. The treated spikes could then continue to develop. The resulting seeds of these flowers were harvested, and the descendants were examined for targeted editing events (Itoh et al., 2005).

Example 16: Transient Transformation Methods

In particular for in planta transformation of meristematic tissue, there is a large interest in creating transient transformation methods, in particular for the introduction of CRISPR tools of interest, because as a result, only the targeted modification that is to be introduced, and not the tool itself, can be passed on to the descendants of a cell. Methods that are controlled and can be controlled in this manner have become increasingly important in the field of plant breeding, due to the regulatory provisions and contingent on safety concerns.

Transformation methods, both transient and stable, must, as a matter of course, be adapted to the tissue that is to be transformed. For this reason, the following experiments were carried out, which can be used, in part broadly and in general, and in part for specific tissues (pollen, meristems, flowers, etc.).

Cas9:

Cas9 was obtained from New England Biolabs (NEB), PNA BIO, ToolGen, LDBIOPHARMA or ABM, or Cas9 was purified, as described in Liu et al. (2015).

In Vitro Transcription of sgRNAs:

The in vitro transcription was carried out as described by Zuris et al. (2015). Linear DNA fragments containing a T7 promoter bonding site followed by the 20 bp sgRNA target sequence were transcribed in vitro using the T7 RNA High Yield Synthesis kit (NEB) in accordance with the directions by the manufacture. RNA, transcribed in vitro, was precipitated with ethanol, and purified by gel electrophoresis on a 10% polyacrylamide criterion TBE urea gel (Bio-Rad). Excised gel fragments were extracted in 420 µl 300 mM NaCl overnight, on a shaker surface at 4° C. Gel-purified sgRNA was precipitated with ethanol, and dissolved in water, and the sgRNA concentration was then quantified through UV absorption. The sgRNA could then be snap-frozen and stored at −80° C. Alternatively, gRNAs were obtained as described in Kim et al. (2014). For this, RNA was transcribed in vitro through a T7-RNA-polymerase run-off reaction, using the MEGAshortscript T7 kit (Ambion). Templates for sgRNA or crRNA were generated through accumulation and extension of two complementary oligonucleotides. The transcribed RNA was purified through phenol-chloroform extraction, chloroform extraction, and ethanol precipitation. The purified RNA was quantified through spectrometry.

Alternatively, another protocol (described in Ramakrishna et al., 2014) could be carried out. For this, the RNA was transcribed in vitro, through run-off reactions through the T7-RNA polymerase. Templates for the sgRNA transcription were generated through annealing/hybridisation and extension of two complementary oligonucleotides. The transcribed RNA was separated on a 8% denatured urea-PAGE gel. The RNA was received in nuclease-free water, and subsequently purified and obtained through phenol-chloroform extraction, chloroform extraction, and ethanol precipitation. The purified RNA was quantified through spectrometry.

Complexation Protein Cas9 and gRNA:

As described in Zuris et al. (2015), 1 µl 200 µM Cas9 protein was mixed with 2 µl 50 µM sgRNA and incubated for 5 minutes at room temperature for the introduction of Cas9-sgRNA complexes, prior to mixing the complex with 3 µl of either RNAiMAX or Lipofectamine 2000, and incubated for a further 30 minutes, prior to the injection. Alternatively, the complexation is carried out as described in Kim et al., 2014. For this, Cas9 protein (4.5-45 mg) was pre-mixed with in vitro-transcribed sgRNA (6-60 mg). Cas0 protein in a storage buffer (20 mM HEPES, pH 7.5, 150 mM KCl, 1 mM DTT, and 10% glycerine) were dissolved with sgRNA in nuclease-free water, mixed, and incubated for 10 minutes at room temperature.

*Agrobacterium* (Ab)

Pollen Transformation with Ab:

The pollen transformation was carried out as described in Li et al. (2004). For this, flowers with freshly developed and exposed anthers were collected. An aliquot of an Ab solution was transferred into sterilized 1.5 ml test tubes, and centrifuged for 10 minutes at 3,000 rpm. The pellet was resuspended (in pollen germination medium, with ca. 50 mg pollen/ml) and a vacuum (−80 Pa) was applied for 30 minutes, and then slowly released. The suspension was subsequently centrifuged at 3,000 rpm for 5 minutes, and the pellets, i.e. the pollen, were used directly for pollination.

Shoot Apical Meristem Transformation with Ab:

Meristems from seedlings were transformed on the basis of the protocol from Chee et al., 1989. Inoculations were carried out at three different sites, in that a 30'/2 gauge needle was inserted into the plumule, cotyledon nodes and adjacent regions, and 30 ml of the Ab cells were injected at each injection point. The germination process of the seeds infected with Ab was continued in that the seeds were transferred to sterilized moist paper and further incubated at 28° C. (in darkness for about 4 hours). For full development, the seedlings were then planted in the ground. Alternatively, the protocol described in Keshamma et al. (2008) can be used. The seedlings were then infected, as soon as the plumule exists, by separating the cotyledons, without destroying them, such that the meristem is visible. The meristems were then pierced, and then dipped in an *Agrobacterium* culture for 60 minutes. After the infection, the seedlings were washed briefly with sterilized water, and later placed on autoclaved Soilrite.

Particle Bombardment:

Bombardment, or bombarding, of embryo meristems was carried out as follows: embryos in the coleoptile stage, or the heart stage, were placed in in embryo maturation medium supplemented with osmoticum 0-6 hours prior to the bombardment. The particle processing and preparation was carried out according to a routine DNA precipitation with spermidine. With protein/RNA mixtures, the protocol from Martin-Ortigosa et al. (2014) was carried out, wherein the mixture was dried or freeze-dried, together with the gold particles. 16-24 hours after the bombardment, the embryos were placed on a ripening medium without osmoticum.

Bombardment of Anthers:

Bombardment of anthers can be carried out in accordance with Twell et al., 1989. For this, 1d plant anthers were surface-sterilized prior to releasing pollen in 10% Clorox for 10 minutes, and rinsed in sterilized distilled water. The anthers were sliced transversely with a sterilized razor blade, and 20 anther sections were placed on solid MSO medium with a surface area of 4 $cm^2$, with exposed thecae. In another approach, anthers were bombarded, as described in Obert (Obert et al., 2008). For this, spikes/anthers were harvested as soon as the microspores were in a middle mononuclear development stage. Two different pre-treatments were used in our studies, together with the use of untreated material. For a cold treatment, the plant material was placed on a moist filter paper in a cold room at 5° C. (Dedicova et al., 1999). After the pre-treatment of the material (14 days in cold storage), the specific portions of the spikes that contain microspores were selected in exactly the suitable stage, and used as further experimental material. The material is surface-sterilized (in 70% (vol./vol.) alcohol), and washed three times with sterilized distilled water. For the mannitol pre-treatment, suitable portions of the fresh spikes containing microspores in the correct stage were surface-sterilized (in 70% alcohol) and washed three times with sterilized distilled water. The anthers were isolated in sterile conditions, or placed on the surface of a cultivation medium (FHG media, Kasha et al., 2001) after pre-treatment. The bombardment conditions were: distance (macrocarrier—anthers in Petri dishes): 9 cm; pressure settings of 650, 900 and 1,100 psi. Anther cultures were then cultivated at 26° C. in darkness, in a tissue culture growth chamber.

In another approach, (Touraev et al. (1997)), single-cell microspores and pollen grains in a middle bi-cellular stage were bombarded in the respective culture media immediately after isolation. The suspension (0.7 ml), containing ca. $5\times10^5$ cells, was evenly spread on a sterile filter paper (Whatman No. 1), and transferred into a 10 cm Petri dish (Sterilin, Great Britain). The helium-driven PDS-1000/He particle discharge system (Bio-Rad, USA) was used for the biolistic transformation. The bombardment was substantially carried out as described in Sanfor et al. (1993). Plasmid DNA was precipitated onto gold particles (Bio-Rad, USA), having a mean diameter of 1.1 μm. Each transformation comprised three bombardments.

The bombarded microspores, or mid-bi-cellular pollen grains, were washed off of the filter paper, and incubated in a separate ripening medium.

Bombardment of Flowers:

On the basis of a protocol from Twell et al., 1989, groups of 10 flowers with intact curved petals were bombarded, wherein the truncated pedicels were suspended in distilled water.

Bombardment of Pollen:

On the basis of a protocol from Twell et al., 1989, pollen from mature flowers was collected in sterilized microcentrifuge test tubes. Prior to bombardment, dried pollen samples were suspended in a liquid MSO medium with a density of approx. 106 grains/ml. The pollen suspension (1 ml) was immediately pipetted onto the surface of a 9 cm Petri dish, containing an MSO medium thickened with agar, on which a sterile Whatman no. 1 filter paper with a nylon membrane (Genescreen, NEN) was previously placed. The bombardment was carried out within 60 minutes after the plant material was transferred to the MSO medium. The precipitation of plasmid DNA onto tungsten micro-projectiles and the bombardment took place as described in Klein et al. After bombardment, the Petri dishes or intact flowers were incubated in distilled water at 26° C., in light.

In another approach, pollen bombardment was carried out as described in Horikawa et al. (1997). For this, mature pollen grains were collected from extruded tassels. The subsequent bombardment preparation steps were carried out very quickly, because the life expectancy of the pollen decreases quickly. The pollen was immersed in a liquid MS medium containing 30 g/l sucrose (pH 5.8). The $4.0\times10^5$ pollen grains (in 1 ml medium) were adsorbed on the surface of a piece of microfilter (pore size 0.45 um, Fuji Film Co., Tokyo) through vacuum filtration. The microfilter was placed on 1% agar plates in a Petri dish in preparation for the bombardment with a particle cannon.

Pollination with the Treated Pollen:

For the pollination with the bombarded pollen, the protocol described in Touraev et al., 1997, was carried out. For this, mature flowers were emasculated shortly before flowering, while they still had closed anthers, one day prior to pollination. The pollen that matured in vitro was washed repeatedly in a GK medium without quercetin, and then transferred to scar tissue in droplets of 3 μl. Those scars that display a good scar secretion production were selected for the pipette pollination. To prevent cross-pollination, all of the other flower buds in the climate chamber were removed one day before opening. Mature seed capsules or pods were collected 3-4 weeks later.

In another approach, the method described in Horikawa et al. (1997) is used. For this, pollen was placed in 1 ml liquid MS medium. The pollen was used immediately for pollination by pipetting it onto the threads of a spike (previously covered with spike sacs), three days after thread development. The pollination treatments were carried out on 20 spikes. As control, pollen was pollinated by a sample without DNA.

Bombardment of Flowers with HELIOS:

The bombardment of flowers or inflorescence was carried out with the hand pistol "Helios" from Bio-Rad, according to the manufacture's instructions. As soon as the inflorescence or the flowers were exposed, they were bombarded with 1 to 5 shots at 50-300 psi. The exposed meristems were then covered and the inflorescence, or the flowers, were able to continue ripening.

In another approach, the protocol described by Gounaris et al., 2005, was carried out. Flowers that are to serve as pollen receptors were emasculated two days prior to the expected pollination. On the morning of the pollination day, intact stamens were collected from the donor flowers 1-2 hours after opening. Each of the donor flowers was treated with 4-5 shots from the particle cannon while they lay on a flat surface in a Petri dish, covered with a nylon net. The particle cannon was operated with a helium pressure of 400 psi, and was equipped with a particle diffusion screen. The helium gas purity was class 4.5 (99.994%). Each bombarded inflorescence was used to pollinate ca. 15-20 emasculated receptor flowers. The pollinated flowers were able to continue developing, and thus produce seeds.

Microinjection: DNA/RNA/Protein and Combinations

Embryo Microinjection:

The method described in Neuhaus et al., 1987, was used for the embryo microinjection. For this, embryos positioned on a cover glass were individually selected visually using a manual micro-capillary, connected to a silicone tube, and transferred into a medium on a object carrier in ca. 2 μl droplets for the microinjection (Spangenberg et al., 1986). The microinjection was carried out in that the embryoid bodies were secured in place with a retention capillary, and microinjected into the respective cells. Exogenous DNA was injected as a 1:1 mixture of lineated (through cleaving the plasmids outside the inserted genes) and super-coiled molecules, in a quantity of ca. 0.5 μg/μl in 50 mM NaCl, 50 mM tris-HCl, pH 7.8.

Microinjection of Shoot Meristems with *Agrobacterium* (Ab):

Shoot meristem microinjection with Ab was carried out as described by Sivakumar et al. (2014). 100 μl of the culture was microinjected with an insulin syringe into the embryonic shoot apical meristems of germinated cotton seeds. The culture was microinjected 1-5 times (0.5-1.0 mm depth), in order to check the effect of the number of microinjections in and around the embryonic shoot apical meristem. Excess bacteria culture was removed after dabbing the infected seeds on sterilized filter paper (Whatman no. 1). The seeds were co-cultivated in darkness for two days on a % strength MS medium. After the co-cultivation, the seedlings were washed with cefotaxime (200 mg/l), and transferred into an antibiotic selection medium, containing cefotaxime and hygromycin B.

Microinjection of DNA in Shoot Meristems:

The microinjection was carried out as described in Lusardi et al., (1994). Mature, dried seeds were washed for 30 seconds with absolute ethanol, followed by sterilization with commercial bleach (2.5% NaClO), supplemented with 0.01% Tween 80 (20 minutes while shaking). The seeds were then rinsed four to five times with sterilized distilled water. The germination was induced by incubating the seeds in a 9 cm Petri dish between filter papers with sterilized distilled water at 27° C. in the dark for 3-4 days. During this time, the shoot passed through nucleus integument and reached a length of ca. 0.8 to 1.0 cm. At this point, the shoot was removed from the seed at the scutellar node level. The coleoptile and the five or six embryonic cotyledons were removed under a stereomicroscope. After the embryonic leaves were prepared, the uncovered apices, surrounded by two leaf layers, were exposed in various stages of development. The isolated apices were cultivated in 9 cm Petri dishes in an MS medium (Murashige and Skoog, 1962), supplemented with 2% sucrose and thickened with 0.8% Difco Bacto-Agar (Difco Lab. Detroit), and grown further with a 27° C./22° C. temperature regimen and a 16/8 hour light/dark lighting schedule. Normal plants developed within 10 days. Over the next 15-20 days, they reached a sufficient size for transferring into pots, and were placed in the greenhouse. For the microinjection, the plasmids for the injection were dissolved in injection buffer (10 mM Tris-HCl and 0.1 M EDTA, pH 7.5). The injection buffer was filtered through a 0.2 μm disposable filter unit (Schleicher and Schuell, Germany), in order to sterilize the solution and prevent particle contamination. All of the injections were carried out under sterile conditions. The isolated shoot meristems from maize were transferred into 9 cm Petri dishes, the MS medium was supplemented with 2% sucrose, and thickened with 0.8% Difco Bacto Agar. The apices were oriented on the medium such that the apical domes were clearly visible. The cells of the L2 layers of the meristems were injected with a (high power) stereomicroscope (up to 200× enlargement; SV 8, Zeiss, Germany) equipped with an embryo splitter system from Research Instruments (UK). In some experiments, a co-injection of FITC dextran was used in order to better identify the injected cells (Neuhaus et al., 1993; Schnorf et al., 1991). An injection capillary (tip diameter of less than 1 μm) was mounted on the mechanical micromanipulator of the system, which was connected to a microinjector (Eppendorf 5242 microinjector), which delivered approximately 3 μl into the cells at a constant volume (Neuhaus et al., 1986, 1987; Schnorf et al., 1991). The second manipulator of the embryo splitter system was used to stabilize and move the apices during the injection. The manipulator was also equipped with a micro-needle for this, in order to be able to move and secure the apical meristems, such that they could be treated in the correct position.

Whiskers

Delivery by whiskers in the various meristems was carried out as described in Frame et al. (1994). The exposed tissue was treated with 40 μl 5% whisker suspension in 25 μl of plasmid DNA. The contents of the reaction vessel were first lightly stirred, and then placed either upright in a multi-sample head on a Vortex Genie II vortex mixer (Scientific Industries Inc., Bohemia, N.Y.), or horizontally in the retainer of a Mixomat amalgam mixer (Degussa Canada Ltd. Burlington, Ontario). The transformation was carried out for 60 seconds by mixing at full speed (Vortex Genie II), or at a fixed speed for 1 second (Mixomat).

Alternatively, whiskers were loaded, together with DNA/RNA or protein mix whiskers, into the pipette of a micromanipulator, and then macroinjected into meristematic tissue.

Cell Penetrating Peptides: DNA/RNA/Protein and Combinations Thereof

Mixing Cell Penetrating Peptides and Cas9 Protein and gRNA:

A protocol on the basis of Ramakrishna et al., 2014, was used for the use of cell penetrating peptides. One day after plating, the cells were washed with Opti-MEM and with Ca9-M9R and sgRNA:9R, either successively or simultaneously. The sgRNA:9R complex was formed during a 30 minute incubation of 10 mg sgRNA and 30-50 mg 9R peptide in 250 ml (for the sequential treatment) or 100 ml (for the simultaneous treatment) of Opti-MEM medium at room temperature.

Embryo:

TAT peptides (Tat, Tat2, M-Tat) were used for introducing GUS enzymes into wheat embryos. The TAT peptide and GUS enzyme are first prepared in separate micro-centrifuge test tubes. An unmarked TAT peptide (4 μg) was added to sterilized water (end volume: 100 μl). Likewise, 1 μg of the GUS enzyme (Sigma Aldrich) was added to sterilized water, to obtain an end volume of 100 μl. The contents of the two test tubes were mixed together, resulting in a 4:1 ratio of peptide to protein in the mixture. The mixture was incubated for 1 hour at room temperature, and then added to the isolated, immature embryos (in a 2 ml micro-centrifuge test tube) in the presence or absence of the permeating agent (tuluol/ethanol 1:40, vol./vol. with respect to the overall volume of the peptide/protein mixture). After 1 hour incubation at room temperature, the embryos were washed twice with the buffer, and subjected to a permeability and trypsin treatment (1:1 (vol./vol.) permeability buffer) for 5 minutes at room temperature. The embryos were washed twice with permeability buffer, followed by a histochemical GUS analysis of the embryos. 1 μg of the GUS enzyme is transfected for the delivery by the Chariot Protein Transduction kit (Active Motif, Carlsbad, Calif., USA), according to the manufacturer's instructions. Permeable and non-permeable embryos were incubated for 1 hour with the chariot-GUS complex. All of the post-incubation steps were the same as those described for the TAT peptides.

Transformation of Microspores:

The transformation of microspores using cell-penetrating peptides was carried out in accordance with Shim et al. (2012). The extraction of microspores was carried out in accordance with Eudes and Amundsen (2005), and all of the steps for isolating microspores were carried out using the NPB-99 liquid medium (Zheng et al., 2001; Eudes and Amundsen, 2005). After washing the microspores with NPB-99, 2-3 ml microspore solution were layered onto 2 to 3 ml 30% Percoll solution, containing 400 mM mannitol and 10 mM MES, pH 7.0. The microspores were centrifuged for 5 minutes at 100×g, at 4° C. The cells that formed a band at the Percoll/NPB-99 cleavage site were diluted to 15 ml in a fresh 15 ml centrifuge test tube with NPB-99, and then centrifuged again. The precipitation was decanted off, and the microspores were re-suspended in approximately 1 ml NPB-99 medium. The microspore concentration was determined using a hemocytometer, and adjusted to $2.5\times10^5$ cells/ml. Five treatments, including the control, were applied to microspore suspensions of the same extraction as follows: T1, control treatment, comprising 200 μl sterilized water; T2, 1 μg dsDNA in 100 μl sterilized water was added to 4 μg TAT2, diluted in 100 μl sterilized water, and mixed lightly, resulting in a 1:4 ratio of dsDNA to TAT2 (dsDNA: TAT2); T3, 1 μg dsDNA, diluted in 100 μl sterilized water, and 6 μl Chariot (Active Motif, Carlsbad, Calif.), diluted in 100 μl sterilized water, were mixed together (dsDNA-Pep1); T4, 4 μg RecA (MJS Biolynx, Brockville, Canada; #UB-70028) in 50 μl sterilized water and 1 μg dsDNA in 50 μl sterilized water were mixed together for 15 minutes, and 6 μl Chariot in 100 μl sterilized water was added to the dsDNA-RecA solution, to obtain an end volume of 200 μl in a 2 ml micro-centrifuge test tube (dsDNA-RecA-TAT2). After incubation for 15 minutes at room temperature (RT), 5 μl Lipofectamine (Invitrogen, Carlsbad, Ca; #11,668 to 019) was added to all of the preparations, and they were then incubated for a further five minutes at RT. The mixtures were then added immediately to 50,000 pelleted microspores in 2 ml micro-centrifuge test tubes, and incubated for 15 minutes. 100 μl NPB-99 was then added to each test tube, and they were incubated for 45 minutes at RT. The transfected microspores were then pelleted, the precipitation was removed, and the cells were washed twice with NPB-99. 1 ml NPB-99 was then added to the microspores in each of the test tubes, they were carefully mixed, and aliquots of 500 μl were pipetted into 35 mm Petri dishes, containing 3 ml NPB-99+10% Ficoll (Sigma, St. Louis, Mo.; F4375; NPB-99-10F) and 100 mg/l of the antibiotic cefotaxime (Sigma; #C7039).

Electroporation

Pollen Transformation:

Pollen transformation through electroporation was carried out according to the protocol established by Shi et al. (1996). For this, mature pollen, germinating pollen, or pollen without an exine layer was electroporated with a field strength of 750-1250 V/cm, having a constant impulse of 13 ms.

Ultrasonic Treatment

Pollen Ultrasonic Treatment:

Pollen transformation through ultrasonic treatment was carried out as described by Wang et al. (2000). For this, 0.3 g fresh pollen was collected in the morning, and mixed in 20 ml of a solution containing 5% sucrose with approximately 10 μg of the plasmid DNA of interest. The solution was treated with ultrasound, both before and after the plasmid DNA was added. Using a JY92-II ultrasound device from the Ningbo Xinzi Scientific Instrument Institute, the parameters that were used for the ultrasonic treatment were: sonic intensity: 300 W, eight treatments for 5 and 10 second intervals. Subsequently clipped maize silk was pollinated with the treated pollen.

LIST OF REFERENCES CITED IN THE EXAMPLE PORTION

Aragão, F. J., et al. (2005). "Germ line genetic transformation in cotton (*Gossypium hirsutum* L.) by selection of transgenic meristematic cells with a herbicide molecule." *Plant Science* 168(5): 1227-1233/Record #: 2408

Artschwager, E. (1926). "Anatomy of the vegetative organs of the sugar beet." *J. aqric. Res* 33: 143-176/Record #: 2352

Barnabas, B., et al. (1992). "In vitro pollen maturation and successful seed production in detached spikelet cultures in wheat (*Triticum aestivum* L.)." *Sexual Plant Reproduction* 5(4): 286-291/Record #: 2374

Buchheim, J. A., et al. (1989). "Maturation of Soybean Somatic Embryos and the Transition to Plantlet Growth." *Plant Physioloqy* 89(3): 768-775/Record #: 2402

Chee, P. P., et al. (1989). "Transformation of soybean (*Glycine max*) by infecting germinating seeds with *Agrobacterium tumefaciens.*" *Plant Physioloqy* 91(3): 1212-1218/Record #: 2392

Chowrira, G., et al. (1995). "Electroporation-mediated gene transfer into intact nodal meristemsin planta." *Molecular Biotechnoloqy* 3(1): 17-23/Record #: 2393

Eapen, S. (2011). "Pollen grains as a target for introduction of foreign genes into plants: an assessment." *Physioloqy and Molecular Biology of Plants* 17(1): 1-8/Record #: 2384

Frame, B. R., et al. (1994). "Production of fertile transgenic maize plants by silicon carbide whisker-mediated transformation." *The Plant Journal* 6(6): 941-948/Record #: 1755

Gounaris, Y., et al. (2005). "Pollen-mediated genetic transformation of cotton with the *Arabidopsis thaliana* hmgr cDNA using the particle gun." *Journal of Food Agriculture and Environment* 3(2): 157-160/Record #: 2330

Grandjean, O., et al. (2004). "In Vivo Analysis of Cell Division, Cell Growth, and Differentiation at the Shoot Apical Meristem in *Arabidopsis." The Plant Cell* 16(1): 74-87/Record #: 2387

Hermann, K., et al. (2007). "1-Aminocyclopropane-1-carboxylic acid and abscisic acid during the germination of sugar beet (*Beta vulgaris* L.): a comparative study of fruits and seeds." *Journal of Experimental Botany* 58(11): 3047-3060/Record #: 2370

Horikawa, Y., et al. (1997). "Transformants through pollination of mature maize (*Zea mays* L.) pollen delivered bar gene by particle gun." *Journal of Japanese Society of Grassland Science* (*Japan*)/Record #: 2383

Huang, Y., et al. (2009). "Probing the endosperm gene expression landscape in *Brassica napus." BMC Genomics* 10(1): 256/Record #: 2377

Itoh, J.-I., et al. (2005). "Rice Plant Development: from Zygote to Spikelet." *Plant and Cell Physiology* 46(1): 23-47/Record #: 2416

Keshamma, E., et al. (2008). "Tissue culture-independent in planta transformation strategy: an *Agrobacterium tumefaciens*-mediated gene transfer method to overcome recalcitrance in cotton (*Gossypium hirsutum* L.)." *Journal of Cotton Science* 12(3): 264-272/Record #: 2405

Kim, S., et al. (2014). "Highly efficient RNA-guided genome editing in human cells via delivery of purified Cas9 ribonucleoproteins." *Genome Research* 24(6): 1012-1019/Record #: 2288

Ko, S.-W., et al. (1983). "A simplified method of embryo culture in rice of *Oryza sativa* L." *Bot. Bull. Acad. Sin* 24: 97-101/Record #: 2415

Krens, F. A., et al. (1988). "Transformation and regeneration in sugar beet (*Beta vulgaris* L.) induced by 'shooter' mutants of *Agrobacterium tumefaciens." Euphytica* 39(3): 185-194/Record #: 1426

Leduc, N., et al. (1994). "Gene transfer to inflorescence and flower meristems using ballistic micro-targeting." *Sexual Plant Reproduction* 7(2): 135-143/Record #: 2345

Li, X., et al. (2004). "Improvement of cotton fiber quality by transforming the acsA and acsB genes into *Gossypium hirsutum* L. by means of vacuum infiltration." *Plant Cell Reports* 22(9): 691-697/Record #: 2419

Liu, J., et al. (2015). "Efficient delivery of nuclease proteins for genome editing in human stem cells and primary cells." *Nat. Protocols* 10(11): 1842-1859/Record #: 2421

Lusardi, M. C., et al. (1994). "An approach towards genetically engineered cell fate mapping in maize using the Lc gene as a visible marker: transactivation capacity of Lc vectors in differentiated maize cells and microinjection of <i>Lc</i> vectors into somatic embryos and shoot apical meristems." *The Plant Journal* 5(4): 571-582/Record #: 82

Mahn, A., et al. (1995). "Transient gene expression in shoot apical meristems of sugarbeet seedlings after particle bombardment." *Journal of Experimental Botany* 46(10): 1625-1628/Record #: 2367

Martin-Ortigosa, S., et al. (2014). "Proteolistics: a biolistic method for intracellular delivery of proteins." *Transgenic Research:* 1-14/Record #: 2260

Matthys-Rochon, E., et al. (1998). "In vitro development of maize immature embryos: a tool for embryogenesis analysis." *Journal of Experimental Botany* 49(322): 839-845/Record #: 2285

Mauney, J. R. (1961). "The Culture In vitro of Immature Cotton Embryos." *Botanical Gazette* 122(3): 205-209/Record #: 2409

McCabe, D. E., et al. (1993). "Transformation of elite cotton cultivars via particle bombardment of meristems." *Nature Biotechnoloqy* 11(5): 596-598/Record #: 2404

McCabe, D. E., et al. (1988). "Stable transformation of soybean (*Glycine max*) by particle acceleration." *Nature Biotechnoloqy* 6(8): 923-926/Record #: 2391

Muniz de Péadua, V., et al. (2001). "Transformation of Brazilian elite Indica-type rice (*Oryza sativa* L.) by electroporation of shoot apex explants." *Plant Molecular Biology Reporter* 19(1): 55-64/Record #: 2412

Naseri, G., et al. (2014). "In planta transformation of rice (*Oryza sativa*) using thaumatin-like protein gene for enhancing resistance to sheath blight." *African Journal of Biotechnoloqy* 11(31)/Record #: 2411

Neuhaus, G., et al. (1987). "Transgenic rapeseed plants obtained by the microinjection of DNA into microspore-derived embryoids." *Theoretical and Applied Genetics* 75(1): 30-36/Record #: 2123

Obert, B., et al. (2008). "Genetic transformation of barley microspores using anther bombardment." *Biotechnoloqy Letters* 30(5): 945-949/Record #: 2068

Olvera, H. F., et al. (2008). "Floral and Inflorescence Morphology and Ontogeny in *Beta vulgaris*, with Special Emphasis on the Ovary Position." *Annals of Botany* 102(4): 643-651/Record #: 2372

Rajasekaran, K. (2013). Biolistic Transformation of Cotton Zygotic Embryo Meristem. *T Transgenic Cotton.* 958: 47-57/Record #: 2403

Ramakrishna, S., et al. (2014). "Gene disruption by cell-penetrating peptide-mediated delivery of Cas9 protein and guide RNA." *Genome Research* 24(6): 1020-1027/Record #: 2287

Ritchie, G. L., et al. (2007). "Cotton growth and development." from cotton.tamu.edu/mwg-internal/de5fs23hu73ds/progress?id=-gCnQaUKI-guBsRa08L1m_QG1EFw5-bHQ3iPfT8R-CI, /Record #: 2410

Rod-in, W., et al. (2014). "The floral-dip method for rice (*Oryza sativa*) transformation." *Journal of Agricultural Technology* 10(2): 467-474/Record #: 2414

Sautter, C., et al. (1995). Ballistic microtargeting of visible marker genes to the shoot meristem of wheat. *Gene Transfer to Plants*, Springer: 152-156/Record #: 2339

Sautter, C., et al. (1995). "Shoot apical meristems as a target for gene transfer by microballistics." *Euphytica* 85(1-3): 45-51/Record #: 2373

Shi, H., et al. (1996). "Exine-detached pollen of *Nicotiana tabacum* as an electroporation target for gene transfer." *Acta Botanica Sinica* 38(8): 626-630/Record #: 2417

Shim, Y.-S., et al. (2012). "dsDNA and protein co-delivery in triticale microspores." *In Vitro Cellular & Developmental Biology—Plant:* 1-10/Record #: 1253

Shou, H., et al. (2002). “Irreproducibility of the soybean pollen-tube pathway transformation procedure.” *Plant Molecular Biology Reporter* 20(4): 325-334/Record #: 2399

Sivakumar, S., et al. (2014). “Optimization of factors influencing microinjection method for *Agrobacterium*-Mediated transformation of Embryonic Shoot Apical Meristem in Cotton (*Gossypium hirsutum* L. cv.SVPR-2).” *International Journal of Current Biotechnology*/Record #: 2420

Touraev, A., et al. (1997). “Plant male germ line transformation.” *The Plant Journal* 12(4): 949-956/Record #: 2380

Twell, D., et al. (1989). “Transient expression of chimeric genes delivered into pollen by microprojectile bombardment.” *Plant Physiology* 91(4): 1270-1274/Record #: 2316

Vain, P., et al. (1993). “Osmotic treatment enhances particle bombardment-mediated transient and stable transformation of maize.” *Plant Cell Reports* 12(2): 84-88/Record #: 20

Wang, J., et al. (2000). “Transgenic maize plants obtained by pollen-mediated transformation.” *Acta Botanica Sinica* 43(3): 275-279/Record #: 2418

Wiebold, W. J. (2012). “Arrested Development in the Soybean Field.” from ipm.missouri.edu/IPCM/2012/10/Arrested-Development-in-the-Soybean-Field//Record #: 2400

Zapata, C., et al. (1999). “Transformation of a Texas cotton cultivar by using *Agrobacterium* and the shoot apex.” *Theoretical and Applied Genetics* 98(2): 252-256/Record #: 2407

Zhang, C.-L., et al. (2008). “Efficient somatic embryogenesis in sugar beet (*Beta vulgaris* L.) breeding lines.” *Plant Cell, Tissue and Organ Culture* 93(2): 209-221/Record #: 1461

Zuris, J. A., et al. (2015). “Cationic lipid-mediated delivery of proteins enables efficient protein-based genome editing in vitro and in vivo.” *Nat Biotech* 33(1): 73-80/Record #: 2303

The invention claimed is:

1. A method for the production of a plant comprising (i) providing a target plant structure which is at least one meristematic cell in an inner layer L2 or inner layer L3 of a mature or immature plant embryo, wherein the at least one meristematic cell comprises at least one target nucleic acid region, and wherein the target plant structure is placed scutellum side down;

(ii) providing (I) at least one gRNA; or providing a first recombinant construct, the first recombinant construct comprising (a) a nucleic acid sequence coding for a gRNA, (b) optionally at least one regulatory sequence and/or a localization sequence, and (c) optionally at least one DNA repair matrix, and providing at least one CRISPR nuclease or a catalytically active fragment thereof and/or an effector domain; or providing a second recombinant construct, the second recombinant construct comprising (A) a nucleic acid sequence coding for a CRISPR nuclease or a catalytically active fragment thereof, and/or at least one effector domain or a sequence coding for an effector domain, and (B) optionally at least one regulatory sequence and/or a localization sequence, or providing (II) one recombinant construct, the one recombinant construct comprising (a) at least one gRNA or a nucleic acid sequence coding for a gRNA, and (b) at least one CRISPR nuclease, or a catalytically active fragment thereof, or a nucleic acid sequence coding for a CRISPR nuclease or a catalytically active fragment thereof, and/or at least one effector domain or a sequence coding for an effector domain, and (c) optionally at least one regulatory sequence and/or a localization sequence, wherein the gRNA is both able to hybridize with a section of the target nucleic acid region and to interact with the CRISPR nuclease or the catalytically active fragment thereof and/or the effector domain;

(iii) introducing by bombardment into the target plant structure (a) the gRNA or the first recombinant construct; and (b) the CRISPR nuclease or the catalytically active fragment thereof and/or the effector domain or the second recombinant construct; or (c) the one recombinant construct;

(iv) culturing the target plant structure under conditions which allow activation of the introduced gRNA or the first recombinant construct and CRISPR nuclease or the catalytically active fragment thereof and/or the effector domain or the second recombinant construct or the one recombinant construct and thus a specific modification of the target nucleic acid region in the target plant structure, in order to obtain a target plant structure comprising at least one meristematic cell which comprises the specific modification of the target nucleic acid region, wherein the target plant structure has the capacity to germinate without an intermediate step of cell culture in the form of callus production and regeneration and without manipulation of the target plant structure;

(v) obtaining a plant directly without an intermediate step of cell culture in the form of callus production and regeneration, from the specifically modified at least one meristematic cell by cell division and differentiation and optionally by an additional step of cross-fertilization or self-fertilization;

wherein the obtained plant comprises the specific modification of the target nucleic acid region.

2. The method of claim 1, wherein the first recombinant construct and/or the second recombinant construct or the one recombinant construct are transiently transformed into the plant cell of step (v).

3. The method of claim 1, in which in step (ii), the gRNA or the nucleic acid sequence coding for the gRNA and/or the CRISPR nuclease or a catalytically active fragment thereof or a nucleic acid sequence coding for CRISPR nuclease or a catalytically active fragment thereof and/or the effector domain or a sequence coding for an effector domain is adapted to application in a plant cell.

4. The method of claim 1, further comprising providing at least one vector for introducing the first and/or second recombinant constructs or the one recombinant construct between steps (ii) and (iii).

5. The method of claim 1, wherein at least one third recombinant construct comprising a recombinant nucleic acid fragment is provided between steps (ii) and (iii) for specific homology-directed repair of the target nucleic acid region in the target plant structure or insertion into the target nucleic acid region in the target plant structure and optionally at least one further vector for introducing the at least one third recombinant construct.

6. The method of claim 1, wherein the at least one meristematic cell is a cell of a monocotyledonous or dicotyledonous plant.

7. The method of claim 4, wherein the at least one vector is selected from the group consisting of *Agrobacterium* spp., a virus comprising a nucleic acid sequence selected from the group consisting of SEQ ID NOs:12-15 and 25-38, as well as sequences with at least 95% sequence identity with a sequence of SEQ ID NOs:12-15 or 25-38, or an agent which is suitable for transfection of a peptide or polypeptide sequence or of nucleic acid sequences or a combination thereof.

8. The method of claim 1, wherein (a) the gRNA is introduced into the target plant structure directly as a synthetic nucleic acid;

(b) the CRISPR nuclease, or the catalytically active fragment thereof, is introduced directly as a polypeptide; and/or (c) the effector domain is introduced as a nucleic acid or polypeptide.

9. The method of claim 1, wherein the gRNA or the nucleic acid sequence coding for the gRNA or the CRISPR nuclease or the catalytically active fragment thereof or the nucleic acid sequence coding for the CRISPR nuclease or the catalytically active fragment thereof or the effector domain or the sequence coding for the effector domain additionally comprises a localization sequence selected from a nuclear localization sequence, a plastid localization sequence, a mitochondrial localization sequence and a chloroplast localization sequence.

10. The method of claim 1, wherein an inhibitor of endogenous non-homologous end joining repair mechanism is introduced into the target plant structure.

11. The method of claim 1, wherein the recombinant construct comprises a nucleic acid sequence selected from SEQ ID NOs: 23 and 24, as well as sequences with at least 95% sequence identity with SEQ ID NOs: 23 or 24.

12. A recombinant construct comprising a nucleic acid selected from SEQ ID NOs: 23 and 24, and sequences with at least sequence identity with SEQ ID NOs: 23 or 24.

13. A recombinant construct comprising utilizing a nucleic acid sequence selected from the group consisting of SEQ ID NOs:12-15 and 25-38, as well as sequences with at least 95% sequence identity with SEQ ID NOs:12-15 or 25-38.

* * * * *